(12) United States Patent
Feder et al.

(10) Patent No.: US 7,141,381 B2
(45) Date of Patent: Nov. 28, 2006

(54) HUMAN LEUCINE-RICH REPEAT-CONTAINING PROTEINS SPECIFICALLY EXPRESSED IN THE NERVOUS SYSTEM

(75) Inventors: John N. Feder, Belle Mead, NJ (US);
Gabriel Mintier, Hightstown, NJ (US);
Chandra S. Ramanathan, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/424,233

(22) Filed: Apr. 25, 2003

(65) Prior Publication Data

US 2003/0220263 A1    Nov. 27, 2003

Related U.S. Application Data

(60) Provisional application No. 60/375,335, filed on Apr. 25, 2002.

(51) Int. Cl.
*G01N 33/53* (2006.01)
*C12Q 1/68* (2006.01)
*C12P 21/02* (2006.01)
*A61K 38/17* (2006.01)
*C07H 21/00* (2006.01)

(52) U.S. Cl. .......................... 435/7.1; 435/6; 435/69.1; 435/320.1; 435/325; 514/12; 530/350; 530/388.1; 536/23.5

(58) Field of Classification Search ................ 424/9.1; 435/6, 7.1, 69.1; 530/350
See application file for complete search history.

(56) References Cited

U.S. PATENT DOCUMENTS

| | | |
|---|---|---|
| 2003/0027988 A1 | 2/2003 | Baker et al. |
| 2003/0036635 A1 | 2/2003 | Baker et al. |
| 2003/0044934 A1 | 3/2003 | Baker et al. |
| 2003/0045687 A1 | 3/2003 | Baker et al. |
| 2003/0050448 A1 | 3/2003 | Baker et al. |
| 2003/0065147 A1 | 4/2003 | Baker et al. |
| 2003/0069397 A1 | 4/2003 | Baker et al. |
| 2003/0073814 A1 | 4/2003 | Baker et al. |
| 2003/0073816 A1 | 4/2003 | Baker et al. |
| 2003/0073817 A1 | 4/2003 | Baker et al. |
| 2003/0088063 A1 | 5/2003 | Baker et al. |
| 2003/0088064 A1 | 5/2003 | Baker et al. |
| 2003/0088065 A1 | 5/2003 | Baker et al. |
| 2003/0088066 A1 | 5/2003 | Baker et al. |
| 2003/0088067 A1 | 5/2003 | Baker et al. |
| 2003/0088068 A1 | 5/2003 | Baker et al. |
| 2003/0088070 A1 | 5/2003 | Baker et al. |
| 2003/0088071 A1 | 5/2003 | Baker et al. |
| 2003/0088072 A1 | 5/2003 | Baker et al. |
| 2003/0092886 A1 | 5/2003 | Baker et al. |
| 2003/0092887 A1 | 5/2003 | Baker et al. |
| 2003/0092888 A1 | 5/2003 | Baker et al. |
| 2003/0092889 A1 | 5/2003 | Baker et al. |
| 2003/0092890 A1 | 5/2003 | Baker et al. |
| 2003/0096362 A1 | 5/2003 | Baker et al. |
| 2003/0096959 A1 | 5/2003 | Baker et al. |
| 2003/0096960 A1 | 5/2003 | Baker et al. |
| 2003/0096961 A1 | 5/2003 | Baker et al. |
| 2003/0096962 A1 | 5/2003 | Baker et al. |
| 2003/0096963 A1 | 5/2003 | Baker et al. |
| 2003/0096964 A1 | 5/2003 | Baker et al. |
| 2003/0096965 A1 | 5/2003 | Baker et al. |
| 2003/0096966 A1 | 5/2003 | Baker et al. |
| 2003/0096967 A1 | 5/2003 | Baker et al. |
| 2003/0096968 A1 | 5/2003 | Baker et al. |
| 2003/0096969 A1 | 5/2003 | Baker et al. |
| 2003/0096970 A1 | 5/2003 | Baker et al. |
| 2003/0096971 A1 | 5/2003 | Baker et al. |
| 2003/0096972 A1 | 5/2003 | Baker et al. |
| 2003/0100064 A1 | 5/2003 | Baker et al. |
| 2003/0100708 A1 | 5/2003 | Baker et al. |
| 2003/0100709 A1 | 5/2003 | Baker et al. |
| 2003/0100710 A1 | 5/2003 | Baker et al. |
| 2003/0100711 A1 | 5/2003 | Baker et al. |
| 2003/0100712 A1 | 5/2003 | Baker et al. |
| 2003/0100713 A1 | 5/2003 | Baker et al. |
| 2003/0100714 A1 | 5/2003 | Baker et al. |
| 2003/0100715 A1 | 5/2003 | Baker et al. |
| 2003/0100716 A1 | 5/2003 | Baker et al. |
| 2003/0100717 A1 | 5/2003 | Baker et al. |
| 2003/0100718 A1 | 5/2003 | Baker et al. |
| 2003/0100719 A1 | 5/2003 | Baker et al. |
| 2003/0100720 A1 | 5/2003 | Baker et al. |

(Continued)

FOREIGN PATENT DOCUMENTS

EP        1 270 724        1/2003

(Continued)

OTHER PUBLICATIONS

Kobe et al., Trends Biochem. Sci. 1994, vol. 19(10), pp. 415-421.*

(Continued)

*Primary Examiner*—Janet L. Andres
*Assistant Examiner*—Gregory S. Emch
(74) *Attorney, Agent, or Firm*—Stephen C. D'Amico

(57) ABSTRACT

The present invention describes two newly discovered Human Leucine Rich Repeat (LRR)-containing proteins, HLRRNS-2 and HLRRNS-3, and their encoding polynucleotides. Also described are expression vectors, host cells, agonists, antagonists, antisense molecules, and antibodies associated with the polynucleotides and/or polypeptides of the present invention. In addition, methods involving the new HLRR-containing proteins HLRRNS-2 and HLRRNS-3, or modulators thereof, for treating, diagnosing, preventing, and screening for disorders associated with aberrant cell growth, neurological conditions, and diseases or disorders related to the brain are illustrated.

12 Claims, 32 Drawing Sheets

U.S. PATENT DOCUMENTS

| | | | |
|---|---|---|---|
| 2003/0100721 A1 | 5/2003 | Baker et al. |
| 2003/0100722 A1 | 5/2003 | Baker et al. |
| 2003/0100723 A1 | 5/2003 | Baker et al. |
| 2003/0100724 A1 | 5/2003 | Baker et al. |
| 2003/0100725 A1 | 5/2003 | Baker et al. |
| 2003/0100726 A1 | 5/2003 | Baker et al. |
| 2003/0100727 A1 | 5/2003 | Baker et al. |
| 2003/0100728 A1 | 5/2003 | Baker et al. |
| 2003/0100729 A1 | 5/2003 | Baker et al. |
| 2003/0100730 A1 | 5/2003 | Baker et al. |
| 2003/0100731 A1 | 5/2003 | Baker et al. |
| 2003/0100732 A1 | 5/2003 | Baker et al. |
| 2003/0100733 A1 | 5/2003 | Baker et al. |
| 2003/0100734 A1 | 5/2003 | Baker et al. |
| 2003/0100735 A1 | 5/2003 | Baker et al. |
| 2003/0100736 A1 | 5/2003 | Baker et al. |
| 2003/0100737 A1 | 5/2003 | Baker et al. |
| 2003/0100738 A1 | 5/2003 | Baker et al. |
| 2003/0105288 A1 | 6/2003 | Baker et al. |
| 2003/0105289 A1 | 6/2003 | Baker et al. |
| 2003/0105290 A1 | 6/2003 | Baker et al. |
| 2003/0105291 A1 | 6/2003 | Baker et al. |
| 2003/0220263 A1 | 11/2003 | Feder et al. |
| 2004/0006206 A1 | 1/2004 | Baker et al. |
| 2004/0018594 A1 | 1/2004 | Alsobrook, II et al. |
| 2004/0019183 A1 | 1/2004 | Baker et al. |
| 2004/0044179 A1 | 3/2004 | Baker et al. |
| 2004/0044180 A1 | 3/2004 | Baker et al. |

FOREIGN PATENT DOCUMENTS

| | | |
|---|---|---|
| WO | WO 01/34769 | 5/2001 |
| WO | WO 01/66690 | 9/2001 |
| WO | WO 01/77137 | 10/2001 |
| WO | WO 02/08288 | 1/2002 |
| WO | WO 02/20569 | 3/2002 |
| WO | WO 02/090504 | 11/2002 |
| WO | WO 03/004615 | 1/2003 |
| WO | WO 03/035831 | 5/2003 |
| WO | WO 03/059256 | 7/2003 |
| WO | WO 03/104429 | 12/2003 |

OTHER PUBLICATIONS

Chen, G. et al. Molecular and Cellular Proteomics, 2002, vol. 1, pp. 304-313.*

Andreasen et al. Cerebrospinal fluid beta-amyloid(1-42) in Alzheimer disease: differences between early- and late-onset Alzheimer disease and stability during the course of disease. Arch. Neurol. Jun.56(6):673-80, 1999.*

Michell et al. Biomarkers and Parkinson's Disease. Brain. Aug; 127: 1693-1705, 2004.*

Mickle JE et al. Genotype-phenotype relationships in cystic fibrosis. Med Clin North Am. May 2000;84(3):597-607.*

Voet et al. Biochemistry. 1990. John Wiley & Sons, Inc. 126-128 and 228-234.*

Yan et al. Two-amino acid molecular switch in a epithelial morphogen that regulates binding to two distinct receptors. Science 290: 523-527, 2000.*

NCBI Entrez Accession No. gi|NP_115928, Aruga, J. et al., Dec. 22, 2003.

NCBI Entrez Accession No. gi|11877257, Heath, P., Dec. 16, 2000.

NCBI Entrez Accession No. gi|14017925, Nagase, T. et al., Jun. 5, 2001.

NCBI Entrez Accession No. gi|18073098, Redolfi, E. et al., Jan. 4, 2002.

NCBI Entrez Accession No. gi|20984229, NCBI Annotation Project, Nov. 18, 2002.

NCBI Entrez Accession No. gi|21749288, Suzuki, O. et al., Jul. 15, 2002.

NCBI Entrez Accession No. gi|23342567, Parham, C.L. et al., Sep. 26, 2002.

NCBI Entrez Accession No. gi|25031235, Oct. 30, 2003.

NCBI Entrez Accession No. gi|37546329, Oct. 17, 2003.

Aruga, J. et al., "Human SLITRK family genes: genomic organization and expression profiling in normal brain and brain tumor tissue", Gene, vol. 315, pp. 87-94 (2003).

Nagase, T. et al., "Prediction of the Coding Sequences of Unidentified Human Genes. XX. The Complete Sequences of 100 New cDNA Clones from Brain Which Code for Large Proteins in vivo", DNA Research, vol. 8, pp. 85-95 (2001).

NCBI Entrez Accession No. gi|26328293, Carninci, P. et al., Apr. 3, 2004.

NCBI Entrez Accession No. gi|NP_079269, Clark, H.F. et al., Jun. 24, 2004.

Swiss-Prot Accession No. Q8JZS8, Release 22, Oct. 2002.

NCBI Entrez Accession No. AAB45703 (gi:1831249), Hudson, D. et al., Feb. 7, 1997.

NCBI Entrez Accession No. AAB50905 (gi:1911844), Heid, H.W. et al., Mar. 28, 1997.

NCBI Entrez Accession No. AAB61227 (gi:2196755), Corbo, J.C. et al., Jun. 15, 1997.

NCBI Entrez Accession No. AAB61228 (gi:2196757), Ropp, P.A. et al., Oct. 27, 1999.

NCBI Entrez Accession No. AAE01312 (gi:5941780), Gruenwald, S. et al., Sep. 29, 1999.

NCBI Entrez Accession No. AAE06789 (gi:5954285), Vlasuk, G. et al., Sep. 29, 1999.

NCBI Entrez Accession No. AAE06798 (gi:5954294), Vlasuk, G. et al., Sep. 29, 1999.

NCBI Entrez Accession No. AAO67545 (gi:29540614), Lauren, J. et al., Apr. 16, 2003.

NCBI Entrez Accession No. AAO67552 (gi:29542647), Lauren, J. et al., Apr. 16, 2003.

NCBI Entrez Accession No. AK056644 (gi:16552103), Ota, T. et al., Jan. 30, 2004.

NCBI Entrez Accession No. AY182024 (gi:29540613), Lauren, J. et al., Apr. 2003.

NCBI Entrez Accession No. BAB71240 (gi:16552104), Ota, T. et al., Jan. 30, 2004.

NCBI Entrez Accession No. CAB63072 (gi:6572272), Corby, N., Jan. 12, 2001.

NCBI Entrez Accession No. NP_083156 (gi:21312700), Kawai, J. et al., Sep. 19, 2002.

NCBI Entrez Accession No. NP_115928 (gi:33504581), Aruga, J. et al., Oct. 27, 2004.

NCBI Entrez Accession No. NP_849161 (gi:30520365), Clark, H.F. et al., Oct. 27, 2004.

NCBI Entrez Accession No. NT_005087 (gi:16158989), NCBI Annotation Project, Oct. 16, 2001.

NCBI Entrez Accession No. NT_025408 (gi:11422945), International Human Genome Project collaborators, Feb. 10, 2001.

NCBI Entrez Accession No. O43300 (gi:50400808), Lauren, J. et al., Jan. 25, 2005.

NCBI Entrez Accession No. O94933 (gi:14424222), Nagase, T. et al., Jan. 25, 2005.

NCBI Entrez Accession No. O94991 (gi:46397810), Nagase, T. et al., Jan. 25, 2005.

NCBI Entrez Accession No. XP_086884 (gi:29746658), International Human Genome Sequencing Consortium, Apr. 28, 2003.

Swiss-Prot Accession No. Q86XY1, Release 24, Jun. 2003.

Swiss-Prot Accession No. Q9BGP6, Release 17, Jun. 2001.

Swiss-Prot Accession No. Q9DBB9, Release 45, Oct. 2004.

Swiss-Prot Accession No. Q9H5Y7, Release 44, Jul. 2004.

Swiss-Prot Accession No. Q9H9T0, Release 16, Mar. 2001.

Swiss-Prot Accession No. Q96E60, Release 19, Dec. 2001.

Altschul, S.F. et al., "Gapped BLAST and PSI-BLAST: a new generation of protein database search programs", Nucleic Acids Research, vol. 25, No. 17, pp. 3389-3402 (1997).

Buchanan, S.G.S.C. et al., "Structural and Functional Diversity in the Leucine-Rich Repeat Family of Proteins", Prog. Biophys. Molec. Biol., vol. 65, No. 1/2, pp. 1-44 (1996).

Burge, B.W. et al., "Glycopeptides of the Membrane Glycoprotein of Sindbis Virus", J. Mol. Biol., vol. 47, pp. 449-466 (1970).

Dixon, M.S. et al., "Genetic complexity of pathogen perception by plants: The example of Rcr3, a tomato gene required specifically by Cf-2", Proc. Natl. Acad. Sci., vol. 97, No. 16, pp. 8807-8814 (2000).

Eldon, E. et al., "The *Drosophila 18 wheeler* is required for morphogenesis and has striking similarities to *Toll*", Development, vol. 120, pp. 885-899 (1994).

Halfon, M.S. et al., "The *Drosophila Toll* Gene Functions Zygotically and Is Necessary for Proper Motoneuron and Muscle Development", Developmental Biology, vol. 169, pp. 151-167 (1995).

Harton, J.A. et al., "Class II Transactivator: Mastering the Art of Major Histocompatibility Complex Expression", Molecular and Cellular Biology, vol. 20, No. 17, pp. 6185-6194 (2000).

Hoffman, H.M. et al., "Mutation of a new gene encoding a putative pyrin-like protein causes familial cold autoinflammatory syndrome and Muckle-Wells syndrome", Nature Genetics, vol. 29, pp. 301-305 (2001).

Hugot, J.-P. et al., "Association of NOD2 leucine-rich repeat variants with susceptibility to Crohn's disease", Nature, vol. 411, pp. 599-603 (2001).

Inohara, N. et al., "An Induced Proximity Model for NF-κB Activation in the Nod1/RICK and RIP Signaling Pathways", The Journal of Biological Chemistry, vol. 275, No. 36, pp. 27823-27831 (2000).

Inohara, N. et al., "Nod1, an Apaf-1-like Activator of Caspase-9 and Nuclear Factor-κB", The Journal of Biological Chemistry, vol. 274, No. 21, pp. 14560-14567 (1999).

Jacobs, J.R. et al., "Embryonic Development of Axon Pathways in the *Drosophila* CNS. I. A Glial Scafford Appears Before the First Growth Cones", The Journal of Neuroscience, vol. 9, No. 7, pp. 2402-2411 (1989).

Kennaway, D.J. et al., "Melatonin and Circadian Rhythms", Current Topics in Medicinal Chemistry, vol. 2, No. 2, pp. 199-209 (2002).

Liang, Y. et al., "Mammalian Homologues of the *Drosophila* Slit Protein Are Ligands of the Heparan Sulfate Proteoglycan Glypican-1 in Brain", The Journal of Biological Chemistry, vol. 274, No. 25, pp. 17885-17892 (1999).

Schneider, D.S. et al., "Dominant and recessive mutations define functional domains of *Toll*, a transmembrane protein required for dorsal-ventral polarity in the *Drosophila* embryo", Genes & Development, vol. 5, pp. 797-807 (1991).

Simpson, J.H. et al., "Short-Range and Long-Range Guidance by Slit and Its Robo Receptors: A Combinatorial Code of Robo Receptors Controls Lateral Position", Cell, vol. 103, pp. 1019-1032 (2000).

Takahashi, N. et al., "Periodicity of leucine and tandem repetition of a 24-amino acid segment in the primary structure of leucine-rich $\alpha_2$-glycoprotein of human serum", Proc. Natl. Acad. Sci. USA, vol. 82, pp. 1906-1910 (1985).

van der Voort, R. et al., "Regulation of Cytokine Signaling by B Cell Antigen Receptor and CD40-controlled Expression of Heparan Sulfate Proteoglycans", J. Exp. Med., vol. 192, No. 8, pp. 1115-1124 (2000).

Verbeek, M.M. et al., "Agrin Is a Major Heparan Sulfate Proteoglycan Accumulating in Alzheimer's Disease Brain", American Journal of Pathology, vol. 155, No. 6, pp. 2115-2125 (1999).

* cited by examiner

FIG. 1A

```
GGACAAGGGCTGCCTCCCAGCACAGCTACAAAACACTTTAAACCTGACCA
GCTAAATGGATAAACCTAGCCTGCATAGCTTTTAAACTGGGGTCTCATAC
AGCACAGGAGGCCTACTTGCTTCAAGAACTGAAAATCCAGAGGATGAATT
GCTTTATCTGGGAATGGCAAAAGCCAGCACAATAAGGAATGCCAGTTTGT
ATGGGGCTACTAGCTCACATGCGGGATCAGAATGGTGTGAATGACAGCCG
CACTGTGTCATGAAGGTGGTGGTGGTTTCCGCACAAGAGACCAAATAAGA
AGAAAGCTGAGAGAGGGGGGAAACGTTTTTGGATGACAAAGGATGGGTTT
CCATTTAATTACGCAGCTGAAAGGCATGAGTGTGGTGCTGGTGCTACTTC
CTACACTGCTGCTTGTTATGCTCACGGGTGCTCAGAGAGCTTGCCCAAAG
AACTGCAGATGTGATGGCAAAATTGTGTACTGTGAGTCTCATGCTTTCGC
AGATATCCCTGAGAACATTTCTGGAGGGTCACAAGGCTTATCATTAAGGT
TCAACAGCATTCAGAAGCTCAAATCCAATCAGTTTGCCGGCCTTAACCAG
CTTATATGGCTTTATCTTGACCATAATTACATTAGCTCAGTGGATGAAGA
TGCATTTCAAGGGATCCGTAGACTGAAAGAATTAATTCTAAGCTCCAACA
AAATTACTTATCTGCACAATAAAACATTTCACCCAGTTCCCAATCTCCGC
AATCTGGACCTCTCCTACAATAAGCTTCAGACATTGCAATCTGAACAATT
TAAAGGCCTTCGGAAACTCATCATTTTGCACTTGAGATCTAACTCACTAA
AGACTGTGCCCATAAGAGTTTTTCAAGACTGTCGGAATCTTGATTTTTTG
GATTTGGGTTACAATCGTCTTCGAAGCTTGTCCCGAAATGCATTTGCTGG
CCTCTTGAAGTTAAAGGAGCTCCACCTGGAGCACAACCAGTTTTCCAAGA
TCAACTTTGCTCATTTTCCACGTCTCTTCAACCTCCGCTCAATTTACTTA
CAATGGAACAGGATTCGCTCCATTAGCCAAGGTTTGACATGGACTTGGAG
TTCCTTACACAACTTGGATTTATCAGGGAATGACATCCAAGGAATTGAGC
CGGGCACATTTAAATGCCTCCCAATTTACAAAAATTGAATTTGGATTCC
AACAAGCTCACCAATATCTCACAGGAAACTGTCAATGCGTGGATATCATT
AATATCCATCACATTGTCTGGAAATATGTGGGAATGCAGTCGGAGCATTT
GTCCTTTATTTTATTGGCTTAAGAATTTCAAAGGAAATAAGGAAAGCACC
ATGATATGTGCGGGACCTAAGCACATCCAGGGTGAAAAGGTTAGTGATGC
AGTGGAAACATATAATATCTGTTCTGAAGTCCAGGTGGTCAACACAGAAA
GATCACACCTGGTGCCCCAAACTCCCCAGAAACCTCTGATTATCCCTAGA
```

FIG. 1B

CCTACCATCTTCAAACCTGACGTCACCCAATCCACCTTTGAAACACCAAG
CCCTTCCCCAGGGTTTCAGATTCCTGGCGCAGAGCAAGAGTATGAGCATG
TTTCATTTCACAAAATTATTGCCGGGAGTGTGGCTCTCTTTCTCTCAGTG
GCCATGATCCTCTTGGTGATCTATGTGTCTTGGAAACGCTACCCAGCCAG
CATGAAACAACTCCAGCAACACTCTCTTATGAAGAGGCGGCGGAAAAAGG
CCAGAGAGTCTGAAAGACAAATGAATTCCCCTTTACAGGAGTATTATGTG
GACTACAAGCCTACAAACTCTGAGACCATGGATATATCGGTTAATGGATC
TGGGCCCTGCACATATACCATCTCTGGCTCCAGGGAATGTGAGATGCCAC
ACCACATGAAGCCCTTGCCATATTACAGCTATGACCAGCCTGTGATCGGG
TACTGCCAGGCCCACCAGCCACTCCATGTCACCAAGGGCTATGAGACAGT
GTCTCCAGAGCAGGACGAAAGCCCCGGCCTGGAGCTGGGCCGAGACCACA
GCTTCATCGCCACCATCGCCAGGTCGGCAGCACCGGCCATCTACCTAGAG
AGAATTGCAAACTAACGCTGAAGCCAACTCCTCACTGGGGAGCTCCATGG
GGGGGAGGGAGGCCCTTCATCTTAAAGGAGAATGGGTGTCCACAATCGCG
CAATCGAGCAAGCTCATCGTTCCTGTTAAACATTTATGGCATAGAGAAA
AGAAAAAAAAAAAAAAA

FIG. 2

MGFHLITQLKGMSVVLVLLPTLLLVMLTGAQRACPKNCRCDGKIVYCESHAFADIPENISGGSQGLSLRFN
SIQKLKSNQFAGLNQLIWLYLDHNYISSVDEDAFQGIRRLKELILSSNKITYLHNKTFHPVPNLRNLDLSY
NKLQTLQSEQFKGLRKLIILHLRSNSLKTVPIRVFQDCRNLDFLDLGYNRLRSLSRNAFAGLLKLKELHLE
HNQFSKINFAHFPRLFNLRSIYLQWNRIRSISQGLTWTWSSLHNLDLSGNDIQGIEPGTFKCLPNLQKLNL
DSNKLTNISQETVNAWISLISITLSGNMWECSRSICPLFYWLKNFKGNKESTMICAGPKHIQGEKVSDAVE
TYNICSEVQVVNTERSHLVPQTPQKPLIIPRPTIFKPDVTQSTFETPSPSPGFQIPGAEQEYEHVSFHKII
AGSVALFLSVAMILLVIYVSWKRYPASMKQLQQHSLMKRRRKKARESERQMNSPLQEYYVDYKPTNSETMD
ISVNGSGPCTYTISGSRECEMPHHMKPLPYYSYDQPVIGYCQAHQPLHVTKGYETVSPEQDESPGLELGRD
HSFIATIARSAAPAIYLERIAN

FIG. 3A

```
TCCTGATTCCTGATTTTCCACCCCCTTTTTGCGCTTTTTTTTTTTTCCTAAAGCGATTG
CGATTTCTGCTGGGAGCTCAAGACGGGCGAGCTGCCCGAGATCTCTTCGAGATACCCCAG
GGGAGGAGGAGATGGGCAGGATTTAGTAGGACAACTCGGTTACTAATGACTTGGCGGCTG
GCTGCGACCCCCGGGAAATCAGGTTTGCCTGTAGGTACCTGAGTTGACACCGAAGGTGC
CTAAAGATGCTGAGCGGCGTTTGGTTCCTCAGTGTGTTAACCGTGGCCGGGATCTTACAG
ACAGAGAGTCGCAAAACTGCCAAAGACATTTGCAAGATCCGCTGTCTGTGCGAAGAAAAG
GAAAACGTACTGAATATCAACTGTGAGAACAAAGGATTTACAACAGTTAGCCTGCTCCAG
CCCCCCCAGTATCGAATCTATCAGCTTTTTCTCAATGGAAACCTCTTGACAAGACTGTAT
CCAAACGAATTTGTCAATTACTCCAACGCGGTGACTCTTCACCTAGGTAACAACGGGTTA
CAGGAGATCCGAACAGGGGCATTCAGTGGCCTGAAAACTCTCAAAAGACTGCATCTCAAC
AACAACAAGCTTGAGATATTGAGGGAGGACACCTTCCTAGGCCTGGAGAGCCTGGAGTAT
CTCCAGGCCGACTACAATTACATCAGTGCCATCGAGGCTGGGGCATTCAGCAAACTTAAC
AAGCTCAAAGTGCTCATCCTGAATGACAACCTTCTGCTTTCACTGCCCAGCAATGTGTTC
CGCTTTGTCCTGCTGACCCACTTAGACCTCAGGGGGAATAGGCTAAAAGTAATGCCTTTT
GCTGGCGTCCTTGAACATATTGGAGGGATCATGGAGATTCAGCTGGAGGAAAATCCATGG
AATTGCACTTGTGACTTACTTCCTCTCAAGGCCTGGCTAGACACCATAACTGTTTTTGTG
GGAGAGATTGTCTGTGAGACTCCCTTTAGGTTGCATGGGAAAGACGTGACCCAGCTGACC
AGGCAAGACCTCTGTCCCAGAAAAGTGCCAGTGATTCCAGTCAGAGGGGCAGCCATGCT
GACACCCACGTCCAAAGGCTGTCACCTACAATGAATCCTGCTCTCAACCCAACCAGGGCT
CCGAAAGCCAGCCGGCCGCCCAAAATGAGAAATCGTCCAACTCCCCGAGTGACTGTGTCA
AAGGACAGGCAAAGTTTTGGACCCATCATGGTGTACCAGACCAAGTCTCCTGTGCCTCTC
ACCTGTCCCAGCAGCTGTGTCTGCACCTCTCAGAGCTCAGACAATGGTCTGAATGTAAAC
TGCCAAGAAAGGAAGTTCACTAATATCTCTGACCTGCAGCCCAAACCGACCAGTCCAAAG
AAACTCTACCTAACAGGGAACTATCTTCAAACTGTCTATAAGAATGACCTCTTAGAATAC
AGTTCTTTGGACTTACTGCACTTAGGAAACAACAGGATTGCAGTCATTCAGGAAGGTGCC
TTTACAAACCTGACCAGTTTACGCAGACTTTATCTGAATGGCAATTACCTTGAAGTGCTG
TACCCTTCTATGTTTGATGGACTGCAGAGCTTGCAATATCTCTATTTAGAGTATAATGTC
ATTAAGGAAATTAAGCCTCTGACCTTTGATGCTTTGATTAACCTACAGCTACTGTTTCTG
AACAACAACCTTCTTCGGTCCTTACCTGATAATATATTTGGGGGACGGCCCTAACCAGG
CTGAATCTGAGAAACAACCATTTTTCTCACCTGCCCGTGAAAGGGGTTCTGGATCAGCTC
CCGGCTTTCATCCAGATAGATCTGCAGGAGAACCCCTGGGACTGTACCTGTGACATCATG
GGGCTGAAAGACTGGACAGAACATGCCAATTCCCCTGTCATCATTAATGAGGTGACTTGC
GAATCTCCTGCTAAGCATGCAGGGGAGATACTAAAATTTCTGGGGAGGGAGGCTATCTGT
CCAGACAGCCCAAACTTGTCAGATGGAACCGTCTTGTCAATGAATCACAATACAGACACA
CCTCGGTCGCTTAGTGTGTCTCCTAGTTCCTATCCTGAACTACACACTGAAGTTCCACTG
TCTGTCTTAATTCTGGGATTGCTTGTTGTTTTCATCTTATCTGTCTGTTTTGGGGCTGGT
TTATTCGTCTTTGTCTTGAAACGCCGAAAGGGAGTGCCGAGCGTTCCAGGAATACCAAC
AACTTAGACGTAAGCTCCTTTCAATTACAGTATGGGTCTTACAACACTGAGACTCACGAT
AAAACAGACGGCCATGTCTACAACTATATCCCCCACCTGTGGGTCAGATGTGCCAAAAC
CCCATCTACATGCAGAAGGAAGGAGACCCAGTAGCCTATTACCGAAACCTGCAAGAGTTC
AGCTATAGCAACCTGGAGGAGAAAAAGAAGAGCCAGCCACACCTGCTTACACAATAAGT
GCCACTGAGCTGCTAGAAAAGCAGGCCACACCAAGAGAGCCTGAGCTGCTGTATCAAAAT
ATTGCTGAGCGAGTCAAGGAACTTCCCAGCGCAGGCCTAGTCCACTATAACTTTTGTACC
TTACCTAAAAGGCAGTTTGCCCCTTCCTATGAATCTCGACGCCAAAACCAAGACAGAATC
AATAAAACCGTTTTATATGGAACTCCCAGGAAATGCTTTGTGGGGCAGTCAAAACCCAAC
```

FIG. 3B

```
CACCCTTTACTGCAAGCTAAGCCGCAATCAGAACCGGACTACCTCGAAGTTCTGGAAAAA
CAAACTGCAATCAGTCAGCTGTGAAGGGAAATCATTTACAACCCTAAGGCATCAGAGGAT
GCTGCTCCGAACTGTTGGAAACAAGGACATTAGCTTTTGTGTTTGTTTTTGTTCTCCCTT
TCCCAGTGTTAATGGGGACTTTGAAAATGTTTGGGAGATAGGATGAAGTCATGATTTTG
CTTTTGCAAGTTTTCCTTTAAATTATTTCTCTCTCGCTCTCCTCCCCTCCTTTTTTTTTT
TTTTTTTTCTTTTTCCCTTCTCTTCTTAGGAACCATCAGTGGACATGAATGTTTCTACA
ATGCATTTCTTCATAGATTTTGTTTATGGTTTTGTTTCTTTTTTCTTCTTTGTTTTTCAG
TGTGGGAGTGGGAAGAGGAGATTATAGTGACTGAAGAAAGAATAGGCAAACTTTTCAAAT
GAAAATGGATATTTAGTGTATTTTGTAGAAGATCTCCAAAGATCTTTTGTGACTACAACT
TCTTTTGTAAATAATGATATATGGTATTTCCATCGTCAGTTACCGAGTATAGCCACTGGG
TATCACTACTTTGTGTTAAAGTGCCTTCGCACTTTAAGTACATTACTTAAATGTTGCTTT
TAGCTTTGATAAATTGAAAATATTTTAATGTGTTGTATTTTTGAAATTGAAAACACTGTA
AAATAGATTGATGTGTCAGCTATATTAAGTCAACGTACAGTTTGCTTGAGTTATAGAAAC
CAGCCTGTCATCAAATGATTCTAGTTCTAGGACTTTGTAGGCTTAACTATAAAATATTTC
CTTTCCTCTGGGTTTAAGTGATTTTATTTAAGTCAACTAAGGGGATTTAACAGTGGACTA
GAGGTAATAAGCCACCTCAGTCAGGATTAATAATTCATTAATAAAATATATTTAACCCAA
AAAAAAAAAAAAAAAAAAAAAAAAAAAAAAAAAAAAAAAAAAAAAAAAAAAAAAAAAAAA
```

FIG. 4

MLSGVWFLSVLTVAGILQTESRKTAKDICKIRCLCEEKENVLNINCENKGFTTVSLLQPPQYRIYQLFLNG
NLLTRLYPNEFVNYSNAVTLHLGNNGLQEIRTGAFSGLKTLKRLHLNNNKLEILREDTFLGLESLEYLQAD
YNYISAIEAGAFSKLNKLKVLILNDNLLLSLPSNVFRFVLLTHLDLRGNRLKVMPFAGVLEHIGGIMEIQL
EENPWNCTCDLLPLKAWLDTITVFVGEIVCETPFRLHGKDVTQLTRQDLCPRKSASDSSQRGSHADTHVQR
LSPTMNPALNPTRAPKASRPPKMRNRPTPRVTVSKDRQSFGPIMVYQTKSPVPLTCPSSCVCTSQSSDNGL
NVNCQERKFTNISDLQPKPTSPKKLYLTGNYLQTVYKNDLLEYSSLDLLHLGNNRIAVIQEGAFTNLTSLR
RLYLNGNYLEVLYPSMFDGLQSLQYLYLEYNVIKEIKPLTFDALINLQLLFLNNNLLRSLPDNIFGGTALT
RLNLRNNHFSHLPVKGVLDQLPAFIQIDLQENPWDCTCDIMGLKDWTEHANSPVIINEVTCESPAKHAGEI
LKFLGREAICPDSPNLSDGTVLSMNHNTDTPRSLSVSPSSYPELHTEVPLSVLILGLLVVFILSVCFGAGL
FVFVLKRRKGVPSVPRNTNNLDVSSFQLQYGSYNTETHDKTDGHVYNYIPPPVGQMCQNPIYMQKEGDPVA
YYRNLQEFSYSNLEEKKEEPATPAYTISATELLEKQATPREPELLYQNIAERVKELPSAGLVHYNFCTLPK
RQFAPSYESRRQNQDRINKTVLYGTPRKCFVGQSKPNHPLLQAKPQSEPDYLEVLEKQTAISQL

FIG. 5

```
gaaactcatcatttgCACTTGAGATCTAac
ttcACTAAAGACTGtgcccaTAAGAgttt
tttccaAGACTGTCGGAATCTTGATTTTTT
GGATTTGGGTTACAATCGTCTTCGAAGCTT
GTCCCGAAATGCATTTGCTGGCCTCTTGAA
GTTAAAGGAGCTCCACCTGGAGCACAACCA
GTTTTCCAAGATCAACTTTGCTCATTTTCC
ACGTCTCTTCAACCTCCGCTCAATTTACTT
ACAATGGAACAGGATTCGCTCCATTAGCCA
AGGTTTGACATGGACTTGGAGTTCCTTACA
CAACTTGGATTTATCAGGGAATGACATCCA
AGGAATTGAGCCGGGCACATTTAAATGCCT
CCCCAATTTACAAAATTGAATTTGGATTC
CAACAAGCTCACCAATATCTCACAGGAAAC
TGTCAATGCGTGGATATCATTAATATCCAT
CACATTGTCTGGAAATATGTGGGAATGCAG
TCGGAGCATTTGTCCTTTATTTTATTGGCT
TAAGAATTTCAAGGAAATAAGGAAAGCAC
CATGATATGTGCGGGACCTAAGCACATCCA
GGGTGAAAAGGTTAGTGATGCAGTGGAAAC
ATATAATATCTGTTCTGAAGTCCAGGTGGT
CAACACAGAAAGATCACACCTGGTGCCCA
AACTCCCagaaacctctgattatccctag
AcctaccatcttcaaacctgacgtcaccCa
```

FIG. 6

```
CCAGTCCCTCCCTGGCAGCTCGGCTTCCCTCAGCTCCAACTCTTCTCTTCCGCTCCTGCC
TCCTGTCGGATTTTTAATTTCTGCGCACCCCCAGTCAAATTAAATCAACCAACAAAAAGC
AGGCATCCCCCCTGGAAGCAGCGTCTTATTTTACCTTGTTCTCCCACTTCCTGAAGATGC
TAAACTCCTGGTGGACTGCAGAGGAGAGGGATTCAGTCTTCTCCTGATGTCGATTGCGAT
TTCTGCTGGGAGCTCAAGACGGGCGAGCTGCCCGAGATCTCTTCGAGATACCCCAGggga
GgAGGAGATGGGCAGGATTTAGTAGGACAACTCGGTTACTAATGACTTGGCGGCTGGCTG
CGACCCCCGGGAAATCAGGTTTGCCTGTAGGTACCTGAGTTGACACCGAAGGTGCCTAA
AGATGCTGAGCGGCGTTTGGTTCCTCAGTGTGTTAACCGTGGCCGGGATCTTACAGACAG
AGAGTCGCAAAACTGCCAAAGACATTTGCAAGATCCGCTGTCTGTGCGAAGAAAAGGAAA
ACGTACTGAATATCAACTGTGAGAACAAAGGATTTACAACAGTTAGCCTGCTCCAGCCCC
CCCAGTATCGAATCTATCAGCTTTTTCTCAATGGAAACCTCTTGACAAGACTGTATCCAA
ACGAATTTGTCAATTACTCCAACGCGGTGACTCTTCACCTAGGTAACAACGGGTTACAGG
AGATCCGAACGGGGGCATTCAGTGGCCTGAAAACTCTCAAAAGACTGCATCTCAACAACA
ACAAGCTTGAGATATTGAGGGAGGACACCTTCCTAGGCCTGGAGAGCCTGGAGTATCTCC
AGGCCGACTACAATTACATCAGTGCCATCGAGGCTGGGGCATTCAGCAAACTTAACAAGC
TCAAAGTGCTCATCCTGAATGACAACCTTCTGCTTTCACTGCCCAGCAATGTGTTCCGCT
TTGTCCTGCTGACCCACTTAGACCTCAGGGGGAATAGGCTAAAAGTAATGCCTTTTGCTG
GCGTCCTTGAACATATTGGAGGGATCATGGAGATTCAGCTGGAGGAAAATCCATGGAATT
GCACTTGTGACTTACTTCCTCTCAAGGCCTGGCTAGACACCATAACTGTTTTTGTGGGAG
AGATTGTCTGTGAGACTCCCTTTAGGTTGCATGGGAAAGACGTGACCCAGCTGACCAGGC
AAGACCTCTGTCCCAGAAAAAGTGCCAGTGATTCCAGTCAGAGGGGCAGCCATGCTGACA
CCCACGTCCAAAGGCTGTCACCTACAATGAATCCTGCTCTCAACCCAACCAGGGCTCCGA
AAGCCAGCCGGCCGCCCAAAATGAGAAATCGTCCAACTCCCCGAGTGACTGTGTCAAAGG
ACAGGCAAAGTTTTGGACCCATCATGGTGTACCAGACCAAGTCTCCTGTGCCTCTCACCT
GTCCCAGCAGCTGTGTCTGCACCTCTCAGAGCTCAGACAATGGTCTGAATGTAAACTGCC
AAGAAAGGAAGTTCACTAATATCTCTGACCTGCAGCCCAAACCGACCAGTCCAAAGAAAC
TCTACCTAACAGGGAACTATCTTCAAACTGTCTATAAGAATGACCTCTTAGAATACAGTT
CTTTGGACTTACTGCACTTAGGAAACAACAGGATTGCAGTCATTCAGGAAGGTGCCTTTA
CAAACCTGACCAGTTTACGCAGACTTTATCTGAATGGCAATTACCTTGAAGTGCTGTACC
CTTCTATGTTTGATGGACTGCAGAGCTTGCAATATCTCTATTTAGAGTATAATGTCATTA
AGGAAATTAAGCCTCTGACCTTTGATGCTTTGATTAACCTACAGCTACTGTTTCTGAACA
ACAACCTTCTTCGGTCCTTACCTGATAATATATTTGGGGGACGGCCCTAACCAGGCTGA
ATCTGAGAAACAACCATTTTTCTCACCTGCCCGTGAAAGGGGTTCTGGATCAGCTCCCGG
CTTTCATCCAGATAGATCTGCAGGAGAaCccCCTGGGACTGTccTGTGACATCATGggGC
TGAAaGACTGGACAGAACAtGCCaattcCCCTgtcATcat
```

FIG. 7A

```
HLRRNS2    ------------------------------------------------------------
Q9H9T0     ------------------------------------------------------------
Q9BGP6     ------------------------------------------------------------
AAY66713   ------------------------------------------------------------
Q9D686     ------------------------------------------------------------
O43300     ------------------------------------------------------------
AAB45703   ------------------------------------------------------------
AAB61228   ------------------------------------------------------------
AAE06789   ------------------------------------------------------------
AAE06798   ------------------------------------------------------------
AAB61227   ------------------------------------------------------------
Q9DBB9     ------------------------------------------------------------
Q9UGS3     MVQGGIQSSSVASGKSLPPLGLSEAGGQGLWGLPGVLQEGGLPRPRSSTHVPLVLPLLVL

HLRRNS2    ------------------------------------------------------------
Q9H9T0     ------------------------------------------------------------
Q9BGP6     ------------------------------------------------------------
AAY66713   ------------------------------------------------------------
Q9D686     ------------------------------------------------------------
O43300     ------------------------------------------------------------
AAB45703   ------------------------------------------------------------
AAB61228   ------------------------------------------------------------
AAE06789   ------------------------------------------------------------
AAE06798   ------------------------------------------------------------
AAB61227   ------------------------------------------------------------
Q9DBB9     ------------------------------------------------------------
Q9UGS3     LLLAPARQAAAQRCPQACICDNSRRHVACRYQNLTEVPDAIPELTQRLDLQGNLLKVIPA

HLRRNS2    ------------------------------------------------------------
Q9H9T0     ------------------------------------------------------------
Q9BGP6     ------------------------------------------------------------
AAY66713   ------------------------------------------------------------
Q9D686     ------------------------------------------------------------
O43300     ------------------------------------------------------------
AAB45703   ------------------------------------------------------------
AAB61228   ------------------------------------------------------------
AAE06789   ------------------------------------------------------------
AAE06798   ------------------------------------------------------------
AAB61227   ------------------------------------------------------------
Q9DBB9     ------------------------------------------------------------
Q9UGS3     AAFQGVPHLTHLDLRHCEVELVAEGAFRGLGRLLLLNLASNHLRELPQEALDGLGSLRRL

HLRRNS2    ------------------------------------------------------------
Q9H9T0     ------------------------------------------------------------
Q9BGP6     ------------------------------------------------------------
AAY66713   ------------------------------------------------------------
Q9D686     ------------------------------------------------------------
O43300     ------------------------------------------------------------
AAB45703   ------------------------------------------------------------
AAB61228   ------------------------------------------------------------
```

FIG. 7B

```
AAE06789    ~~~~~~~~~~~~~~~~~~~~~~~~~~~~~~~~~~~~~~~~~~~~~~~~~~~~~~~~
AAE06798    ~~~~~~~~~~~~~~~~~~~~~~~~~~~~~~~~~~~~~~~~~~~~~~~~~~~~~~~~
AAB61227    ~~~~~~~~~~~~~~~~~~~~~~~~~~~~~~~~~~~~~~~~~~~~~~~~~~~~~~~~
Q9DBB9      ~~~~~~~~~~~~~~~~~~~~~~~~~~~~~~~~~~~~~~~~~~~~~~~~~~~~~~~~
Q9UGS3      ELEGNALEELRPGTFGALGALATLNLAHNALVYLPAMAFQGLLRVRWLRLSHNALSVLAP

HLRRNS2     ~~~~~~~~~~~~~~~~~~~~~~~~~~~~~~~~~~~~~~~~~~~~~~~~~~~~~~~~
Q9H9T0      ~~~~~~~~~~~~~~~~~~~~~~~~~~~~~~~~~~~~~~~~~~~~~~~~~~~~~~~~
Q9BGP6      ~~~~~~~~~~~~~~~~~~~~~~~~~~~~~~~~~~~~~~~~~~~~~~~~~~~~~~~~
AAY66713    ~~~~~~~~~~~~~~~~~~~~~~~~~~~~~~~~~~~~~~~~~~~~~~~~~~~~~~~~
Q9D686      ~~~~~~~~~~~~~~~~~~~~~~~~~~~~~~~~~~~~~~~~~~~~~~~~~~~~~~~~
O43300      ~~~~~~~~~~~~~~~~~~~~~~~~~~~~~~~~~~~~~~~~~~~~~~~~~~~~~~~~
AAB45703    ~~~~~~~~~~~~~~~~~~~~~~~~~~~~~~~~~~~~~~~~~~~~~~~~~~~~~~~~
AAB61228    ~~~~~~~~~~~~~~~~~~~~~~~~~~~~~~~~~~~~~~~~~~~~~~~~~~~~~~~~
AAE06789    ~~~~~~~~~~~~~~~~~~~~~~~~~~~~~~~~~~~~~~~~~~~~~~~~~~~~~~~~
AAE06798    ~~~~~~~~~~~~~~~~~~~~~~~~~~~~~~~~~~~~~~~~~~~~~~~~~~~~~~~~
AAB61227    ~~~~~~~~~~~~~~~~~~~~~~~~~~~~~~~~~~~~~~~~~~~~~~~~~~~~~~~~
Q9DBB9      ~~~~~~~~~~~~~~~~~~~~~~~~~~~~~~~~~~~~~~~~~~~~~~~~~~~~~~~~
Q9UGS3      EALAGLPALRRLSLHHNELQALPGPVLSQARGLARLELGHNPLTYAGEEDGLALPGLREL

HLRRNS2     ~~~~~~~~~~~~~~~~~~~~~~~~~~~~~~~~~~~~~~~~~~~~~~~~~~~~~~~~
Q9H9T0      ~~~~~~~~~~~~~~~~~~~~~~~~~~~~~~~~~~~~~~~~~~~~~~~~~~~~~~~~
Q9BGP6      ~~~~~~~~~~~~~~~~~~~~~~~~~~~~~~~~~~~~~~~~~~~~~~~~~~~~~~~~
AAY66713    ~~~~~~~~~~~~~~~~~~~~~~~~~~~~~~~~~~~~~~~~~~~~~~~~~~~~~~~~
Q9D686      ~~~~~~~~~~~~~~~~~~~~~~~~~~~~~~~~~~~~~~~~~~~~~~~~~~~~~~~~
O43300      ~~~~~~~~~~~~~~~~~~~~~~~~~~~~~~~~~~~~~~~~~~~~~~~~~~~~~~~~
AAB45703    ~~~~~~~~~~~~~~~~~~~~~~~~~~~~~~~~~~~~~~~~~~~~~~~~~~~~~~~~
AAB61228    ~~~~~~~~~~~~~~~~~~~~~~~~~~~~~~~~~~~~~~~~~~~~~~~~~~~~~~~~
AAE06789    ~~~~~~~~~~~~~~~~~~~~~~~~~~~~~~~~~~~~~~~~~~~~~~~~~~~~~~~~
AAE06798    ~~~~~~~~~~~~~~~~~~~~~~~~~~~~~~~~~~~~~~~~~~~~~~~~~~~~~~~~
AAB61227    ~~~~~~~~~~~~~~~~~~~~~~~~~~~~~~~~~~~~~~~~~~~~~~~~~~~~~~~~
Q9DBB9      ~~~~~~~~~~~~~~~~~~~~~~~~~~~~~~~~~~~~~~~~~~~~~~~~~~~~~~~~
Q9UGS3      LLDGGALQALGPRAFAHCPRLHTLDLRGNQLDTLPPLQGPGQLRRLRLQGNPLWCGCQAR

HLRRNS2     ~~~~~~~~~~~~~~~~~~~~~~~~~~~~~~~~~~~~~~~~~~MGFHLITQLKGMS
Q9H9T0      ~~~~~~~~~~~~~~~~~~~~~~~~~~~~~~~~~~~~~~~~~~~~~~~~~~~~~~~~
Q9BGP6      ~~~~~~~~~~~~~~~~~~~~~~~~~~~~~~~~~~~~~~~~~~MGFNVIRLLSGSA
AAY66713    ~~~~~~~~~~~~~~~~~~~~~~~~~~~~~~~~~~~~~~~MDFLLLGLCLYWLRRPS
Q9D686      ~~~~~~~~~~~~~~~~~~~~~~~~~~~~~~~~~~~~~~~MDFLLLGLCLHWLRRPS
O43300      ~~~~~~~~~~~~~~~~~~~~~~~~~~~~~~~~~~~~~~~~~~MGLHFKWPLGAPM
AAB45703    ~~~~~~~~~~~~~~~~~~~~~~~~~~~~~~~~~~~~~~~~~MCGLQFSLPCLRLFL
AAB61228    ~~~~~~~~~~~~~~~~~~~~~~~~~~~~~~~~~~~~~~~~~~~~~~~~~~~~~~~~
AAE06789    ~~~~~~~~~~~~~~~~~~~~~~~~~~~~~~~~~~~~~~~~~MCGLQFSLPCLRLFL
AAE06798    ~~~~~~~~~~~~~~~~~~~~~~~~~~~~~~~~~~~~~~~~~~~~~~~~~~~~~~~~
AAB61227    ~~~~~~~~~~~~~~~~~~~~~~~~~~~~~~~~~~~~~~~~~~~~~~~~~~~~~~~~
Q9DBB9      ~~~~~~~~~~~~~~~~~~~~~~~~~~~~~~~MKFSSVSEEKPGLLAPPAQPLTTMFPGA
Q9UGS3      PLLEWLARARVRSDGACQGPRRLRGEALDALRPWDLRCPGDAAQEEEELEERAVAGPRAP
```

FIG. 7C

```
HLRRNS2    VVLVLLPTLLLVMLTGAQRACPKNCRCDGKIVYCESHAFADIPENISGGSQGLSLRFNSL
Q9H9T0     ~~~~~~~~~~~~~~~~~~~~~~~~~~~~~~~~~~~~~~~~~~~~~~~~~~~~~~~~~~~
Q9BGP6     VALVIAPTVLLTMLSSAERGCPKGCRCEGKMVYCESQKLQEIPSSISAGCLGLSLRYNSL
AAY66713   GVVLCLLGACFQMLPAAPSGCPQLCRCEGRLLYCEALNLTEAPHNL.SGLLGLSLRYNSL
Q9D686     GVVLCLLGACFQMLPAAPSGCPGQCRCEGRLLYCEALNLTEAPHNL.SGLLGLSLRYNSL
O43300     LAAIYAMSMVLKMLPALGMACPPKCRCEKLLFYCDSQGFHSVPNATDKGSLGLSLRHNHI
AAB45703   VVTCYLLLLLHKEILGCSSVC.QLCT..GRQINCRNLGISSIPKNFPESTVFLYLTGNNI
AAB61228   ~~~~~~~~~~~~~~~~~CSSVC.QLCT..GRQINCRNLGISSIPKNFPESTVFLYLTGNNI
AAE06789   VVTCYLLLLLHKEILGCSSVC.QLCT..GRQINCRNLGISSIPKNFPESTVFLYLTGNNI
AAE06798   ~~~~~~~~~~HKEILGCSSVC.QLCT..GRQINCRNLGISSIPKNFPESTVFLYLTGNNI
AAB61227   ~~~~~~~~~~~~~~~~~CSSVC.QLCT..GRQINCRNLGISSIPKNFPESTVFLYLTGNNI
Q9DBB9     WLCWVSLLLLARLTQPCPVGC.D.CF...GREVFCSDEQLADIEPDIEPHITDIVFVETAF
Q9UGS3     PRGPPRGPGEERAVAPCPRAC..VCVPESRHSSCEGCGLQAVPRGFPSDTQLLDLRRNHF

HLRRNS2    QKLKSNQFAGLNQLIWLYLDHNYISSVDEDAFQGIRRLKELILSSNKITYLHNKTFHPVP
Q9H9T0     ~~~~~~~~~~~~~~~~~~~~~~~~~~~~~~~~~~~~~~~~~~~~~~~~~~~~~~~~~~~
Q9BGP6     QKLKYNQFKGLNQLTWLYLDHNHTSNIDENAFNGIRRLKELILSSNRLSYFLNNTFRPVT
AAY66713   SELRAGQFTGIMQLTWLYLDHNHICSVQGDAFQKLRRVKELTLSSNQITQLPNTTFRPMP
Q9D686     SELRAGQFTGLMQLTWLYLDHNHICSVQGDAFQKLRRVKELTLSSNQITELANTTFRPMP
O43300     TELERDQFASFSQLTWLHLDHNQISTVKEDAFQGLYKLKELILSSNKIFYLPNTTFTQLI
AAB45703   SYINESELTGLHSLVALYLDNSNILYVYPKAFVQLRHLYFLFLNNNFIKRLDPGIFKGL.
AAB61228   SYINESELTGIHSLVALYLDNSNILYVYPKAFVQLRHLYFLFLNNNFIKRLDPGIFKGL.
AAE06789   SYINESELTGLHSLVALYLDNSNILYVYPKAFVQLRHLYFLFLNNNFIKRLDPGIFKGL.
AAE06798   SYINESELTGIHSLVALYLDNSNILYVYPKAFVQLRHLYFLFLNNNFIKRLDPGIFKGL.
AAB61227   SYINESELTGLHSLVALYLDNSNILYVYPKAFVQLRHLYFLFLNNNFIKRLDPGIFKGL.
Q9DBB9     TTVRTRAFSGSPNLTKVVFLNTQVRHLEPDAFGGLPRLQDLEITGSPVSNLSAHIESNLS
Q9UGS3     PSVPRAAFPGLGHLVSLHLQHCGTAELEAGALAGLGRLIYLYLSDNQLAGLSAAALEGAP

HLRRNS2    NLRNLDLSYNKLQTLQSEQFKGLRKLIILHLRSNSLKTVPIRVFQDCRNLDFLDLGYNRL
Q9H9T0     ~~~~~~~~~~~~~~~~~~~~~~~~~~~~~~~~~~~~~~~~~~~~~~~~~~~~~~~~~~~
Q9BGP6     NLRNLDLSYNQLHSLGSEQFRGLRKLLSLHLRSNSTLRTIPVRIFQDCRNLELLDLGYNRI
AAY66713   NLRSVDLSYNKLQALAPDLFHGLRKLTTLHMRANAIQFVFVRLFQDCRSLKFLDIGYNQL
Q9D686     NLRSVDLSYNKLQALAPDLFHGLRKLTTLHMRANAIQFVPVRLFQDCRSLKFLDLSTNRL
O43300     NLQNLDLSFNQLSSLHPELFYGLRKLQTLHLRSNSLRTIPVPRGVFNDLVSVQYLNLQRNRL
AAB45703   ......LN..................LRNLYLQYNQVSFVPRGVFNDLVSVQYLNLQRNRL
AAB61228   ......LN..................LRNLYLQYNQVSFVPRGVFNDLVSVQYLNLQRNRL
AAE06789   ......LN..................LRNLYLQYNQVSFVPRGVFNDLVSVQYLNLQRNRL
AAE06798   ......LN..................LRNLYLQYNQVSFVPRGVFNDLVSVQYLNLQRNRL
AAB61227   ......LN..................LRNLYLQYNQVSFVPRGVFNDLVSVQYLNLQRNRL
Q9DBB9     SLEKLTLDFDRLAGLPEDLFCHMDILESLQLQGNQLRTIPGRLFQSLRDLRTLNIAQNLL
Q9UGS3     RLGYLYLERNRFLQVPGAALRALPSLFSLHLQDNAVDRLAPGDLGRTRALRWVYLSGNRI

HLRRNS2    RSLSRNAFAGLLKLKELHLEHNQFSKINFAHFPRLFNLRSIYLQWNRIRSISQG.LTWTW
Q9H9T0     ~~~~~~~~~~~~~~~~~~~~~~~~~~~~~~~~~~~~~~~~~~~~~~~~~~~~~~~~~~~
Q9BGP6     RSLARNVEAGMIRLKELHLEHNQFSKLNLALFPRLVSLQNLYLQWNKISVIGQT.MSWTW
AAY66713   KSLARNSFAGLFKLTELHLEHNDLVKVNFAHFPRLISLHSLCLRRNKVAIVVSS.LDWVW
Q9D686     KSLARNSFAGLFKLTELHLEHNDLIKVNFAHFPRLISLLHSLCLRRNKVAIVVSS.LDWVW
O43300     RSLARNGFAGLIKLRELHLEHNQLTKINFAHFLRLSSLHTLFLQWNKISNLTCG.MEWTW
AAB45703   TVLGSGTFVGMVALRILDLSNNNILRISESGFQHLENLACLYIGSNNLTKVPSNAFEVL.
AAB61228   TVLGSGTFVGMVALRILDLSNNNILRISESGFQHLENLACLYIGSNNLTKVPSNAFEVL.
AAE06789   TVLGSGTFVGMVALRILDLSNNNILRISESGFQHLENLACLYIGSNNLTKVPSNAFEVL.
```

FIG. 7D

```
AAE06798  TVLGSGTFVGMVALRILDLSNNNILRISESGFQHLENLACLYLGSNNLTKVPSNAFEVL.
AAB61227  TVLGSGTFVGMVALRILDLSNNNILRISESGFQHLENLACLYLGSNNLTKVPSNAFEVL.
Q9DBB9    TQLPKGAFQSLTGLQMLKLSNNMLARLPEGALGSLSSIQELFLDGNATTELSPHLESQL.
Q9UGS3    TEVSLGALGPARELEKIHLDRNQLREVPTGALEGLPALLELQLSGNPLRALRDGAEQPVG

HLRRNS2   SSLHNLDLSGNDTQGIE.PGTFKCL.PNLQKLNLDSNKLTNLSQETVNAWISLISLTLSG
Q9H9T0    ~~~~~~~~~~~~~~~~~~~~~~~~~~~~~~~~~~~~~~~~~~~~~~~~~~~~~~~~~~~
Q9BGP6    SSLQRLDLSGNEIEAFSGPSVFQCV.PNLQRLNLDSNKLTFLGQEILDSWISLNDTSLAG
AAY66713  .NLEKMDLSGNEIEYME.PHVFETV.PHLQSLQLDSNRLTYLEPRILNSWKSLTSITLAG
Q9D686    .NLEKMDLSGNEIFYME.PHVFETV.PYLQTLQLDSNRLTYLEPRILNSWKSLTSITLAG
O43300    GTLEKLDLTGNEIKAID.LTVFETM.PNLKILLMDNNKLNSLDSKILNSLRSLTTVGLSG
AAB45703  KSLRRLSLSHNPIEAIQ.PFAFKGLA.NLEYLLLKNSRIRNVTRDGFSGINNLKHLILSH
AAB61228  KSLRRLSLSHNPIEAIQ.PFAFKGLA.NLEYLLLKNSRIRNVTRDGFSGINNLKHLILSH
AAE06789  KSIRRLSLSHNPIEAIQ.PFAFKGLA.NLEYLLLKNSRIRNVTRDGFSGINNLKHLILSH
AAE06798  KSLRRLSLSHNPIEATQ.PFAFKGLA.NLEYLLLKNSRIRNVTRDGFSGINNLKHLILSH
AAB61227  KSLRRLSLSHNPIEAIQ.PFAFKGLA.NLEYLLLKNSRIRNVTRDGFSGINNLKHLILSH
Q9DBB9    FSLEMLWLQHNAICHLP.VSLFSSLH.NLTFLSLKDNALRTLPEGLFAHNQGLLHLSLSY
Q9UGS3    RSLQHLFLNSSGLEQIC.PGAFSGLGPGLQSLHLQKNQLRALP..ALPSLSQLELIDLSS

HLRRNS2   N.MWECSRSTCPLFYWLKNFKGNKESTMLCAGPKHIQGEKVSDAVETYNICSEVQVVNTE
Q9H9T0    ~~MWECSRSTCPLFYWLKNFKGNKESTMTCAGPKHIQGEKVSDAVETYNICSEVQVVNTE
Q9BGP6    N.IWECSRNICSLVNWLKSFKGLRENTIICASPKELQGVNVIDAVKNYSICGK...STTE
AAY66713  N.LWDCGRNVCALASWLSNFQGRYDGNLQCASPEYAQGEDVLDAVYAFHLCEDGAEP...
Q9D686    N.LWDCGRNVCALASWLSNFQGRYDANLQCASPEYAQGRTSWMQCMLSTCVRMGPSPPAA
O43300    N.LWECSARLCALASWIGSFQGRWEHSILCHSPDHTQGEDILDAVHGFQLCWN.....LS
AAB45703  NDLENLNSDTFSLLKNLIYLK..LDRNRIISIDN........DTFE..NMGASLKILNLS
AAB61228  NDLENLNSDTFSLLKNLIYLK..LDRNRIISIDN........DTFE..NMGASLKILNLS
AAE06789  NDLENLNSDTFSLLKNLIYLK..LDRNRIISIDN........DTFE..NMGASLKILNLS
AAE06798  NDLENLNSDTFSLLKNLIYLK..LDRNRIISIDN........DTFE..NMGASLKILNLS
AAB61227  NDLENLNSDTFSLLKNLIYLK..LDRNRIISIDN........DTFE..NMGASLKILNLS
Q9DBB9    NQLETIPEGAFTNLSRLVSLT..LSHNATTDLPE........HVFR..NLEQLVKLSLD
Q9UGS3    NPF.HCDCQLLPLHRWLTGLN..LRVGATCATPP........NA.....RGQRVKAAAAV

HLRRNS2   RSHLVPQTFQKPLIIPRPTIFKPDVTQSTFETPSPSP...GFQIPGAE..QEYEH.VSFH
Q9H9T0    RSHLVPQTFQKPLIIPRPTIFKPDVTQSTFETPSPSP...GFQIPGAE..QEYEH.VSFH
Q9BGP6    RFDLA.......RALPKPT.FKPKLPRPKHESKPPLPPTVGATEPGPETDADAEH.ISFH
AAY66713  TSGH..LLSAVTNRSDLGPPASSATTLA.DGGEGQHDGTFEPATVALPGGEHAENAVQIH
Q9D686    TSCRWPSLTAVT~~~~~~~~~~~~~~~~~~~~~~~~~~~~~~~~~~~~~~~~~~~~~~~~
O43300    TT...VTVMATTYRDETTEYLKRISSSSYHVGDKEIPTTAGIAVTTEEHFPEEDNAIFTQ
AAB45703  FNNLTALHPRVLK..PLS...SLIHLQAN.......................SNPWECNCKL
AAB61228  FNNLTALHPRVLK..PLS...SLIHLQAN.......................SNPWECNCKL
AAE06789  FNNLTALHPRVLK..PLS...SLIHLQAN.......................SNPWECNCKL
AAE06798  FNNLTALHPRVLK..PLS...SLIHLQAN.......................SNPWECNCKL
AAB61227  FNNLTALHPRVLK..PLS...SLIHLQAN.......................SNPWECNCKL
Q9DBB9    SNNLTALHPALFH..NLSRLQLLNLSRNQLTTLPGGTFDTNYDLFNLALLGNPWQCDCIIL
Q9UGS3    FEDCPGWAARKAKRTPASRPSARRTPIKGRQCGADKVG~~~~~~~~~~~~~~~~~~~~~~
```

FIG. 7E

```
HLRRNS2    KITAGSVALFLSVAMILIVIYVSWKRYPASMKQLQQHSLMKRRRKKARESERQM.NSPLQ
Q9H9T0     KITAGSVALFLSVAMILIVIYVSWKRYPASMKQLQQHSLMKRRRKKARESERQM.NSPLQ
Q9BGP6     KITAGSVALFLSVLVILIVIYVSWKRYPASMRQLQQRSLMRRHRKKKRQSLKQM.TPSTQ
AAY66713   KVVTGTMALIFSFLIVVLVLYVSWKCFPASLRQLRQCFVTQRRKQKQKQTMHQMAAMSAQ
Q9D686     ~~~~~~~~~~~~~~~~~~~~~~~~~~~~~~~~~~~~~~~~~~~~~~~~~~~~~~~~~~~
O43300     RVITGTMALLFSFFFIIFIVEISRKCCPPTLRRIRQCSMVQNHRQLRSQTRLHMSNMSDQ
AAB45703   LGLRDWLA...SSAIT.LNIYCQ...NPPSMRGRALRYINITN..CVTSS...INVS.RA
AAB61228   LGLRDWLA...SSAIT.LNIYCQ...NPPSMRGRALRYINITN..CVTSS...INVS.RA
AAE06789   LGLRDWLA...SSAIT.LNIYCQ...NPPSMRGRALRYINITN..CVTSS...INVS.RA
AAE06798   LGLRDWLA...SSAIT.LNIYCQ...NPPSMRGRALRYINITN..CVTSS...INVS.RA
AAB61227   LGLRDWLA...SSAIT.LNIYCQ...NPPSMRGRALRYINITN..CVTSS...INVS.RA
Q9DBB9     SYLTSWLRY.NNQISNTHTFCA...GPAYLKGQLVPNLKQEQLICPVNP...GHLSFRA
Q9UGS3     ~~~~~~~~~~~~~~~~~~~~~~~~~~~~~~~~~~~~~~~~~~~~~~~~~~~~~~~~~~~

HLRRNS2    EYYVDYKPTNSETMDISVNGSGPCYTISGSRECEMPHHMKPLPYYSYDQPVIGYCQAHQ
Q9H9T0     EYYVDYKPTNSETMDISVNGSGPCYTISGSRECEV~~~~~~~~~~~~~~~~~~~~~~~~
Q9BGP6     EFYVDYKPTNTETSEMLLNGTGPCYNKSGSRECEIPLSMNVSTFLAYDQPTISYCGVHH
AAY66713   EYYVDYKPNHIEGALVIINEYGSCTCHQQPARECEV~~~~~~~~~~~~~~~~~~~~~~~
Q9D686     ~~~~~~~~~~~~~~~~~~~~~~~~~~~~~~~~~~~~~~~~~~~~~~~~~~~~~~~~~~~
O43300     GPYNEYEPTH.EGPFIIINGYGQCKCQQLPYKECEV~~~~~~~~~~~~~~~~~~~~~~~
AAB45703   WAVVK.SPHIHHKTTALMMAWHKVTTNGSPLENTE....TENITFWERIP.TSPAGRFFQ
AAB61228   WAVVK.SPHIHHKTTALMMAWHKVTTNGSPLENTE....TENITFWERIP.TSPAGRFFQ
AAE06789   WAVVK.SPHIHHKTTALMMAWHKVTTNGSPLENTE....TENITFWERIP.TSPAGRFFQ
AAE06798   WAVVK.SPHIHHKTTALMMAWHKVTTNGSPLENTE....TENITFWERIP.TSPAGRFFQ
AAB61227   WAVVK.SPHIHHKTTALMMAWHKVTTNGSPLENTE....TENITFWERIP.TSPAGRFFQ
Q9DBB9     LGLDEGEPAGSWDLTVEGRAAHSQCAYSNP.EGTVLLACEESRCRWLNIQLSSRDGSDSA
Q9UGS3     ~~~~~~~~~~~~~~~~~~~~~~~~~~~~~~~~~~~~~~~~~~~~~~~~~~~~~~~~~~~

HLRRNS2    PLHVTKGYETVSPEQDESPGLELGRDHSFIATIARSAAPAIYLERIAN~~~~~~~~~~~~
Q9H9T0     ~~~~~~~~~~~~~~~~~~~~~~~~~~~~~~~~~~~~~~~~~~~~~~~~~~~~~~~~~~~~
Q9BGP6     ELLSHKSFETNAQEDTMETHLFTELDLSTITTAGRISDHKQQLA~~~~~~~~~~~~~~~~
AAY66713   ~~~~~~~~~~~~~~~~~~~~~~~~~~~~~~~~~~~~~~~~~~~~~~~~~~~~~~~~~~~~
Q9D686     ~~~~~~~~~~~~~~~~~~~~~~~~~~~~~~~~~~~~~~~~~~~~~~~~~~~~~~~~~~~~
O43300     ~~~~~~~~~~~~~~~~~~~~~~~~~~~~~~~~~~~~~~~~~~~~~~~~~~~~~~~~~~~~
AAB45703   ENAFGNPLETTAVLP.VQIQLTTSVTLNLEKNSALPNDAASMSGKTSLICTQEVEKLNEA
AAB61228   ENAFGNPLETTAVLP.VQIQLTTSVTLNLEKNSALPNDAASMSGKTSLICTQEVEKLNEA
AAE06789   ENAFGNPLETTAVLP.VQIQLTTSVTLNLEKNSALPNDAASMSGKTSLICTQEVEKLNEA
AAE06798   ENAFGNPLETTAVLP.VQIQLTTSVTLNLEKNSALPNDAASMSGKTSLICTQEVEKLNEA
AAB61227   ENAFGNPLETTAVLP.VQIQLTTSVTLNLEKNSALPNDAASMSGKTSLICTQEVEKLNEA
Q9DBB9     AMVYNSSQEWG..LR.SSCGL.LRVTVSIEAPAAGP~~~~~~~~~~~~~~~~~~~~~~~~
Q9UGS3     ~~~~~~~~~~~~~~~~~~~~~~~~~~~~~~~~~~~~~~~~~~~~~~~~~~~~~~~~~~~~

HLRRNS2    ~~~~~~~~~~~~~~~~~~~~~~~~~~~~~~~~~~~~~~~~~~~~~~~~~~~~~~~~~~~~
Q9H9T0     ~~~~~~~~~~~~~~~~~~~~~~~~~~~~~~~~~~~~~~~~~~~~~~~~~~~~~~~~~~~~
Q9BGP6     ~~~~~~~~~~~~~~~~~~~~~~~~~~~~~~~~~~~~~~~~~~~~~~~~~~~~~~~~~~~~
AAY66713   ~~~~~~~~~~~~~~~~~~~~~~~~~~~~~~~~~~~~~~~~~~~~~~~~~~~~~~~~~~~~
Q9D686     ~~~~~~~~~~~~~~~~~~~~~~~~~~~~~~~~~~~~~~~~~~~~~~~~~~~~~~~~~~~~
O43300     ~~~~~~~~~~~~~~~~~~~~~~~~~~~~~~~~~~~~~~~~~~~~~~~~~~~~~~~~~~~~
```

FIG. 7F

```
AAB45703  FDILLAFFILACVLIIFLIYKVVQFKQKLKASENSRENRLEYYSFYQSARYNVTASICNT
AAB61228  FD~~~~~~~~~~~~~~~~~~~~~~~~~~~~~~~~~~~~~~~~~~~~~~~~~~~~~~~~~
AAE06789  FDILLAFFILACVLIIFLIYKVVQFKQKLKASENSRENRLEYYSFYQSARYNVTASICNT
AAE06798  FDILLAFFILACVLIIFLIYKVVQFKQKLKASENSRENRLEYYSFYQSARYNVTASICNT
AAB61227  FDILLAFFILACVLIIFLIYKVVQFKQKLKASENSRENRLEYYSFYQSARYNVTASICNT
Q9DBB9    ~~~~~~~~~~~~~~~~~~~~~~~~~~~~~~~~~~~~~~~~~~~~~~~~~~~~~~~~~~~
Q9UGS3    ~~~~~~~~~~~~~~~~~~~~~~~~~~~~~~~~~~~~~~~~~~~~~~~~~~~~~~~~~~~

HLRRNS2   ~~~~~~~~~~~~~~~~~~~~~~~~~~~~~~~~~~~~~~~~
Q9H9T0    ~~~~~~~~~~~~~~~~~~~~~~~~~~~~~~~~~~~~~~~~
Q9BGP6    ~~~~~~~~~~~~~~~~~~~~~~~~~~~~~~~~~~~~~~~~
AAY66713  ~~~~~~~~~~~~~~~~~~~~~~~~~~~~~~~~~~~~~~~~
Q9D686    ~~~~~~~~~~~~~~~~~~~~~~~~~~~~~~~~~~~~~~~~
O43300    ~~~~~~~~~~~~~~~~~~~~~~~~~~~~~~~~~~~~~~~~
AAB45703  SPNSLESPGLEQIRLHKQIVPENEAQVILFEHSAL
AAB61228  ~~~~~~~~~~~~~~~~~~~~~~~~~~~~~~~~~~
AAE06789  SPNSLESPGLEQIRLHKQIVPENEAQVILFEHSAL
AAE06798  SPNSLESPGLEQIRLHKQIVPENEAQVILFEHSAL
AAB61227  SPNSLESPGLEQIRLHKQIVPENEAQVILFEHSAL
Q9DBB9    ~~~~~~~~~~~~~~~~~~~~~~~~~~~~~~~~~~
Q9UGS3    ~~~~~~~~~~~~~~~~~~~~~~~~~~~~~~~~~~
```

FIG. 8A

```
AAB50905   ~~~~~~~~~~~~~~~~~~~~~~~~~~~~~~~~~~~~~~~~~~~~~~~~~~
AAY94963   ~~~~~~~~~~~~~~~~~~~~~~~~~~~~~~~~~~~~~~~~~~~~~~~~~~
AAE01312   ~~~~~~~~~~~~~~~~~~~~~~~~~~~~~~~~~~~~~~~~~~~~~~~~~~
HLRRNS3    ~~~~~~~~~~~~~~~~~~~~~~~~~~~~~~~~~~~~~~~~~~~~~~~~~~
Y918_HUMAN ~~~~~~~~~~~~~~~~~~~~~~~~~~~~~~~~~~~~~~~~~~~~~~~~~~
Q9H5Y7     ~~~~~~~~~~~~~~~~~~~~~~~~~~~~~~~~~~~~~~~~~~~~~~~~~~
Y848_HUMAN ~~~~~~~~~~~~~~~~~~~~~~~~~~~~~~~~~~~~~~~~~~~~~~~~~~
Q9UGS3     MVQGGIQSSSVASGKSLPPLGLSEAGGQGLWGLPGVLQEGGLPRPRSSTHVPLVLPLLVL

AAB50905   ~~~~~~~~~~~~~~~~~~~~~~~~~~~~~~~~~~~~~~~~~~~~~~~~~~
AAY94963   ~~~~~~~~~~~~~~~~~~~~~~~~~~~~~~~~~~~~~~~~~~~~~~~~~~
AAE01312   ~~~~~~~~~~~~~~~~~~~~~~~~~~~~~~~~~~~~~~~~~~~~~~~~~~
HLRRNS3    ~~~~~~~~~~~~~~~~~~~~~~~~~~~~~~~~~~~~~~~~~~~~~~~~~~
Y918_HUMAN ~~~~~~~~~~~~~~~~~~~~~~~~~~~~~~~~~~~~~~~~~~~RRGAQGGKMHTCCPP
Q9H5Y7     ~~~~~~~~~~~~~~~~~~~~~~~~~~~~~~~~~~~~~~~~~~~~~~~~~~
Y848_HUMAN ~~~~~~~~~~~~~~~~~~~~~~~~~~~~~~~~~~~~~~~~~~~~~~~~~MK
Q9UGS3     LLLAPARQAAAQRCPQACICDNSRRHVACRYQNLTEVPDAIPELTQRLDLQGNLLKVIPA

AAB50905   ~~~~~~~~~~~~~~~~~~MLLWILLLETSLCFAAGNVTGDVCKEKICSCNEIEGDLHV.
AAY94963   ~~~~~~~~~~~~~~~~~~MLLWILLLETSLCFAAGNVTGDVCKEKICSCNEIEGDLHV.
AAE01312   ~~~~~~~~~~~~~~~~~~~~~~~~~~~RKTAKDICKIR.CLCEEKENVLNI.
HLRRNS3    ~~~~~~~~~~~~~MLSGVWFLSVLTVAGILQTESRKTAKDICKIR.CLCEEKENVLNI.
Y918_HUMAN VTLEQDLHRKMHSWMLQTLAFAVTSLVLSCAETID..YYGEICDNA.CPCEEKDGILTV.
Q9H5Y7     ~~~~~~~~~~~~~~~~~~~~~~~~~~~~~~~~~~~~~~~~~~~~~~~MLI.
Y848_HUMAN PSIAEMLHRGRMLWIIL.LSTIALGWTTPIPLIEDSEEIDEPCFDP.CYCEVKESLFHI.
Q9UGS3     AAFQGVPHLTHLDLRHCEVELVAEGAFRGLGRLLLLNLASN..HLRELPQEALDGLGSLR

AAB50905   DCEKKGFTSLQRFTAPTS....QFYHLFIHGNSLTRLEPNEEANEYNAVSLHMENNGIHE
AAY94963   DCEKKGFTSLQRFTAPTS....QFYHLFIHGNSLTRLEPNEEANEYNAVSLHMENNGIHE
AAE01312   NCENKGFTTVSLLQPPQY....RIYQLFINGNLLTRLYPNEFVNYSNAVTLHLGNNCLQE
HLRRNS3    NCENKGFTTVSLLQPPQY....RIYQLFINGNLLTRLYPNEFVNYSNAVTLHLGNNGLQE
Y918_HUMAN SCENRGIISLSEISPPRE....PIYHLLLSGNLLNRLYPNEFVNYTGASILHLGSNVIQD
Q9H5Y7     NCEAKGIKMVSEISVEPS....RPFQLSLLNNGLTMLHTNDFSGLTNAISIHLGENNIAD
Y848_HUMAN HCDSKGFTNISQITEFWS....RPFKLYLQRNSMRKLYTNSELHLNNAVSINLGNNALQD
Q9UGS3     RLFLEG.NALEELRFGTEGALCALATLNLAHNALVYLPAMAEQGLLRVRWLRLSHNALSV

AAB50905   IVPGAELGLQLVKRLHINNNKLKSFRKQTFLGLDDLEYLQADENLLRDIDPGAEQDLNKL
AAE01312   IRTGAFSGLKTLKRLHLNNNKLEILREDTFLGLESLEYLQADYNYISAIEAGAFSKLNKL
HLRRNS3    IRTGAFSGLKTLKRLHLNNNKLEILREDTFLGLESLEYLQADYNYISAIEAGAFSKLNKL
Y918_HUMAN IETGAEHGLRGLRRLHLNNNKLELLRDDTFLGLENLEYLQVDYNYISVIEPNAFGKLHLL
Q9H5Y7     IEIGAENGIGLIKQLHINHNSLEILKEDTFHGLENLELQADNNEITVIEPSAFSKLNRL
Y848_HUMAN IQTGAENGIKILKRLYLIENKLDVFRNDTFLGLFSLEYLQADYNVIKRIESCAFRNLSKL
Q9UGS3     LAPEALAGIPALRRLSLHHNELQALPGPVLSQARGLARLELGHNPLTYAGEEDGLALPGL

AAB50905   EVLILNDNLISTLPANVFQYVPITH.LDLRGNRLKTLPYEEVLEQI.PGLAEILLEDNP.
AAY94963   EVLILNDNIISTLPANVFQYVPITH.LDLRGNRLKRCPMRS.LGAN.PWYCGDPARDNP.
AAE01312   KVLILNDNLLSLPSNVFRFVLLTH.LDLRGNRLKVMPFAGVLEHIGG.IMEQLEENP.
HLRRNS3    KVLILNDNLLSLPSNVFRFVLLTH.LDLRGNRLKVMPFAGVLEHIGG.IMEIQLEENP.
Y918_HUMAN QVLILNDNLISSLPNNIFRFVPLTH.LDLRGNRLKLLPYVGLLQHMDK.VVEIQLEENP.
Q9H5Y7     KVLILNDNATESLPPNIFREVPLTH.LDLRGNQLQTLPYVGFLEHIGR.ILDLQLEDNK.
Y848_HUMAN RVLILNDNIIPMLETNLEKAVSLTH.LDLRGNRLKVLFYRGMLDHIGRSLMELQEENP.
```

FIG. 8B

```
Q9UGS3      RELLLDGGALQALGPRAEAHCERLHTLDLRGNQLDTLP...PLQGPG.QLRRLRLQGNPL

AAB50905    WDCTCDLLSLKEWLENTPKNALIGRVVCEAPTRLQGKDLNETTEQDL.CPLKNRVDSSLP
AAY94963    WDCTCDLLSLKEWLENIPKNALIGRVVCEAPTRLQGKDLNETTEQDL.CPLKNRVDSSLP
AAE01312    WNCTCDLLPLKAWLDTI..TVEVGEIVCETPFRLHGKDVTQLTRQDL.CPRKSASDSSQR
HLRRNS3     WNCTCDLLPLKAWLDTI..TVEVGEIVCETPFRLHGKDVTQLTRQDL.CPRKSASDSSQR
Y918_HUMAN  WNCSCELLSLKDWLDSTSYSALVGDVVCETPFRLHGRDLDEVSKQEL.CPRRLISDYEMR
Q9H5Y7      WACNCDLLQLKTWLENMPPQSTIGDVVCNSPPFFKGSILSRLKKEST.CPTPPVYEEHED
Y848_HUMAN  WNCTCEIVQLKSWLERIPYTALVGDITCETPFHFHGKDIRETRKTEL.CPLLSDSEVEAS
Q9UGS3      W.CGCQARPILEWLARARVRS...DGACQGPRRLRGEALDALRPWDLRCPGDAAQEEEEL

AAB50905    APPAQEETFAPGPLETPFKTNGQEDHATPGSA.PNGGTKIPG....NWQIKIRPTAALAT
AAY94963    APPAQEETFAPGPLETPFKTNGQEDHATPGSA.PNGGTKIPG....NWQIKIRPTAALAT
AAE01312    GSH..ADTHVQRLSP.............TMNPAL..NPTRAPKASRPP.KMRNRPTPRVTV
HLRRNS3     GSH..ADTHVQRLSP.............TMNPAL..NPTRAPKASRPP.KMRNRPTPRVTV
Y918_HUMAN  PQTPLSTTGYLHTTPASVNSVA.....TSSSAVYKPPLKPPKGTRQPNKPRVRPTSR.QP
Q9H5Y7      PS...GSLHLAATSSINDSRMS.....TKTTSILKLPTKAPGL..........IPYIT.
Y848_HUMAN  LGIPHSSSSKENAWPTKPSSMLSSVHFTASSVEYKSSNKQPKPTKQPRTPR....PPSTS
Q9UGS3      EERAVAGPRAPPRGEPRGPGEERAVAPCPRACVCVPESRHSSCEGCGLQAVPRGFESDIQ

AAB50905    GSSRNK......PLA.....NSLP..CPGGCSCD................HIPGS...GL
AAY94963    GSSRNK......PLA.....NSLP..CPGGCSCD................HIPGS...GL
AAE01312    SKD..RQSFG..EIMVYQTKSPVPLTCPSSCVCT................SQSSDN...GL
HLRRNS3     SKD..RQSFG..EIMVYQTKSPVPLTCPSSCVCT................SQSSDN...GL
Y918_HUMAN  SKDLGYSNYG..PSIAYQTKSPVPLECPTACSCN................LQISDL...GL
Q9H5Y7      .K..........P....STQLFGPY.CPIPCNCK................V.LSPS...GI
Y848_HUMAN  QALYPGPNQP..PLAPYQTRPPIPIICPTGCTCN................LHINDL...GI
Q9UGS3      LLDLRRNHFPSVERAAFPGLGHLVSLHLQHCGIAELEAGALAGLGRLIYLYLSDNQLAGL

AAB50905    K............MNCNNRNVSSL..ADLKPKLSNVQELELRDNKIHSIRKSHFVDYKNL
AAY94963    K............MNCNNRNVSSL..ADLKPKLSNVQELELRDNKIHSIRKSHFVDYKNL
AAE01312    N............VNCQERKFTNT..SDLQPKPTSPKKLYLTGNYLQTVYKNDLLEYSSL
HLRRNS3     N............VNCQERKFTNT..SDLQPKPTSPKKLYLTGNYLQTVYKNDLLEYSSL
Y918_HUMAN  N............VNCQERKIESI..AELQPKPYNPKKMYLTENYIAVVRRTDFLEATGL
Q9H5Y7      L............IHCQERNIESL..SDLRPPPQNPRKLILAGNIIHSLMKSDIVFYFTL
Y848_HUMAN  T............VNCKERGFNNI..SELLPRPLNAKKKLYLSSNLIQKLYRSDFWNFSSL
Q9UGS3      SAAALEGAPRLGYLYLERNRFLQVPGAALRALE.SLFSLHIQDNAVDRLAPGDLGRTRAL

AAB50905    ILLDLGNNNIATVENNTFKNLLDLRWLYMDSNYLDTLSREKEAGLQNLEYLNVEYNATQL
AAY94963    ILLDLGNNNIATVENNTFKNLLDLRWLYMDSNYLDTLSREKEAGLQNLEYLNVEYNATQL
AAE01312    DLLHLGNNRIAVIQEGAFTNLTSLRRLYLNGNYLEVLYPSMFDGLQSLQYLYLEYNVLKE
HLRRNS3     DLLHLGNNRIAVIQEGAFTNLTSLRRLYLNGNYLEVLYPSMFDGLQSLQYLYLEYNVLKE
Y918_HUMAN  DLLHLGNNRISMIQDRAFGDLTNLRRLYLNGNRIERLSPELFYGLQSLQYLELQYNLIRE
Q9H5Y7      EMLHLGNNRIEVLEEGSFMNLTRLQKLYLNGNHLTKISKGMELGIHNLEYLYLEYNAIKE
Y848_HUMAN  DLLHLGNNRISYVQDGAFINLPNLKSLELNGNDIEKLTFGMERGLQSLHYLYFEENVIRE
Q9UGS3      RWVYLSGNRITEVSLGALGPARELEKLHLDRNQLREVPTGALEGLPALLELQLSGNPLRA

AAB50905    ILPGTFNAM.PKLRILILNNNLLRSLPVDVFAGV..SLSKLSLHNNYFMYLPVAGVLDQL
AAY94963    ILPGTFNAM.PKLRILILNNNLLRSLPVDVFAGV..SLSKLSLHNNYFMYLPVAGVLDQL
AAE01312    IKPLTFDAL.INLQLLXLNNNLLRSLPDNIFGGT..ALTRLNLRNNHFSHLPVKGVLDQL
HLRRNS3     IKPLTFDAL.INLQLLFLNNNLLRSLPDNIFGGT..ALTRLNLRNNHFSHLPVKGVLDQI
```

FIG. 8C

```
Y918_HUMAN  IQSGTFDPV.PNLQLIFLNNNLLQAMPSGVFSGL...TLLRLNLRSNHFTSLPVSGVLDQL
Q9H5Y7      ILPGTFNPM.PKLKVLYLNNTSSKFYHHIFFQGF..L~~~~~~~~~~~~~~~~~~~~~~~
Y848_HUMAN  IQPAAFSLM.PNIKLLFLNNNLLRFLPTDAFAGT...SLARLNLRKNYFLYLPVAGVFEHL
Q9UGS3      LRDGAFQPVGRSLQHLFLNSSGLEQICPGAFSGLGPGLQSLHLQKNQLRALFALPSFSQL

AAB50905    TSIIQIDLHGNPWECSCTIVPFKQWAERLGSEVLMSDLKCETPVNFFRKDFMLFSND.EL
AAY94963    TSIIQIDLHGNPWECSCTIVPFKQWAERLGSEVLMSDLKCETPVNFFRKDFMLFSND.EL
AAE01312    PAFIQIDLQENPWDCTCDIMGLKDWTEHANSPVIINEVTCESPAKHAGEILKFLGRE.AI
HLRRNS3     PAFIQIDLQENPWDCTCDIMGLKDWTEHANSPVIINEVTCESPAKHAGEILKFLGRE.AI
Y918_HUMAN  KSLIQIDIHDNPWDCTCDTVGMKLWVEQLKVGVLVDEVICKAPKKFAETDMRSIKSE.LL
Q9H5Y7      ~~~~~~~~~~~~~~~~~~~~~~~~~~~~~~~~~~~~~~~~~~~~~~~~~~~~~~~~~~~
Y848_HUMAN  NAIVQIDINFNPWDCTCDLVPFKQWIFTISSVSVVGDVLCRSPENLTHRDVRTIELF.VL
Q9UGS3      EL...IDLSSNPFHCDCQLLPLHRWLTGLNLRV...GATCATPPNARCQRVKAAAAVFED

AAB50905    CPQLYARISPTLTSHSKNSTGLAETGTHSNSYLDT............SRVSISVLVPGLL
AAY94963    CPQLYARISPTLTSHSKNSTGLAETGTHSNSYLDT............SRVSISVLVPGLL
AAE01312    CPDSPN..LSDGTVLSMN..HNTD...TP...RSLSV.SPSSYPE..LHTEVP~~~~~~~
HLRRNS3     CPDSPN..LSDGTVLSMN..HNTD...TP...RSLSV.SPSSYPE..LHTEVPLSVLILGLL
Y918_HUMAN  CPDYSDVVVSTPTPSSIQVPARTSAVTPAVRLNSTGAPASLGAGGGASSVPLSVLILSLL
Q9H5Y7      ~~~~~~~~~~~~~~~~~~~~~~~~~~~~~~~~~~~~~~~~~~~~~~~~~~~~~~~~~~~
Y848_HUMAN  CPEMLHVAPAGESPAQPGDSHLIGAPFSA.......SFYEFSPPG..GPVPLSVLILSLL
Q9UGS3      CPGWAAR.KAKRTPASRPSARRTPIKGRQCGADKVG~~~~~~~~~~~~~~~~~~~~~~~~

AAB50905    IVFVTSAFTVVGMLVFIL.RNRKRSKRRDANSSASEINSLQTVCDSSYWHNGPYNADGAH
AAY94963    IVFVTSAFTVVGMLVFIL.RNRKRSKRRDANSSASEINSLQTVCDSSYWHNGPYNADGAH
AAE01312    ~~~~~~~~~~~~~~~~~~~~~~~~~~~~~~~~~~~~~~~~~~~~~~~~~~~~~~~~~~~
HLRRNS3     VVFILSVCFGAGLFVFVL.KRRKGVPSVPRNTNNLDVSSFQLQY.GSY..........NT
Y918_HUMAN  LVFIMSVFVAAGLFVLVM.KRRKNQSDHTSTNNSDVSSFNMQY.SVMGGGGGTGGHPHA
Q9H5Y7      ~~~~~~~~~~~~~~~~~~~~~~~~~~~~~~~~~~~~~~~~~~~~~~~~~~~~~~~~~~~
Y848_HUMAN  VIFFSAVFVAAGLFAYVLRRRRKKLPFRSKRQEGVDLTGIQMQC.HRLFEDGGGGGGSG
Q9UGS3      ~~~~~~~~~~~~~~~~~~~~~~~~~~~~~~~~~~~~~~~~~~~~~~~~~~~~~~~~~~~

AAB50905    RVYDCGSHSLSD~~~~~~~~~~~~~~~~~~~~~~~~~~~~~~~~~~~~~~~~~~~~~~~
AAY94963    RVYDCGSHSLSD~~~~~~~~~~~~~~~~~~~~~~~~~~~~~~~~~~~~~~~~~~~~~~~
AAE01312    ~~~~~~~~~~~~~~~~~~~~~~~~~~~~~~~~~~~~~~~~~~~~~~~~~~~~~~~~~~~
HLRRNS3     ETHD........KTD.GHVYNYIPPPVGQMCQNPIYMQKEGDPVAYYRNLQEF..SYS..
Y918_HUMAN  HVHHRGPALPKVKTPAGHVYFYIPHPLGHMCKNPIYRSREGNSVEDYKDLHELKVTYSSN
Q9H5Y7      ~~~~~~~~~~~~~~~~~~~~~~~~~~~~~~~~~~~~~~~~~~~~~~~~~~~~~~~~~~~
Y848_HUMAN  GGGRPTLSSPEKAPPVGHVYEYIPHPVTQMCNNPIYKPREEEEVA....VSSAQEAGSAE
Q9UGS3      ~~~~~~~~~~~~~~~~~~~~~~~~~~~~~~~~~~~~~~~~~~~~~~~~~~~~~~~~~~~

AAB50905    ~~~~~~~~~~~~~~~~~~~~~~~~~~~~~~~~~~~~~~~~~~~~~~~~~~~~~~~~~~~
AAY94963    ~~~~~~~~~~~~~~~~~~~~~~~~~~~~~~~~~~~~~~~~~~~~~~~~~~~~~~~~~~~
AAE01312    ~~~~~~~~~~~~~~~~~~~~~~~~~~~~~~~~~~~~~~~~~~~~~~~~~~~~~~~~~~~
HLRRNS3     .NLEEKKEEP......................ATPAYTISATELLEKQATP.R
Y918_HUMAN  HHLQQQQQPPPPPQQPQQQPPPQLQLQPGEEERRESHHLRSPAYSVSTIEPREDLLSPVQ
Q9H5Y7      ~~~~~~~~~~~~~~~~~~~~~~~~~~~~~~~~~~~~~~~~~~~~~~~~~~~~~~~~~~~
Y848_HUMAN  RGGPGTQPPGMGEALLGSEQFAETPKENHSNYRTLLEKEKEWALAVSSSQLNTIVTVNHH
Q9UGS3      ~~~~~~~~~~~~~~~~~~~~~~~~~~~~~~~~~~~~~~~~~~~~~~~~~~~~~~~~~~~
```

FIG. 8D

```
AAB50905    ~~~~~~~~~~~~~~~~~~~~~~~~~~~~~~~~~~~~~~~~~~~~~~~~~~~~~~
AAY94963    ~~~~~~~~~~~~~~~~~~~~~~~~~~~~~~~~~~~~~~~~~~~~~~~~~~~~~~
AAE01312    ~~~~~~~~~~~~~~~~~~~~~~~~~~~~~~~~~~~~~~~~~~~~~~~~~~~~~~
HLRRNS3     EPEL.LYQNIAERVKELPS..AG..LVHY.NF.CTLPKRQFAPSYESRRQNQ........
Y918_HUMAN  DADR.FYRGILEPDKHCSTTPAGNSLPEYPKFPCSPAAYTFSPNYDLRRPHQYLHPGAGD
Q9H5Y7      ~~~~~~~~~~~~~~~~~~~~~~~~~~~~~~~~~~~~~~~~~~~~~~~~~~~~~~
Y848_HUMAN  HPHHPAVGGVSGVVGGTGGDLAGFRHHEKNGGVVLFPPGGGCGSGSMLLDRERPQPAPCT
Q9UGS3      ~~~~~~~~~~~~~~~~~~~~~~~~~~~~~~~~~~~~~~~~~~~~~~~~~~~~~~

AAB50905    ~~~~~~~~~~~~~~~~~~~~~~~~~~~~~~~~~~~~~~~~~~~~~~~~~~~~~~
AAY94963    ~~~~~~~~~~~~~~~~~~~~~~~~~~~~~~~~~~~~~~~~~~~~~~~~~~~~~~
AAE01312    ~~~~~~~~~~~~~~~~~~~~~~~~~~~~~~~~~~~~~~~~~~~~~~~~~~~~~~
HLRRNS3     DRINKTVLYGTP..RKCFVGQSKPNHPLLQAKPQSEPDYLEVLEKQTAISQL~~~~~~~~
Y918_HUMAN  SRLREPVLYSPP..SAVFVEPNRNEYLELKAKLNVEPDYLEVLEKQTTFSQF~~~~~~~~
Q9H5Y7      ~~~~~~~~~~~~~~~~~~~~~~~~~~~~~~~~~~~~~~~~~~~~~~~~~~~~~~
Y848_HUMAN  VGFVDCLYGTVPKLKELHVHPPGMQYPDLQQDARLKETLLFSAEKGFTDHQTQKSDYLEL
Q9UGS3      ~~~~~~~~~~~~~~~~~~~~~~~~~~~~~~~~~~~~~~~~~~~~~~~~~~~~~~

AAB50905    ~~~~~~~~~~~~~~~~~~~~~~~
AAY94963    ~~~~~~~~~~~~~~~~~~~~~~~
AAE01312    ~~~~~~~~~~~~~~~~~~~~~~~
HLRRNS3     ~~~~~~~~~~~~~~~~~~~~~~~
Y918_HUMAN  ~~~~~~~~~~~~~~~~~~~~~~~
Q9H5Y7      ~~~~~~~~~~~~~~~~~~~~~~~
Y848_HUMAN  RAKLQTKPDYLEVLEKTTYRF
Q9UGS3      ~~~~~~~~~~~~~~~~~~~~~~~
```

FIG. 9A

```
Domain 1 of 9:
 QS =      86   QE =      109   TS =       1   TE =       25

Q      86  QLIWLYLDHNYIS-SVDEDAFQGIR
            +L +L+L+HN ++ S+ +++F++ +
 T       1  NLQHLDLSHNQLTGSIPPESFGNLP

Domain 2 of 9:
 QS =     110   QE =      133   TS =       1   TE =       25

Q     110  RLKELILSSNKIT-YLHNKTFHPVP
            +L++L LS+N++T   +++ +F    P
 T       1  NLQHLDLSHNQLTGSIPPESFGNLP

Domain 3 of 9:
 QS =     134   QE =      157   TS =       1   TE =       25

Q     134  NLRNLDLSYNKLQ-TLQSEQFKGLR
            NL+ LDLS+N+L+ ++ +E F++L+
 T       1  NLQHLDLSHNQLTGSIPPESFGNLP

Domain 4 of 9:
 QS =     158   QE =      181   TS =       1   TE =       25

Q     158  KLIILHLRSNSLK-TVPIRVFQDCR
            +L   L+L++N+L+ ++P  +F++++
 T       1  NLQHLDLSHNQLTGSIPPESFGNLP

Domain 5 of 9:
 QS =     182   QE =      205   TS =       1   TE =       25

Q     182  NLDFLDLGYNRLR-SLSRNAFAGLL
            NL +LDL +N+L+ S++  ++F++L
 T       1  NLQHLDLSHNQLTGSIPPESFGNLP

Domain 6 of 9:
 QS =     206   QE =      229   TS =       1   TE =       25

Q     206  KLKELHLEHNQFS-KINFAHFPRLF
            +L++L+L HNQ++ +I     F   L
 T       1  NLQHLDLSHNQLTGSIPPESFGNLP
```

FIG. 9B

```
Domain 7 of 9:
  QS =     230  QE =      253  TS =       1  TE =       25

Q     230 NLRSIYLQWNRIR-SISQGLTWTWS
          NL++++L+ N+++ SI++++    +
T       1 NLQHLDLSHNQLTGSIPPESFGNLP

Domain 8 of 9:
  QS =     254  QE =      277  TS =       1  TE =       25

Q     254 SLHNLDLSGNDIQ-GIEPGTFKCLP
          +L   LDLS+N ++ +I+P++F+ LP
T       1 NLQHLDLSHNQLTGSIPPESFGNLP

Domain 9 of 9:
  QS =     278  QE =      301  TS =       1  TE =       25

Q     278 NLQKLNLDSNKLT-NISQETVNAWI
          NLQ L+L++N+LT   I++E+
T       1 NLQHLDLSHNQLTGSIPPESFGNLP
```

FIG. 10A

```
RANK 2 Score =  20.38   P_Score -  7.3e-007
 Q = CGI_597ews1c0c3e.seq          QF =  1 #Q Symbols = 518
 T = LRRNT                         TF =  1 #T Symbols = 31
 A = PF01462
 D = LRRNT PF01462 Leucine rich repeat N-terminal domain
 Identical Match = 9  Similar = 18  Total # Of Gaps = 2
 Identity: Alignment = 29% Query = 2% Target = 29%
 Similarity: Alignment = 58% Query = 3% Target = 58%
 QS =      33  QE =      60  TS =       1  TE =      31

Q     33 ACPKNCRCD--GKIVYCESHAFA-DIPENIS
          +CP +C+C    ++ VYC ++    +P  I+
 T      1 QCPRPCHCHPFHTHVYCDDRNLTNEVPRDIP
```

FIG. 10B

```
RANK 3 Score =  9.26  P_Score =  0.000004
 Q = CGI_597ews1c0c3e.seq             QF =  1 #Q Symbols = 518
 T = LRRCT                            TF =  1 #T Symbols = 54
 A = PF01463
 D = LRRCT PF01463 Leucine rich repeat C-terminal domain
 Identical Match = 14  Similar = 33  Total # Of Gaps = 2
 Identity: Alignment = 25% Query = 3% Target = 26%
 Similarity: Alignment = 60% Query = 6% Target = 61%
 QS =      311  QE =      361  TS =       1  TE =       54

Q      311 NMWECSRSICPLFYWLKN----FKGNKESTMICAGPKHIQGEKVSDAVETYNICS
           N W+C+ ++ ++  WL++     ++++E  + CA+P H +G +V D +    +C+
T        1 NPWHCDCHLRWFQRWLREWHPRHIWDQE-DYRCANPPHLRGQPVLDYPHSDFSCP
```

FIG. 11

1 MGFHLITQLKGMSVVLVLLPTLLLVMLTGA^QR 32

Score: 7.9
   Probability: 5.417E-01
   SP length: 30
   McGeoch scan succeeded:
     Charged-region statistics:
       Length: 10   Charge: 1
     Hydrophobic-region statistics:
       Length: 9   Offset: 11   Total hydropathy: 64.8
       Maximum 8-residue hydropathy: 60.7, starting at 13

FIG. 12A

```
Domain 1 of 10:
  QS =      87   QE =      110   TS =      1   TE =      25

Q       87  NAVTLHLGNNGLQ-EIRTGAFSGLK
            N +L+L +N L+ +I  ++F++L+
T        1  NLQHLDLSHNQLTGSIPPESFGNLP

Domain 2 of 10:
  QS =     111   QE =      134   TS =      1   TE =      25

Q      111  TLKRLHLNNNKLE-ILREDTFLGLE
            L++L+L++N+L+   + +++F +L
T        1  NLQHLDLSHNQLTGSIPPESFGNLP

Domain 3 of 10:
  QS =     135   QE =      158   TS =      1   TE =      25

Q      135  SLEYLQADYNYIS-AIEAGAFSKLN
            +L++L  ++N ++   I++++F++L
T        1  NLQHLDLSHNQLTGSIPPESFGNLP

Domain 4 of 10:
  QS =     159   QE =      181   TS =      1   TE =      25

Q      159  KLKVLILNDNLLL-SLPSNVFR-FV
            +L++L L++N L   S+P+++F+
T        1  NLQHLDLSHNQLTGSIPPESFGNLP

Domain 5 of 10:
  QS =     182   QE =      203   TS =      1   TE =      25

Q      182  LLTHLDLRGNRLK-VMPF--AGVLE
            L+HLDL++N+L+     P    G L
T        1  NLQHLDLSHNQLTGSIPPESFGNLP

Domain 6 of 10:
  QS =     400   QE =      423   TS =      1   TE =      25

Q      400  SLDLLHLGNNRIA-VIQEGAFTNLT
            +L  L+L +N++    I +++F NL+
T        1  NLQHLDLSHNQLTGSIPPESFGNLP
```

FIG. 12B

```
Domain 7 of 10:
 QS =     424  QE =       447  TS =        1  TE =       25

Q     424  SLRRLYLNGNYLE-VLYPSMFDGLQ
           +L++L+L++N L+   + P+ F +L+
T       1  NLQHLDLSHNQLTGSIPPESFGNLP

Domain 8 of 10:
 QS =     448  QE =       471  TS =        1  TE =       25

Q     448  SLQYLYLEYNVIK-EIKPLTFDALI
           +LQ+L+L +N ++ +I P +F  L
T       1  NLQHLDLSHNQLTGSIPPESFGNLP

Domain 9 of 10:
 QS =     472  QE =       494  TS =        1  TE =       25

Q     472  NLQLLFLNNNLLR-SLPDN-IFGGT
           NLQ L L++N L+ S+P++ + + +
T       1  NLQHLDLSHNQLTGSIPPESFGNLP

Domain 10 of 10:
 QS =     495  QE =       519  TS =        1  TE =       25

Q     495  ALTRLNLRNNHFSHLPVKGVLDQLP
           L++L+L++N+++      +++ +LP
T       1  NLQHLDLSHNQLTGSIPPESFGNLP
```

FIG. 13A

```
Domain = LRRNT PF01462 Leucine rich repeat N-terminal domain
  Identical Match = 16   Similar = 40   Total # Of Gaps = 4
  Identity: Alignment = 5%  Query = 2%  Target = 52%
  Similarity: Alignment = 11%  Query = 5%  Target = 100%

Domain 1 of 2:
  QS =       28   QE =       59   TS =        1   TE =       31

Q       28 ICKIRCLCEEKENVLNINCENKGFT-TVSLLQP
           +C+ +C C++      + ++C +++ T +V      P
T        1 QCPRPCHCHP--FHTHVYCDDRNLTNEVPRDIP

Domain 2 of 2:
  QS =      339   QE =      372   TS =        1   TE =       31

Q      339 TCPSSCVCTSQSSDNGLNVNCQERKFT-NISDLQP
           CP +C+C++       ++ V+C++R+ T   + +  P
T        1 QCPRPCHCHP----FHTHVYCDDRNLTNEVPRDIP
```

FIG. 13B

```
Domain = LRRCT PF01463 Leucine rich repeat C-terminal domain
  Identical Match = 27  Similar = 76  Total # Of Gaps = 6
  Identity: Alignment = 7% Query = 3% Target = 50%
  Similarity: Alignment = 20% Query = 9% Target = 100%

Domain 1 of 2:
  QS =      216  QE =      264  TS =        1  TE =       54

Q      216 NPWNCTCDLLPLKAWLDT-ITVFVG---EIVCETPFRLHGKDVTQLTR-QDLCP
           NPW+C+C+L++++ WL +  ++ ++    ++ C+ P +L+G+ V ++++   + CP
T        1 NPWHCDCHLRWFQRWLREWHPRHIWDQEDYRCANPPHLRGQPVLDYPHSDFSCP

Domain 2 of 2:
  QS =      529  QE =      579  TS =        1  TE =       54

Q      529 NPWDCTCDIMGLKDWTEH-ANSPVIIN-EVTCESPAKHAG-EILKFLGREAICP
           NPW+C+C+++  +++W ++ +++ +     +++C++P + +G  +L ++  + +CP
T        1 NPWHCDCHLRWFQRWLREWHPRHIWDQEDYRCANPPHLRGQPVLDYPHSDFSCP
```

HUMAN LEUCINE-RICH REPEAT-CONTAINING PROTEINS SPECIFICALLY EXPRESSED IN THE NERVOUS SYSTEM

This application claims benefit to provisional application U.S. Ser. No. 60/375,335 filed Apr. 25, 2002, under 35 U.S.C. 119(e). The entire teachings of the referenced application are incorporated herein by reference.

FIELD OF THE INVENTION

The present invention relates to the fields of pharmacogenomics, diagnostics, and patient therapy. More specifically, the present invention relates to methods of diagnosing and/or treating diseases involving human leucine-rich repeat containing proteins specifically expressed in the nervous system (HLRRNS-2 and HLRRNS-3).

BACKGROUND OF THE INVENTION

Leucine-rich repeats ("LRRs") were first discovered in leucine-rich α2-glycoprotein isolated from human serum (Takashashi, et al. (1985) *Proc. Natl. Acad. Sci. USA* 82:1906–1910). LRR-containing proteins represent a diverse group of molecules with differing functions and cellular locations in a variety of organisms (for review, see Kobe and Deisenhofer (1994) *Trends Biochem. Sci.* 19:415–421).

Given the wide range of important functions of LRR-containing proteins, such as protein:protein interactions, matrix association, cell adhesion, caspase recruitment (CARD), nucleotide binding, and signal transduction, there exists a need for identifying novel LRR containing proteins as well as for modulators of such molecules for use in regulating a variety of cellular responses. Proteins within this group have also been found to play a role in cell adhesion during various developmental processes. Adhesion proteins represent the largest group in the LRR superfamily.

As the name implies, LRRs are distinguished by a consensus sequence containing predominently of leucines. LRRs are short protein modules characterized by a periodic distribution of hydrophobic amino acids, especially leucine residues, separated by hydrophilic residues (Sean et al., *Prog. Biophys. Molec. Biol.* 65:1–44, 1996). The basic structure of the repeat is as follows: X-L-X-X-L-X-L-X-X-N-X-a-X-X-X-a-X-X-L-X (SEQ ID NO:75), where X is any amino acid, L is leucine, N is asparagine and "a" denotes an aliphatic residue, such as glycine, alanine, valine, leucine and isoleucine. The asparagine at position 10 can be replaced by cysteine, threonine, or glutamine. The average repeat length is 24 amino acids but can vary between 22 and 29 amino acids. In transmembrane proteins, LRRs and their flanking sequences always occur in the presumed extracellular portions. In these situations, the LRRs are generally flanked on either side by cysteine-rich regions. Generally, the cysteines are present in the oxidized disulphide link form.

A class of cell surface proteins, having a leucine-rich repeat (LRR) in the carboxy terminus of the polypeptide chain, has been described in both plants and animals that are involved in pathogen perception, MHC class II trans-activation, inflammation, and the regulation of apoptosis (Dixon et al., *Proc. Natl. Acad. Sci, USA.* 97:8807–14:2000; Harton and Ting, *Mol. Cell. Biol.* 20:6185–6194:2000; Inohara et al., *J. Biol. Chem.* 275:27823–27831, 2000; Inohara et al., *J. Biol. Chem.* 274:14560–14567, 1999).

An example of a transmembrane protein containing an LRR is Toll, a *Drosophila* gene that functions to establish dorsal-ventral patterning. Dominant ventralizing mutants that map to the cysteine-rich regions surrounding the LRR domain have been described (Schneider et al., *Genes and Development* 5:797–807, 1991). The cysteine regions associated with LRRs act to regulate receptor activity. The LRRs, within the Toll protein, have been shown to function in heterotypic cell adhesion, a process required for proper motoneuron and muscle development (Halfon et al., *Dev. Biol.* 169:151–167, 1995).

Another *Drosophila* LRR-containing transmembrane protein, 18 wheeler, which is regulated by homeotic genes, also promotes heterophilic cell adhesion in cell migration events during development (Eldon et al., *Development* 120:885–899, 1994). Mammalian CD14, which binds lipopolysaccharide (LPS), and signals through NF-κB, is thought to have analogies to the Toll signal transduction pathway. CD14 also contains a region of LRRs that has been shown in deletion mutants to be responsible for LPS binding.

Slit is another LRR-containing *Drosophila* secreted protein that functions in the development of the midline glial cells and the commissural axon tracts that cross the midline (Jacobs and Goodman, *J. Neurosci.* 9:2402–2411, 1989). Slit is secreted by midline glia and forms a gradient by diffusion. Another protein, Robo, responds to the Slit gradient and specifies the lateral position of axons in developing the central nervous system (Simpson et al., *Cell* 103: 1019–1032, 2000). Mammalian homologues of *Drosophila* Slit have been shown to bind the heparin sulfate proteoglycan, glypican-1 (Liang et al., *J. Biol. Chem.* 274:17885–1792, 1999). In general, heparin sulfate proteoglycans have been shown to accummulate in Alzheimer's diseased brains and specifically, glypican-1 is a component of both senile plaques and neurofibrillary tangles (Verbeek et al., *Am. J. Pathol.* 155:2115–2125, 1999). Heparin sulfate proteoglycans are also implicated in the regulation of cytokine signaling in B cells through the activation of CD40 (van Der Voort et al., *J. Exptl. Med.* 192:1115–1124, 2000).

Direct evidence that mutations in proteins that contain LRRs can lead to human disease has recently been demonstrated. For example, one of the genes associated with susceptibility to Crohn's disease, NOD2, a member of the Apaf-1/Ced-4 superfamily of apoptosis regulators, contains mutations that alter the structure of either the LRR or the adjacent region (Hugot et al., *Nature* 411:599–603, 2000). Other examples are mutations in a pyrin-like LRR-containing gene that causes familial cold autoinflammatory syndrome and Muckle-Wells syndrome (Hoffman et al., *Nature Genetics* 29:301–305, 2001).

LRR-containing proteins have been identified in prokaryotes, plants, yeast, and mammals. Although these proteins were initially thought to be secreted proteins, it is now appreciated that they inhabit a variety of cellular locations and participate in a diverse set of critical functions in developmental and cellular homeostasis. These LRRs, being extracellular, are capable of directing protein-protein interactions with other receptors that are involved in regulating developmental processes, apoptosis, inflammation, and immune responses. LRR-containing proteins can also bind to other extracellular ligands derived from infectious agents and participate in triggering and or modulating immune responses. Therefore, agonists and antagonists for these LRR-containing proteins can be useful for therapeutic purposes.

SUMMARY OF THE INVENTION

The present invention relates to nucleic acid and protein molecules, referred to herein as human leucine-rich repeat molecules, specifically, HLRRNS-2 and HLRRNS-3. HLRRNS-2 and HLRRNS-3 are useful as modulating agents in regulating a variety of cellular processes. In one aspect, this invention provides isolated nucleic acid molecules encoding human leucine-rich repeat proteins HLRRNS-2 and HLRRNS-3, or biologically active portions thereof, as well as nucleic acid fragments suitable as primers or hybridization probes for the detection of human leucine-rich repeat HLRRNS-2- and HLRRNS-3-encoding nucleic acids.

In particular, one aspect of the present invention provides isolated nucleic acid molecules that encode transmembrane proteins that contain leucine-rich repeats (LRR) on their carboxy terminal ends and whose amino acid sequences are shown in FIGS. 2 and 4, or the amino acid sequences encoded by the cDNA clones. These newly isolated human LRR-containing sequences each display a neuronal specific pattern of expression. The specificity by which the transcripts are expressed relates to their importance in various biologically processes.

It is another aspect of the present invention to provide an isolated HLRRNS-2 polynucleotide sequence as depicted in SEQ ID NO: 1 (FIG. 1) and an isolated HLRRNS-3 polynucleotide sequence as depicted in SEQ ID NO: 3 (FIG. 3).

It is another aspect of the present invention to provide a newly isolated and substantially purified polynucleotide that encodes HLRRNS-2, or a fragment thereof. In a particular aspect, the polynucleotide comprises the nucleotide sequence of SEQ ID NO: 1. The present invention also provides a polynucleotide sequence comprising the complement of SEQ ID NO: 1, or variants thereof. In addition, the present invention features polynucleotide sequences, which hybridize under conditions of moderate stringency or high stringency to the polynucleotide sequence of SEQ ID NO: 1.

It is another aspect of the present invention to provide a newly isolated and substantially purified polynucleotide that encodes HLRRNS-3, or a fragment thereof. In a particular aspect, the polynucleotide comprises the nucleotide sequence of SEQ ID NO: 3. The present invention also provides a polynucleotide sequence comprising the complement of SEQ ID NO: 3, or variants thereof. In addition, the present invention features polynucleotide sequences, which hybridize under conditions of moderate stringency or high stringency to the polynucleotide sequence of SEQ ID NO: 3.

It is an aspect of the present invention to further provide the human leucine-rich repeat-containing HLRRNS-2 and HLRRNS-3 nucleic acid sequences and an antisense of the nucleic acid sequences, as well as, oligonucleotides, fragments, or portions of the nucleic acid molecules or antisense molecules. Also provided are expression vectors and host cells comprising polynucleotides that encode the human leucine-rich repeat HLRRNS-2 and HLRRNS-3 polypeptides.

It is also an aspect of the present invention to provide the HLRRNS-2 polypeptide, encoded by the polynucleotide of SEQ ID NO: 1 (CDS=343 to 2112; FIG. 1) and having the amino acid sequence of SEQ ID NO: 2 (FIG. 2), or a functional or biologically active portion thereof. In a further aspect of the present invention, the HLRRNS-3 polypeptide, encoded by the polynucleotide of SEQ ID NO:3 (CDS=247 to 2781; FIG. 3) and having the amino acid sequence of SEQ ID NO:4 (FIG. 4), or a functional or biologically active portion thereof, is also provided.

One aspect of the present invention encompasses a polynucleotide lacking the initiating start codon, in addition to, the resulting encoded polypeptide of HLRNNS-2. Specifically, the present invention encompasses the polynucleotide corresponding to nucleotides 346 thru 2112 of SEQ ID NO: 1, and the polypeptide corresponding to amino acids 2 thru 590 of SEQ ID NO: 2. Also encompassed are recombinant vectors comprising said encoding sequence, and host cells comprising said vector.

Yet another aspect of the present invention encompasses a polynucleotide lacking the initiating start codon, in addition to, the resulting encoded polypeptide of HLRNNS-3. Specifically, the present invention encompasses the polynucleotide corresponding to nucleotides 250 thru 2781 of SEQ ID NO: 3, and the polypeptide corresponding to amino acids 2 thru 845 of SEQ ID NO: 4. Also encompassed are recombinant vectors comprising said encoding sequence, and host cells comprising said vector.

It is a further aspect of the present invention to provide compositions comprising the HLRRNS-2 polynucleotide sequence, or a fragment or portion thereof, or the encoded HLRRNS-2 polypeptide (MW=67.22 kDa), or a fragment or portion thereof. Also provided by the present invention are pharmaceutical compositions comprising at least one HLRRNS-2 polypeptide, or a functional portion thereof, wherein the compositions further comprise a pharmaceutically acceptable carrier, excipient, or diluent.

In yet another aspect of the present invention, compositions comprising the HLRRNS-3 polynucleotide sequence, or fragment or portion thereof, or the encoded HLRRNS-3 polypeptide (MW=95.4 kDa), or fragment or portion thereof, are provided. Also, the present invention provides pharmaceutical compositions comprising at least one HLRRNS-3 polypeptide, or a functional portion thereof, wherein the compositions further comprise a pharmaceutically acceptable carrier, excipient, or diluent.

It is yet another aspect of the invention to provide methods for producing a polypeptide comprising the amino acid sequence depicted in SEQ ID NO: 2 or SEQ ID NO: 4, or a fragment thereof, comprising the steps of: a) cultivating a host cell comprising an expression vector containing the polynucleotide sequence encoding the human leucine-rich repeat HLRRNS-2 or HLRRNS-3 protein, or a portion thereof, according to this invention, under conditions suitable for the expression of the encoded polypeptide; and b) recovering the polypeptide from the host cell.

It is another aspect of the present invention to provide human leucine-rich repeat HLRRNS-2 and HLRRNS-3 nucleic acid sequences, polypeptides, peptides and antibodies for use in the diagnosis and/or screening of disorders or diseases associated with expression of the polynucleotide and its encoded polypeptide as described herein.

It is another aspect of the present invention to provide a method for detecting a polynucleotide that encodes an LRR, preferably the HLRRNS-2 and HLRRNS-3 polypeptides as described herein, a homologue, or fragment or portion thereof, in a biological sample comprising the steps of: a) hybridizing the polynucleotide, or complement of the polynucleotide sequence encoding SEQ ID NO: 2 or SEQ ID NO: 4, to a nucleic acid material of a biological sample, thereby forming a hybridization complex; and b) detecting the hybridization complex, wherein the presence of the complex correlates with the presence of a polynucleotide encoding the human leucine-rich repeat HLRRNS-2 or HLRRNS-3 polypeptide, or fragment therof, in the biological sample. The nucleic acid material can be further amplified by the polymerase chain reaction prior to hybridization.

It is yet another aspect of the present invention to provide a substantially purified antagonist or inhibitor of the polypeptide of SEQ ID NO: 2 or SEQ ID NO: 4. In this regard, and by way of example, a purified antibody that binds to a polypeptide comprising the amino acid sequence of SEQ ID NO: 2 or SEQ ID NO: 4 is provided.

It is an aspect of the invention to further provide substantially purified agonists or activators of the HLRRNS-2 polypeptide of SEQ ID NO: 2 or the HLRRNS-3 polypeptide of SEQ ID NO: 4.

It is another aspect of the present invention to provide antibodies, and immunoreactive portions thereof, that recognize and bind to the human leucine-rich HLRRNS-2 or HLRRNS-3 protein, polypeptide, or epitope thereof. Such antibodies can be either polyclonal or monoclonal. Antibodies that bind to the human leucine-rich HLRRNS-2 or HLRRNS-3 protein can be utilized in a variety of diagnostic and prognostic formats, as well as, therapeutic methods.

It is a further aspect of the invention to provide methods for screening for agents which bind to, or modulate the human leucine-rich repeat HLRRNS-2 and HLRRNS-3 polypeptide, as well as, the binding molecules and/or modulators, e.g., agonists and antagonists, particularly those that are obtained from the screening methods described herein.

It is also an aspect of the instant invention to provide methods and compositions to detect and diagnose alterations in the human leucine-rich repeat HLRRNS-2 or HLRRNS-3 sequence in tissues and cells as they relate to ligand response.

It is a further aspect of the present invention to provide compositions for diagnosing neuronal-related disorders, diseases, or conditions, and for diagnosing or monitoring response to the human leucine-rich repeat molecules HLRRNS-2 or HLRRNS-3 in humans. In accordance with the invention, the compositions detect an alteration of the normal or wild type human leucine-rich repeat HLRRNS-2 or HLRRNS-3 sequence, or its expression product in a patient sample of cells or tissue.

It is an aspect of the present invention to provide diagnostic probes for screening diseases and monitoring a patient's response to therapy. The probe sequence comprises the human leucine-rich repeat HLRRNS-2 or HLRRNS-3 locus polymorphism. The probes comprise nucleic acids or amino acids.

It is a further aspect of the instant invention to provide methods for detecting genetic predisposition, susceptibility and response to therapy related to the brain. In accordance with the invention, the method comprises isolating a human sample, for example, blood or tissue from adults, children, embryos or fetuses, and detecting at least one alteration in the wild type human leucine-rich repeat HLRRNS-2 or HLRRNS-3 sequence, or its expression product, in the sample, wherein at least one alteration is indicative of genetic predisposition, susceptibility, or altered response to therapy related to the brain. According to the present invention, SEQ ID NO: 1 constitutes the wild type HLRRNS-2 and SEQ ID NO: 3 constitutes the wild type HLRRNS-3.

It is an aspect of the present invention to provide methods for the treatment or prevention of neurological disorders, immune disorders, or cancers involving administering to an individual in need of treatment or prevention an effective amount of a purified antagonist of the human leucine-rich repeat HLRRNS-2 or HLRRNS-3 polypeptide. Due to its elevated expression in brain, modulators of the novel human leucine-rich repeat proteins HLRRNS-2 and HLRRNS-3 of the present invention are particularly useful in treating or preventing neurological disorders, conditions, or diseases.

It is also an aspect of the present invention to provide diagnostic kits for determining the nucleotide sequence of human leucine-rich repeat HLRRNS-2 and HLRRNS-3 alleles. The kits can comprise amplification-based assays, nucleic acid probe assays, protein nucleic acid probe assays, antibody assays or any combination thereof.

It is also an aspect of the present invention to provide kits for screening and diagnosing of disorders associated with aberrant or uncontrolled neuronal development and with the expression of the polynucleotide and its encoded polypeptide as described herein.

It is an additional aspect of the present invention to provide methods for making determinations concerning drug administration, dosages, duration of treatment and the like, for diseases or disorders related to expression and/or activity or HLRRNS-2 and/or HLRRNS-3.

Further aspects, features, and advantages of the present invention will be better understood upon a reading of the detailed description of the invention when considered in connection with the accompanying figures/drawings.

BRIEF DESCRIPTION OF THE FIGURES

FIGS. 1A–1B show the full-length nucleotide sequence of cDNA clone, HLRRNS-2 (SEQ ID NO: 1), consensus of GPCR-164 clones A and D.

FIG. 2 shows the amino acid sequence (SEQ ID NO: 2) resulting from the translation of the full-length HLRRNS-2 cDNA sequence.

FIGS. 3A–3B show the full-length nucleotide sequence of cDNA clone, HLRRNS-3 (SEQ ID NO: 3), consensus of GPCR-168 clone A.

FIG. 4 shows the amino acid sequence (SEQ ID NO: 4) resulting from the translation of the full-length HLRRNS-3 cDNA sequence.

FIG. 5 shows the EST sequence identified as encoding peptides with homology to various LRR-containing proteins, including those that are found in some GPCRs [Incyte Template ID: 985843.1 (brain, also adrenal tumor, kidney epithelial); GPCR-164; BAC ID: NT_005087; SEQ ID NO: 23].

FIG. 6 shows the EST sequence identified as encoding peptides with homology to various LRR-containing proteins, including those that are found in some GPCRs [Incyte Template ID: 83448.1 (brain); GPCR-168; BAC ID: NT_025408; SEQ ID NO: 24].

FIGS. 7A–7F show the multiple sequence alignment of the translated sequence of the HLRRNS-2, where the GCG (Genetics Computer Group) pileup program was used to generate the alignment with several known sequences related to neuronal guidance, cell adhesion, inflammation, and immune regulation type proteins. The blackened areas represent identical amino acids in more than half of the listed sequences and the grey highlighted areas represent similar amino acids. The following sequences are aligned with HLRRNS-2: AAB45703 (SEQ ID NO: 5); AAB61227 (SEQ ID NO: 6); AAB61228 (SEQ ID NO: 7); AAE06789 (SEQ ID NO: 8); AAE06798 (SEQ ID NO: 9); AAY66713 (SEQ ID NO: 10); O43300 (SEQ ID NO: 11); Q9BGP6 (SEQ ID NO: 12); Q9D686 (SEQ ID NO: 13); Q9DBB9 (SEQ ID NO: 14); Q9H9T0 (SEQ ID NO: 15); and Q9UGS3 (SEQ ID NO:16).

FIGS. 8A–8D show the multiple sequence alignment of the translated sequence of the HLRRNS-3, where the GCG (Genetics Computer Group) pileup program was used to generate the alignment with several known sequences related to inflammation and immune regulation-type proteins. The blackened areas represent identical amino acids in more than half of the listed sequences and the grey highlighted areas represent similar amino acids. The sequences that are aligned with HLRRNS-3 are as follows: AAB50905 (SEQ ID NO: 17); AAE01312 (SEQ ID NO: 18); AAY94963 (SEQ ID NO: 19); Q9H5Y7 (SEQ ID NO: 20); Q9UGS3 (SEQ ID NO: 16); Y848_HUMAN (Acc. No. O94933; SEQ ID NO: 21); and Y918_HUMAN (Acc. No. O94991; SEQ ID NO: 22).

FIGS. 9A–9B show the alignment of HLRRNS-2 (SEQ ID NO:2; Query; Q) against the Target Pfam model (SEQ ID NO: 30; Target, T).

FIGS 10A–10B show the alignment of HLRRNS-2 (SEQ ID NO: 2; Query, Q) and (A) PF01462 Leucine rich repeat N-terminal domain (SEQ ID NO: 31, T); and (B) PF01463 Leucine rich repeat C-terminal domain (SEQ ID NO: 32; T).

FIG. 11 shows an HLRRNS-2 predicted signal peptide at its amino terminal end (SEQ ID NO: 29).

FIGS. 12A–12B show the alignment of HLRRNS-3 (SEQ ID NO: 4; Query, Q) against the Target Pfam model (SEQ ID NO: 30; Target, T).

FIGS. 13A–13B show the alignment of of HLRRNS-3 (SEQ ID NO: 4; Query, Q) and (A) PF01462 Leucine rich repeat N-terminal domain (SEQ ID NO: 31); and (B) PF01463 Leucine rich repeat C-terminal domain (SEQ ID NO: 32).

DESCRIPTION OF THE PRESENT INVENTION

Figure 14:
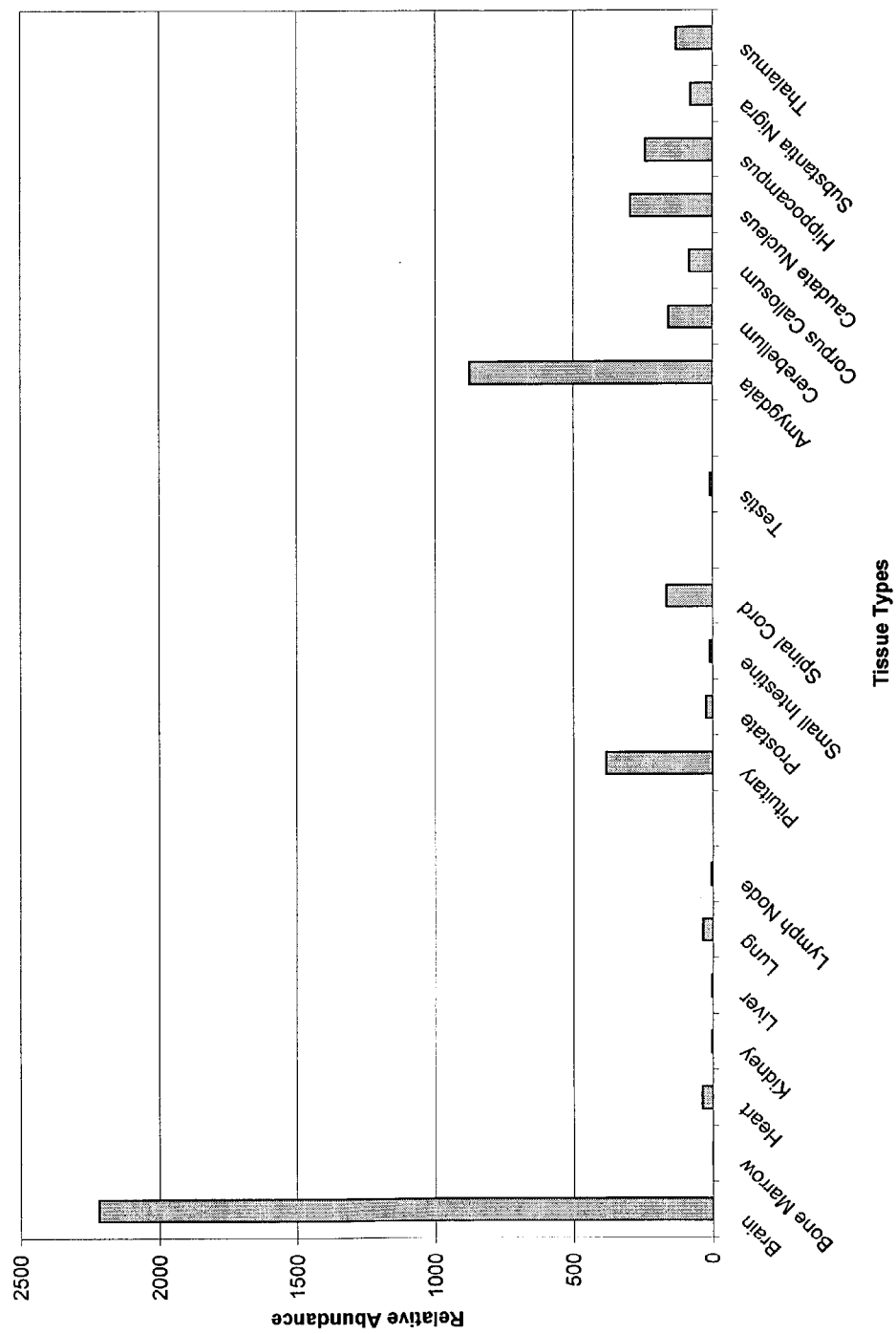
FIG. 14 shows expression profiling of the novel human LRR-containing protein, HLRRNS-2, as described in Example 4.

The present invention relates to newly isolated human leucine-rich repeat polynucleotides and their encoded polypeptides, the expression of which was discovered to be high in brain. These novel polypeptides are termed herein HLRRNS-2 and HLRRNS-3, acronyms for "Human Leucine-rich repeat nervous system-2" and "Human Leucine-rich repeat nervous system-3," respectively. It is to be understood that although HLRRNS-2 and HLRRNS-3 are distinct and novel peptides, they are related showing 14.9% identity and 23.5% similarity, as determined using the CLUSTALW algorithm described herein, and can perfom similar functions. Therefore, the uses including methods and compositions as described herein, encompass HLRRNS-2 and HLRRNS-3 separately, and if desired, in combination.

DEFINITIONS

The human leucine-rich repeat HLRRNS-2 and HLRRNS-3 polypeptides (or proteins) of the present invention refer to the amino acid sequences of substantially purified HLRRNS-2 and HLRRNS-3, respectively, which can be obtained from any species, preferably mammalian, and more preferably, human, and from a variety of sources, including natural, synthetic, semi-synthetic, or recombinant. Functional fragments of the HLRRNS-2 and HLRRNS-3 polypeptides are also embraced by the present invention.

"Nucleic acid sequence," as used herein, refers to an oligonucleotide, nucleotide, or polynucleotide, and fragments or portions thereof, and to DNA or RNA of genomic or synthetic origin which can be single- or double-stranded, and represent the sense or anti-sense strand. By way of non-limiting example, fragments include nucleic acid sequences that are 10–15 nucleotides, preferably greater, 20–60 nucleotides, in length, and preferably include fragments that are at least 70–100 nucleotides, or which are at least 1000 nucleotides or greater in length.

An "allele" or "allelic sequence" is an alternative form of the HLRRNS-2 or the HLRRNS-3 nucleic acid sequence of the invention. Alleles can result from at least one mutation in the nucleic acid sequence and can yield altered mRNAs or polypeptides whose structure or function may or may not be altered. Any given gene, whether natural or recombinant, can have none, one, or many allelic forms. Common mutational changes, which give rise to alleles, are generally ascribed to natural deletions, additions, or substitutions of nucleotides. Each of these types of changes can occur alone, or in combination with the others, one or more times in a given sequence.

"Altered" nucleic acid sequences encoding the HLRRNS-2 or HLRRNS-3 polypeptide include nucleic acid sequences containing deletions, insertions and/or substitutions of different nucleotides resulting in a polynucleotide that encodes the same or a functionally equivalent HLRRNS-2 or HLRRNS-3 polypeptide. Altered nucleic acid sequences can further include polymorphisms of the polynucleotide encoding the HLRRNS-2 or HLRRNS-3 polypeptide; such polymorphisms are preferably detectable using a particular oligonucleotide probe. The encoded protein can also contain deletions, insertions, or substitutions of amino acid residues, which produce a silent change and result in a functionally equivalent HLRRNS-2 or HLRRNS-3 protein. Deliberate amino acid substitutions can be made on the basis of similarity in polarity, charge, solubility, hydrophobicity, hydrophilicity, and/or the amphipathic nature of the residues, as long as the biological activity of HLRRNS-2 and HLRRNS-3 protein is retained. For example, negatively charged amino acids can include aspartic acid and glutamic acid; positively charged amino acids include lysine and arginine; and amino acids with uncharged polar head groups having similar hydrophilicity values include leucine, isoleucine, and valine; glycine and alanine; asparagine and glutamine; serine and threonine; and phenylalanine and tyrosine.

"Peptide nucleic acid" (PNA) refers to an antisense molecule or anti-gene agent which comprises an oligonucleotide ("oligo") linked via an amide bond, similar to the peptide backbone of amino acid residues. PNAs typically comprise oligos of at least 5 nucleotides linked via amide bonds. PNAs may or may not terminate in positively charged amino acid residues to enhance binding affinities to DNA. Such amino acids include, for example, lysine and arginine, among others. These small molecules stop transcript elongation by binding to their complementary strand of nucleic acid (P. E. Nielsen et al., 1993, *Anticancer Drug Des.*, 8:53–63). PNAs can be pegylated to extend their lifespan in the cell where they preferentially bind to complementary single stranded DNA and RNA.

"Oligonucleotides" or "oligomers" refer to a nucleic acid sequence, preferably comprising contiguous nucleotides, of at least about 6 nucleotides to about 60 nucleotides, preferably at least about 8 to 10 nucleotides in length, more preferably at least about 12 nucleotides in length, for example, about 15 to 35 nucleotides, or about 15 to 25 nucleotides, or about 20 to 35 nucleotides, which can typically be used in PCR amplification assays, hybridization assays, or in microarrays. It will be understood that the term oligonucleotide is substantially equivalent to the terms primer, probe, or amplimer, as commonly defined in the art.

The term "antisense" refers to nucleotide sequences, and compositions containing nucleic acid sequences, which are complementary to a specific DNA or RNA sequence. The term "antisense strand" is used in reference to a nucleic acid strand that is complementary to the "sense" strand. Antisense (i.e., complementary) nucleic acid molecules include PNAs and can be produced by any method, including synthesis or transcription. Once introduced into a cell, the complementary nucleotides combine with natural sequences produced by the cell to form duplexes, which block either transcription or translation. The designation "negative" is sometimes used in reference to the antisense strand, and "positive" is sometimes used in reference to the sense strand.

Similarly, "amino acid sequence," as used herein, refers to an oligopeptide, peptide, polypeptide, or protein sequence, and fragments or portions thereof, and to naturally occurring or synthetic molecules. Amino acid sequence fragments are typically by way of non-limiting example from about 5 to about 30, preferably from about 5 to about 15 amino acids in length and retain the biological activity or function of the HLRRNS-2 or HLRRNS-3 polypeptide.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. In addition, the terms polypeptide and protein, in relation to HLRRNS-2 and HLRRNS-3, are used interchangeably herein to refer to the encoded product of the HLRRNS-2 or HLRRNS-3 nucleic acid sequence of the present invention, respectively.

The term "family" when referring to the protein and nucleic acid molecules of the invention is intended to mean two or more proteins or nucleic acid molecules having a common structural domain or motif and having amino acid or nucleotide sequence homology as defined herein. Such family members can be naturally occurring and can be from either the same or different species. For example, a family can contain a first protein of human origin, as well as other, distinct proteins of human origin or alternatively, can contain homologues and orthologues of non-human origin. Members of a family can also have common functional characteristics.

A "variant" of the HLRRNS-2 or HLRRNS-3 polypeptide refers to an amino acid sequence that is altered by one or more amino acids. The variant can have "conservative" changes, wherein a substituted amino acid has similar structural or chemical properties, e.g., replacement of leucine with isoleucine. More rarely, a variant can have "non-conservative" changes, e.g., replacement of a glycine with a tryptophan. Minor variations can also include amino acid deletions or insertions, or both. Guidance in determining which amino acid residues can be substituted, inserted, or deleted without abolishing functional biological or immunological activity can be found using computer programs well known in the art, for example, DNASTAR software.

The term "consensus" refers to the sequence that reflects the most common choice of base or amino acid at each position among a series of related DNA, RNA or protein sequences. Areas of particularly good agreement often represent conserved functional domains.

A "deletion" refers to a change in either the nucleotide or the amino acid sequence and results in the absence of one or more nucleotides or amino acid residues. By contrast, an insertion (also termed "addition") refers to a change in a nucleotide or amino acid sequence that results in the addition of one or more nucleotides or amino acid residues, as compared with the naturally occurring molecule. A substitution refers to the replacement of one or more nucleotides or amino acids by different nucleotides or amino acids.

A "derivative" nucleic acid molecule refers to the chemical modification of a nucleic acid encoding, or complementary to, the encoded HLRRNS-2 or HLRRNS-3 polypeptide. Such modifications include, for example, replacement of hydrogen by an alkyl, acyl, or amino group. A nucleic acid derivative encodes a polypeptide, which retains the essential biological and/or functional characteristics of the natural molecule. A derivative polypeptide is one, which is modified by glycosylation, pegylation, or any similar process that retains the biological and/or functional or immunological activity of the polypeptide from which it is derived.

"Amplification" refers to the production of additional copies of a nucleic acid sequence and is generally carried out using polymerase chain reaction (PCR) technologies, which are well known and practiced in the art (see, D. W. Dieffenbach and G. S. Dveksler, 1995, *PCR Primer, a Laboratory Manual*, Cold Spring Harbor Press, Plainview, N.Y.).

The term "biologically active," i.e., functional, refers to a protein or polypeptide or fragment thereof, having, for example, structural, regulatory, biochemical, biological, or physiological functions of a naturally occurring molecule. Likewise, "immunologically active" refers to the capability of the natural, recombinant, or synthetic HLRRNS-2 or HLRRNS-3, or any oligopeptide thereof, to induce a specific immune response in appropriate animals or cells, for example, to generate and to bind with specific antibodies.

The term "hybridization" refers to any process by which a strand of nucleic acids binds with a complementary strand through base pairing.

Hybridization techniques can be applied to a "microarray," which is an ordered array of molecules, such as but not limited to distinct polynucleotides or oligonucleotides, synthesized or attached on a substrate, such as paper, nylon, or other type of membrane; filter; chip; glass slide; or any other type of suitable solid support. One example of a microarray of nucleic acids is described, for instance, in WO 96/17958. Probes may also be deposited as elements onto the substrate and may be either directly or indirectly labeled. Each probe or element can be from about 0.1 to 2.5 mm in diameter, and more preferably about 2.5 mm in diameter. Such microarrays can be fabricated, for example, using the method described by Schena et al., *Science* 270:487–470 (1995). Techniques capable of producing high density microarrays may also be used (see, e.g., Fodor et al. *Science* 767–773 (1991) and U.S. Pat. No. 5,143,854 to Pirrung, M. C.).

The term "hybridization complex" refers to a complex formed between two nucleic acid sequences by virtue of the formation of hydrogen bonds between complementary G and C bases and between complementary A and T bases. The hydrogen bonds can be further stabilized by base stacking interactions. The two complementary nucleic acid sequences hydrogen bond in an anti-parallel configuration. A hybridization complex can be formed in solution (e.g., Cot or Rot analysis), or between one nucleic acid sequence present in solution and another nucleic acid sequence immobilized on a solid support (e.g., membranes, filters, chips, pins, or glass slides, or any other appropriate substrate to which cells or their nucleic acids have been affixed).

The terms "stringency" or "stringent conditions" refer to the conditions for hybridization as defined by nucleic acid composition, salt, and temperature. These conditions are well known in the art and can be altered to identify and/or detect identical or related polynucleotide sequences in a sample. A variety of equivalent conditions comprising either low, moderate, or high stringency depend on factors such as the length and nature of the sequence (DNA, RNA, base composition), reaction milieu (in solution or immobilized on a solid substrate), nature of the target nucleic acid (DNA, RNA, base composition), concentration of salts and the presence or absence of other reaction components (e.g., formamide, dextran sulfate and/or polyethylene glycol) and reaction temperature (within a range of from about 5° C. below the melting temperature of the probe to about 20° C. to 25° C. below the melting temperature). One or more factors can be varied to generate conditions, either low or high stringency that is different from but equivalent to the aforementioned conditions.

As will be understood by those of skill in the art, the stringency of hybridization can be altered in order to identify or detect identical or related polynucleotide sequences. As will be further appreciated by the skilled practitioner, the melting temperature, Tm, can be approximated by the formulas as known in the art, depending on a number of parameters, such as the length of the hybrid or probe in number of nucleotides, or hybridization buffer ingredients and conditions (see, for example, T. Maniatis et al., *Molecular Cloning: A Laboratory Manual*, Cold Spring Harbor Laboratory, Cold Spring Harbor, N.Y., 1982 and J. Sambrook et al., *Molecular Cloning: A Laboratory Manual*, Cold Spring Harbor Laboratory, Cold Spring Harbor, N.Y., 1989; *Current Protocols in Molecular Biology*, Eds. F. M. Ausubel et al., Vol. 1, "Preparation and Analysis of DNA", John Wiley and Sons, Inc., 1994–1995, Suppls. 26, 29, 35 and 42; pp. 2.10.7–2.10.16; G. M. Wahl and S. L. Berger (1987; *Methods Enzymol*. 152:399–407); and A. R. Kimmel, 1987; *Methods of Enzymol*. 152:507–511). As a general guide, Tm decreases approximately 1° C.–1.5° C. with every 1% decrease in sequence homology. Also, in general, the stability of a hybrid is a function of sodium ion concentration and temperature. Typically, the hybridization reaction is initially performed under conditions of low stringency, followed by washes of varying, but higher stringency. Reference to hybridization stringency, e.g., high, moderate, or low stringency, typically relates to such washing conditions.

Thus, by way of non-limiting example, "high stringency" refers to conditions that permit hybridization of those nucleic acid sequences that form stable hybrids in 0.018M NaCl at about 65° C. (i.e., if a hybrid is not stable in 0.018M NaCl at about 65° C., it will not be stable under high stringency conditions). High stringency conditions can be provided, for instance, by hybridization in 50% formamide, 5×Denhardt's solution, 5×SSPE (saline sodium phosphate EDTA) (1×SSPE buffer comprises 0.15 M NaCl, 10 mM Na2HPO4, 1 mM EDTA, (or 1×SSC buffer containing 150 mM NaCl, 15 mM $Na_3$ citrate•2 $H_2O$, pH 7.0), 0.2% SDS at about 42° C., followed by washing in 1×SSPE (or saline sodium citrate, SSC) and 0.1% SDS at a temperature of at least about 42° C., preferably about 55° C., more preferably about 65° C.

"Moderate stringency" refers, by non-limiting example, to conditions that permit hybridization in 50% formamide, 5×Denhardt's solution, 5×SSPE (or SSC), 0.2% SDS at 42° C. (to about 50° C.), followed by washing in 0.2×SSPE (or SSC) and 0.2% SDS at a temperature of at least about 42° C., preferably about 55° C., more preferably about 65° C.

"Low stringency" refers, by non-limiting example, to conditions that permit hybridization in 10% formamide, 5×Denhardt's solution, 6×SSPE (or SSC), 0.2% SDS at 42° C., followed by washing in 1×SSPE (or SSC) and 0.2% SDS at a temperature of about 45° C., preferably about 50° C.

For additional stringency conditions, see T. Maniatis et al., *Molecular Cloning: A Laboratory Manual*, Cold Spring Harbor Laboratory, Cold Spring Harbor, N.Y. (1982). It is to be understood that the low, moderate, and high stringency hybridization/washing conditions can be modified using a variety of ingredients, buffers, and temperatures well known to and practiced by the skilled artisan.

The terms "complementary" or "complementarity" refer to the natural binding of polynucleotides under permissive salt and temperature conditions by base pairing. For example, the sequence "A-G-T" binds to the complementary sequence "T-C-A". Complementarity-between two single-stranded molecules can be "partial", in which only some of the nucleic acids bind, or it can be complete when total complementarity exists between single stranded molecules. The degree of complementarity between nucleic acid strands has significant effects on the efficiency and strength of hybridization between nucleic acid strands. This is of particular importance in amplification reactions, which depend upon binding between nucleic acids strands, as well as in the design and use of PNA molecules.

The term "homology" refers to a degree of complementarity. There can be partial homology or complete homology, wherein complete homology is equivalent to identity. A partially complementary sequence that at least partially inhibits an identical sequence from hybridizing to a target nucleic acid is referred to using the functional term "substantially homologous." The inhibition of hybridization of the completely complementary sequence to the target sequence can be examined using a hybridization assay (e.g., Southern or Northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. Nonetheless, conditions of low stringency do not permit non-specific binding; low stringency conditions require that the binding of two sequences to one another be a specific (i.e., selective) interaction. The absence of non-specific binding can be tested by the use of a second target sequence which lacks even a partial degree of complementarity (e.g., less than about 30% identity). In the absence of non-specific binding, the probe will not hybridize to the second non-complementary target sequence.

Those having skill in the art will know how to determine percent identity between or among sequences using, for example, algorithms such as those based on the CLUSTALW computer program (J. D. Thompson et al., 1994, *Nucleic Acids Research*, 2(22):4673–4680), or FASTDB (Brutlag et al., 1990, *Comp. App. Biosci.*, 6:237–245), as known in the art. Although the FASTDB algorithm typically does not consider internal non-matching deletions or additions in sequences, i.e., gaps, in its calculation, this can be corrected manually to avoid an overestimation of the percent identity. CLUSTALW, however, does take sequence gaps into account in its identity calculations.

A "composition" comprising a given polynucleotide sequence refers broadly to any composition containing the given polynucleotide sequence. The composition can comprise a dry formulation or an aqueous solution. Compositions comprising polynucleotide sequence (SEQ ID NO: 1) encoding HLRRNS-2 polypeptide (SEQ ID NO: 2), or fragments thereof, can be employed as hybridization probes. Further, compositions comprising polynucleotide sequence (SEQ ID NO: 3) encoding HLRRNS-3 polypeptide (SEQ ID NO: 4), or fragments thereof, can be employed as hybridization probes. The probes can be stored in freeze-dried form and can be in association with a stabilizing agent such as a carbohydrate. In hybridizations, the probe can be employed in an aqueous solution containing salts (e.g., NaCl), detergents or surfactants (e.g., SDS) and other components (e.g., Denhardt's solution, dry milk, salmon sperm DNA, and the like).

The term "substantially purified" refers to nucleic acid sequences or amino acid sequences that are removed from their natural environment, isolated, or separated, and are at least 60% free, preferably 75% to 85% free, and most preferably 90% or greater free from other components with which they are naturally associated.

The term "sample," or "biological sample," is meant to be interpreted in its broadest sense. A biological sample suspected of containing nucleic acid encoding HLRRNS-2 and/or HLRRNS-3 protein, or fragments thereof, or HLRRNS-2 and/or HLRRNS-3 protein itself, can comprise a body fluid, an extract from cells or tissue, chromosomes isolated from a cell (e.g., a spread of metaphase chromosomes), organelle, or membrane isolated from a cell, a cell, nucleic acid such as genomic DNA (in solution or bound to a solid support such as for Southern analysis), RNA (in solution or bound to a solid support such as for Northern analysis), cDNA (in solution or bound to a solid support), a tissue, a tissue print and the like.

"Transformation" refers to a process by which exogenous DNA enters and changes a recipient cell. It can occur under natural or artificial conditions using various methods well known in the art. Transformation can rely on any known method for the insertion of foreign nucleic acid sequences into a prokaryotic or eukaryotic host cell. The method is selected based on the type of host cell being transformed and can include, but is not limited to, viral infection, electroporation, heat shock, lipofection, and partial bombardment. Such "transformed" cells include stably transformed cells in which the inserted DNA is capable of replication either as an autonomously replicating plasmid or as part of the host chromosome. Transformed cells also include those cells, which transiently express the inserted DNA or RNA for limited periods of time.

The term "mimetic" refers to a molecule, the structure of which is developed from knowledge of the structure of HLRRNS-2 and/or HLRRNS-3 protein, or portions thereof, and as such, is able to effect some or all of the actions of HLRRNS-2 and/or HLRRNS-3 protein.

The term "portion" with regard to a protein (as in "a portion of a given protein") refers to fragments, segments, or peptides of that protein. The fragments can range in size from four or five amino acid residues to the entire amino acid sequence minus one amino acid. Thus, for example, a protein "comprising at least a portion of the amino acid sequence of SEQ ID NO: 2" can encompass the full-length human HLRRNS-2 polypeptide, and fragments thereof.

The term "antibody" refers to intact molecules, as well as, fragments thereof, such as Fab, F(ab')$_2$, Fv, or Fc, which are capable of binding an epitopic or antigenic determinant. Antibodies that bind to HLRRNS-2 and/or HLRRNS-3 polypeptides can be prepared using intact polypeptides or fragments containing small peptides of interest, or prepared recombinantly for use as the immunizing antigen. The polypeptide or oligopeptide used to immunize an animal can be derived from the transition of RNA or synthesized chemically, and can be conjugated to a carrier protein, if desired. Commonly used carriers that are chemically coupled to peptides include, but are not limited to, bovine serum albumin (BSA), keyhole limpet hemocyanin (KLH), and thyroglobulin. The coupled peptide is then used to immunize the animal (e.g., a mouse, a rat, or a rabbit).

The term "humanized" antibody refers to antibody molecules in which amino acids have been replaced in the non-antigen binding regions in order to more closely resemble a human antibody, while still retaining the original binding capability, e.g., as described in U.S. Pat. No. 5,585,089 to C. L. Queen, et al.

The term "antigenic determinant" refers to that portion of a molecule that makes contact with a particular antibody (i.e., an epitope). When a protein or fragment of a protein is used to immunize a host animal, numerous regions of the protein can induce the production of antibodies which bind specifically to a given region or three-dimensional structure on the protein; these regions or structures are referred to as antigenic determinants. An antigenic determinant can compete with the intact antigen (i.e., the immunogen used to elicit the immune response) for binding to an antibody.

An "agonist" refers to a molecule which, when bound to the HLRRNS-2 or HLRRNS-3 polypeptide, or a functional fragment thereof, increases or prolongs the duration of the effect of the HLRRNS-2 or HLRRNS-3 polypeptide, respectively. Agonists can include proteins, nucleic acids, carbohydrates, or any other molecules that bind to and modulate the effect of HLRRNS-2 or HLRRNS-3 polypeptide. An antagonist refers to a molecule which, when bound to the HLRRNS-2 or HLRRNS-3 polypeptide, or a functional fragment thereof, decreases or inhibits the amount or duration of the biological or immunological activity of HLRRNS-2 or HLRRNS-3 polypeptide, respectively. "Antagonists" can include proteins, nucleic acids, carbohydrates, antibodies, or any other molecules that decrease or reduce the effect of HLRRNS-2 or HLRRNS-3 polypeptide.

Similarly, the present invention to provide modulators of the HLRRNS-2 or HLRRNS-3 protein and HLRRNS-2 or HLRRNS-3 peptide targets which can affect the function or activity of HLRRNS-2 or HLRRNS-3 in a cell in which HLRRNS-2 or HLRRNS-3 function or activity is to be modulated or affected. In addition, modulators of HLRRNS-2 or HLRRNS-3 can affect downstream systems and molecules that are regulated by, or which interact with, HLRRNS-2 or HLRRNS-3 in the cell. Modulators of HLRRNS-2 or HLRRNS-3 include compounds, materials, agents, drugs, and the like, that antagonize, inhibit, reduce, block, suppress, diminish, decrease, or eliminate HLRRNS-2 or HLRRNS-3 function and/or activity. Such compounds, materials, agents, drugs and the like can be collectively termed "antagonists". Alternatively, modulators of HLRRNS-2 or HLRRNS-3 include compounds, materials, agents, drugs, and the like, that agonize, enhance, increase, augment, or amplify HLRRNS-2 or HLRRNS-3 function in a cell. Such compounds, materials, agents, drugs and the like can be collectively termed "agonists".

As used herein the terms "modulate" or "modulates" refer to an increase or decrease in the amount, quality or effect of a particular activity, DNA, RNA, or protein. The definition of "modulate" or "modulates" as used herein is meant to encompass agonists and/or antagonists of a particular activity, DNA, RNA, or protein.

The terms "specific binding" or "specifically binding" refer to the interaction between a protein or peptide and a binding molecule, such as an agonist, an antagonist, or an antibody. The interaction is dependent upon the presence of a particular structure (e.g., an antigenic determinant, epitope, or secondary or tertiary conformation) of the protein that is recognized by the binding molecule. For example, if an antibody is specific for epitope "A," the presence of a protein containing epitope A (or free, unlabeled A) in a reaction containing labeled "A" and the antibody will reduce the amount of labeled A bound to the antibody.

The term "correlates with expression of a polynucleotide" indicates that the detection of the presence of ribonucleic acid that is similar to SEQ ID NO: 1 by Northern analysis is indicative of the presence of mRNA encoding HLRRNS-2 polypeptide (SEQ ID NO: 2) in a sample and thereby correlates with expression of the transcript from the polynucleotide encoding the protein. Another embodiment relates to the detection of the presence of ribonucleic acid that is similar to SEQ ID NO: 3 by Northern analysis which is indicative of the presence of mRNA encoding HLRRNS-3 polypeptide (SEQ ID NO: 4).

An alteration in the polynucleotide of SEQ ID NO: 1 or SEQ ID NO: 3 comprises any alteration in the sequence of the polynucleotides encoding the HLRRNS-2 polypeptide or the HLRRNS-3 polypeptide, including deletions, insertions, and point mutations that can preferably be detected using hybridization assays. Included within this definition is the detection of alterations to the genomic DNA sequence which encodes the HLRRNS-2 or the HLRRNS-3 polypeptide (e.g., by alterations in the pattern of restriction fragment length polymorphisms capable of hybridizing to SEQ ID NO: 1 or SEQ ID NO: 3, respectively), the inability of a selected fragment of SEQ ID NO: 1 or SEQ ID NO: 3, respectively, to hybridize to a sample of genomic DNA (e.g., using allele-specific oligonucleotide probes), and improper or unexpected hybridization, such as hybridization to a locus other than the normal chromosomal locus for the polynucleotide sequence encoding the HLRRNS-2 or HLRRNS-3 polypeptide (e.g., using fluorescent in situ hybridization (FISH) to metaphase chromosome spreads).

DETAILED DESCRIPTION OF THE INVENTION

The present invention is based on the discovery of newly isolated human molecules, referred to herein as leucine-rich repeat (LRR) proteins and their encoding nucleic acid molecules, which comprise a family of molecules having certain conserved structural and functional features.

In particular, one embodiment of the present invention provides new human LRR protein family members, HLRRNS-2 and HLRRNS-3. Based on sequence homology and sequence predictions, the HLRRNS-2 and HLRRNS-3 proteins are newly isolated human LRRs. These particular LRRs are expressed highly in neuronal cells, such as brain.

HLRRNS-2 (SEQ ID NO: 2) encodes a 590 amino acid protein containing 9 LRR domains, including 1 LRR C-terminal domain, and 1 LRR N-terminal domain (FIG. 2). The protein has a predicted signal peptide at its amino terminal end (see FIG. 11; SEQ ID NO: 29) and one putative transmembrane domain located between amino acids 425 and 444. HLRRNS-2 shows substantial homology and similarity to a variety of other proteins having roles in neuronal guidance, cell adhesion, and inflammation and immune regulation. Transcripts for HLRRNS-2 are found in approximately 2250 fold greater amounts in the brain relative to other tissues examined (FIG. 14). The pituitary gland and the spinal cord also show appreciable levels of HLRRNS-2 transcripts. Within the brain, HLRRNS-2 is most highly expressed in the amygdala (3–9 fold greater) versus other brain subregions tested. HLRRNS-2 can be an important regulator of developmental processes, apoptosis, inflammation, and immune responses in the human nervous system. Over- and under-expression of this protein can contribute to the onset of dementia and neural degenerative processes, such as, but not limited to, Alzheimer's and Parkinson's disease. It can also contribute in the development of various affective disorders, such as, but not limited to, depression and schizophrenia, as well as various anxiety, fear, and learning disorders.

Figure 15:
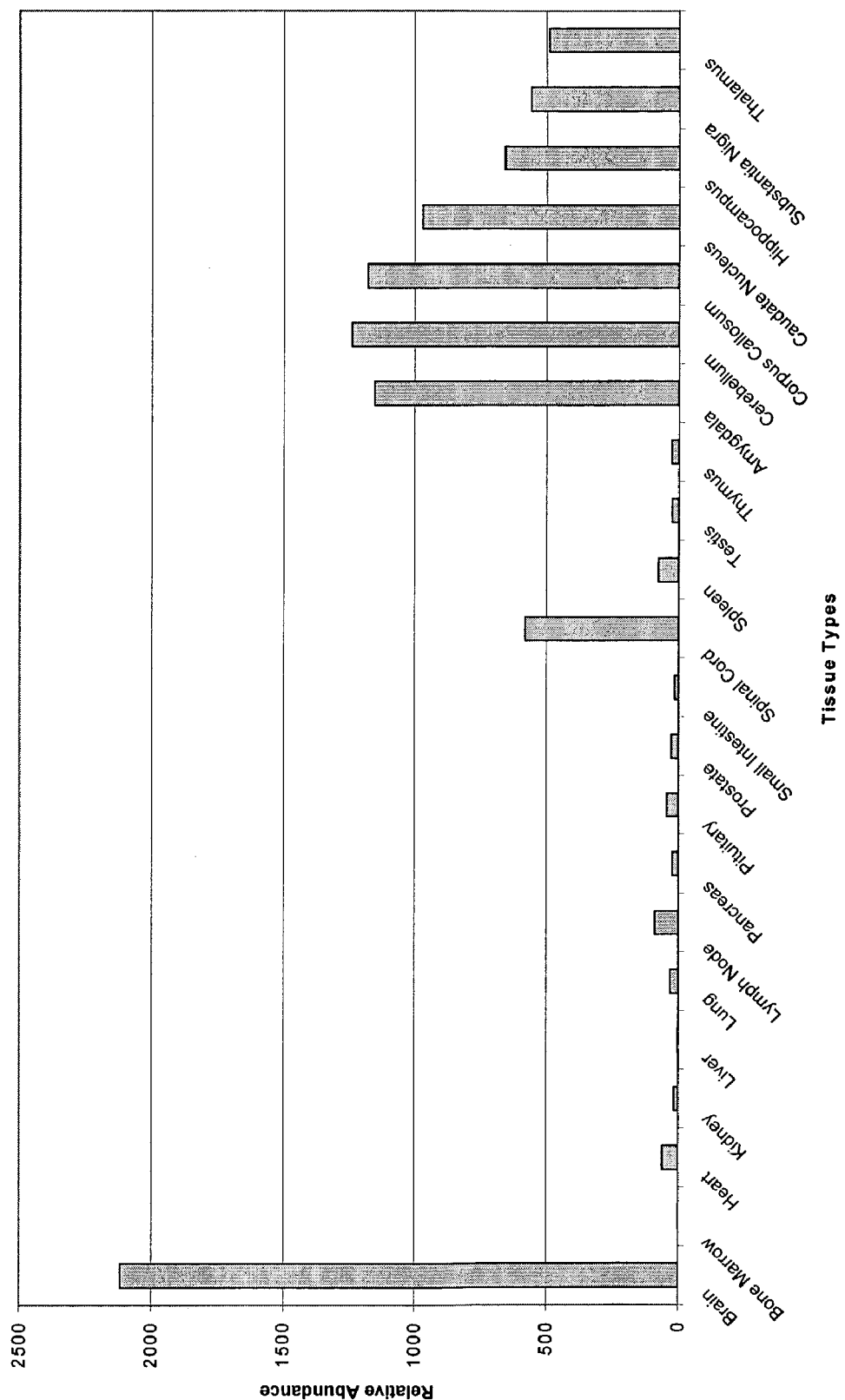
FIG. 15 shows expression profiling of the novel human LRR-containing protein, HLRRNS-3, as described in Example 4.

HLRRNS-3 (SEQ ID NO: 4) encodes an 845 amino acid protein containing 10 LRR domains, 2 LRR C-terminal domains, and 2 LRR N-terminal domains (FIG. 4). The protein also contains one putative transmembrane region located between amino acids 621 and 639. HLRRNS-3 shows substantial homology and similarity to a variety of other proteins having roles in inflammation and immune regulation. Transcripts for HLRRNS-3 are found in approximately 2000 fold greater amounts in the brain relative to other tissues examined (FIG. 15). Within the brain, HLRRNS-3 transcripts are widely expressed. HLRRNS-3 is also found in sufficient amounts in the spinal cord. Based on the expression pattern, HLRRNS-3 can be an important regulator of developmental processes, apoptosis, inflammation and immune responses in the human nervous system. Similar to HLRRNS-2, over- and under-expression of HLRRNS-3 can contribute to the onset of dementia and neural degenerative processes such as Alzheimer's and Parkinson's disease. It can also have a contributory role in the development of various affective disorders such as depression and schizophrenia.

The LRR polypeptides and polynucleotides of the invention are useful for diagnosing diseases related to over- and under-expression of LRR proteins by identifying mutations in the LRR gene using LRR probes, or by determining LRR protein or mRNA expression levels. In particular, the LRR polypeptides of the invention, HLRRNS-2 and HLRRNS-3, are also useful for screening compounds that affect the activity or function of the protein. The invention encompasses the polynucleotides, i.e. SEQ ID NOs: 1 and 3, encoding the LRR polypeptides SEQ ID NOs: 2 and 4, respectively, of this invention, and the use of the LRR polynucleotides or polypeptides, or compositions thereof, in the screening, diagnosis, treatment, or prevention of disorders associated with aberrant or uncontrolled cellular growth and/or function, such as neoplastic diseases (e.g., cancers and tumors), with particular regard to neurological diseases or disorders, i.e. those related to the brain.

In one embodiment, the invention relates to a method for predicting the likelihood that an individual will have a disorder associated with the reference allele at a given nucleotide position of interest of SEQ ID NO: 1 or SEQ ID NO: 3. The presence of the variant allele at this position can indicate that the individual has a greater likelihood of having a disorder associated therewith than an individual having the reference allele at that position, or a greater likelihood of having more severe symptoms.

Yet another embodiment relates to a method for predicting the likelihood (or diagnosing or aiding in the diagnosis of such a disorder) that an individual will have a disorder associated with the variant allele at a given nucleotide position of SEQ ID NO: 1 or SEQ ID NO: 3 comprising, obtaining a DNA sample from an individual to be assessed and determining the nucleotide present at particular positions of SEQ ID NO: 1 or SEQ ID NO: 3. The presence of the variant allele at this position indicates that the individual has a greater likelihood of having a disorder associated with the variant allele, than an individual having the reference allele at that position, or a greater likelihood of having more severe symptoms.

In a further embodiment, the present invention encompasses a polypeptide comprising the amino acid sequence of SEQ ID NO: 2 as shown in FIG. 2. The HLRRNS-2 polypeptide is 590 amino acids in length and shares amino acid sequence homology with the the human 7TM clone HDTIE58 protein fragment #1 (Acc. No.: AAB45703). Multiple sequence alignment of HLRRNS-2 is shown in FIGS. 7A–7F. The HLRRNS-2 polypeptide (SEQ ID NO: 2) shares 27% identity and 34.46% similarity with the AAB45703 sequence (Ace. No.:AAB45703; SEQ ID NO: 5), wherein "similar" amino acids are those which have the same/similar physical properties and in many cases, the function is conserved with similar residues. For example, amino acids Lysine and Arginine are similar, while residues such as Proline and Cysteine, which do not share any physical properties, are considered dissimilar. The HLRRNS-2 polypeptide also shares 27.21% identity and 34.71% similarity with the mature human TANGO 325 protein (AAB61227; Acc. No.:AAB61227; SEQ ID NO: 6); 27.5% identity and 35.23% similarity with the human TANGO 325 extracellular domain (AAB61228; Acc. No.:AAB61228; SEQ ID NO: 7); 27% identity and 34.46% similarity with the human neuronal guidance molecule (NGM)-like protein #1 (AAE06789; Acc. No.: AAE06789; SEQ ID NO:8); 26.9% identity and 34.32% similarity with the mature human neuronal guidance molecule (NGM)-like protein #1 (AAE06798; Acc. No.: AAE06798; SEQ ID NO:9); 46.69% identity and 57.2% similarity with the membrane-bound protein PRO1309 (AAY66713; Acc. No.: AAY66713; SEQ ID NO: 10); 44.14% identity and 53.71% similarity with the human KIAA0416 (O43300; Acc. No.: O43300; SEQ ID NO:11); 61.74% identity and 68.7% similarity with the *Macaca fascicularis* hypothetical 65.9kDa protein (Q9BGP6; Acc. No.:Q9BGP6; SEQ ID NO: 12); 49.6% identity and 59.1% similarity with the Mus musculus 4632401D06RIK protein (Q9D686; Acc. No.: Q9D686; SEQ ID NO: 13); 25.66% identity and 33.85% similarity with the Mus musculus 1300018K11RIK protein (Q9DBB9; Acc. No.: Q9DBB9; SEQ ID NO: 14); 99.52% identity and 99.52% similarity with the human cDNA FLJ12568 FIS clone NT2RM4000857, weakly similar to leucine-rich alpha-2-glycoprotein (Q9H9T0; Acc. No.: Q9H9T0; SEQ ID NO: 15); and 26.48% identity and 33.68% similarity with the human DJ756G23.1 novel leucine rich protein fragment (Q9UGS3; Acc. No.:Q9UGS3; SEQ ID NO: 16).

Based upon the observed homology, the HLRNNS-2 polypeptide of the present invention is expected to share at least some biological activity with the aforementioned polypeptides, and possibly with other leucine-rich repeat polypeptides known in the art or described herein.

In yet another embodiment, the present invention encompasses a polypeptide comprising the amino acid sequence of SEQ ID NO: 4 as shown in FIG. 4. The HLRRNS-3 polypeptide is 845 amino acids in length and shares amino acid sequence homology with the the human PRO266 protein (AAB50905; Acc. No.:AAB50905; SEQ ID NO: 17). Multiple sequence alignment of HLRRNS-3 is shown in FIGS. 8A–8D. The HLRRNS-3 polypeptide (SEQ ID NO: 2) shares 43% identity and 50.88% similarity with the AAB50905 sequence. The HLRRNS-3 polypeptide shares 99.83% identity and 99.83% similarity with the human gene 1 encoded secreted protein fragment (AAE01312; Acc. No.: AAE01312; SEQ ID NO: 18); 41.61% identity and 49.34% similarity with the human secreted protein clone nf56_3 protein sequence (AAY94963; Acc. No.: AAY94963; SEQ ID NO: 19); 48.17% identity and 59.13% similarity with the human cDNA FLJ22774 FIS, KAIA1575 clone (Q9H5Y7; Acc. No.: Q9H5Y7; SEQ ID NO: 20); 30.22% identity and 37.52% similarity with the human DJ756G23.1 novel leucine rich protine fragment (Q9UGS3; Acc. No.:Q9UGS3; SEQ ID NO: 16); 44.66% identity and 54.26% similarity with the human hypothetical protein KIAA0848 (Y848_HUMAN; Acc. No.: O94933; SEQ ID NO: 21); and 53.92% identity and 61.64% similarity with the human hypothetical protein KIAA0918 fragment (Y918_HUMAN; Acc. No.: O94991; SEQ ID NO: 22).

Based upon the observed homology, the HLRNNS-3 polypeptide of the present invention is expected to share at least some biological activity with the aforementioned polypeptides, and possibly with other leucine-rich repeat polypeptides known in the art or described herein.

Variants of the LRR polypeptides of the invention are also encompassed by the present invention. An HLRRNS-2 and/or HLRRNS-3 variant has at least about 75% to about 80%, preferably at least about 85% to about 90%, and more preferably at least about 90% to about 95%, and most preferably about 98–100%, amino acid sequence identity to the amino acid sequence claimed herein, and which retains at least one biological, immunological, or other functional characteristic or activity of the HLRRNS-2 or HLRRNS-3 polypeptide. Preferred is an HLRRNS-2 or HLRRNS-3 variant having at least about 95% amino acid sequence identity to that of SEQ ID NO: 2 or SEQ ID NO: 4, respectively. For example, FIGS. 7A–7F and 8A–8D show multiple sequence alignments of HLRRNS-2 and HLRRNS-3, respectively. Highlighted are the differences in sequence.

Polynucleotide and polypeptide polymorphisms are also contemplated by the invention. Polymorphisms of the invention are useful as genetic markers for any study that attempts to look for a linkage between HLRRNS-2 or HLRRNS-3 and a disease or disease state related to one of these two polypeptides. In one embodiment, the following polynucleotides containing single nucleotide polymorphisms (SNPs) related to HLRRNS-2 and/or HLRRNS-3 are encompassed by the present invention.

The present invention further relates to isolated proteins or polypeptides comprising, or alternatively, consisting of all or a portion of the encoded variant amino acid sequence of the HLRRNS-2 or HLRRNS-3 polypeptides (e.g., wherein the reference or wildtype HLRRNS-2 polypeptide is exemplified by SEQ ID NO: 2; and the reference of wildtype HLRRNS-3 polypeptide is exemplified by SEQ ID NO: 4). Preferred portions are at least about 10, preferably at least about 20, more preferably at least about 40, even more preferably at least about 50–100, contiguous polypeptides and comprise any one of the amino acid variant alleles of the HLRRNS-2 or HLRRNS-3 polypeptides, or a portion of SEQ ID NO: 2 or SEQ ID NO: 4, respectively. The invention further relates to isolated nucleic acid molecules encoding such polypeptides or proteins, as well as to antibodies that bind to such proteins or polypeptides.

The present invention relates to isolated nucleic acid molecules comprising, or alternatively, consisting of all or a portion of the variant allele of the HLRRNS-2 or the HLRRNS-3 gene (e.g., where HLRRNS-2 gene is exemplified by SEQ ID NO: 1, and the the reference or wildtype HLRRNS-3 gene is exemplified by SEQ ID NO: 3). Portions are at least about 10, preferably at least about 20, more preferably at least 40, and even more preferably at least about 50–100 contiguous polynucleotides comprising any one of the HLRRNS-2 or HRRNS-3 gene or alleles described herein and exemplified in FIGS. 1 and 3.

In another embodiment, the present invention encompasses polynucleotides which encode the HLRRNS-2 or HLRRNS-3 polypeptide. Accordingly, a nucleic acid sequence, which encodes the amino acid sequence of the HLRRNS-2 or the HLRRNS-3 polypeptide, can be used to produce recombinant molecules that express HLRRNS-2 or HLRRNS-3 protein, respectively. In a particular embodiment, the present invention encompasses the HLRRNS-2 polynucleotide comprising the nucleic acid sequence of SEQ ID NO: 1 as shown in FIG. 1, and the HLRRNS-3 polynucleotide comprising the nucleic acid sequence of SEQ ID NO: 3 (FIG. 3). In particular, the present invention provides the HLRRNS-2 cDNA clone and HLRRNS-3 clone, and their nucleotide sequences, wherein HLRRNS-3 was deposited at the American Type Culture Collection (ATCC), 10801 University Boulevard, Manassas, Va. 20110-2209 on Dec. 22, 2001 under ATCC Accession PTA-3949, according to the terms of the Budapest Treaty.

As will be appreciated by the skilled practitioner in the art, the degeneracy of the genetic code results in the production of a number of nucleotide sequences encoding HLRRNS-2 or the HLRRNS-3 polypeptides. Accordingly, the present invention contemplates each and every possible variation of nucleotide sequence that could be made by selecting combinations based on possible codon choices. These combinations are made in accordance with the standard triplet genetic code as applied to the nucleotide sequences of naturally occurring HLRRNS-2 and HLRRNS-3, and all such variations are to be considered as being specifically disclosed.

In another embodiment of the present invention, polynucleotide sequences or portions thereof which encode the novel LRR polypeptides or peptides can comprise recombinant DNA molecules to direct the expression of LRR polypeptide products, peptide fragments, or functional equivalents thereof, in appropriate host cells. Because of the inherent degeneracy of the genetic code, other DNA sequences, which encode substantially the same or a functionally equivalent amino acid sequence, can be produced and these sequences can be used to clone and express the LRR proteins as described.

Although nucleotide sequences which encode the HLRRNS-2 and the HLRRNS-3 polypeptides and their variants are preferably capable of hybridizing to the nucleotide sequences of the naturally occurring HLRRNS-2 and HLRRNS-3 polypeptides under appropriately selected conditions of stringency, it can be advantageous to produce nucleotide sequences encoding the HLRRNS-2 and the HLRRNS-3 polypeptides, or their derivatives, which possess a substantially different codon usage. Codons can be selected to increase the rate at which expression of the peptide or polypeptide occurs in a particular prokaryotic or eukaryotic host in accordance with the frequency with which particular codons are utilized by the host. Other reasons for substantially altering the nucleotide sequences encoding the HLRRNS-2 and the HLRRNS-3 polypeptides, and their derivatives, without altering the encoded amino acid sequences, include the production of RNA transcripts having more desirable properties, such as a greater half-life, than transcripts produced from the naturally occurring sequence.

The present invention also encompasses the production of DNA sequences, or portions thereof, which encode the HLRRNS-2 and the HLRRNS-3 polypeptides, fragments, and their derivatives, entirely by synthetic chemistry. After production, the synthetic sequences can be inserted into any of the many available expression vectors and cell systems using reagents that are well known and commonly practiced by those in the art. Moreover, synthetic chemistry and other known techniques can be used to introduce mutations into a sequence encoding an HLRRNS-2 or an HLRRNS-3 polypeptide, or any fragment thereof.

The HLRRNS-2 and HLRRNS-3 nucleotide sequences of the present invention can be engineered using methods generally known in the art in order to alter the HLRRNS-2 or the HLRRNS-3 polypeptide-encoding sequences for a variety of reasons, including, but not limited to, alterations which modify the cloning, processing, and/or expression of the gene product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, or introduce mutations, and the like.

To express a biologically active HLRRNS-2 or HLRRNS-3 polypeptide or peptide, the nucleotide sequence encoding the HLRRNS-2 and that encoding the HLRRNS-3 polypeptide, or functional equivalents, can be inserted into an appropriate expression vector, i.e., a vector, which contains the necessary elements for the transcription and translation of the inserted coding sequence.

In an embodiment of the present invention, a gene delivery vector containing an HLRRNS-2 or HLRRNS-3 polynucleotide, or functional fragment thereof is provided. Preferably, in one embodiment, a gene delivery vector contains the isolated and purified HLRRNS-2 polynucleotide encoding the respective human LRR, or functional fragment thereof, comprising an isolated and purified polynucleotide encoding the HLRRNS-2 having the nucleic acid sequence as set forth in SEQ ID NO: 1 and encoding the amino acid sequence of SEQ ID NO: 3. In another embodiment, the vector contains the isolated and purified HLRRNS-3 polynucleotide encoding the respective human LRR, or functional fragment thereof, comprising an isolated and purified polynucleotide encoding the HLRRNS-3 having the nucleic acid and amino acid sequences of HLRRNS-3 as set forth in SEQ ID NOs: 2 and 4, respectively. Alternatively, an expression vector can contain the complement of the aforementioned LRR nucleic acid sequences.

Expression vectors derived from retroviruses, adenovirus, herpes or vaccinia viruses, or from various bacterial plasmids can be used for the delivery of nucleotide sequences to a target organ, tissue or cell population. Methods, which are well known to those skilled in the art, can be used to construct expression vectors containing sequences encoding one or more of the LRR polypeptides along with appropriate transcriptional and translational control elements. These methods include in vitro recombinant DNA techniques, synthetic techniques, and in vivo genetic recombination. Such techniques are described in J. Sambrook et al., 1989, *Molecular Cloning: A Laboratory Manual*, Cold Spring Harbor Press, Plainview, N.Y. and in F. M. Ausubel et al., 1989, *Current Protocols in Molecular Biology*, John Wiley & Sons, New York, N.Y.

A variety of expression vectors or host systems can be utilized to contain and express sequences encoding the LRR polypeptides or peptides. Such expression vectors or host systems include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) and tobacco mosaic virus (TMV)), or with bacterial expression vectors (e.g., Ti or pBR322 plasmids); or animal cell systems, including mammalian cell systems. The host cell employed is not limiting to the present invention. Preferably, the host cell of the invention contains an expression vector comprising an isolated and purified polynucleotide having a nucleic acid sequence selected from any one of SEQ ID NOs: 1 and 3, and encoding the human LRR of this invention, or a functional fragment thereof, comprising the amino acid sequence as set forth in any one of SEQ ID NOs: 2 and 4.

Bacterial artificial chromosomes (BACs) can be used to deliver larger fragments of DNA that can be contained and expressed in a plasmid vector. BACs are vectors used to clone DNA sequences of about 100–300 kb, on average 150 kb, in size in *E. coli* cells. BACs are constructed and delivered via conventional delivery methods (e.g., liposomes, polycationic amino polymers, or vesicles) for therapeutic purposes.

Additionally, human artificial chromosomes (HACs) are also used to deliver larger fragments of DNA that can be contained and expressed in a plasmid vector. HACs are linear microchromosomes which can contain DNA sequences of 10K to 10M in size, and contain all of the elements that are required for stable mitotic chromosome segregation and maintenance (see, J. J. Harrington et al., 1997, *Nature Genet.*, 15:345–355). HACs of 6 to 10M are constructed and delivered via conventional delivery methods (e.g., liposomes, polycationic amino polymers, or vesicles) for therapeutic purposes.

"Control elements" or "regulatory sequences" are those non-translated regions of the vector, e.g., enhancers, promoters, 5' and 3' untranslated regions, which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters, such as the hybrid lacZ promoter of the BLUESCRIPT phagemid (Stratagene; La Jolla, Calif.) or PSPORT1 plasmid (Life Technologies; Rockville, Md.), and the like, can be used. The baculovirus polyhedrin promoter can be used in insect cells. Promoters or enhancers derived from the genomes of plant cells (e.g., heat shock, RUBISCO; and storage protein genes), or from plant viruses (e.g., viral promoters or leader sequences), can be cloned into the vector. In mammalian cell systems, promoters from mammalian genes or from mammalian viruses are preferred. If it is necessary to generate a cell line that contains multiple copies of the sequence encoding HLRRNS-2 or HLRRNS-3, vectors based on SV40 or EBV can be used with an appropriate selectable marker.

Specific initiation signals can also be used to achieve more efficient translation of sequences encoding the HLRRNS-2 or HLRRNS-3 polypeptide. Such signals include the ATG initiation codon and adjacent sequences. In cases where sequences encoding the HLRRNS-2 or HLRRNS-3 polypeptide, its initiation codon, and upstream sequences are inserted into the appropriate expression vector, no additional transcriptional or translational control signals may be needed. However, in cases where only a coding sequence, or a fragment thereof, is inserted, exogenous translational control signals, including the ATG initiation codon, should be provided. Furthermore, the initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system that is used, such as those described in the literature (D. Scharf et al., 1994, *Results Probl. Cell Differ.*, 20:125–162).

In bacterial systems, a number of expression vectors can be selected, depending upon the use intended for the expressed LRR product. For example, when large quantities of expressed protein are needed for the generation of antibodies, vectors that direct high level expression of fusion proteins that can be readily purified are used. Such vectors include, but are not limited to, the multifunctional *E. coli* cloning and expression vectors such as BLUESCRIPT (Stratagene), in which the sequence encoding the LRR polypeptide can be ligated into the vector in-frame with sequences for the amino-terminal Met and the subsequent 7 residues of β-galactosidase, so that a hybrid protein is produced; pIN vectors (see, G. Van Heeke and S. M. Schuster, 1989, *J. Biol. Chem.*, 264:5503–5509); and the like. pGEX vectors (Promega; Madison, Wis.) can also be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. Proteins made in such systems can be designed to include heparin, thrombin, or factor XA protease cleavage sites so that the cloned polypeptide of interest can be released from the GST moiety at will.

An insect system can also be used to express an HLRRNS-2 or an HLRRNS-3 polypeptide. For example, in one such system, *Autographa californica* nuclear polyhedrosis virus (AcNPV) is used as a vector to express foreign genes in *Spodoptera frugiperda* cells or in *Trichoplusia* larvae. The sequences encoding the HLRRNS-2 or HLRRNS-3 polypeptide can be cloned into a non-essential region of the virus such as the polyhedrin gene and placed under control of the polyhedrin promoter. Successful insertion of HLRRNS-2 or HLRRNS-3-encoding polynucleotide will render the polyhedrin gene inactive and produce recombinant virus lacking coat protein. The recombinant viruses can then be used to infect, for example, *S. frugiperda* cells or *Trichoplusia* larvae in which the HLRRNS-2 or the HLRRNS-3 polypeptide product can be expressed (E. K. Engelhard et al., 1994, *Proc. Nat. Acad. Sci.*, 91:3224–3227).

In the yeast *Saccharomyces cerevisiae*, a number of vectors containing constitutive or inducible promoters such as alpha factor, alcohol oxidase, and PGH can be used. (For reviews, see F. M. Ausubel et al., supra, and Grant et al., 1987, *Methods Enzymol*, 153:516–544).

Should plant expression vectors be desired and used, the expression of sequences encoding the HLRRNS-2 or HLRRNS-3 polypeptide can be driven by any of a number of promoters. For example, viral promoters such as the 35S and 19S promoters of CaMV can be used alone or in combination with the omega leader sequence from TMV (N. Takamatsu, 1987, *EMBO J.*, 6:307–311). Alternatively, plant promoters such as the small subunit of RUBISCO, or heat shock promoters, can be used (G. Coruzzi et al., 1984, *EMBO J.*, 3:1671–1680; R. Broglie et al., 1984, *Science*, 224:838–843; and J. Winter et al., 1991, *Results Probl. Cell Differ.* 17:85–105). These constructs can be introduced into plant cells by direct DNA transformation or pathogen-mediated transfection. Such techniques are described in a number of generally available reviews (see, for example, S. Hobbs or L. E. Murry, In: *McGraw Hill Yearbook of Science and Technology* (1992) McGraw Hill, New York, N.Y.; pp. 191–196).

In mammalian host cells, a number of viral-based expression systems can be utilized. In cases where an adenovirus is used as an expression vector, sequences encoding the LRR polypeptide can be ligated into an adenovirus transcription or translation complex containing the late promoter and tripartite leader sequence. Insertion into a non-essential E1 or E3 region of the viral genome can be used to obtain a viable virus which is capable of expressing LRR polypeptide in infected host cells (J. Logan and T. Shenk, 1984, *Proc. Natl. Acad. Sci.*, 81:3655–3659). In addition, transcription enhancers, such as the Rous sarcoma virus (RSV) enhancer, can be used to increase expression in mammalian host cells. Other expression systems can also be used, such as, but not limited to, yeast, plant, and insect vectors.

Moreover, a host cell strain can be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein can also be used to facilitate correct insertion, folding and/or function. Different host cells having specific cellular machinery and characteristic mechanisms for such post-translational activities (e.g., CHO, HeLa, MDCK, HEK293, and W138) are available from the American Type Culture Collection (ATCC), 10801 University Boulevard, Manassas, Va. 20110-2209, and can be chosen to ensure the correct modification and processing of the foreign protein.

Host cells transformed with nucleotide sequences encoding the HLRRNS-2 or the HLRRNS-3 protein, or fragments thereof, can be cultured under conditions suitable for the expression and recovery of the protein from cell culture. The protein produced by a recombinant cell can be secreted or contained intracellularly depending on the sequence and/or the vector used. As will be understood by those having skill in the art, expression vectors containing polynucleotides which encode the HLRRNS-2 or HLRRNS-3 protein can be designed to contain signal sequences which direct secretion of the HLRRNS-2 or HLRRNS-3 protein through a prokaryotic or eukaryotic cell membrane. Other constructions can be used to join nucleic acid sequences encoding the HLRRNS-2 or HLRRNS-3 protein to nucleotide sequences encoding a polypeptide domain, which will facilitate purification of soluble proteins. Such purification facilitating domains include, but are not limited to, metal chelating peptides such as histidine-tryptophan modules that allow purification on immobilized metals; protein A domains that allow purification on immobilized immunoglobulin; and the domain utilized in the FLAGS extension/affinity purification system (Immunex Corp.; Seattle, Wash.).

The inclusion of cleavable linker sequences such as those specific for Factor XA or enterokinase (Invitrogen; San Diego, Calif.) between the purification domain and the HLRRNS-2 or HLRRNS-3 protein can be used to facilitate purification. One such expression vector provides for expression of a fusion protein containing the HLRRNS-2 or HLRRNS-3 and a nucleic acid encoding 6 histidine residues preceding a thioredoxin or an enterokinase cleavage site. The histidine residues facilitate purification on IMAC (immobilized metal ion affinity chromatography) as described by J. Porath et al., 1992, *Prot. Exp. Purif.*, 3:263–281, while the enterokinase cleavage site provides a means for purifying from the fusion protein. For a discussion of suitable vectors for fusion protein production, see D. J. Kroll et al., 1993; *DNA Cell Biol.*, 12:441–453.

Alternatively, host cells which contain the nucleic acid sequence encoding the HLRRNS-2 or HLRRNS-3 polypeptide and which express the HLRRNS-2 or HLRRNS-3 polypeptide product, can be identified by a variety of procedures known to those having skill in the art. These procedures include, but are not limited to, DNA-DNA or DNA-RNA hybridizations and protein bioassay or immunoassay techniques, including membrane, solution, or chip based technologies, for the detection and/or quantification of nucleic acid or protein.

Any number of selection systems can be used to recover transformed cell lines. These include, but are not limited to, the Herpes Simplex Virus thymidine kinase (HSV TK), (M. Wigler et al., 1977, *Cell*, 11:223–32) and adenine phosphoribosyltransferase (I. Lowy et al., 1980, *Cell*, 22:817–23) genes which can be employed in tk⁻ or aprt⁻ cells, respectively. Also, anti-metabolite, antibiotic or herbicide resistance can be used as the basis for selection; for example, dhfr, which confers resistance to methotrexate (M. Wigler et al., 1980, *Proc. Natl. Acad. Sci.*, 77:3567–70); npt, which confers resistance to the aminoglycosides neomycin and G-418 (F. Colbere-Garapin et al., 1981, *J. Mol. Biol.*, 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (S. C. Hartman and R. C. Mulligan, 1988, *Proc. Natl. Acad. Sci.*, 85:8047–51). Recently, the use of visible markers has gained popularity with such markers as the anthocyanins, β-glucuronidase and its substrate GUS, and luciferase and its substrate luciferin, which are widely used not only to identify transformants, but also to quantify the amount of transient or stable protein expression that is attributable to a specific vector system (C. A. Rhodes et al., 1995, *Methods Mol. Biol.*, 55:121–131).

Although the presence or absence of marker gene expression suggests that the gene of interest is also present, the presence and expression of the desired gene of interest may need to be confirmed. For example, if the nucleic acid sequence encoding the HLRRNS-2 or HLRRNS-3 polypeptide is inserted within a marker gene sequence, recombinant cells containing sequences encoding the HLRRNS-2 or HLRRNS-3 polypeptide can be identified by the absence of marker gene function. Alternatively, a marker gene can be placed in tandem with a sequence encoding the HLRRNS-2 or HLRRNS-3 polypeptide under the control of a single promoter. Expression of the marker gene in response to induction or selection usually indicates co-expression of the tandem gene.

A wide variety of labels and conjugation techniques are known and employed by those skilled in the art and can be used in various nucleic acid and amino acid assays. Means for producing labeled hybridization or PCR probes for detecting sequences related to polynucleotides encoding an LRR polypeptide include oligo-labeling, nick translation, end-labeling, or PCR amplification using a labeled nucleotide. Alternatively, the sequences encoding an LRR polypeptide of this invention, or any portion or fragment thereof, can be cloned into a vector for the production of a mRNA probe. Such vectors are known in the art, are commercially available, and can be used to synthesize RNA probes in vitro by addition of an appropriate RNA polymerase, such as T7, T3, or SP(6) and labeled nucleotides.

These procedures can be conducted using a variety of commercially available kits (e.g., Amersham Pharmacia Biotech (Piscataway, N.J.); Promega (Madison, Wis.); and U.S. Biochemical Corp. (Cleveland, Ohio)). Suitable reporter molecules or labels which can be used include radionuclides, enzymes, fluorescent, chemiluminescent, or chromogenic agents, as well as substrates, cofactors, inhibitors, magnetic particles, and the like.

It will also be appreciated by those skilled in the pertinent art that a longer LRR oligonucleotide probe or mixture of probes, e.g., degenerate probes, can be used to detect longer, or more complex nucleic acid sequences, for example, genomic DNA. In such cases, the probe can comprise at least about 20 to about 300 nucleotides, preferably, at least about 30 to about 100 nucleotides, and more preferably, about 50 to about 100 nucleotides.

Yet a further embodiment relates to sequences encoding the HLRRNS-2 or HLRRNS-3 polypeptide which can be synthesized in whole, or in part, using chemical methods well known in the art (see, for example, M. H. Caruthers et al., 1980, *Nucl. Acids Res. Symp. Ser.*, 215–223 and T. Horn et al., 1980, *Nucl. Acids Res. Symp. Ser.*, 225–232). Alternatively, the protein itself can be produced using chemical methods to synthesize the amino acid sequence of HLRRNS-2 or HLRRNS-3 polypeptide, or a fragment or portion thereof. For example, peptide synthesis can be performed using various solid-phase techniques (J. Merrifield, 1963, *J. Am. Chem. Soc.*, 85:2149–2154; J. Y. Roberge et al., 1995, *Science*, 269:202–204), performed using manual techniques, and automated synthesis can be achieved, for example, using the ABI 431A Peptide Synthesizer (PE Biosystems; Gaithersburg, Md.). Various fragments of the HLRRNS-2 or HLRRNS-3 polypeptide can be chemically synthesized separately and then combined using chemical methods to produce the full-length molecule.

The newly synthesized peptide can be substantially purified by preparative high performance liquid chromatography (e.g., T. Creighton, 1983, *Proteins, Structures and Molecular Principles*, W. H. Freeman and Co., New York, N.Y.), by reversed-phase high performance liquid chromatography, or other purification methods as are known in the art. The composition of the synthetic peptides can be confirmed by amino acid analysis or sequencing (e.g., the Edman degradation procedure; Creighton, supra). In addition, the amino acid sequence of the HLRRNS-2 or HLRRNS-3 polypeptide, or any portion thereof, can be altered during direct synthesis and/or combined using chemical methods with sequences from other proteins, or any part thereof, to produce a variant polypeptide.

The present invention also relates to methods of obtaining the full length sequence of the HLRRNS-2 or the HLRRNS-3 polypeptide as described herein. In one instance, the method of multiplex cloning is provided as a means of extending large numbers of bioinformatic gene predictions into full length sequences by multiplexing probes and cDNA libraries in an effort to minimize the overall effort typically required for cDNA cloning. The method relies on the conversion of plasmid-based, directionally cloned cDNA libraries into a population of pure, covalently-closed, circular, single-stranded molecules and long biotinylated DNA oligonucleotide probes designed from predicted gene sequences.

Probes and libraries are subjected to solution hybridization in a formamide buffer which can be superior to aqueous buffers typically used in other biotin/streptavidin cDNA capture methods (i.e., GeneTrapper). Hybridization is performed two times without prior knowledge of the clones represented in the libraries. After the first selection, the isolated sequences are screened with PCR primers specific for the targeted clones. The second hybridization is carried out with only those oligo probes whose gene-specific PCR assays give positive results.

The secondary hybridization serves to 'normalize' the selected library, thereby decreasing the number of screenings necessary to identify particular clones. This method is robust and sensitive. Typically, dozens of cDNAs are isolated for any one particular gene, thereby increasing the chances of obtaining a full length cDNA. The entire complexity of any cDNA library is screened in the solution hybridization process, which is advantageous for finding rare sequences. The procedure is scaleable, where 50 oligonucleotide probes per experiment can be used, although this is not to be considered a limiting number.

Using bioinformatic predicted gene sequence, the following types of PCR primers and cloning oligos can be designed: A) PCR primer pairs that reside within a single predicted exon; B) PCR primer pairs that cross putative exon/intron boundaries; and C) 80-mer antisense and sense oligos containing a biotin moiety on the 5' end. The primer pairs of the A type above are optimized on human genomic DNA; the B type primer pairs are optimized on a mixture of first strand cDNAs made with and without reverse transcriptase. Primers are optimized using mRNA derived from appropriate tissues sources, for example, brain, lung, uterus, cartilage, and testis poly A+ RNA.

The information obtained with the B type primers is used to assess those putative expressed sequences which can be experimentally observed to have reverse transcriptase-dependent expression. The primer pairs of the A type are less stringent in terms of identifying expressed sequences. However, because they amplify genomic DNA as well as cDNA, their ability to amplify genomic DNA provides for the necessary positive control for the primer pair. Negative results with the B type are subject to the caveat that the sequence(s) may not be expressed in the tissue first strand that is under examination.

The biotinylated 80-mer oligonucleotides are added en mass to pools of single strand cDNA libraries. Up to 50 probes have been successfully used on pools for 15 different libraries. After the primary selection is performed, all of the captured DNA is repaired to double strand form using the T7 primer for the commercial libraries in pCMVSPORT, and the Sp6 primer for other constructed libraries in pSPORT. The resulting DNA is electroporated into *E. coli* DH12S and plated onto 150 mm plates with nylon filters. The cells are scraped and a frozen stock is made, thereby comprising the primary selected library.

One-fifth of the library is generally converted into single-stranded form and the DNA is assayed with gene specific primer pairs (GSPs). The next round of solution hybridization capture is carried out with 80-mer oligos for only those sequences that are positive with the gene-specific primers. After the second round, the captured single-stranded DNAs are repaired with a pool of GSPs, where only the primer complementary to polarity of the single-stranded circular DNA is used (i.e., the antisense primer for pCMVSPORT and pSPORT1 and the sense primer for pSPORT2).

The resulting colonies are screened by PCR using the GSPs. Typically, greater than 80% of the clones are positive for any given GSP. The entire 96 well block of clones is subjected to "mini-prep," to prepare DNA, as known in the art, and each of the clones is sized by either PCR or restriction enzyme digestion. A selection of different sized clones for each targeted sequence is chosen for transposon-hopping and DNA sequencing.

Preferably, the libraries employed for established cDNA cloning methods used by the skilled practitioner are of high quality. High complexity and large average insert size are optimal. High Pressure Liquid Chromatography (HPLC) can be employed as a means of fractioning cDNA for the purpose of constructing libraries.

Another embodiment of the present invention provides a method of identifying full-length genes encoding the disclosed HLRRNS-2 polypeptide or the HLRRNS-3 polypeptide. The LRR polynucleotides encoding the LRR polypeptides of the present invention and/or the polypeptides encoded by the deposited clone(s), preferably represent the complete coding region (i.e., full-length gene).

Several methods are known in the art for the identification of the 5' or 3' non-coding and/or coding portions of a given gene. The methods described herein are exemplary and should not be construed as limiting the scope of the invention. These methods include, but are not limited to, filter probing, clone enrichment using specific probes, and protocols similar or identical to 5' and 3' rapid amplification of cDNA ends, "RACE," protocols that are well known in the art. For instance, a method similar to 5' RACE is available for generating the missing 5' end of a desired full-length transcript (Fromont-Racine, et al. *Nucleic Acids Res.* 21(7): 1683–1684, 1993).

Briefly, in the RACE method, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product can then be sequenced and used to generate the full-length gene.

The above-described method utilizes total RNA isolated from the desired source, although poly-A+ RNA can be used. The RNA preparation is treated with phosphatase, if necessary, to eliminate 5' phosphate groups on degraded or damaged RNA that can interfere with the later RNA ligase step. The phosphatase is preferably inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

The modified RNA preparation, as described above, used as a template for first strand CDNA synthesis employs a gene specific oligonucleotide. The first strand synthesis reaction as a template for PCR amplification of the desired 5' end uses a primer specific to the ligated RNA oligonucleotide and a primer specific to the known sequence of the gene of interest, such as, for example, HLRRNS-2 or HLRRNS-3. The resultant product is then sequenced and analyzed to confirm that the 5' end sequence belongs to the desired gene. It can also be advantageous to optimize the RACE protocol to increase the probability of isolating additional 5' or 3' coding or non-coding sequences. Various methods of optimizing a RACE protocol are known in the art, for example, a detailed description summarizing these methods can be found in B. C. Schaefer, *Anal. Biochem.*, 227:255–273, 1995.

An alternative method for carrying out 5' or 3' RACE for the identification of coding or non-coding nucleic acid sequences is provided by Frohman, M. A., et al. (*Proc. Natl. Acad. Sci. USA*, 85:8998–9002, 1988). Briefly, a cDNA clone missing either the 5' or 3' end can be reconstructed to include the absent base pairs extending to the translational start or stop codon, respectively. In some cases, cDNAs are missing the start of translation for an encoded product. A brief description of a modified 5' RACE procedure is as follows. Poly A+ or total RNA is reverse transcribed with Superscript II (Gibco/BRL) and an antisense or an I complementary primer specific to any one of the cDNA sequences provided as SEQ ID NOs: 1 and 3. The primer is removed from the reaction with a Microcon Concentrator (Amicon). The first strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoIJ SaiI and ClaI) at the 5' end and a primer containing only these restriction sites. This double-stranded cDNA is PCR amplified for 40 cycles with the same primers, as well as a nested cDNA-specific antisense primer. The PCR products are size-separated on an ethidium bromide-agarose gel and the region of gel containing cDNA products having the predicted size of missing protein-coding DNA is removed.

cDNA is purified from the agarose with the Magic PCR Prep kit (Promega), restriction digested with XhoI or SalI, and ligated to a plasmid such as pBluescript SKII (Stratagene) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco/BRL for both 5' and 3' RACE for recovery of full length genes. A second kit is available from Clontech which is a modification of a related technique, called single-stranded ligation to single-stranded cDNA, (SLIC), developed by Dumas et al. (*Nucleic Acids Res.*, 19:5227–32, 1991). The major difference in the latter procedure is that the RNA is alkaline hydrolyzed after reverse transcription and RNA ligase is used to join a restriction enzyme site-containing anchor primer to the first strand cDNA. This obviates the necessity for the dA-tailing reaction which results in a polyT stretch that can impede sequencing.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

Also encompassed by the present invention are polynucleotide sequences that are capable of hybridizing to the novel LRR nucleic acid sequences, as set forth in SEQ ID NOs: 1 and 3, under various conditions of stringency. Hybridization conditions are typically based on the melting temperature ($T_m$) of the nucleic acid binding complex or probe (see, G. M. Wahl and S. L. Berger, *Methods Enzymol.* 152:399–407, 1987; and A. R. Kimmel, *Methods of Enzymol.* 152:507–511, 1987), and can be used at a defined stringency. For example, included in the present invention are sequences capable of hybridizing under moderately stringent conditions to the LRR sequences of SEQ ID NOs: 1 and 3, and other sequences which are degenerate to those which encode the novel LRR polypeptides. For example, a non-limiting example of moderate stringency conditions include prewashing solution of 2×SSC, 0.5% SDS, 1.0mM EDTA, pH 8.0, and hybridization conditions of 50° C., 5×SSC, overnight.

The nucleic acid sequence encoding the LRR proteins of the present invention can be extended by utilizing a partial nucleotide sequence and employing various methods known in the art to detect upstream sequences such as promoters and regulatory elements. For example, one method that can be employed is restriction enzyme site PCR, which utilizes universal primers to retrieve unknown sequence adjacent to a known locus (See, e.g., G. Sarkar *PCR Methods Applic.*, 2:318–322, 1993). In particular, genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR can also be used to amplify or extend sequences using divergent primers based on a known region or sequence (T. Triglia et al. *Nucleic Acids Res.*, 16:8186, 1988). The primers can be designed using OLIGO 4.06 Primer Analysis software (National Biosciences, Inc.; Plymouth, Minn.), or another appropriate program, such that the primers are 22–30 nucleotides in length, have a GC content of 50% or more, and anneal to the target sequence at temperatures about 68° C.–72° C. The method uses several restriction enzymes to generate a suitable fragment in the known region of the gene. The fragment is then circularized by intramolecular ligation and used as a PCR template.

Another method which can be used to amplify or extend sequences is capture PCR which involves PCR amplification of DNA fragments adjacent to a known sequence in human and yeast artificial chromosome (YAC) DNA (M. Lagerstrom et al. *PCR Methods Applic.*, 1:111–119, 1997). In this method, multiple restriction enzyme digestions and ligations can be used to place an engineered double-stranded sequence into an unknown portion of the DNA molecule before performing PCR. J. D. Parker et al. (*Nucleic Acids Res.*, 19:3055–3060, 1991) provide another method which can be used to retrieve unknown sequences. Bacterial artificial chromosomes (BACs) are also used for such applications. In addition, PCR, nested primers, and PROMOTER-FINDER libraries can be used to "walk" genomic DNA (Clontech; Palo Alto, Calif.). This process avoids the need to screen libraries and is useful in finding intron/exon junctions.

When screening for full length cDNAs, it is preferable to use libraries that have been size-selected to include larger cDNAs. Also, random-primed libraries are also preferable, since such libraries contain more sequences comprising the 5' regions of genes. The use of a randomly primed library can be especially preferable for situations in which an oligo d(T) library does not yield a full-length cDNA. Genomic libraries can be useful for extension of sequence into the 5' and 3' non-transcribed regulatory regions.

The embodiments of the present invention can be practiced using methods for DNA sequencing which are well known and generally available in the art. The methods can employ such enzymes as the Klenow fragment of DNA polymerase I, SEQUENASE (US Biochemical Corp.; Cleveland, Ohio), Taq polymerase (PE Biosystems; Gaithersburg, Md.), thermostable T7 polymerase (Amersham Pharmacia Biotech; Piscataway, N.J.), or combinations of recombinant polymerases and proofreading exonucleases such as the ELONGASE Amplification System marketed by Life Technologies (Gaithersburg, Md.). Preferably, the process is automated with machines such as the Hamilton Micro Lab 2200 (Hamilton; Reno, Nev.), Peltier Thermal Cycler (PTC200; MJ Research; Watertown, Mass.) and the ABI Catalyst and 373 and 377 DNA sequencers (PE Biosystems). Commercially available capillary electrophoresis systems can be used to analyze the size or confirm the nucleotide sequence of sequencing or PCR products. Capillary electrophoresis is especially preferable for the sequencing of small pieces of DNA, which might be present in limited amounts in a particular sample.

Commercially available capillary electrophoresis systems can be used to analyze the size or confirm the nucleotide sequence of sequencing or PCR products. In particular, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate software (e.g., GENOTYPER and SEQUENCE NAVIGATOR, PE Biosystems; Gaithersburg, Md.) and the entire process—from loading samples to computer analysis and electronic data display—can be computer controlled. Capillary electrophoresis is especially preferable for the sequencing of small pieces of DNA, which might be present in limited amounts in a particular sample.

The nucleotide sequences of the present invention can be engineered using methods generally known in the art in order to alter the LRR polypeptide-encoding sequences for a variety of reasons, including, but not limited to, alterations which modify the cloning, processing, and/or expression of the gene product. DNA shuffling by random fragmentation, PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, or introduce mutations, and the like.

In yet another embodiment of the present invention, a natural, modified, or recombinant nucleic acid sequence encoding either the HLRRNS-2 or the HLRRNS-3 polypeptide can be ligated to a heterologous sequence to encode a fusion (or chimeric or hybrid) protein. For example, a fusion protein can comprise any one of the amino acid sequence, or portion thereof, as set forth in SEQ ID NOs: 2 and 4, and an amino acid sequence of an Fc portion (or constant region) of a human immunoglobulin protein. The fusion protein can further comprise an amino acid sequence that differs from SEQ ID NO: 2 or 4 only by conservative substitutions. As another example, screening peptide libraries for inhibitors of LRR activity can be useful to encode a chimeric HLRRNS-2 or HLRRNS-3 protein recognizable by a commercially available antibody. A fusion protein can also be engineered to contain a cleavage site located between the HLRRNS-2 or HLRRNS-3 protein-encoding sequence and the heterologous protein sequence, so that the HLRRNS-2 or HLRRNS-3 protein can be cleaved and purified away from the heterologous moiety.

For long-term, high-yield production of recombinant proteins, stable expression is preferred. For example, cell lines which stably express the HLRRNS-2 or the HLRRNS-3 protein can be transformed using expression vectors which can contain viral origins of replication and/or endogenous expression elements and a selectable marker gene on the same, or on a separate, vector. Following the introduction of the vector, cells can be allowed to grow for 1–2 days in an enriched cell culture medium before they are switched to selective medium. The purpose of the selectable marker is to confer resistance to selection, and its presence allows the growth and recovery of cells, which successfully express the introduced sequences. Resistant clones of stably transformed cells can be proliferated using tissue culture techniques appropriate to the cell type.

Diagnostic Assays

In another embodiment of the present invention, the presence of a polynucleotide sequence encoding the HLRRNS-2 or the HLRRNS-3 polypeptide can be detected by DNA-DNA or DNA-RNA hybridization, or by amplification using probes or portions or fragments of a polynucleotide encoding the HLRRNS-2 or the HLRRNS-3 polypeptide. Nucleic acid amplification based assays involve the use of oligonucleotides or oligomers, based on the sequences encoding the HLRRNS-2 or the HLRRNS-3 polypeptide, to detect transformants containing DNA or RNA encoding the HLRRNS-2 or HLRRNS-3 polypeptide.

In yet another embodiment, an HLRRNS-2- or HLRRNS-3-encoding polynucleotide sequence can be used to purify a molecule or compound in a sample, wherein the molecule or compound specifically binds to the polynucleotide, comprising: a) combining the LRR-encoding polynucleotide, or fragment thereof, under conditions to allow specific binding; b) detecting specific binding between the LRR-encoding polynucleotide and the molecule or compound; c) recovering the bound polynucleotide; and d) separating the polynucleotide from the molecule or compound, thereby obtaining a purified molecule or compound.

This invention also relates to the use of HLRRNS-2 or HLRRNS-3 polynucleotides as diagnostic reagents. Detection of a mutated form of the HLRRNS-2 or HLRRNS-3 gene associated with a dysfunction provides a diagnostic tool that can add to or define a diagnosis of a disease or susceptibility to a disease which results from under-expression, over-expression, or altered expression of HLRRNS-2 or HLRRNS-3. Individuals carrying mutations in the HLRRNS-2 or HLRRNS-3 gene can be detected at the DNA level by a variety of techniques.

Nucleic acids for diagnosis can be obtained from a subject's cells, such as from blood, urine, saliva, tissue biopsy or autopsy material. The genomic DNA can be used directly for detection or can be amplified enzymatically by using PCR or other amplification techniques prior to analysis. RNA or cDNA can also be used in similar fashion. Deletions and insertions can be detected by a change in size of the amplified product in comparison to the normal genotype. Hybridizing amplified DNA to labeled HLRRNS-2 or HLRRNS-3 polynucleotide sequence can identify point mutations. Perfectly matched sequences can be distinguished from mismatched duplexes by RNase digestion or by differences in melting temperatures. DNA sequence differences can also be detected by alterations in electrophoretic mobility of DNA fragments in gels, with or without denaturing agents, or by direct DNA sequencing. See, e.g., Myers et al., Science (1985) 230:1242. Sequence changes at specific locations can also be revealed by nuclease protection assays, such as RNase and S1 protection or the chemical cleavage method. See Cotton et al., Proc. Natl. Acad. Sci., USA (1985) 85:43297–4401.

In another embodiment, an array of oligonucleotides probes comprising the HLRRNS-2 or HLRRNS-3 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, 274:610–613, 1996).

The diagnostic assays offer a process for diagnosing or determining, for example, a susceptibility to infections such as, for example, bacterial, fungal, and viral infections, particularly infections caused by HIV-1 or HIV-2 through detection of a mutation in the HLRRNS-2 or HLRRNS-3 gene by the methods described. The invention also provides diagnostic assays for determining or monitoring susceptibility to the following conditions, diseases, or disorders: HIV infections; asthma; allergies; obesity; anorexia; bulimia; ulcers; acute heart failure; hypotension; hypertension; angina pectoris; myocardial infarction; urinary retention; osteoporosis; benign prostatic hypertrophy; cancers; brain-related disorders; Alzheimer's Disease, Parkinson's disease; neuropathic pain; immune; metabolic; cardiovascular; and psychotic and neurological disorders, including anxiety, schizophrenia, manic depression, delirium, dementia, severe mental retardation and dyskinesias, such as Huntington's disease or Gilles dela Tourett's syndrome; Sydenham chorea; major depressive disorder; and obsessive-compulsive disorder (OCD). Movement- or kinesis-type diseases, disorders, or conditions can also be targeted. Both HLRRNS-2 and HLRRNS-3 are widely expressed throughout the brain.

Decreased or increased expression of the LRR proteins of this invention can be measured at the RNA level using any of the methods well known in the art for the quantification of polynucleotides, such as, for example, PCR, RT-PCR, RNAse protection, Northern blotting and other hybridization methods. Assay techniques that can be used to determine levels of a protein, such as an HLRRNS-2 or HLRRNS-3 protein, in a sample derived from a host are well known to those of skill in the art. Such assay methods include radioimmunoassays, competitive-binding assays, Western Blot analysis and ELISA assays.

The HLRRNS-2 or HLRRNS-3 polynucleotide, which can be used in the diagnostic assays according to the present invention, includes oligonucleotide sequences, complementary RNA and DNA molecules, and PNAs. The polynucleotides can be used to detect and quantify HLRRNS-2- or HLRRNS-3-encoding nucleic acid expression in biopsied tissues in which expression (or under- or overexpression) of the HLRRNS-2 or HLRRNS-3 the polynucleotide can be correlated to disease. The diagnostic assays can be used to distinguish between the absence, presence, and excess expression of HLRRNS-2 or HLRRNS-3, and to monitor regulation of HLRRNS-2 or HLRRNS-3 polynucleotide expression levels during therapeutic treatment or intervention.

In a related aspect, hybridization with PCR probes which are capable of detecting polynucleotide sequences, including genomic sequences, encoding the HLRRNS-2 or HLRRNS-3 polypeptide, or closely related molecules, can be used to identify nucleic acid sequences which encode the HLRRNS-2 or HLRRNS-3 polypeptide. The specificity of the probe, whether it is made from a highly specific region, e.g., about 8 to 10 contiguous nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding the HLRRNS-2 or HLRRNS-3 polypeptide, alleles, or related sequences.

Probes can also be used for the detection of related sequences, and should preferably contain at least about 50% of the nucleotides, most optimally about 15–35 nucleotides, encoding the HLRRNS-2 or HLRRNS-3 polypeptide. The hybridization probes of this invention can be DNA or RNA, and can be derived from the nucleotide sequence of SEQ ID NO: 1 or SEQ ID NO: 3, respectively, or from the genomic sequence including promoter, enhancer elements, and introns of the naturally occurring HLRRNS-2 or HLRRNS-3 protein.

Methods for producing specific hybridization probes for DNA encoding the HLRRNS-2 or HLRRNS-3 polypeptide include the cloning of a nucleic acid sequence that encodes the HLRRNS-2 or HLRRNS-3 polypeptide or derivatives thereof, into vectors for the production of mRNA probes. Such vectors are known in the art, commercially available, and can be used to synthesize RNA probes in vitro by means of the addition of the appropriate RNA polymerases and the appropriate labeled nucleotides. Hybridization probes can be labeled by a variety of detector/reporter groups, e.g., radionuclides such as $^{32}P$ or $^{35}S$, or enzymatic labels, such as alkaline phosphatase coupled to the probe via avidin/biotin coupling systems, and the like.

The polynucleotide sequences encoding the HLRRNS-2 polypeptide or that encoding the HLRRNS-3 polypeptide, or fragments thereof, can be used for the diagnosis of diseases or disorders associated with expression of HLRRNS-2 or HLRRNS-3. Examples of such disorders or conditions are described in "Therapeutic Assays". The polynucleotide sequence encoding the HLRRNS-2 or HLRRNS-3 polypeptide can be used in Southern or Northern analysis, dot blot, or other membrane-based technologies; in PCR technologies; or in dip stick, pin, ELISA or chip assays utilizing fluids or tissues from patient biopsies to detect the status of, e.g., levels or overexpression of HLRRNS-2 or HLRRNS-3, or to detect altered HLRRNS-2 or HLRRNS-3 expression. Such qualitative or quantitative methods are well known in the art.

In a particular aspect, the nucleotide sequence encoding the HLRRNS-2 or HLRRNS-3 polypeptide can be used in assays that detect activation or induction of various neoplasms or cancers, particularly those mentioned supra. The nucleotide sequence or portion thereof encoding the HLRRNS-2 or HLRRNS-3 polypeptide can be labeled by standard methods, and added to a fluid or tissue sample from a patient, under conditions suitable for the formation of hybridization complexes. After a suitable incubation period, the sample is washed and the signal is quantified and compared with a standard value. If the amount of signal in the biopsied or extracted sample is significantly altered from that of a comparable control sample, the nucleotide sequence has hybridized with nucleotide sequence present in the sample, and the presence of altered levels of nucleotide sequence encoding the HLRRNS-2 or HLRRNS-3 polypeptide in the sample indicates the presence of the associated disease. Such assays can also be used to evaluate the efficacy of a particular therapeutic treatment regimen in animal studies, in clinical trials, or in monitoring the treatment of an individual patient.

To provide a basis for the diagnosis of disease associated with the expression of the HLRRNS-2 or HLRRNS-3 protein, a normal or standard profile for expression is established. This can be accomplished by combining body fluids or cell extracts taken from normal subjects, either animal or human, with a sequence, or a fragment thereof, which encodes the HLRRNS-2 or HLRRNS-3 polypeptide, under conditions suitable for hybridization or amplification. Standard hybridization can be quantified by comparing the values obtained from normal subjects with those from an experiment where a known amount of a substantially purified polynucleotide is used. Standard values obtained from normal samples can be compared with values obtained from samples from patients who are symptomatic for disease. Deviation between standard and subject (patient) values is used to establish the presence of disease.

Once disease is established and a treatment protocol is initiated, hybridization assays can be repeated on a regular basis to evaluate whether the level of expression in the patient begins to approximate that which is observed in a normal individual. The results obtained from successive assays can be used to show the efficacy of treatment over a period ranging from several days to months.

With respect to cancer, the presence of an abnormal amount of transcript in biopsied tissue from an individual can indicate a predisposition for the development of the disease, or can provide a means for detecting the disease prior to the appearance of actual clinical symptoms. A more definitive diagnosis of this type can allow health professionals to employ preventative measures or aggressive treatment earlier, thereby preventing the development or further progression of the cancer.

Additional diagnostic uses for oligonucleotides designed from the nucleic acid sequence encoding the HLRRNS-2 or HLRRNS-3 polypeptide can involve the use of PCR. Such oligomers can be chemically synthesized, generated enzymatically, or produced from a recombinant source. Oligomers will preferably comprise two nucleotide sequences, one with sense orientation (5'→3') and another with antisense (3'→5'), employed under optimized conditions for identification of a specific gene or condition. The same two oligomers, nested sets of oligomers, or even a degenerate pool of oligomers, can be employed under less stringent conditions for detection and/or quantification of closely related DNA or RNA sequences.

Methods suitable for quantifying the expression of HLRRNS-2 or HLRRNS-3 include radiolabeling or biotinylating nucleotides, co-amplification of a control nucleic acid, and standard curves onto which the experimental results are interpolated (P. C. Melby, et al. *J. Immunol. Methods*, 159:235–244, 1993; and C. Duplaa, et al. *Anal. Biochem.*, 229–236, 1993). The speed of quantifying multiple samples can be accelerated by running the assay in an ELISA format where the oligomer of interest is presented in various dilutions and a spectrophotometric or colorimetric response gives rapid quantification.

A variety of protocols for detecting and measuring the expression of the HLRRNS-2 or HLRRNS-3 polypeptide using either polyclonal or monoclonal antibodies specific for the protein are known and practiced in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive with two non-interfering epitopes on the HLRRNS-2 or HLRRNS-3 polypeptide is preferred, but a competitive binding assay can also be employed. These and other assays are described in the art as represented by the publication of R. Hampton et al., 1990; *Serological Methods, a Laboratory Manual*, APS Press, St Paul, Minn.; and D. E. Maddox et al., 1983; *J. Exp. Med.*, 158:1211–1216).

Several assay protocols including ELISA, RIA, and FACS for measuring the HLRRNS-2 or HLRRNS-3 polypeptide are known in the art and provide a basis for diagnosing altered or abnormal expression levels of the HLRRNS-2 or HLRRNS-3 polypeptide. Normal or standard values for HLRRNS-2 or HLRRNS-3 polypeptide expression are established by combining body fluids or cell extracts taken from normal mammalian subjects, preferably human, with antibody to the HLRRNS-2 or HLRRNS-3 polypeptide under conditions suitable for complex formation. The amount of standard complex formation can be quantified by various methods; photometric means are preferred. Quantities of the HLRRNS-2 or HLRRNS-3 polypeptide expressed in a subject sample, control sample, and disease sample from biopsied tissues are compared with the standard values. Deviation between standard and subject values establishes the parameters for diagnosing disease.

In another of its aspects, the present invention relates to a diagnostic kit for detecting a disease or susceptibility to a disease, particularly brain-related disorders; Alzheimer's or Parkinson's disease; neuropathic pain; immune; metabolic; cardiovascular; and psychotic and neurological disorders, including anxiety, schizophrenia, manic depression, delirium, dementia, severe mental retardation and dyskinesias, such as Huntington's disease or Gilles dela Tourett's syndrome, which comprises:

(a) an LRR-associated polynucleotide, preferably the nucleotide sequence of SEQ ID NO: 1 or SEQ ID NO:3, or a fragment thereof; or (b) a nucleotide sequence complementary to that of (a); or (c) an LRR-associated polypeptide, preferably the polypeptide of SEQ ID NO: 2 or SEQ ID NO: 4, or a fragment thereof; or (d) an antibody to the LRR-associated polypeptide, preferably to the polypeptide of SEQ ID NO: 2 or SEQ ID NO:4, or an epitope-containing fragment thereof, or combinations thereof.

The LRR-associated polynucleotide and polypeptide are preferably HLRRNS-2 or HLRRNS-3. It will be appreciated that in any such kit, (a), (b), (c) or (d) can comprise a substantial component, and instructions are frequently included.

In another embodiment of the present invention, antibodies which specifically bind to the HLRRNS-2 or the HLRRNS-3 polypeptide can be used for the diagnosis of conditions or diseases characterized by expression (or overexpression) of the HLRRNS-2 or the HLRRNS-3 polynucleotide or polypeptide, or in assays to monitor patients being treated with the LRR polypeptide, or its agonists, antagonists, or inhibitors. The antibodies useful for diagnostic purposes can be prepared in the same manner as those described above for use in therapeutic methods. Diagnostic assays for the HLRRNS-2 or the HLRRNS-3 polypeptide include methods, which utilize the antibody and a label to detect the protein in human body fluids or extracts of cells or tissues. The antibodies can be used with or without modification, and can be labeled by joining them, either covalently or non-covalently, with a reporter molecule. A wide variety of reporter molecules, which are known in the art, can be used, several of which are described above. In particular, a method of detecting an LRR-containing protein, a homologue thereof, or an antibody-reactive fragment of an LRR-containing protein, in a sample, comprising: a) contacting the sample with an antibody specific for the polypeptide, or an antigenic fragment thereof, under conditions in which an antigen-antibody complex can form between the antibody and the polypeptide or antigenic fragment thereof in the sample; and b) detecting an antigen-antibody complex formed in step (a), wherein detection of the complex indicates the presence of an antigenic fragment thereof, in the sample.

Monoclonal antibodies to the HLRRNS-2 polypeptide or the HLRRNS-3 polypeptide, or immunogenic fragments thereof, can be prepared using any technique which provides for the production of antibody molecules by continuous cell lines in culture. These include, but are not limited to, the hybridoma technique, the human B-cell hybridoma technique, and the EBV-hybridoma technique (G. Kohler et al., 1975, *Nature*, 256:495–497; D. Kozbor et al., 1985, *J. Immunol. Methods*, 81:31–42; R. J. Cote et al., 1983, *Proc. Natl. Acad. Sci. USA*, 80:2026–2030; and S. P. Cole et al., 1984, *Mol. Cell Biol.*, 62:109–120). The production of monoclonal antibodies is well known and routinely used in the art.

In addition, techniques developed for the production of "chimeric antibodies," the splicing of mouse antibody genes to human antibody genes to obtain a molecule with appropriate antigen specificity and biological activity can be used (S. L. Morrison et al., 1984, *Proc. Natl. Acad. Sci. USA*, 81:6851–6855; M. S. Neuberger et al., 1984, *Nature*, 312: 604–608; and S. Takeda et al., 1985, *Nature*, 314:452–454). Alternatively, techniques described for the production of single chain antibodies can be adapted, using methods known in the art, to produce HLRRNS-2- or HLRRNS-3- polypeptide-specific single chain antibodies. Antibodies with related specificity, but of distinct idiotypic composition, can be generated by chain shuffling from random combinatorial immunoglobulin libraries (D. R. Burton, 1991, *Proc. Natl. Acad. Sci. USA*, 88:11120–3). Antibodies can also be produced by inducing in vivo production in the lymphocyte population or by screening recombinant immunoglobulin libraries or panels of highly specific binding reagents as disclosed in the literature (R. Orlandi et al., 1989, *Proc. Natl. Acad. Sci. USA*, 86:3833–3837 and G. Winter et al., 1991, *Nature*, 349:293–299).

Antibodies specific for the HLRRNS-2 polypeptide or the HLRRNS-3 polypeptide, or immunogenic peptide fragments thereof, can be generated using methods that have long been known and conventionally practiced in the art. Such antibodies can include, but are not limited to, polyclonal, monoclonal, chimeric, single chain, Fab fragments, and fragments produced by an Fab expression library. Neutralizing antibodies, (i.e., those which inhibit dimer formation) are especially preferred for therapeutic use. Antibody fragments, which contain specific binding sites for the HLRRNS-2 or HLRRNS-3 polypeptide, can also be generated. For example, such fragments include, but are not limited to, $F(ab')_2$ fragments which can be produced by pepsin digestion of the antibody molecule and Fab fragments which can be generated by reducing the disulfide bridges of the $F(ab')_2$ fragments. Alternatively, Fab expression libraries can be constructed to allow rapid and easy identification of monoclonal Fab fragments with the desired specificity (W. D. Huse et al., 1989, *Science*, 254:1275–1281).

Various immunoassays can be used for screening antibodies having the desired specificity. Numerous protocols for competitive binding or immunoradiometric assays using either polyclonal or monoclonal antibodies with established specificities are well known in the art. Such immunoassays typically involve measuring the formation of complexes between the HLRRNS-2 or HLRRNS-3 polypeptide and its specific antibody. A two-site, monoclonal-based immunoassay utilizing monoclonal antibodies reactive with two non-interfering HLRRNS-2 or HLRRNS-3 polypeptide epitopes is preferred, but a competitive binding assay can also be employed (Maddox, supra).

Therapeutic Assays

The HLRRNS-2 polypeptide of SEQ ID NO: 2 and the HLRRNS-3 polypeptide- of SEQ ID NO: 4 share homology with leucine-rich repeat-containing proteins. The HLRRNS-2 or the HLRRNS-3 protein can play a role in neurological disorders, and/or in cell cycle regulation, and/or in cell signaling. Additionally, the HLRRNS-2 and/or the HLRRNS-3 protein can be involved in neoplastic, cardiovascular, and immunological disorders.

One embodiment of the present invention relates to the HLRRNS-2 protein and to the HLRRNS-3 protein, antagonists, antibodies, agonists, complementary sequences, or vectors thereof of the present invention that can be administered in combination with other appropriate therapeutic agents for treating or preventing a neurological disease, disorder, or condition. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one can achieve therapeutic efficacy with lower dosages of each agent, thus reducing the potential for adverse side effects.

In a further embodiment of the present invention, an antagonist or inhibitory agent of the HLRRNS-2 or the HLRRNS-3 polypeptide can be administered to an individual to prevent or treat a neurological disorder, particularly since both HLRRNS-2 and HLRRNS-3 are highly expressed in the brain. Such disorders can include, but are not limited to, akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, Parkinson's disease, paranoid psychoses, schizophrenia, and Tourette's disorder.

Nervous system diseases, disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507–3515 (1990)); increased sprouting of neurons may be detected by methods known in the art, such as, for example, the methods set forth in Pestronk et al. (Exp. Neurol. 70:65–82 (1980)) or Brown et al. (Ann. Rev. Neurosci. 4:17–42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterrestial radiation levels by decreasing the level of internal oxidative/metabolic damage acquired during normal basal energy requirements; and/or (iii) enabling recipient to subsist at a lower metabolic temperature (i.e., cryogenic, and/or sub-cryogenic environment).

Antagonists or inhibitors of the HLRRNS-2 polypeptide of the present invention can be produced using methods which are generally known in the art. For example, an HLRRNS-2 or an HLRRNS-3 encoding polynucleotide sequence can be transfected into particular cell lines useful for the identification of agonists and antagonists of the HLRRNS-2 or the HLRRNS-3 polypeptide. Representative uses of these cell lines would be their inclusion in a method of identifying HLRRNS-2 or HLRRNS-3 agonists and antagonists. Preferably, the cell lines are useful in a method for identifying a compound that modulates the biological activity of the LRR polypeptide, comprising the steps of (a) combining a candidate modulator compound with a host cell expressing the HLRRNS-2 or HLRRNS-3 polypeptide having the sequence as set forth in SEQ ID NO: 2 and SEQ ID NO: 4, respectively; and (b) measuring an effect of the candidate modulator compound on the activity of the expressed HLRRNS-2 polypeptide or the expressed HLRRNS-3 polypeptide. Representative vectors for expressing the HLRRNS-2 or HLRRNS-3 polypeptides are known in the art.

The cell lines are also useful in a method of screening for a compound that is capable of modulating the biological activity of the HLRRNS-2 or the HLRRNS-3 polypeptide, comprising the steps of: (a) determining the biological activity of the HLRRNS-2 or the HLRRNS-3 polypeptide in the absence of a modulator compound; (b) contacting a host cell expressing the HLRRNS-2 or HLRRNS-3 polypeptide with the modulator compound; and (c) determining the biological activity of the HLRRNS-2 or the HLRRNS-3 polypeptide in the presence of the modulator compound; wherein a difference between the activity of the HLRRNS-2 or the HLRRNS-3 polypeptide in the presence of the modulator compound and in the absence of the modulator compound indicates a modulating effect of the compound. Additional uses for these cell lines are described herein or otherwise known in the art. In particular, purified HLRRNS-2 or HLRRNS-3 protein, or fragments thereof, can be used to produce antibodies, or used to screen libraries of pharmaceutical agents to identify those which specifically bind HLRRNS-2 or HLRRNS-3.

Polypeptides used in treatment can also be generated endogenously in the subject, in treatment modalities often referred to as "gene therapy". Thus for example, cells from a subject can be engineered with a polynucleotide, such as DNA or RNA, encoding an HLRRNS-2 or an HLRRNS-3 polypeptide ex vivo, and for example, by the use of a retroviral plasmid vector. The cells can then be introduced into the subject.

The present invention also encompasses the polypeptide sequences that intervene between the predicted HLRRNS-2 transmembrane domain or the HLRRNS-3 transmembrane domain. Since these regions are solvent accessible either extracellularly or intracellularly, they are particularly useful for designing antibodies specific to each region. Such antibodies can be useful as antagonists or agonists of the HLRRNS-2 or the HLRRNS-3 full-length polypeptide and can modulate its activity.

The following serve as non-limiting examples of HLRRNS-2 peptides or fragments that can be used to generate antibodies:

| | |
|---|---|
| QLIWLYLDHNYISSVDEDAFQGIR | (SEQ ID NO:33) |
| RLKELILSSNKITYLHNKTFHPVP | (SEQ ID NO:34) |
| NLRNLDLSYNKLQTLQSEQFKGLR | (SEQ ID NO:35) |
| KLIILHLRSNSLKTVPIRVFQDCR | (SEQ ID NO:36) |

-continued

| | |
|---|---|
| NLDFLDLGYNRLRSLSRNAFAGLL | (SEQ ID NO:37) |
| KLKELHLEHNQFSKINFAHFPRLF | (SEQ ID NO:38) |
| NLRSIYLQWNRIRSISQGLTWTWS | (SEQ ID NO:39) |
| SLHNLDLSGNDIQGIEPGTFKCLP | (SEQ ID NO:40) |
| NLQKLNLDSNKLTNISQETVNAWI | (SEQ ID NO:41) |
| ACPKNCRCDGKIVYCESHAFADIPENIS | (SEQ ID NO:42) |
| NMWECSRSICPLFYWLKNFKGNKESTMICAGPKHIQ GEKVSDAVETYNICS | (SEQ ID NO:43) |

The following serve as non-limiting examples of HLR-RNS-3 peptides or fragments that can be used to generate antibodies:

| | |
|---|---|
| NAVTLHLGNNGLQEJRTGAFSGLK | (SEQ ID NO:44) |
| TLKRLHLNNNKLEILREDTFLGLE | (SEQ ID NO:45) |
| SLEYLQADYNYISATEAGAFSKLN | (SEQ ID NO:46) |
| KLKVLIILNDNLLLSLPSNVFRFV | (SEQ ID NO:47) |
| LLTHLDLRGNRLKVMPFAGVLE | (SEQ ID NO:48) |
| SLDLLHLGNNRIAVIQEGAFTNLT | (SEQ ID NO:49) |
| SLRRLYLNGNYLEVLYPSMFDGLQ | (SEQ ID NO:50) |
| SLQYLYLEYNVIKEIKPLTFDALI | (SEQ ID NO:51) |
| NLQLLFLNNNLLRSLPDNIFGGT | (SEQ ID NO:52) |
| ALTRLNLRNNHFSHLPVKGVLDQLP | (SEQ ID NO:53) |
| ICKTRCLCEEKENVLNINCENKGFTTVSLLQP | (SEQ ID NO:54) |
| TCPSSCVCTSQSSDNGLNVNCQERKFTNISDLQP | (SEQ ID NO:55) |
| NPWNCTCDLLPLKAWLDTITVFVGEIVCETPFRLHG KDVTQLTRQDLCP | (SEQ ID NO:56) |
| NPWDCTCDIMGLKDWTEHANSPVIINEVTCESPAKH AGEILKFLGREAICP | (SEQ ID NO:57) |

For the production of antibodies, various hosts including goats, rabbits, sheep, rats, mice, humans, and others, can be immunized by injection with the HLRRNS-2 or the HLRRNS-3 polypeptide, or any fragment or oligopeptide thereof, which has immunogenic properties. Depending on the host species, various adjuvants can be used to increase the immunological response. Non-limiting examples of suitable adjuvants include Freund's (complete and incomplete) adjuvant, mineral gels such as aluminum hydroxide or silica, and surface active substances such as lysolecithin, pluronic polyols, polyanions, peptides, oil emulsions, KLH, and dinitrophenol. Adjuvants typically used in humans include BCG (bacilli Calmette Guèrin) and *Corynebacterium parvumn*.

Preferably, the peptides, fragments, or oligopeptides used to induce antibodies to the HLRRNS-2 or the HLRRNS-3 polypeptide (i.e., immunogens) have an amino acid sequence of at least five amino acids and more preferably, at least 7–10 amino acids. It is also preferable that the immunogens are identical to a portion of the amino acid sequence of the natural protein; they can also contain the entire amino acid sequence of a small, naturally occurring molecule. The peptides, fragments or oligopeptides can comprise a single epitope or antigenic determinant or multiple epitopes. Short stretches of HLRRNS-2 amino acids or those of HLRRNS-3 can be fused with those of another protein, such as KLH, and antibodies are produced against the chimeric molecule.

Another aspect of the invention relates to a method for inducing an immunological response in a mammal which comprises inoculating the mammal with the HLRRNS-2 or the HLRRNS-3 polypeptide, or a fragment thereof, adequate to produce antibody and/or T cell immune response to protect said animal from infections such as, for example, bacterial, fungal, and viral infections, particularly infections caused by HIV-1 or HIV-2. Yet another aspect of the invention relates to a method of inducing immunological response in a mammal which comprises, delivering the HLRRNS-2 or the HLRRNS-3 polypeptide via a vector directing expression of the LRR polynucleotide in vivo in order to induce such an immunological response to produce antibody to protect said animal from diseases.

A further aspect of the invention relates to an immunological or vaccine formulation (composition) which, when introduced into a mammalian host, induces an immunological response in that mammal to an HLRRNS-2 or HLRRNS-3 polypeptide wherein the composition comprises a the LRR polypeptide or gene. The vaccine formulation can further comprise a suitable carrier, diluent, or excipient. Since the HLRRNS-2 or HLRRNS-3 polypeptide can be broken down in the stomach, it is preferably administered parenterally (including subcutaneous, intramuscular, intravenous, intradermal, etc., injection). Formulations suitable for parenteral administration include aqueous and non-aqueous sterile injection solutions which can contain antioxidants, buffers, bacteriostats and solutes which render the formulation isotonic with the blood of the recipient; and aqueous and non-aqueous sterile suspensions which can include suspending agents or thickening agents. The formulations can be presented in unit-dose or multi-dose containers, for example, sealed ampoules and vials, and can be stored in a freeze-dried condition requiring only the addition of the sterile liquid carrier immediately prior to use. The vaccine formulation can also include adjuvant systems for enhancing the immunogenicity of the formulation, such as oil-in-water systems and other systems known in the art. The dosage will depend on the specific activity of the vaccine and can be readily determined by routine experimentation.

In an embodiment of the present invention, the polynucleotide encoding the HLRRNS-2 or the HLRRNS-3 polypeptide, or any fragment or complement thereof, can be used for therapeutic purposes. In one aspect, antisense to the polynucleotide encoding the HLRRNS-2 or HLRRNS-3 polypeptide, can be used in situations in which it would be desirable to block the transcription of the mRNA. In particular, cells can be transformed with sequences complementary to polynucleotides encoding the HLRRNS-2 polypeptide or encoding the HLRRNS-3 polypeptide. Thus, complementary molecules can be used to modulate the HLRRNS-2 or HLRRNS-3 polynucleotide and polypeptide activity, or to achieve regulation of gene function. Such technology is now well known in the art, and sense or antisense oligomers or oligonucleotides, or larger fragments, can be designed from various locations along the coding or control regions of polynucleotide sequences encoding the HLRRNS-2 or HLRRNS-3 polypeptide.

The genes encoding the HLRRNS-2 or the HLRRNS-3 polypeptide can be turned off by transforming a cell or tissue with an expression vector that expresses high levels of the HLRRNS-2 or the HLRRNS-3 polypeptide-encoding polynucleotide, or a fragment thereof. Such constructs can be used to introduce untranslatable sense or antisense sequences into a cell. Even in the absence of integration into the DNA, such vectors can continue to transcribe RNA molecules until they are disabled by endogenous nucleases. Transient expression can last for a month or more with a non-replicating vector, and even longer if appropriate replication elements are designed to be part of the vector system.

Modifications of gene expression can be obtained by designing antisense molecules or complementary nucleic acid sequences (DNA, RNA, or PNA), to the control, 5', or regulatory regions of the gene encoding the HLRRNS-2 or HLRRNS-3 polypeptide, (e.g., signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described (see, for example, J. E. Gee et al., 1994, In: B. E. Huber and B. I. Carr, *Molecular and Immunologic Approaches*, Futura Publishing Co., Mt. Kisco, N.Y.). The antisense molecule or complementary sequence can also be designed to block translation of mRNA by preventing the transcript from binding to ribosomes.

Ribozymes, i.e., enzymatic RNA molecules, can also be used to catalyze the specific cleavage of RNA. The mechanism of ribozyme action involves sequence-specific hybridization of the ribozyme molecule to complementary target RNA, followed by endonucleolytic cleavage. Suitable examples include engineered hammerhead motif ribozyme molecules that can specifically and efficiently catalyze endonucleolytic cleavage of sequences encoding the HLRRNS-2 or HLRRNS-3 polypeptide.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site can be evaluated for secondary structural features which can render the oligonucleotide inoperable. The suitability of candidate targets can also be evaluated by testing accessibility to hybridization with complementary oligonucleotides using ribonuclease protection assays.

Complementary ribonucleic acid molecules and ribozymes according to the invention can be prepared by any method known in the art for the synthesis of nucleic acid molecules. Such methods include techniques for chemically synthesizing oligonucleotides, for example, solid phase phosphoramidite chemical synthesis. Alternatively, RNA molecules can be generated by in vitro and in vivo transcription of DNA sequences encoding the HLRRNS-2 or HLRRNS-3. Such DNA sequences can be incorporated into a wide variety of vectors with suitable RNA polymerase promoters such as T7 or SP. Alternatively, the cDNA constructs that constitutively or inducibly synthesize complementary RNA can be introduced into cell lines, cells, or tissues.

RNA molecules can be modified to increase intracellular stability and half-life. Possible modifications include, but are not limited to, the addition of flanking sequences at the 5' and/or 3' ends of the molecule, or the use of phosphorothioate or 2' O-methyl, rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytosine, guanine, thymine, and uridine which are not as easily recognized by endogenous endonucleases.

In one embodiment of the present invention, an expression vector containing the polynucleotide encoding the HLRRNS-2 or HLRRNS-3 polypeptide can be administered to an individual to treat or prevent a neurological disorder, including, but not limited to, the types of diseases, disorders, or conditions described above. Additionally, an expression vector containing the complement of the polynucleotide encoding the HLRRNS-2 or HLRRNS-3 polypeptide can be administed to an individual.

Many methods for introducing vectors into cells or tissues are available and are equally suitable for use in vivo, in vitro, and ex vivo. For ex vivo therapy, vectors can be introduced into stem cells taken from the patient and clonally propagated for autologous transplant back into that same patient. Delivery by transfection and by liposome injections can be achieved using methods, which are well known in the art.

Any of the therapeutic methods described above can be applied to any individual or subject in need of such therapy, including but not limited to, for example, mammals such as dogs, cats, cows, horses, rabbits, monkeys, and most preferably, humans.

A further embodiment of the present invention embraces the administration of a pharmaceutical composition, in conjunction with a pharmaceutically acceptable carrier, diluent, or excipient, for any of the above-described therapeutic uses and effects. Such pharmaceutical compositions can comprise the HLRRNS-2 or HLRRNS-3 nucleic acid, polypeptide, or peptides, antibodies to the LRR polypeptide, mimetics, agonists, antagonists, or inhibitors of the LRR polypeptide or polynucleotide. The compositions can be administered alone, or in combination with at least one other agent, such as a stabilizing compound, which can be administered in any sterile, biocompatible pharmaceutical carrier, including, but not limited to, saline, buffered saline, dextrose, and water. The compositions can be administered to a patient alone, or in combination with other agents, drugs, hormones, or biological response modifiers.

The pharmaceutical compositions for use in the present invention can be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, vaginal, or rectal means.

In addition to the active ingredients (i.e., the HLRRNS-2 or HLRRNS-3 nucleic acid or polypeptide, or functional fragments thereof), the pharmaceutical compositions can contain suitable pharmaceutically acceptable carriers, diluents, or excipients comprising auxiliaries which facilitate processing of the active compounds into preparations which can be used pharmaceutically. Further details on techniques for formulation and administration are provided in the latest edition of *Remington's Pharmaceutical Sciences* (Mack Publishing Co.; Easton, Pa,).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained by the combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropyl-methylcellulose, or sodium carboxymethylcellulose; gums, including arabic and tragacanth, and proteins such as gelatin and collagen. If desired, disintegrating or solubilizing agents can be added, such as cross-linked polyvinyl pyrrolidone, agar, alginic acid, or a physiologically acceptable salt thereof, such as sodium alginate.

Dragee cores can be used in conjunction with physiologically suitable coatings, such as concentrated sugar solutions, which can also contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification, or to characterize the quantity of active compound, i.e., dosage.

Pharmaceutical preparations, which can be used orally, include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances, which increase the viscosity of the suspension, such as sodium carboxymethyl cellulose, sorbitol, or dextran. In addition, suspensions of the active compounds can be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension can also contain suitable stabilizers or agents which increase the solubility of the compounds to allow for the preparation of highly concentrated solutions.

For topical or nasal administration, penetrants or permeation agents that are appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes.

The pharmaceutical composition can be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms. In other cases, the preferred preparation can be a lyophilized powder which can contain any or all of the following: 1–50 mM histidine, 0. 1%–2% sucrose, and 2–7% mannitol, at a pH range of 4.5 to 5.5, combined with a buffer prior to use. After the pharmaceutical compositions have been prepared, they can be placed in an appropriate container and labeled for treatment of an indicated condition. For administration of the HLRRNS-2 or HLRRNS-3 product, such labeling would include amount, frequency, and method of administration.

Pharmaceutical compositions suitable for use in the present invention include compositions in which the active ingredients are contained in an effective amount to achieve the intended purpose. The determination of an effective dose or amount is well within the capability of those skilled in the art. For any compound, the therapeutically effective dose can be estimated initially either in cell culture assays, e.g., using neoplastic cells, or in animal models, usually mice, rabbits, dogs, or pigs. The animal model can also be used to determine the appropriate concentration range and route of administration. Such information can then be used and extrapolated to determine useful doses and routes for administration in humans.

A therapeutically effective dose refers to that amount of active ingredient, for example, the HLRRNS-2 or HLRRNS-3 polypeptide, or fragments thereof, antibodies to LRR polypeptides, agonists, antagonists or inhibitors of the LRR polypeptide, which ameliorates, reduces, or eliminates the symptoms or condition. Therapeutic efficacy and toxicity can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, which can be expressed as the ratio, $LD_{50}/ED_{50}$. Pharmaceutical compositions which exhibit large therapeutic indices are preferred. The data obtained from cell culture assays and animal studies are used in determining a range of dosages for human use. Preferred dosage contained in a pharmaceutical composition is within a range of circulating concentrations that include the $ED_{50}$ with little or no toxicity. The dosage varies within this range depending upon the dosage form employed, sensitivity of the patient, and the route of administration.

The practitioner, who will consider the factors related to the individual requiring treatment, will determine the exact dosage. Dosage and administration are adjusted to provide sufficient levels of the active moiety or to maintain the desired effect. Factors, which can be taken into account, include the severity of the individual's disease state, general health of the patient, age, weight, and gender of the patient, diet, time and frequency of administration, drug combination(s), reaction sensitivities, and tolerance/response to therapy. As a general guide, long-acting pharmaceutical compositions can be administered every 3 to 4 days, every week, or once every two weeks, depending on half-life and clearance rate of the particular formulation. Variations in these dosage levels can be adjusted using standard empirical routines for optimization, as is well understood in the art.

Normal dosage amounts can vary from 0.1 to 100,000 micrograms (µg), up to a total dose of about 1 gram (g), depending upon the route of administration. Guidance as to particular dosages and methods of delivery is provided in the literature and is generally available to practitioners in the art. Those skilled in the art will employ different formulations for nucleotides than for proteins or their inhibitors. Similarly, delivery of polynucleotides or polypeptides will be specific to particular cells, conditions, locations, and the like.

Microarrays and Screening Assays

In another embodiment of the present invention, oligonucleotides, or longer fragments derived from the HLRRNS-2 or HLRRNS-3 polynucleotide sequence described herein can be used as targets in a microarray. The microarray can be used to monitor the expression level of large numbers of genes simultaneously (to produce a transcript image), and to identify genetic variants, mutations and polymorphisms. This information can be used to determine gene function, to understand the genetic basis of a disease, to diagnose disease, and to develop and monitor the activities of therapeutic agents. In a particular aspect, the microarray is prepared and used according to the methods described in WO 95/11995 (Chee et al.); D. J. Lockhart et al., 1996, *Nature Biotechnology*, 14:1675–1680; and M. Schena et al., 1996, *Proc. Natl. Acad. Sci. USA*, 93:10614–10619). Microarrays are further described in U.S. Pat. No. 6,015,702 to P. Lal et al.

In another embodiment of this invention, the nucleic acid sequence, which encodes the HLRRNS-2 or HLRRNS-3 polypeptide, can also be used to generate hybridization probes, which are useful for mapping the naturally occurring genomic sequence. The sequences can be mapped to a particular chromosome, to a specific region of a chromosome, or to artificial chromosome constructions (HACs), yeast artificial chromosomes (YACs), bacterial artificial chromosomes (BACs), bacterial PI constructions, or single chromosome cDNA libraries, as reviewed by C. M. Price, 1993, *Blood Rev.*, 7:127–134 and by B. J. Trask, 1991, *Trends Genet.*, 7:149–154.

Fluorescent In Situ Hybridization (FISH), (as described in I. Verma et al., 1988, *Human Chromosomes: A Manual of Basic Techniques* Pergamon Press, New York, N.Y.) can be correlated with other physical chromosome mapping techniques and genetic map data. Examples of genetic map data can be found in numerous scientific journals, or at Online Mendelian Inheritance in Man (OMIM). Correlation between the location of the gene encoding the HLRRNS-2 or the HLRRNS-3 polypeptide on a physical chromosomal map and a specific disease, or predisposition to a specific disease, can help delimit the region of DNA associated with that genetic disease. The nucleotide sequences, particularly that of SEQ ID NO: 1 and SEQ ID NO:3, respectively, or fragments thereof, according to this invention can be used to detect differences in gene sequences between normal, carrier, or affected individuals.

In situ hybridization of chromosomal preparations and physical mapping techniques such as linkage analysis using established chromosomal markers can be used for extending genetic maps. Often the placement of a gene on the chromosome of another mammalian species, such as mouse, can reveal associated markers, even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (R. A. Gatti et al., 1988, *Nature*, 336:577–580), any sequences mapping to that area can represent associated or regulatory genes for further investigation. The nucleotide sequence of the present invention can also be used to detect differences in the chromosomal location due to translocation, inversion, and the like, among normal, carrier, or affected individuals.

In another embodiment of the present invention, the HLRRNS-2 or HLRRNS-3 polypeptide, its catalytic or immunogenic fragments or oligopeptides thereof, can be used for screening libraries of compounds in any of a variety of drug screening techniques. The fragment employed in such screening can be free in solution, affixed to a solid support, borne on a cell surface, or located intracellularly. The formation of binding complexes, between the HLRRNS-2 or HLRRNS-3 polypeptide, or portion thereof, and the agent being tested, can be measured utilizing techniques commonly practiced in the art. In particular, a method of screening a library of molecules or compounds with an HLRRNS-2 or HLRRNS-3 polynucleotide, or fragment thereof, to identify at least one molecule or compound therein which specifically binds to the LRR polynucleotide sequence, preferably the HLRRNS-2 or HLRRNS-3 polynucleotide sequence, or fragment thereof, comprising: a) combining the LRR polynucleotide, or fragment thereof, with a library of molecules or compounds under conditions to allow specific binding; and b) detecting specific binding, thereby identifying a molecule or compound, which specifically binds to an LRR-encoding polynucleotide sequence. In a further embodiment, the screening method is a high throughput screening method. Preferably, the library is selected from the group consisting of DNA molecules, RNA molecules, artificial chromosome constructions, PNAs, peptides and proteins. In a preferred embodiment, the candidate small molecules or compounds are a drug or therapeutic agent.

Another embodiment of this invention embraces a method of screening for candidate compounds capable of modulating the activity of an LRR-encoding polypeptide, comprising: a) contacting a test compound with a cell or tissue expressing the LRR polypeptide, homologue, or fragment thereof; and b) selecting as candidate modulating compounds those test compounds that modulate activity of the LRR polypeptide. Preferably, the candidate compounds are agonists or antagonists of LRR activity. More preferably, the polypeptide activity is neurologically-associated, e.g., in the brain.

Another technique for drug screening provides for high throughput screening of compounds having suitable binding affinity to the protein of interest as described in WO 84/03564 (Venton, et al.). In this method, as applied to the HLRRNS-2 or HLRRNS-3 protein, large numbers of different small test compounds are synthesized on a solid substrate, such as plastic pins or some other surface. The test compounds are reacted with the HLRRNS-2 or HLRRNS-3 polypeptide, or fragments thereof, and washed. The bound HLRRNS-2 or HLRRNS-3 polypeptide is then detected by methods well known in the art. Purified HLRRNS-2 or HLRRNS-3 polypeptide can also be coated directly onto plates for use in the aforementioned drug screening techniques. Alternatively, non-neutralizing antibodies can be used to capture the peptide and immobilize it on a solid support.

In a further embodiment of this invention, competitive drug screening assays can be used in which neutralizing antibodies, capable of binding the HLRRNS-2 or HLRRNS-3 polypeptide, specifically compete with a test compound for binding to the HLRRNS-2 or HLRRNS-3 polypeptide. In this manner, the antibodies can be used to detect the presence of any HLRRNS-2-specific or HLRRNS-3-specific peptide, which share one or more antigenic determinants with the HLRRNS-2 or HLRRNS-3 polypeptide, respectively.

Other screening and small molecule (e.g., drug) detection assays which involve the detection or identification of small molecules or compounds that can bind to a given protein, i.e., the HLRRNS-2 or HLRRNS-3 polypeptide, are encompassed by the present invention. Particularly preferred are assays suitable for high throughput screening methodologies. In such binding-based screening or detection assays, a functional assay is not typically required. All that is needed is a target protein, preferably substantially purified, and a library or panel of compounds (e.g., ligands, drugs, small molecules) to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP; Exton, Pa.) as described in U.S. Pat. Nos. 6,020,141 and 6,036,920 to Pantoliano et al.; see also, J. Zimmerman, 2000, *Gen. Eng. News*, 20(8)). The assay allows for the detection of small molecules (e.g., drugs, ligands) that bind to expressed, and preferably purified, HLRRNS-2 or HLR-RNS-3 polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

EXAMPLES

The Examples herein are meant to exemplify the various aspects of carrying out the invention and are not intended to limit the scope of the invention in any way. The Examples do not include detailed descriptions for conventional methods employed, such as in the construction of vectors, the insertion of cDNA into such vectors, or the introduction of the resulting vectors into the appropriate host. Such methods are well known to those skilled in the art and are described in numerous publications, for example, Sambrook, Fritsch, and Maniatis, *Molecular Cloning: A Laboratory Manual*, 2$^{nd}$ Edition, Cold Spring Harbor Laboratory Press, USA, (1989).

using the BLAST 2 algorithm according to the default parameters (S. F. Altschul, et al., *Nucleic Acids Res.* 25:3389–3402, 1997). The BLAST results were analyzed for potential novel GPCR candidates. The candidate sequences, from genomic or EST data, were then characterized. The characterization methods include sequence and profile-based analyses. The functional prediction is based on sequence identity and homology and/or domain information. FIGS. 7A–7F show the regions of local identity and similarity of the novel human LRR gene encoding the amino acid sequence SEQ ID NO:2 of HLRRNS-2 and other sequences while FIGS. 8A–8D show the multiple homology of HLR-RNS-3 of SEQ ID NO:4 and other sequences. The GAP global alignment program in GCG was used to calculate percent identity and similarity values. The following parameters were used in the GAP program: gap creation penalty-6 and gap extension penalty-2. This program used an algorithm based on the following paper: Needleman S B, Wunsch C D: A general method applicable to the search for similarities in the amino acid sequence of two proteins. *J Mol. Biol.* 48:443–453, 1970.

Example 2

Cloning of the Novel Human Leucine-Rich Repeat Genes

The following EST sequences were identified as encoding putative peptides with homology to various LRR-containing proteins, including those that are found in some G protein-coupled receptors (GPCRs). In particular, the GPCR-164 Incyte clone of SEQ ID NO:23 (Incyte template ID: 98584.1; BAC ID: NT_005087) expressed in brain, adrenal tumor, and kidney epithelial was identified. Also, the GPCR-168 Incyte clone of SEQ ID NO:24 (Incyte template ID: 83448.1; BAC ID: NT_025408) expressed in brain was identified. Using these EST sequences, an 80 base pair antisense oligonucleotide with biotin on the 5' end complementary to the putative coding region of GPCR was designed and obtained from Genset Oligos (San Diego, Calif.).

```
GPCR-164 5'-b-GGGGAGGCATTTAAATGTGCCCGGCTCAATTCCTTGGA    (SEQ ID NO:58)
            TGTCATTCCCTGATAAATCCAAGTTGTGTAAGGAACTCCAA
            G-3'

GPCR-168 5'-b-CACAAGTGCAATTCCATGGATTTTCCTCCAGCTGAATC    (SEQ ID NO:59)
            TCCATGATCCCTCCAATATGTTCAAGGACGCCAGCAAAAG
            GC-3'
```

Example 1

Bioinformatics Analysis

Currently, one approach used for identifying and characterizing the genes distributed throughtout the human genome includes utilizing large fragments of genomic DNA which are isolated, cloned, and sequenced. Open reading frames in these genomic sequences were identified using bioinformatics software.

The LRR polynucleotide sequence and its encoded polypeptide sequence were obtained from publically accessible databases which include, for example, the non-redundant GenBank database, SWISS-PROT database, and the EMBL database. These sequences (more than 1300 protein sequences) were used as probes to search the human genomic, public and private EST databases. The search program used was BLAST2. The alignment was performed The biotinylated (b) oligo is incubated with a mixture of single-stranded covalently closed circular cDNA libraries, which contain DNA corresponding to the sense strand. Hybrids between the biotinylated oligo and the circular cDNA are captured on streptavidin magnetic beads. Upon thermal release of the cDNA from the biotinylated oligo, the single stranded cDNA is converted into double strands using a primer homologous to a sequence on the cDNA cloning vector. The double stranded cDNA is introduced into *E. coli* by electroporation and the resulting colonies are screened by PCR, using a primer pair designed from the EST sequence to identify the proper cDNA. Oligos used to identify the cDNA of a LRR gene of this invention by PCR can be selected from any one of LRR sequences as represented, for example, in SEQ ID NOs: 25–28.

Example 3

Multiplex Cloning

Method for the Construction of a Size Fractionated Brain and Testis cDNA Library PolyA+ RNA was purchased from Clontech, treated with DNase I to remove traces of genomic DNA contamination and converted into double-stranded cDNA using the SuperScript™ Plasmid System for cDNA Synthesis and Plasmid Cloning (Life Technologies). No radioisotope was incorporated in either of the cDNA synthesis steps. The cDNA was then size fractionated on a TransGenomics HPLC system equipped with a size exclusion column (TosoHass; Montgomeryville, Pa.) with dimensions of 7.8 mm×30 cm and a particle size of 10 µm. Tris buffered saline (TBS) was used as the mobile phase, and the column was run at a flow rate of 0.5 mL/min. The system was calibrated by running a 1 kb ladder through the column and analyzing the fractions by agarose gel electrophoresis. Using these data, it can be determined which fractions are to be pooled to obtain the largest cDNA library. Generally, fractions that eluted in the range of 12 to 15 minutes were pooled.

The cDNA was precipitated, concentrated, and then ligated into the SalI/NotI sites of the pSPORT vector. After electroporation into *E. coli* DH12S, colonies were subjected to a miniprep procedure and the resulting cDNA was digested using SalI/NotI restriction enzymes. Generally, the average insert size of libraries made in this fashion was greater than 3.5 Kb; the overall complexity of the library is optimally greater than $10^7$ independent clones. The library was amplified in semi-solid agar for 2 days at 30° C. An aliquot (200 microliters) of the amplified library was inoculated into a 200 mL culture for single-stranded DNA isolation by super-infection with an f1 helper phage. The single-stranded circular DNA was concentrated by ethanol precipitation, resuspended at a concentration of one microgram per microliter and used for cDNA capture experiments.

Method for cDNA Isolation

One microliter (one hundred and fifty nanograms) of each biotinylated oligo was added to six microliters (six micrograms) of a mixture of single-stranded covalently closed circular brain and testis cDNA libraries and seven microliters of 100% formamide in a 0.5 ml PCR tube. The mixture was heated in a thermal cycler to a temperature of 95° C. for 2 mins. Fourteen microliters of 2× hybridization buffer (50% formamide, 1.5 M NaCl, 0.04 M NaPO$_4$, pH 7.2, 5 mM EDTA, 0.2% SDS) was added to the heated probe/cDNA library mixture and incubated at 42° C. for 26 hours. Hybrids between the biotinylated oligo and the circular cDNA were isolated by diluting the hybridization mixture to 220 microliters in a solution containing 1 M NaCl, 10 mM Tris-HCl pH 7.5, 1 mM EDTA, pH 8.0 and adding 125 microliters of streptavidin magnetic beads. This solution was incubated at 42° C. for 60 mins, mixing every 5 mins to resuspend the beads. The beads were separated from the solution with a magnet, and then the beads were washed three times in 200 microliters of 0.1×SSPE, 0.1% SDS at 45° C.

The single stranded cDNAs were released from the biotinylated oligo/streptavidin magnetic bead complex by adding 50 microliters of 0.1 N NaOH and incubating at room temperature for 10 mins. Six microliters of 3 M Sodium Acetate were added along with 15 micrograms of glycogen and the solution was ethanol precipitated with 120 microliters of 100% ethanol. The DNA was resuspended in 12 microliters of TE (10 mM Tris-HCl, pH 8.0, 1 mM EDTA, pH 8.0). The single-stranded cDNA was converted into double strands in a thermal cycler by mixing 5 microliters of the captured DNA with 1.5 microliters of 10 micromolar standard SP6 primer (homologous to a sequence on the cDNA cloning vector) and 1.5 microliters of 10× PCR buffer. The mixture was heated to 95° C. for 20 seconds and then ramped down to 59° C. At this time, 15 microliters of a preheated (70° C.) repair mix containing 4 microliters of 5 mM dNTPs (1.25 mM each), 1.5 microliters of 10× PCR buffer, 9.25 microliters of water, and 0.25 microliters of Taq polymerase was added. The solution was ramped back to 73° C. and incubated for 23 mins. The repaired DNA was ethanol precipitated and resuspended in 10 microliters of TE. Two microliters were electroporated in *E. coli* DH 12S cells and the resulting colonies were screened by PCR, using primer pairs designed from the genomic sequence to identify the correct cDNAs. Those cDNA clones that were positive by PCR had the inserts sized and two clones were chosen for DNA sequencing.

Oligos used for PCR identification of HLRRNS-2 included the following sense (s) and antisense (a) sequences:

GPCR-164s 5'-CCATTAGCCAAGGTTTGACA-3' (SEQ ID NO:25)

GPCR-164a 5'-TTGGTGAGCTTGTTGGAATC-3' (SEQ ID NO:26)

Oligos used for PCR identification of HLRRNS-3 included the following sense (s) and antisense (a) sequences:

GPCR-168s 5'-TGTCCTGCTGACCCACTTAG-3' (SEQ ID NO:27)

GPCR-168a 5'-CCAGGCCTTGAGAGGAAGTA-3' (SEQ ID NO:28)

Example 4

Novel Human LRR Expression Profiling

Briefly, first strand cDNA was made from commercially available mRNA (Clontech) and subjected to real time quantitative PCR using a PE 5700 instrument (Applied Biosystems; Foster City, Calif.) which detects the amount of DNA amplified during each cycle by the fluorescent output of SYBR green, a DNA binding dye specific for double strands. The specificity of the primer pair for its target was verified by performing a thermal denaturation profile at the end of the run which indicated the number of different DNA sequences present by determining the melting temperature, Tm. In the case of each of the novel HLRR gene primer pairs, only one DNA fragment was detected having a homogeneous melting point. The contribution of contaminating genomic DNA to the assessment of tissue abundance was controlled for by performing the PCR with first strand made with and without reverse transcriptase. In all cases, the contribution of material amplified in the controls without reverse transcriptase was negligible.

Small variations in the amount of cDNA used in each tube were determined by performing a parallel experiment using a primer pair for the cyclophilin gene, which was expressed in equal amounts in all tissues. These data were used to normalize the data obtained with the primer pairs. The PCR data were converted into a relative assessment of the differences in transcript abundance among the tissues tested. The data are presented in bar graph form in FIGS. 14 and 15 corresponding to HLRRNS-2 and HLRRNS-3, respectively.

Transcripts corresponding to the newly discovered HLR-RNS-2 were found to be highly expressed in brain and appreciable levels of transcripts were found in the pituitary gland and the spinal cord. HLRRNS-3 transcripts were found to be expressed highly in brain, specifically the amygdala, and with appreciable levels in spinal cord.

Example 5

Taqman™ Quantitative PCR Analysis of HLRRNS-2 and HLRRNS-3

HLRRNS-2

Figure 16:
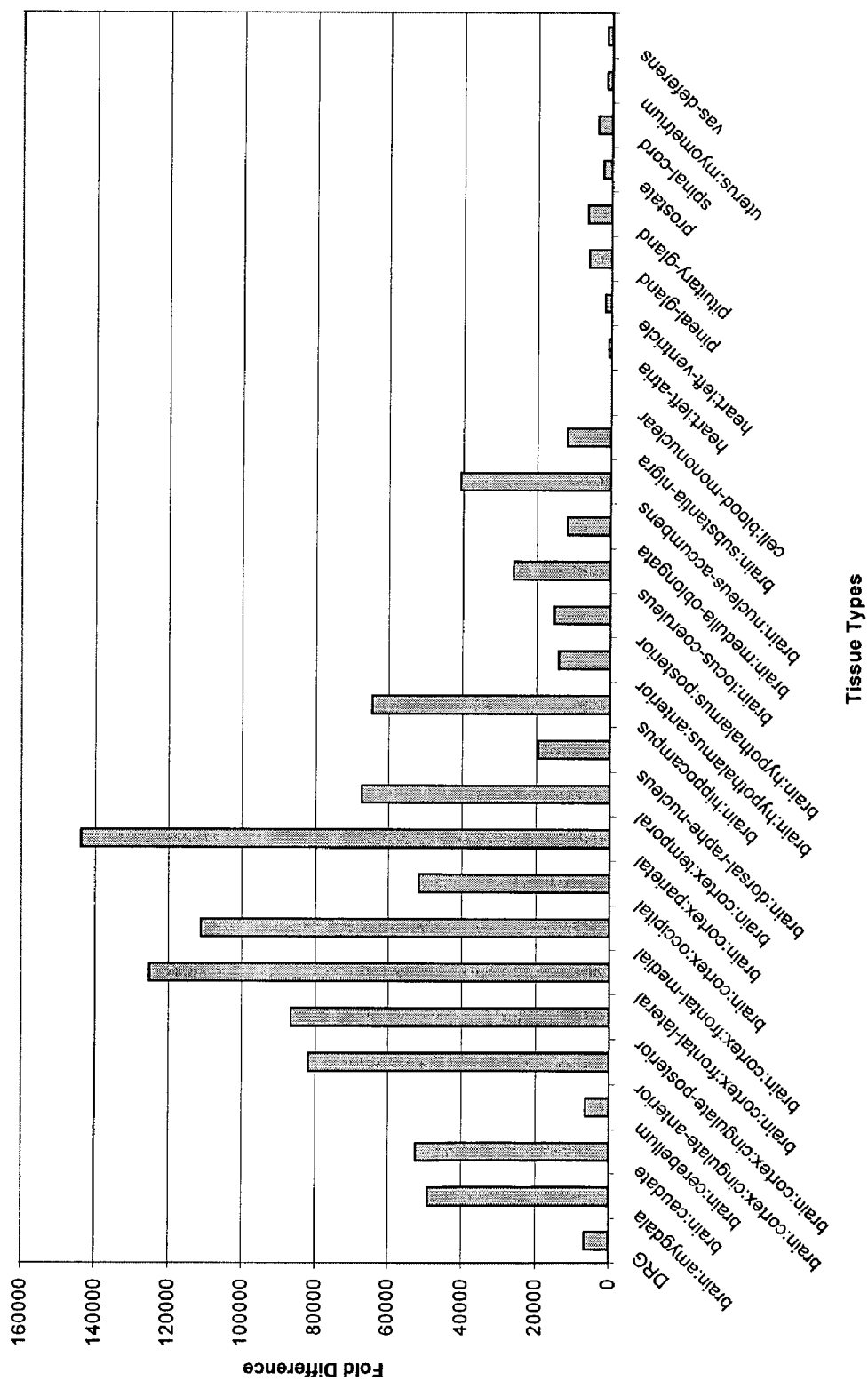
FIG. 16 shows expression profiling of the novel human LRR-containing protein, HLRRNS-2, as described in Example 5.

SYBR green quantitative PCR analysis of HLLRNS-2 in human adult tissue RNAs indicated that this gene has a neuronal expression pattern. Analysis of HLRRNS-2 by TAQMAN™ quantitative PCR on an extended panel of tissue RNAs confirmed and extended these observations. HLLRNS-2 was observed to essentially be restricted to the nervous system, however extremely low levels of expression was detected in other tissues, such as, heart, prostate, uterus and vas-deferens. Within the brain, the highest expression was observed in the various sub regions of the cortex followed by the hippocampus, the caudate and the amygdala. Lower amounts were observed in the accumbens, locus-coeruleus, dorsal-raphae, the hypothalamus and the substantia-nigra. (FIG. 16).

Figure 17:
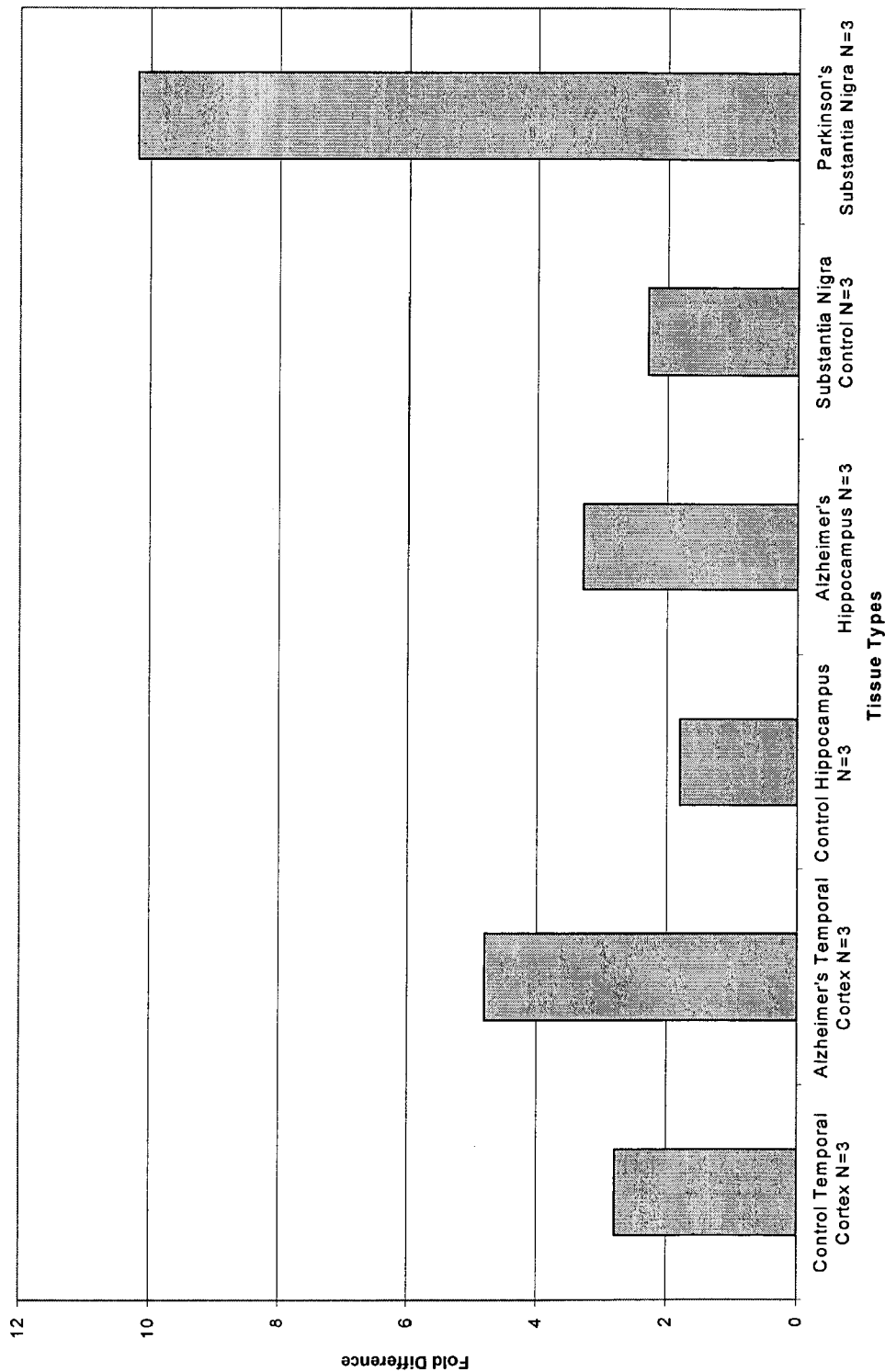
FIG. 17 shows expression profiling of the novel human LRR-containing protein, HLRRNS-2, in selected diseased brain subregions, as described in Example 5.

Analysis of HLRRNS-2 steady state transcript levels in RNA isolated various Alzheimer's and Parkinson's brain subregions indicates a slight increase in the Alzheimer's cortex, hippocampus and Parkinson's substantia nigra over that observed in control RNA samples (FIG. 17). These data suggest that modulators of HLRRNS-2 may have utility in the treatment of cognitive and movement disorders such as Alzheimer's and Parkinson's.

HLRRNS-3

Figure 18:
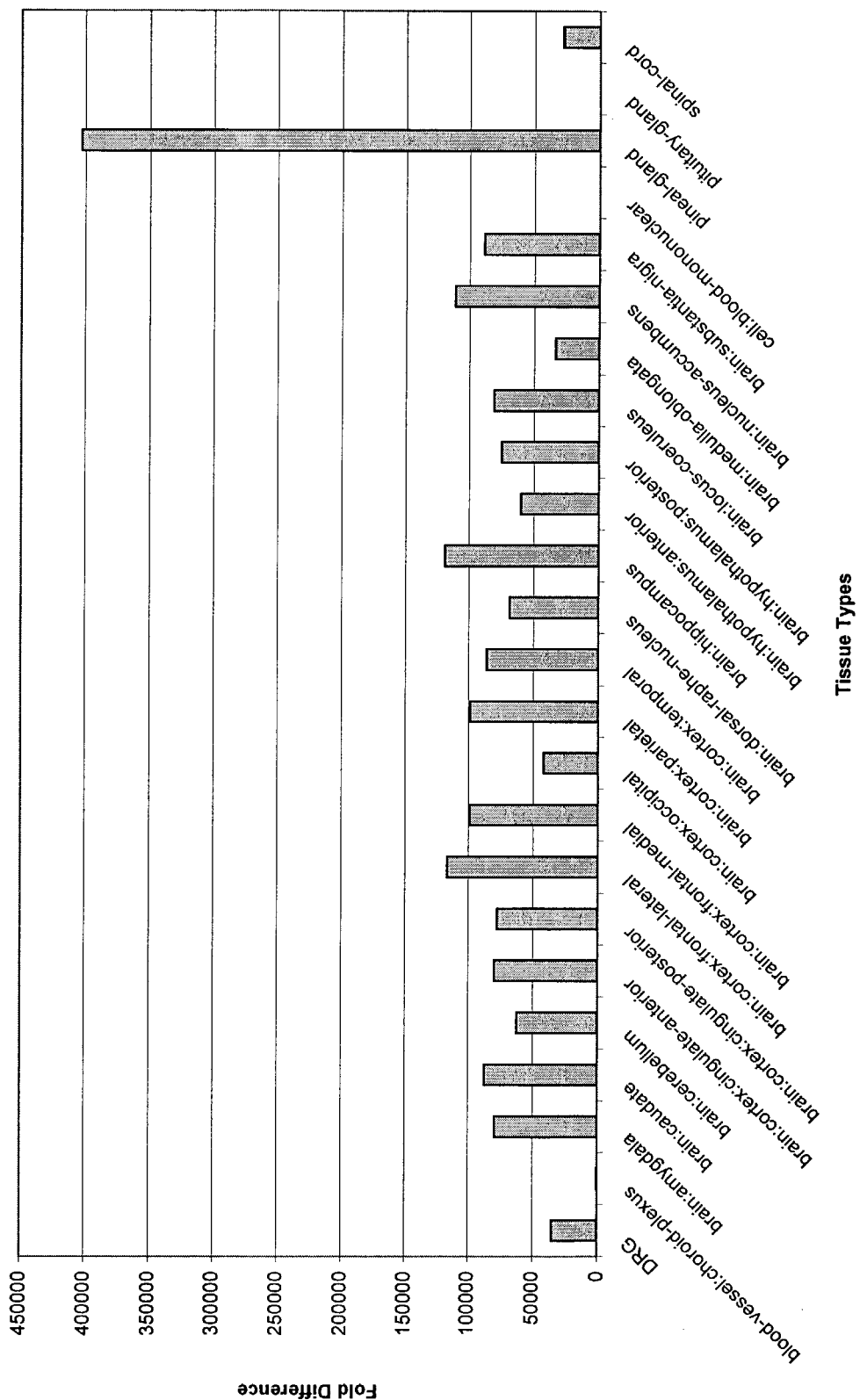
FIG. 18 shows expression profiling of the novel human LRR-containing protein, HLRRNS-3, as described in Example 5.

SYBR green quantitative PCR analysis of HLLRNS-3 in human adult tissue RNAs indicated that this gene also had a neuronal expression pattern. Analysis of HLRRNS-3 by TAQMAN™ quantitative PCR on an extended panel of tissue RNAs confirms and extends these observations. Similar to HLRRNS-2, HLLRNS-3 is essentially restricted to the nervous system. The brain subregion with the highest relative expression level is the pineal gland, where transcripts for HLRRNS-3 are found 40,000 times higher than most of the other tissue RNAs tested. HLRRNS-3 expression is approximately 4 times higher in the pineal gland than the other brain subregions analyzed (FIG. 18). Since melatonin synthesis and secretion by the pineal gland is under the control of the suprachiasmatic nucleus which has a profound effect on circadian rhythms (Kennaway, D J and Wright H. *Curr Top Med Chem* 2(2): 199–209, 2002), these data suggested additional indications that modulators of HLRRNS-3 activity may be of use, namely in sleep disorders and alterations of circadian rhythms.

Methods

Total RNA from tissues was isolated using the TriZol protocol (Invitrogen) and quantified by determining absorbance at 260 nM. An assessment of the 18 s and 28 s ribosomal RNA bands is made by denaturing gel electrophoresis to determine RNA integrity.

The specific sequence to be measured was aligned with related genes found in GenBank to identity regions of significant sequence divergence to maximize primer and probe specificity. Gene-specific primers and probes are designed using the ABI primer express software to amplify small amplicons (150 base pairs or less) to maximize the likelihood that the primers function at 100% efficiency. All primer/probe sequences are searched against Public Genbank databases to ensure target specificity. Primers and probes were obtained from ABI.

The sequences of the HLRRNS-2 and HLLRNS-3 primer/probe set are as follows:

| HLRRNS-2 | | |
|---|---|---|
| Forward Primer: | 5'-GCTACCCAGCCAGCATGAA-3' | (SEQ ID NO:60) |
| Reverse Primer: | 5'-TCAGACTCTCTGGCCTTTTTCC-3' | (SEQ ID NO:61) |
| Probe: | 5'-ACTCCAGCAACACTCTCTTATGAAGAGGCG-3' | (SEQ ID NO:62) |

| HLRRNS-3 | | |
|---|---|---|
| Forward Primer: | 5'-CCTGCTCTCAACCCAACCA-3' | (SEQ ID NO:63) |
| Reverse Primer: | 5'-GGAGTTGGACGATTTCTCATTTTG-3' | (SEQ ID NO:64) |
| Probe: | 5'-CCGAAAGCCAGCCGGCCG-3' | (SEQ ID NO:65) |

DNA Contamination

To access the level of contaminating genomic DNA in the RNA, the RNA was divided into 2 aliquots and one half in treated with Rnase-free Dnase (Invitrogen). Samples from both the Dnase-treated and -untreated were then subjected to reverse transcription reactions with (RT+) and without (RT−) the presence of reverse transcriptase. TAQMAN™ assays were carried out with gene-specific primers (see below) and the contribution of genomic DNA to the signal detected was evaluated by comparing the threshold cycles obtained with the RT+/RT− Dnase-untreated RNA to that on the RT+/RT− Dnase-treated RNA. The amount of signal contributed by genomic DNA in the Dnase-treated RT− RNA must be less that 10% of that obtained with Dnase-treated RT+ RNA. Otherwise, the RNA was not used in the experiments.

Reverse Transcription Reaction And Sequence Detection

Dnase-treated total RNA (100 ng) was annealed to 2.5 μM of the gene-specific reverse primer in the presence of 5.5 mM magnesium chloride by heating the sample to 72° C. for 2 min and then cooling to 55° C. for 30 min. MuLv reverse transcriptase (1.25 U/μl) and 500 μM of each dNTP were added to the reaction and the tube was incubated at 37° C. for 30 min. The sample was then heated to 90° C. for 5 min to denature the enzyme.

Quantitative sequence detection was carried out on a ABI PRISM 7700 by adding to the reverse transcribed reaction 2.5 μM forward and reverse primers, 500μM of each dNTP, buffer, and 5 U AMPLITAQ GOLD™. The PCR reaction was then held at 94° C. for 12 min, followed by 40 cycles of 94° C. for 15 sec, and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$ Example 6

Functional Characterization of Novel Human LRR

The role of the newly described human LRR proteins in either promoting or inhibiting apoptosis is determined by generating transfected cell lines, either transient or stable, and any combination of commonly used assays for detecting of DNA fragmentation. One example is the TUNEL assay (Gavrieli, Y., Sherman, Y., and Ben-Sasson, S. A. J. Cell Biol. 119, 493–501, 1992) which involves end labeling the broken ends of double-stranded DNA with biotin-conjugated dUTP using terminal transferase. Cells undergoing cell death are then easily detected by staining with FITC-conjugated streptavidin and flow cytometric quantitation.

In a further embodiment, human LRR proteins play an important role in promoting cell adhesion events. They can also be identified by generating transfected cell lines, either transient or stable, and evaluating the relative importance of various receptor/ligand interactions in cell-cell and cell-substrate adhesion through hydrodynamic assays. Dynamic adhesion assays simulate the forces found in the bloodstream and can be used to estimate the strength of the bonds between cells and ligands (Jones, D. A., McIntire, L. V., Smith, C. W., and Picker, L. J. J. Clin. Invest. 94, 2443–2450, 1994).

Yet another role of the newly described HLRR proteins relates to modulating the molecular events involved in autoimmunity and inflammation. These proteins can be assayed in a variety of ways, including both in vitro (cell culture models) and in vivo (animal models). The development of over-expressing cell lines can also be used to determine the effect of the newly isolated human LRR proteins on the induction of TNF-α, NFκB activation and various cytokine release profiles after stimulation with bacterial derived lipopolysaccharide (LPS).

Example 7

Phage Display Methods for Identifying Peptide Ligands or Modulators of Human LRR Creation of Peptide Libraries Two types of libraries may be created: i) libraries of 12- and 15-mer peptides for finding peptides that may function as (ant-)agonists; and ii) libraries of peptides with 23–33 random residues that are for finding natural ligands through database searches.

The 15-mer library may be i) an aliquot of the fUSE5-based 15-mer library originally constructed by G P Smith (Scott, J K and Smith, G P. 1990, *Science* 249, 386–390). Such a library may be made essentially as described therein; or ii) a library that is constructed at Bristol-Myers Squibb Company in vector M13KE (New England Biolabs) using a single-stranded library oligonucleotide extension method (S. S. Sidhu, H. B. Lowman, B. C. Cunningham, J. A. Wells. *Methods Enzymol.*, 328: 333–363, 2000).

The 12 mer library is an aliquot of the M13KE-based 'PhD' 12 mer library (New England Biolabs).

The libraries with 27–33 random residues are also constructed at Bristol-Myers Squibb Company in vector M13KE (New England Biolabs) using the method described in (S. S. Sidhu, H. B. Lowman, B. C. Cunningham, J. A. Wells. *Methods Enzymol.*, 328: 333–363, 2000).

All libraries in vector M13KE utilize the standard NNK motif to encode the specified number of random residues, where N=A+G+C+T and where K=G+T.

Sequencing of Bound Phage

Standard procedure: Phage in eluates are infected into *E. coli* host strain (TG1 for fUSE5-based 15 mer library; ER2738 (New England Biolabs) for all M13KE-based libraries) and are plated for single colonies (fUSE5 vector) or plaques (all M13KE-based libraries). Colonies are grown in liquid and sequenced by standard procedure which involves 1) generating PCR product with suitable primers that anneal adjacent to the library segments in the vectors; and 2) sequencing of the PCR products using one primer of each PCR primer pair. Sequences are analyzed for homologies by visual inspection or by using the Vector NTI alignment tool.

Peptide Synthesis

Peptides are synthesized on Fmoc-Knorr amide resin [N-(9-fluorenyl)methoxycarbonyl-Knorr amide-resin, Midwest Biotech; Fishers, IN] with an Applied Biosystems (Foster City, Calif.) model 433A synthesizer and the Fast-Moc chemistry protocol (0.25 mmol scale) supplied with the instrument. Amino acids are double coupled as their N-alpha-Fmoc derivatives and reactive side chains are protected as follows: Asp, Glu: t-Butyl ester (OtBu); Ser, Thr, Tyr: t-Butyl ether (tBu); Asn, Cys, Gln, His: Triphenylmethyl (Trt); Lys, Trp: t-Butyloxycarbonyl (Boc); Arg: 2,2,4,6,7-Pentamethyldihydrobenzofuran-5-sulfonyl (Pbf). After the final double coupling cycle, the N-terminal Fmoc group is removed by the multi-step treatment with piperidine in N-Methylpyrrolidone described by the manufacturer. The N-terminal free amines are then treated with 10% acetic anhydride, 5% Diisopropylamine in N-Methylpyrrolidone to yield the N-acetyl-derivative. The protected peptidyl-resins are simultaneously deprotected and removed from the resin by standard methods. The lyophilized peptides are purified on $C_{18}$ to apparent homogeneity as judged by RP-HPLC analysis. Predicted peptide molecular weights are verified by electrospray mass spectrometry (Burke, J., et al. *J. Biol. Chem.* 273:12041–12046, 1998)

Cyclic analogs are prepared from the crude linear products. The cysteine disulfide may be formed using one of the following methods:

Method 1

A sample of the crude peptide is dissolved in water at a concentration of 0.5 mg/mL and the pH adjusted to 8.5 with $NH_4OH$. The reaction is stirred, open to room air, and monitored by RP-HPLC. Once complete, the reaction is brought to pH 4 with acetic acid and lyophilized. The product is purified and characterized as above.

Method 2

A sample of the crude peptide is dissolved at a concentration of 0.5 mg/mL in 5% acetic acid. The pH is adjusted to 6.0 with NH$_4$OH. DMSO (20% by volume) is added and the reaction is stirred overnight. After analytical RP-HPLC analysis, the reaction is diluted with H$_2$O and triple lyophilized to remove DMSO. The crude product is purified by preparative RP-HPLC. (*JACS*. 113:6657, 1991)

Assessing Affect of Peptides on GPCR Function

The effect of any one of these peptides on the function of the GPCR of the present invention can be determined by adding an effective amount of each peptide to each functional assay. Representative functional assays are described more specifically herein.

Uses of the Peptide Modulators of the Present Invention

The aforementioned peptides of the present invention are useful for a variety of purposes, though most notably for modulating the function of the HLRRNS-2 and/or HLRRNS-3 polypeptides of the present invention, and potentially with other leucine rich repeat proteins known in the art. For example, the peptide modulators of the present invention may be useful as HLRRNS-2 and/or HLRRNS-3 polypeptide agonists. Alternatively, the peptide modulators of the present invention may be useful as HLRRNS-2 and/or HLRRNS-3 polypeptide antagonists of the present invention. In addition, the peptide modulators of the present invention may be useful as competitive inhibitors of the HLRRNS-2 and/or HLRRNS-3 cognate ligand(s), or may be useful as non-competitive inhibitors of the HLRRNS-2 and/or HLRRNS-3 protein cognate ligand(s).

Furthermore, the peptide modulators of the present invention may be useful in assays designed to either identify the endogenous ligand(s) of the HLRRNS-2 and/or HLRRNS-3 polypeptides of the present invention, or to identify other agonists or antagonists of the HLRRNS-2 and/or HLRRNS-3 polypeptides of the present invention, particularly small molecule modulators.

Example 8

Method of Enhancing the Biological Activity or Functional Characteristics of Human LRR Protein Through Molecular Evolution Although many of the most biologically active proteins known are highly effective for their specified function in an organism, they often possess characteristics that make them undesirable for transgenic, therapeutic, pharmaceutical, and/or industrial applications. Among these traits, a short physiological half-life is the most prominent problem, and is present either at the level of the protein, or at the level of the protein's mRNA. The ability to extend the half-life, for example, would be particularly important for a protein's use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to enhancing specific characteristics of the human LRR proteins of the invention through directed molecular evolution. Such an enhancement can, in a non-limiting example, benefit the invention's utility as an essential component in a kit, the invention's physical attributes such as its solubility, structure, or codon optimization, the invention's specific biological activity, including any associated enzymatic activity, the protein's enzyme kinetics, the proteins $K_t$, $K_{cat}$, $K_m$, $V_{max}$, $K_d$, protein-protein activity, protein-DNA binding activity, antagonist/inhibitory activity (including direct or indirect interaction), agonist activity (including direct or indirect interaction), the protein's antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use as a preventative treatment for disease or disease states, or as an effector for targeting diseased genes. Moreover, the ability to enhance specific characteristics of a protein can also be applicable to changing the characterized activity of an enzyme to an activity completely unrelated to its initially characterized activity. Other desirable enhancements of the invention are specific to each individual protein, and thus are well known in the art and contemplated by the present invention.

For example, an engineered leucine-rich repeat protein may be constitutively active upon binding of its cognate ligand. Alternatively, an engineered leucine-rich repeat protein may be constitutively active in the absence of ligand binding. In yet another example, an engineered leucine-rich repeat protein may be capable of being activated with less than all of the regulatory factors and/or conditions typically required for leucine-rich repeat protein activation (e.g., ligand binding, phosphorylation, conformational changes, etc.). Such leucine-rich repeat proteins would be useful in screens to identify leucine-rich repeat protein modulators, among other uses described herein.

Directed evolution comprises several steps. The first step is to establish a library of variants for the gene or protein of interest. The most important step is to then select for those variants having the activity of interest. The design of the screen is essential since the screen should be selective enough to eliminate non-useful variants, yet not too stringent as to eliminate all variants. The last step is then to repeat the above steps using the best variant from the previous screen. Each successive cycle, can then be tailored as necessary, such as increasing the stringency of the screen, for example.

There have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, *Molecular Cloning: A Laboratory Manual*, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR, as described by Moore, J., et al. (*Nature Biotechnology* 14:458, 1996), or through the application of randomized synthetic oligonucleotides corresponding to specific regions of interest as described by Derbyshire, K. M. et al. (*Gene*, 46:145–152, 1986), and Hill, D E, et al. (*Methods Enzymol.*, 55:559–568, 1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis can counter or inhibit the desired benefit of a useful mutation.

While both of the aforementioned methods are effective for creating randomized pools of macromolecule variants, a third method, termed "DNA Shuffling", or "sexual PCR" (W P C, Stemmer, *Proc. Natl. Acad. Sci., USA*, 91:10747, (1994)) has recently been elucidated. DNA shuffling has also been referred to as "directed molecular evolution", "exon-shuffling", "directed enzyme evolution", "in vitro evolution", and "artificial evolution." Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also can hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments—further diversifying the potential hybridization sites during the annealing step of the reaction.

A variety of reaction conditions could be utilized to carry-out the DNA shuffling reaction. However, specific reaction conditions for DNA shuffling are provided, for example, by Stemmer, et al. (*Proc. Natl. Acad. Sci., USA*, 91:10747–51, 1994). Briefly, the DNA substrate to be subjected to the DNA shuffling reaction is prepared. Preparation can be in the form of simply purifying the DNA from contaminating cellular material, chemicals, buffers, oligonucleotide primers, deoxynucleotides, RNAs, etc., and can entail the use of DNA purification kits as those provided by Qiagen, Inc., or by the Promega, Corp., for example.

Once the DNA substrate has been purified, it is subjected to Dnase I digestion. About 2–4 µg of the DNA substrate(s) are digested with 0.0015 units of Dnase I (Sigma) per microliter in 100 µl of 50 µM Tris-HCL, pH 7.4/1 mM $MgCl_2$ for 10–20 min. at room temperature. The resulting fragments of 10–50 bp are then purified by running them through a 2% low-melting point agarose gel by electrophoresis onto DE81 ion-exchange paper (Whatmann), purified using Microcon concentrators (Amicon) of the appropriate molecular weight cutoff, or by using oligonucleotide purification columns (Qiagen), in addition to other methods known in the art. If using DE81 ion-exchange paper, the 10–50 bp fragments are eluted from the paper using 1M NaCl, followed by ethanol precipitation.

The resulting purified fragments are then subjected to a PCR assembly reaction by re-suspending in a PCR mixture containing: 2 mM of each dNTP, 2.2 mM $MgCl_2$, 50 mM KCl, 10 mM Tris•HCL, pH 9.0, and 0.1% Triton X-100, at a final fragment concentration of 10–30 ng/µl. No primers are added at this point. Taq DNA polymerase (Promega) is used at 2.5 units per 100 ul of reaction mixture. A PCR program of 94° C. for 60 s; 94° C. for 30 s, 50–55° C. for 30 s, and 72° C. for 30 s using 30–45 cycles, followed by 72° C. for 5 min using an MJ Research PTC-150 thermocycler (Cambridge, Mass.). After the assembly reaction is completed, a 1:40 dilution of the resulting primeness product is then introduced into a PCR mixture (the same buffer mixture used for the assembly reaction) containing 0.8 µM of each primer and subjecting this mixture to 15 cycles of PCR (using 94° C. for 30 s, 50° C. for 30 s, and 72° C. for 30 s). The preferred primers are those primers corresponding to the nucleic acid sequences of the polynucleotide(s) utilized in the shuffling reaction. The primers consist of modified nucleic acid base pairs using methods commonly known in the art and referred to elsewhere herein, or contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations are obvious to the skilled artisan and are encompassed by the invention. The DNA shuffling method can also be tailored to the desired level of mutagenesis using the methods described by Zhao, et al. (*Nucl Acid Res.*, 25(6):1307–1308, 1997).

As described above, once the randomized pool has been created, it is then subjected to a specific screen identifying the variant possessing the desired characteristic(s). Once the variant has been identified, DNA corresponding to the variant is then used as the DNA substrate for initiating another round of DNA shuffling. This cycle of shuffling, selecting the optimized variant of interest, and then re-shuffling, are repeated until the ultimate variant is obtained. Examples of model screens applied to identify variants created using DNA shuffling technology can be found in the following publications: Moore, J. C. et al., *J. Mol. Biol.*, 272:336–347, 1997), Cross, F. R. et al., *Mol. Cell. Biol.*, 18:2923–2931, 1998), and Crameri., A. et al., *Nat. Biotech.*, 15:436–438, 1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has evolved up to a 16,000 fold increase over the wild-type form of the enzyme. In essence, the background mutagenesis yields the genetic variability on which recombination acts to enhance the activity.

A third feature of recombination is its use for removing deleterious mutations. As discussed above, during the process of the randomization, for every one beneficial mutation, there is at least one or more neutral or inhibitory mutations. Such mutations can be removed by including in the assembly reaction an excess of the wild-type random-sized fragments, in addition to the random-sized fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it is possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention can be created and isolated using DNA shuffling technology. Such a variant has all of the desired characteristics, though can be highly immunogenic in a host due to its novel intrinsic structure. Specifically, the desired characteristic can cause the polypeptide to have a non-native structure which no longer is recognized as a "self" molecule, rather as a "foreign" molecule, and thus activate a host immune response directed against the novel variant. Such a limitation can be overcome, for example, by combining a copy of the gene sequence for a xenobiotic ortholog of the native protein with the gene sequence of the novel variant gene in one or more cycles of DNA shuffling. The molar ratio of the ortholog and novel variant DNAs are varied accordingly. Ideally, the resulting hybrid variant identified contains at least some of the coding sequence which enables the xenobiotic protein to evade the host immune system, and additionally, the coding sequence of the original novel variant that provides the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and/or combination of the above.

In addition to the aforementioned methods, there are a number of related methods that can also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve the invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., *Nat. Biotech.*, 15:436–438, (1997), respectively.

Additional methods of applying "DNA Shuffling" technology to the polynucleotides and polypeptides of the present invention, including their proposed applications, can be found in U.S. Pat. No. 5,605,793; PCT Application No. WO 95/22625; PCT Application No. WO 97/20078; PCT Application No. WO 97/35966; and PCT Application No. WO 98/42832. PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species. Each of the above are hereby incorporated in their entirety herein for all purposes.

Example 9

Method of Discovering Additional Single Nucleotide Polymorphisms (SNPS)

Additional SNPs can be discovered in the polynucleotides of the present invention based on comparative DNA sequencing of PCR products derived from genomic DNA from multiple individuals. The genomic DNA samples can be purchased from Coriell Institute (Collingswood, N.J.). PCR amplicons can be designed to cover the entire coding region of the exons using the Primer3 program (Rozen S, *Methods Mol. Biol.* 132: 365–386, 2000). Exon-intron structure of candidate genes and intron sequences can be obtained by BLASTN search of Genbank cDNA sequences against the human genome draft sequences. The sizes of these PCR amplicons vary according to the exon-intron structure. All the samples can be amplified from genomic DNA (20 ng) in 50 µl reactions containing 10 mM Tris-Cl pH 8.3, 50 mM KCl, 2.5 mM $MgCl_2$, 150 uM dNTPs, 3 uM PCR primers, and 3.75 U TaqGold DNA polymerase (PE Biosystems).

PCR is performed in MJ Research Tetrad machines under a cycling condition of 94 degrees 10 min, 30 cycles of 94 degrees 30 sec, 60 degrees 30 sec, and 72 degrees 30 sec, followed by 72 degrees 7 min. PCR products are purified using QIAquick PCR purification kit (Qiagen) and are sequenced by the dye-terminator method using PRISM 3700 automated DNA sequencer (Applied Biosystems; Foster City, Calif.) following the manufacturer's instruction outlined in the Owner's Manual (which is hereby incorporated herein by reference in its entirety). Sequencing results can be analyzed for the presence of polymorphisms using Poly-Phred software (Nickerson D A, Nuc. Acids Res. 25: 2745–2751, 1997; Rieder M J, et al. Nat. Genet. 22:59–62, 1999). All of the sequence traces of potential polymorphisms can be visually inspected to confirm the presence of SNPs.

Alternative methods for identifying SNPs of the present invention are known in the art. One such method involves resequencing of target sequences from individuals of diverse ethnic and geographic backgrounds by hybridization to probes immobilized to microfabricated arrays. The strategy and principles for the design and use of such arrays are generally described in WO 95/11995.

A typical probe array used in such an analysis has two groups of four sets of probes that respectively tile both strands of a reference sequence. A first probe set comprises a plurality of probes exhibiting perfect complementarily with one of the reference sequences. Each probe in the first probe set has an interrogation position that corresponds to a nucleotide in the reference sequence. That is, the interrogation position is aligned with the corresponding nucleotide in the reference sequence, when the probe and reference sequence are aligned to maximize complementarily between the two. For each probe in the first set, there are three corresponding probes from three additional probe sets. Thus, there are four probes corresponding to each nucleotide in the reference sequence. The probes from the three additional probe sets are identical to the corresponding probe from the first probe set except at the interrogation position, which occurs in the same position in each of the four corresponding probes from the four probe sets, and is occupied by a different nucleotide in the four probe sets. In the present analysis, probes are 17–22 nucleotides long. Arrays tiled for multiple different references sequences are included on the same substrate.

Publicly available sequences for a given gene are assembled into Gap4. PCR primers covering each exon are designed, for example, using Primer 3. Primers are not designed in regions where there are sequence discrepancies between reads. Genomic DNA is amplified from at least two individuals using 2.5 pmol of each primer, 1.5 mM $MgCl_2$, 100 µM dNTPs, 0.75 µM AMPLITAQ GOLD™ polymerase, and about 19 ng DNA in a 15 µl reaction. Reactions are assembled using a PACKARD MultiPROBE robotic pipetting station and then put into MJ 96-well tetrad thermocyclers (96° C. for minutes, followed by cycles of 96° C. for seconds, 59° C. for 2 minutes, and 72° C. for 2 minutes). A subset of the PCR assays for each individual could then be run on 3% NuSieve gels in 0.5× TBE for reaction confirmation.

For a given DNA, 5 µl (about 50 ng) of each PCR or RT-PCR product is pooled (Final volume=150–200 ul). The products are purified using QiaQuick PCR purification from Qiagen. The samples are then eluted once in 35 µl sterile water and 4 µl 10× One-Phor-All buffer (Pharmacia). The pooled samples are then digested with 0.2 U DNaseI (Promega) for 10 minutes at 37° C. and then labeled with 0.5 nmols biotin-N6-ddATP and 15 u Terminal Transferase (GibcoBRL Life Technology) for 60 minutes at 37° C. Both fragmentation and labeling reactions are terminated by incubating the pooled sample for 15 minutes at 100° C.

Low-density DNA chips (Affymetrix, Calif.) are hybridized following the manufacturer's instructions. Briefly, the hybridization cocktail consists of 3M TMACl, mM Tris pH 7.8, 0.01% Triton X-100, 100 mg/ml herring sperm DNA (Gibco BRL), and 200 pM control biotin-labeled oligo. The processed PCR products are then denatured for 7 minutes at 100° C. and then added to prewarmed (37° C.) hybridization solution. The chips are hybridized overnight at 44° C. Chips are washed in 1×SSPET and 6×SSPET followed by staining with 2 µg/ml SARPE and 0.5 mg/ml acetylated BSA in 200 µl of 6×SSPET for 8 minutes at room temperature. Chips are scanned using a Molecular Dynamics scanner.

Chip image files are analyzed using Ulysses (Affymetrix, Calif.) which uses four algorithms to identify potential polymorphisms. Candidate polymorphisms can be visually inspected and assigned a confidence value: where high confidence candidates display all three genotypes, while likely candidates show only two genotypes (homozygous for reference sequence and heterozygous for reference and variant). Some of the candidate polymorphisms can be confirmed by ABI sequencing. Identified polymorphisms are then compared to several databases to determine if they are in fact novel.

Example 10

Method of Determining the Allele Frequency for Each SNP

Allele frequencies of a SNP can be determined by genotyping various DNA samples (Coriell Institute; Collingswood, N.J.) using FP-TDI assay (Chen, X. et al. *Genome Res.* 9:492–498, 1999). Automated genotyping calls are made with an allele calling software developed by Joel Hirschorn (Whitehead Institute/MIT Center for Genome Research).

Briefly, the no template controls (NTCs) are labeled accordingly in column C. The appropriate cells can be completed in column L indicating whether REF (homozygous ROX) or VAR (homozygous TAMRA) are expected to be rare genotypes (<10% of all samples)—the latter is important in helping the program to identify rare homozygotes. The number of 96 well plates genotyped in cell P2 are noted (generally between 0.5 and 4)—the program works best if this is accurate. No more than 384 samples are analyzed at a time. The pairs of mP values from the LJL can be pasted into columns E and F; making sure there is no residual data left at the bottom, fewer than 384 data points are provided. The DNA names can be provided in columns A, B or C; column I will be a concatenation of columns A, B and C. In addition, the well numbers for each sample can be also provided in column D.

With the above information provided, the program automatically cluster the points and identifies genotypes. The program works by converting the mP values into polar coordinates (distance from origin and angle from origin) with the angle being on a scale from 0 to 2; heterozygotes are placed as close to 1 as possible. The cutoff values in columns L and M are adjusted as desired.

Expert parameters or the most important parameters are the maximum angle for REF and minimum angle for VAR. These parameters need to be changed in a particularly skewed assay which is observed when an REF or VAR cluster is close to an angle of 1 and has called as a failed or HETs.

Other parameters are low and high cutoffs that are used to determine which points are considered for the determination of edges of the clusters. With a small number of data points, the high cutoff needs to be increased (to 500 or so). This is the proper protocol for every assay, but certainly when the program fails to identify a small cluster with high signal. NTC TAMRA and ROX indicate the position of the no template control or failed samples as estimated by the computer algorithm.

No signal=mP< represents the threshold below which points are automatically considered failures. "Throw out points with signal above" is the TAMRA or ROX mP value above which points are considered failures. The latter occasionally needs to be adjusted from 250 to 300, but caveat emptor for assays with signals >250. 'Lump' or ' split' describes a subtle difference in the way points are grouped into clusters. Lump generally is better. 'HETs expected' in the rare case where only homozygotes of either class are expected (e.g. a study of X chromosome SNPs in males), change this to "N".

For a method of clustering, the origin is defined by the NTCs or other low signal points (the position of the origin is shown as "NTC TAMRA" and "NTC ROX"); the points with very low or high signal are not considered initially. The program finds the point farthest from the origin and calls that a HET; the ROX/TAMRA ratio is calculated from this point, placing the heterozygotes at 45 degrees from the origin (an angle of "1"). The angles from the origin are calculated (the scale ranges from 0 to 2) and used to define clusters. A histogram of angles is generated. The cluster boundaries are defined by an algorithm that takes into account the shape of the histogram. The homozygote clusters are defined as the leftmost and rightmost big clusters (unless the allele is specified as being rare, in which case the cluster need not be big). The heterozygote is the biggest cluster in between the REF and VAR. If there are two equal clusters, the one best-separated from REF and VAR is called HET. All other clusters are failed. Some fine tuning is applied to lump in scattered points on the edges of the clusters (if "Lump" is selected). The boundaries of the clusters are "Angles" in column L.

Once the clusters are defined, the interquartile distance of signal intensity is defined for each cluster. Points falling more than 3 or 4 interquartiles from the mean are excluded. (These are the "Signal cutoffs" in column M).

The invention encompasses additional methods of determining the allelic frequency of the SNPs of the present invention. Such methods are known in the art, some of which are described elsewhere herein.

Example 11

Alternative Methods of Detecting Polymorphisms

Preparation of Samples

Polymorphisms are detected in a target nucleic acid from an individual being analyzed. For genomic DNA assays, virtually any biological sample (other than pure red blood cells) is suitable. For example, convenient tissue samples include whole blood, semen, saliva, tears, urine, fecal material, sweat, buccal, skin and hair. For cDNA or mRNA assays, the tissue sample must be obtained from an organ in which the target nucleic acid is expressed. For example, if the target nucleic acid is a cytochrome P450, the liver is a suitable source.

Many of the methods described below require amplification of DNA from target samples. This can be accomplished by PCR, for example. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19: 4967, 1991; Eckert et al., *PCR Methods and Applications* 1, 1991; *PCR* (eds. McPherson et al., IRL Press, Oxford); and U.S. Pat. No. 4,683,202.

Other suitable amplification methods include the ligase chain reaction (LCR) (see Wu and Wallace, *Genomics* 4:560 (1989); Landegren et al., *Science* 241:1077 (1988); transcription amplification (Kwoh et al., *Proc. Natl. Acad. Sci. USA* 86, 1173 (1989); and self-sustained sequence replication (Guatelli et al., *Proc. Nat. Acad. Sci. USA*, 87:1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Additional methods of amplification are known in the art or are described elsewhere herein.

Detection of Polymorphisms in Target DNA

There are two distinct types of analysis of target DNA for detecting polymorphisms. The first type of analysis, sometimes referred to as de novo characterization, is carried out to identify polymorphic sites not previously characterized (i.e., to identify new polymorphisms). This analysis compares target sequences in different individuals to identify points of variation, i.e., polymorphic sites. By analyzing groups of individuals representing the greatest ethnic diversity among humans and greatest breed and species variety in plants and animals, patterns characteristic of the most common alleles/haplotypes of the locus are identified, and the frequencies of such alleles/haplotypes in the population are determined. Additional allelic frequencies are determined for subpopulations characterized by criteria such as geography, race, or gender. The de novo identification of polymorphisms of the invention is described in the Examples section.

The second type of analysis determines which form(s) of a characterized (known) polymorphism is present in individuals under test. Additional methods of analysis are known in the art or are described elsewhere herein.

Allele-Specific Probes

The design and use of allele-specific probes for analyzing polymorphisms is described by e.g., Saiki et al. *Nature* 324:163–166, 1986; Dattagupta, EP 235,726; Saiki, WO 89/11548. Allele-specific probes are designed to hybridize to a segment of target DNA from one individual but do not hybridize to the corresponding segment from another individual due to the presence of different polymorphic forms in the respective segments from the two individuals. Hybridization conditions are sufficiently stringent in that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15-mer at the 7 position; in a 16-mer, at either the 8 or 9 position) of the probe. This probe design achieves good discrimination in hybridization between different allelic forms.

Allele-specific probes are often used in pairs, one member of a pair showing a perfect match to a reference form of a target sequence and the other member showing a perfect match to a variant form. Several pairs of probes are then immobilized on the same support for simultaneous analysis of multiple polymorphisms within the same target sequence.

Tiling Arrays

The polymorphisms are also identified by hybridization to nucleic acid arrays, some examples of which are described in WO 95/11995. The same arrays or different arrays are used for analysis of characterized polymorphisms. WO 95/11995 also describes subarrays that are optimized for detection of a variant form of a precharacterized polymorphism. Such a subarray contains probes designed to be complementary to a second reference sequence, which is an allelic variant of the first reference sequence. The second group of probes is designed by the same principles as described, except that the probes exhibit complementarity to the second reference sequence. The inclusion of a second group (or further groups) is particularly useful for analyzing short subsequences of the primary reference sequence in which multiple mutations are expected to occur within a short distance commensurate with the length of the probes (e.g., two or more mutations within 9 to bases).

Allele-Specific Primers

An allele-specific primer hybridizes to a site on target DNA overlapping a polymorphism and only primes amplification of an allelic form to which the primer exhibits perfect complementarity. [See Gibbs, *Nucleic Acid Res.* 17:2427–2448, 1989]. This primer is used in conjunction with a second primer which hybridizes at a distal site. Amplification proceeds from the two primers, resulting in a detectable product which indicates that the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing elongation from the primer (see, e.g., WO 93/22456).

Direct-Sequencing

The direct analysis of the sequence of polymorphisms of the present invention is accomplished using either the dideoxy chain termination method or the Maxam-Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)).

Denaturing Gradient Gel Electrophoresis

Amplification products generated using the polymerase chain reaction are analyzed by using denaturing gradient gel electrophoresis. Different alleles are identified by the different sequence-dependent melting properties and electrophoretic migration of DNA in solution. [Erlich, ed., *PCR Technology. Principles and Applications for DNA Amplification*, W. H. Freeman and Co, New York, 1992, Chapter 7].

Single-Stranded Conformation Polymorphism Analysis

Alleles of target sequences are differentiated using single-stranded conformation polymorphism analysis, which identifies base differences by an alteration in electrophoretic migration of single-stranded PCR products, as described by Orita et al. (*Proc. Nat. Acad. Sci.* 86:2766–2770, 1989). Amplified PCR products are generated as described above, and heated or otherwise denatured, to form single-stranded amplification products. Single-stranded nucleic acids can refold or form secondary structures which are partially dependent on the base sequence. The different electrophoretic mobilities of single-stranded amplification products are related to base-sequence differences between alleles of target sequences.

Single Base Extension

An alternative method for identifying and analyzing polymorphisms is based on single-base extension (SBE) of a fluorescently-labeled primer coupled with fluorescence resonance energy transfer (FRET) between the label of the added base and the label of the primer. Typically, the method, such as that described by Chen et al. (*Proc. Natl. Acad. Sci., USA* 94:10756–61, 1997), uses a locus-specific oligonucleotide primer labeled on the 5' terminus with 5-carboxyfluorescein (FAM). This labeled primer is designed so that the 3' end is immediately adjacent to the polymorphic site of interest. The labeled primer is hybridized to the locus, and single base extension of the labeled primer is performed with fluorescently-labeled dideoxyribonucleotides (ddNTPs) in dye-terminator sequencing fashion. An increase in fluorescence of the added ddNTP in response to excitation at the wavelength of the labeled primer is used to infer the identity of the added nucleotide.

Example 12

Method of Creating N- and C-Terminal Deletion Mutants Corresponding to the HLRRNS-2 or HLRRNS-3 Polypeptide of the Present Invention The present invention also encompasses the creation of N- and C-terminal deletion mutants, in addition to any combination of N- and C-terminal deletions thereof, corresponding to the HLRRNS-2 or HLRRNS-3 polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length HLRRNS-2 or HLRRNS-3 polypeptide sequence (as described in herein, for example), appropriate primers of about 15–25 nucleotides derived from the desired 5' and 3' positions of SEQ ID NO:1 or SEQ ID NO:3 may be designed to PCR amplify, and subsequently clone, the intended N- and/or C-terminal deletion mutant. Such primers could comprise, for example, an initiation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the A30 to N590 HLRRNS-2 N-terminal deletion mutant, the following primers could be used to amplify a cDNA fragment corresponding to this deletion mutant:

```
5' Primer 6'-GCAGCA GCGGCCGC GCTCAGAGAGCTTGCCCAAAGAAC-3'    (SEQ ID NO:66)
                   NotI 3' Primer 5'-GCAGCA GTCGAC GTTTGCAATTCTCTCTAGGTAGATG-3'    (SEQ ID NO:67)
                   SalI
```

For example, in the case of the M1 to I301 HLRRNS-2 C-terminal deletion mutant, the following primers could be used to amplify a cDNA fragment corresponding to this deletion mutant:

```
5' Primer 5'-GCAGCA GCGGCCGC ATGGGTTTCCATTTAATTACGCAGC-3'    (SEQ ID NO:68)
                   NotI 3' Primer 5'-GCAGCA GTCGAC TATCCACGCATTGACAGTTTCCTG-3'       (SEQ ID NO:69)
                   SalI
```

For example, in the case of the N87 to L845 HLRRNS-3 N-terminal deletion mutant, the following primers could be used to amplify a cDNA fragment corresponding to this deletion mutant:

```
5' Primer 5'-GCAGCA GCGGCCGC AACGCGGTGACTCTTCACCTAGG-3'    (SEQ ID NO:70)
                   NotI 3' Primer 5'-GCAGCA GTCGAC CAGCTGACTGATTGCAGTTTG-3'        (SEQ ID NO:71)
                   SalI
```

For example, in the case of the M1 to P519 HLRRNS-3 C-terminal deletion mutant, the following primers could be used to amplify a cDNA fragment corresponding to this deletion mutant:

```
5' Primer 5'-GCAGCA GCGGCCGC ATGCTGAGCGGCGTTTGGTTCCTC-3'    (SEQ ID NO:72)
                   NotI 3' Primer 5'-GCAGCA GTCGAC CGGGAGCTGATCCAGAACCCCTTTC-3'     (SEQ ID NO:73)
                   SalI
```

Representative PCR amplification conditions are provided below, although the skilled artisan would appreciate that other conditions may be required for efficient amplification. A 100 ul PCR reaction mixture may be prepared using 10 ng of the template DNA (cDNA clone of HLRRNS-2 or HLRRNS-3), 200 uM 4 dNTPs, 1 uM primers, 0.25 U Taq DNA polymerase (PE), and standard Taq DNA polymerase buffer. Typical PCR cycling condition are as follows:

| | |
|---|---|
| 20–25 cycles: | 45 sec, 93 degrees |
| | 2 min, 50 degrees |
| | 2 min, 72 degrees |
| 1 cycle: | 10 min, 72 degrees |

After the final extension step of PCR, 5U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). . The skilled artisan would appreciate that other plasmids could be equally substituted, and may be desirable in certain circumstances. The digested fragment and vector are then ligated using a DNA ligase, and then used to transform competent E.coli cells using methods provided herein and/or otherwise known in the art.

The 5' primer sequence for amplifying any additional N-terminal deletion mutants may be determined by reference to the following formula: $(S+(X*3))$ to $((S+(X*3))+25)$, wherein 'S' is equal to the nucleotide position of the initiating start codon of the HLRRNS-2 or HLRRNS-3 gene (SEQ ID NO:1 or SEQ ID NO:3), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1 or SEQ ID NO:3. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula: (S+(X*3)) to ((S+(X*3))–25), wherein 'S' is equal to the nucleotide position of the initiating start codon of the HLRRNS-2 or HLRRNS-3 gene (SEQ ID NO:1 or SEQ ID NO:3), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1 or SEQ ID NO:3. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

Example 13

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84–86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

Human IgG Fc region:

(SEQ ID NO:74)
GGGATCCGGAGCCCAAATCTTCTGACAAAACTCACACATGCCCACC

GTGCCCAGCACCTGAATTCGAGGGTGCACCGTCAGTCTTCCTCTTCCCCCC

AAAACCCAAGGACACCCTCATGATCTCCCGGACTCCTGAGGTCACATGCG

TGGTGGTGGACGTAAGCCACGAAGACCCTGAGGTCAAGTTCAACTGGTAC

GTGGACGGCGTGGAGGTGCATAATGCCAAGACAAAGCCGCGGGAGGAGC

AGTACAACAGCACGTACCGTGTGGTCAGCGTCCTCACCGTCCTGCACCAG

GACTGGCTGAATGGCAAGGAGTACAAGTGCAAGGTCTCCAACAAAGCCCT

CCCAACCCCCATCGAGAAAACCATCTCCAAAGCCAAAGGGCAGCCCCGAG

AACCACAGGTGTACACCCTGCCCCCATCCCGGGATGAGCTGACCAAGAAC

CAGGTCAGCCTGACCTGCCTGGTCAAAGGCTTCTATCCAAGCGACATCGC

CGTGGAGTGGGAGAGCAATGGGCAGCCGGAGAACAACTACAAGACCACG

CCTCCCGTGCTGGACTCCGACGGCTCCTTCTTCCTCTACAGCAAGCTCACC

GTGGACAAGAGCAGGTGGCAGCAGGGGAACGTCTTCTCATGCTCCGTGAT

GCATGAGGCTCTGCACAACCACTACACGCAGAAGAGCCTCTCCCTGTCTC

CGGGTAAATGAGTGCGACGGCCGCGACTCTAGAGGAT

Example 14

Production of an Antibody From a Polypeptide

The antibodies of the present invention can be prepared by a variety of methods. (See, Current Protocols, Chapter 2.) As one example of such methods, cells expressing a polypeptide of the present invention are administered to an animal to induce the production of sera containing polyclonal antibodies. In a preferred method, a preparation of the protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

The contents of all patents, patent applications, published PCT applications and articles, books, references, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A method of diagnosing Alzheimer's disease comprising:
   a) determining the expression level of a polypeptide comprising the sequence of SEQ ID NO:2 in a normal brain sample and a brain test sample, wherein the samples are both derived from either the temporal cortex or hippocampus subregions of the brain; and
   b) comparing said expression level of said polypeptide from said brain test sample with said expression level of said polypeptide from said normal sample; wherein an elevated expression level of said polypeptide in said test sample relative to the expression level of said polypeptide in said normal sample is indicative of Alzheimer's disease.

2. The method according to claim 1, wherein said expression level is determined by the transcript level of RNA encoding said polypeptide.

3. The method according to claim 1, wherein said expression level is determined by protein measurement.

4. The method according to claim 2, wherein the RNA measurement comprises specific hybridization between said RNA to a member of the group consisting of:
   a) an isolated nucleic acid consisting of SEQ ID NO: 1;
   b) an isolated nucleic acid consisting of nucleotides 343 to 2112 of SEQ ID NO:1;
   c) an isolated nucleic acid consisting of nucleotides 346 to 2112 of SEQ ID NO:1; and
   d) an isolated nucleic acid consisting of the complementary sequence of (a), (b), or (c).

5. The method according to claim 2, wherein the RNA measurement comprises specific hybridization between said RNA to an isolated nucleic acid consisting of at least 12 contiguous nucleotides of SEQ ID NO:1, or the complement thereof.

6. The method according to claim 2, wherein the RNA measurement comprises two isolated nucleic acids consisting of at least 12 contiguous nucleotides of SEQ ID NO:1, or the complement thereof, wherein one nucleic acid is directed to the sense strand, and the other nucleic acid is directed to the antisense strand.

7. The method according to claim 3, wherein said protein measurement comprises detecting a member of the group consisting of:
   a.) an isolated polypeptide consisting of SEQ ID NO:2;
   b.) an isolated polypeptide consisting of amino acids 1 to 590 of SEQ ID NO:2; and
   c.) an isolated polypeptide consisting of nucleotides 2 to 590 of SEQ ID NO:2.

8. The method according to claim 3, wherein said protein measurement utilizes an antibody that specifically binds to said polypeptide.

9. A method for diagnosing Alzheimer's disease comprising:
   a) determining transcript level of RNA encoding a polypeptide comprising SEQ ID NO:2 in a normal brain sample and in a brain test sample, wherein the samples are both derived from either the temporal cortex or hippocampus subregions of the brain; and
   b) comparing said transcript level of said mRNA from the brain test sample with said transcript level of said RNA from the normal brain sample; wherein an elevated transcript level of said RNA in said test sample relative to the transcript level of said RNA in said normal sample is indicative of Alzheimer's disease.

10. The method according to claim 9, wherein said RNA transcript level determination comprises specific hybridization between said RNA to a member of the group consisting of:
    a) an isolated nucleic acid consisting of SEQ ID NO:1;
    b) an isolated nucleic acid consisting of nucleotides 343 to 2112 of SEQ ID NO:1;
    c) an isolated nucleic acid consisting of nucleotides 346 to 2112 of SEQ ID NO:1; and
    d) an isolated nucleic acid consisting of the complementary sequence of (a), (b), or (c).

11. The method according to claim 9, wherein said RNA transcript level determination comprises specific hybridization between said RNA to an isolated nucleic acid consisting of at least 12 contiguous nucleotides of SEQ ID NO:1, or the complement thereof.

12. The method according to claim 9, wherein the RNA measurement comprises two isolated nucleic acids consisting of at least 12 contiguous nucleotides of SEQ ID NO:1, or the complement thereof, wherein one nucleic acid is directed to the sense strand, and the other nucleic acid is directed to the antisense strand.

* * * * *

UNITED STATES PATENT AND TRADEMARK OFFICE
CERTIFICATE OF CORRECTION

| | |
|---|---|
| PATENT NO. | : 7,141,381 B2 |
| APPLICATION NO. | : 10/424233 |
| DATED | : November 28, 2006 |
| INVENTOR(S) | : John N. Feder, Gabriel Mintier and Chandra S. Ramanathan |

It is certified that error appears in the above-identified patent and that said Letters Patent is hereby corrected as shown below:

Column 170, Line 16 - please delete "mRNA" and add --RNA--

Signed and Sealed this

Sixteenth Day of March, 2010

David J. Kappos
*Director of the United States Patent and Trademark Office*

SEQUENCE LISTING

```
<160> NUMBER OF SEQ ID NOS: 75

<210> SEQ ID NO 1
<211> LENGTH: 2267
<212> TYPE: DNA
<213> ORGANISM: Homo sapiens
<220> FEATURE:
<221> NAME/KEY: CDS
<222> LOCATION: (343)..(2112)

<400> SEQUENCE: 1
ggacaagggc tgcctcccag cacagctaca aaacacttta aacctgacca gctaaatgga       60
taaacctagc ctgcatagct tttaaactgg ggtctcatac agcacaggag gcctacttgc      120
ttcaagaact gaaaatccag aggatgaatt gctttatctg ggaatggcaa aagccagcac      180
aataaggaat gccagtttgt atggggctac tagctcacat gcgggatcag aatggtgtga      240
atgacagccg cactgtgtca tgaaggtggt ggtggtttcc gcacaagaga ccaaataaga      300
agaaagctga gagagggggg aaacgttttt ggatgacaaa gg atg ggt ttc cat        354
                                                 Met Gly Phe His
                                                  1 tta att acg cag ctg aaa ggc atg agt gtg gtg ctg gtg cta ctt cct        402
Leu Ile Thr Gln Leu Lys Gly Met Ser Val Val Leu Val Leu Leu Pro
 5                  10                  15                  20 aca ctg ctg ctt gtt atg ctc acg ggt gct cag aga gct tgc cca aag        450
Thr Leu Leu Leu Val Met Leu Thr Gly Ala Gln Arg Ala Cys Pro Lys
                 25                  30                  35 aac tgc aga tgt gat ggc aaa att gtg tac tgt gag tct cat gct ttc        498
Asn Cys Arg Cys Asp Gly Lys Ile Val Tyr Cys Glu Ser His Ala Phe
```

-continued

```
                 40                       45                       50
gca gat atc cct gag aac att tct gga ggg tca caa ggc tta tca tta      546
Ala Asp Ile Pro Glu Asn Ile Ser Gly Gly Ser Gln Gly Leu Ser Leu
         55                       60                       65 agg ttc aac agc att cag aag ctc aaa tcc aat cag ttt gcc ggc ctt      594
Arg Phe Asn Ser Ile Gln Lys Leu Lys Ser Asn Gln Phe Ala Gly Leu
 70                       75                       80 aac cag ctt ata tgg ctt tat ctt gac cat aat tac att agc tca gtg      642
Asn Gln Leu Ile Trp Leu Tyr Leu Asp His Asn Tyr Ile Ser Ser Val
 85                       90                       95                      100 gat gaa gat gca ttt caa ggg atc cgt aga ctg aaa gaa tta att cta      690
Asp Glu Asp Ala Phe Gln Gly Ile Arg Arg Leu Lys Glu Leu Ile Leu
                        105                      110                      115 agc tcc aac aaa att act tat ctg cac aat aaa aca ttt cac cca gtt      738
Ser Ser Asn Lys Ile Thr Tyr Leu His Asn Lys Thr Phe His Pro Val
                 120                      125                      130 ccc aat ctc cgc aat ctg gac ctc tcc tac aat aag ctt cag aca ttg      786
Pro Asn Leu Arg Asn Leu Asp Leu Ser Tyr Asn Lys Leu Gln Thr Leu
         135                      140                      145 caa tct gaa caa ttt aaa ggc ctt cgg aaa ctc atc att ttg cac ttg      834
Gln Ser Glu Gln Phe Lys Gly Leu Arg Lys Leu Ile Ile Leu His Leu
 150                      155                      160 aga tct aac tca cta aag act gtg ccc ata aga gtt ttt caa gac tgt      882
Arg Ser Asn Ser Leu Lys Thr Val Pro Ile Arg Val Phe Gln Asp Cys
165                      170                      175                      180 cgg aat ctt gat ttt ttg gat ttg ggt tac aat cgt ctt cga agc ttg      930
Arg Asn Leu Asp Phe Leu Asp Leu Gly Tyr Asn Arg Leu Arg Ser Leu
                        185                      190                      195 tcc cga aat gca ttt gct ggc ctc ttg aag tta aag gag ctc cac ctg      978
Ser Arg Asn Ala Phe Ala Gly Leu Leu Lys Leu Lys Glu Leu His Leu
                 200                      205                      210 gag cac aac cag ttt tcc aag atc aac ttt gct cat ttt cca cgt ctc     1026
Glu His Asn Gln Phe Ser Lys Ile Asn Phe Ala His Phe Pro Arg Leu
         215                      220                      225 ttc aac ctc cgc tca att tac tta caa tgg aac agg att cgc tcc att     1074
Phe Asn Leu Arg Ser Ile Tyr Leu Gln Trp Asn Arg Ile Arg Ser Ile
 230                      235                      240 agc caa ggt ttg aca tgg act tgg agt tcc tta cac aac ttg gat tta     1122
Ser Gln Gly Leu Thr Trp Thr Trp Ser Ser Leu His Asn Leu Asp Leu
245                      250                      255                      260 tca ggg aat gac atc caa gga att gag ccg ggc aca ttt aaa tgc ctc     1170
Ser Gly Asn Asp Ile Gln Gly Ile Glu Pro Gly Thr Phe Lys Cys Leu
                        265                      270                      275 ccc aat tta caa aaa ttg aat ttg gat tcc aac aag ctc acc aat atc     1218
Pro Asn Leu Gln Lys Leu Asn Leu Asp Ser Asn Lys Leu Thr Asn Ile
                 280                      285                      290 tca cag gaa act gtc aat gcg tgg ata tca tta ata tcc atc aca ttg     1266
Ser Gln Glu Thr Val Asn Ala Trp Ile Ser Leu Ile Ser Ile Thr Leu
         295                      300                      305 tct gga aat atg tgg gaa tgc agt cgg agc att tgt cct tta ttt tat     1314
Ser Gly Asn Met Trp Glu Cys Ser Arg Ser Ile Cys Pro Leu Phe Tyr
 310                      315                      320 tgg ctt aag aat ttc aaa gga aat aag gaa agc acc atg ata tgt gcg     1362
Trp Leu Lys Asn Phe Lys Gly Asn Lys Glu Ser Thr Met Ile Cys Ala
325                      330                      335                      340 gga cct aag cac atc cag ggt gaa aag gtt agt gat gca gtg gaa aca     1410
Gly Pro Lys His Ile Gln Gly Glu Lys Val Ser Asp Ala Val Glu Thr
                        345                      350                      355 tat aat atc tgt tct gaa gtc cag gtg gtc aac aca gaa aga tca cac     1458
```

```

Tyr Asn Ile Cys Ser Glu Val Gln Val Val Asn Thr Glu Arg Ser His
        360                 365                 370 ctg gtg ccc caa act ccc cag aaa cct ctg att atc cct aga cct acc     1506
Leu Val Pro Gln Thr Pro Gln Lys Pro Leu Ile Ile Pro Arg Pro Thr
            375                 380                 385 atc ttc aaa cct gac gtc acc caa tcc acc ttt gaa aca cca agc cct     1554
Ile Phe Lys Pro Asp Val Thr Gln Ser Thr Phe Glu Thr Pro Ser Pro
390                 395                 400 tcc cca ggg ttt cag att cct ggc gca gag caa gag tat gag cat gtt     1602
Ser Pro Gly Phe Gln Ile Pro Gly Ala Glu Gln Glu Tyr Glu His Val
405                 410                 415                 420 tca ttt cac aaa att att gcc ggg agt gtg gct ctc ttt ctc tca gtg     1650
Ser Phe His Lys Ile Ile Ala Gly Ser Val Ala Leu Phe Leu Ser Val
                425                 430                 435 gcc atg atc ctc ttg gtg atc tat gtg tct tgg aaa cgc tac cca gcc     1698
Ala Met Ile Leu Leu Val Ile Tyr Val Ser Trp Lys Arg Tyr Pro Ala
            440                 445                 450 agc atg aaa caa ctc cag caa cac tct ctt atg aag agg cgg cgg aaa     1746
Ser Met Lys Gln Leu Gln Gln His Ser Leu Met Lys Arg Arg Arg Lys
        455                 460                 465 aag gcc aga gag tct gaa aga caa atg aat tcc cct tta cag gag tat     1794
Lys Ala Arg Glu Ser Glu Arg Gln Met Asn Ser Pro Leu Gln Glu Tyr
    470                 475                 480 tat gtg gac tac aag cct aca aac tct gag acc atg gat ata tcg gtt     1842
Tyr Val Asp Tyr Lys Pro Thr Asn Ser Glu Thr Met Asp Ile Ser Val
485                 490                 495                 500 aat gga tct ggg ccc tgc aca tat acc atc tct ggc tcc agg gaa tgt     1890
Asn Gly Ser Gly Pro Cys Thr Tyr Thr Ile Ser Gly Ser Arg Glu Cys
                505                 510                 515 gag atg cca cac cac atg aag ccc ttg cca tat tac agc tat gac cag     1938
Glu Met Pro His His Met Lys Pro Leu Pro Tyr Tyr Ser Tyr Asp Gln
            520                 525                 530 cct gtg atc ggg tac tgc cag gcc cac cag cca ctc cat gtc acc aag     1986
Pro Val Ile Gly Tyr Cys Gln Ala His Gln Pro Leu His Val Thr Lys
        535                 540                 545 ggc tat gag aca gtg tct cca gag cag gac gaa agc ccc ggc ctg gag     2034
Gly Tyr Glu Thr Val Ser Pro Glu Gln Asp Glu Ser Pro Gly Leu Glu
    550                 555                 560 ctg ggc cga gac cac agc ttc atc gcc acc atc gcc agg tcg gca gca     2082
Leu Gly Arg Asp His Ser Phe Ile Ala Thr Ile Ala Arg Ser Ala Ala
565                 570                 575                 580 ccg gcc atc tac cta gag aga att gca aac taacgctgaa gccaactcct        2132
Pro Ala Ile Tyr Leu Glu Arg Ile Ala Asn
                585                 590 cactggggag ctccatgggg gggagggagg cccttcatct taaggagaa tgggtgtcca    2192 caatcgcgca atcgagcaag ctcatcgttc ctgttaaaac atttatggca tagagaaaag   2252
aaaaaaaaaa aaaaa                                                    2267

<210> SEQ ID NO 2
<211> LENGTH: 590
<212> TYPE: PRT
<213> ORGANISM: Homo sapiens

<400> SEQUENCE: 2

Met Gly Phe His Leu Ile Thr Gln Leu Lys Gly Met Ser Val Val Leu
1               5                   10                  15

Val Leu Leu Pro Thr Leu Leu Leu Val Met Leu Thr Gly Ala Gln Arg
            20                  25                  30
```

-continued

```
Ala Cys Pro Lys Asn Cys Arg Cys Asp Gly Lys Ile Val Tyr Cys Glu
            35                  40                  45

Ser His Ala Phe Ala Asp Ile Pro Glu Asn Ile Ser Gly Gly Ser Gln
        50                  55                  60

Gly Leu Ser Leu Arg Phe Asn Ser Ile Gln Lys Leu Lys Ser Asn Gln
65                  70                  75                  80

Phe Ala Gly Leu Asn Gln Leu Ile Trp Leu Tyr Leu Asp His Asn Tyr
                85                  90                  95

Ile Ser Ser Val Asp Glu Asp Ala Phe Gln Gly Ile Arg Arg Leu Lys
            100                 105                 110

Glu Leu Ile Leu Ser Ser Asn Lys Ile Thr Tyr Leu His Asn Lys Thr
        115                 120                 125

Phe His Pro Val Pro Asn Leu Arg Asn Leu Asp Leu Ser Tyr Asn Lys
    130                 135                 140

Leu Gln Thr Leu Gln Ser Glu Gln Phe Lys Gly Leu Arg Lys Leu Ile
145                 150                 155                 160

Ile Leu His Leu Arg Ser Asn Ser Leu Lys Thr Val Pro Ile Arg Val
                165                 170                 175

Phe Gln Asp Cys Arg Asn Leu Asp Phe Leu Asp Leu Gly Tyr Asn Arg
            180                 185                 190

Leu Arg Ser Leu Ser Arg Asn Ala Phe Ala Gly Leu Leu Lys Leu Lys
        195                 200                 205

Glu Leu His Leu Glu His Asn Gln Phe Ser Lys Ile Asn Phe Ala His
    210                 215                 220

Phe Pro Arg Leu Phe Asn Leu Arg Ser Ile Tyr Leu Gln Trp Asn Arg
225                 230                 235                 240

Ile Arg Ser Ile Ser Gln Gly Leu Thr Trp Thr Trp Ser Ser Leu His
                245                 250                 255

Asn Leu Asp Leu Ser Gly Asn Asp Ile Gln Gly Ile Glu Pro Gly Thr
            260                 265                 270

Phe Lys Cys Leu Pro Asn Leu Gln Lys Leu Asn Leu Asp Ser Asn Lys
        275                 280                 285

Leu Thr Asn Ile Ser Gln Glu Thr Val Asn Ala Trp Ile Ser Leu Ile
    290                 295                 300

Ser Ile Thr Leu Ser Gly Asn Met Trp Glu Cys Ser Arg Ser Ile Cys
305                 310                 315                 320

Pro Leu Phe Tyr Trp Leu Lys Asn Phe Lys Gly Asn Lys Glu Ser Thr
                325                 330                 335

Met Ile Cys Ala Gly Pro Lys His Ile Gln Gly Glu Lys Val Ser Asp
            340                 345                 350

Ala Val Glu Thr Tyr Asn Ile Cys Ser Glu Val Gln Val Val Asn Thr
        355                 360                 365

Glu Arg Ser His Leu Val Pro Gln Thr Pro Gln Lys Pro Leu Ile Ile
    370                 375                 380

Pro Arg Pro Thr Ile Phe Lys Pro Asp Val Thr Gln Ser Thr Phe Glu
385                 390                 395                 400

Thr Pro Ser Pro Ser Pro Gly Phe Gln Ile Pro Gly Ala Glu Gln Glu
                405                 410                 415

Tyr Glu His Val Ser Phe His Lys Ile Ile Ala Gly Ser Val Ala Leu
            420                 425                 430

Phe Leu Ser Val Ala Met Ile Leu Leu Val Ile Tyr Val Ser Trp Lys
        435                 440                 445

Arg Tyr Pro Ala Ser Met Lys Gln Leu Gln Gln His Ser Leu Met Lys
```

```
                   450                  455                 460
Arg Arg Arg Lys Lys Ala Arg Glu Ser Glu Arg Gln Met Asn Ser Pro
465                 470                 475                 480

Leu Gln Glu Tyr Tyr Val Asp Tyr Lys Pro Thr Asn Ser Glu Thr Met
                    485                 490                 495

Asp Ile Ser Val Asn Gly Ser Gly Pro Cys Thr Tyr Thr Ile Ser Gly
                500                 505                 510

Ser Arg Glu Cys Glu Met Pro His Met Lys Pro Leu Pro Tyr Tyr
            515                 520                 525

Ser Tyr Asp Gln Pro Val Ile Gly Tyr Cys Gln Ala His Gln Pro Leu
        530                 535                 540

His Val Thr Lys Gly Tyr Glu Thr Val Ser Pro Glu Gln Asp Glu Ser
545                 550                 555                 560

Pro Gly Leu Glu Leu Gly Arg Asp His Ser Phe Ile Ala Thr Ile Ala
                565                 570                 575

Arg Ser Ala Ala Pro Ala Ile Tyr Leu Glu Arg Ile Ala Asn
                580                 585                 590

<210> SEQ ID NO 3
<211> LENGTH: 3719
<212> TYPE: DNA
<213> ORGANISM: Homo sapiens
<220> FEATURE:
<221> NAME/KEY: CDS
<222> LOCATION: (247)..(2781)

<400> SEQUENCE: 3
tcctgattcc tgattttcca cccccttttt gcgcttttt tttttttcct aaagcgattg        60
cgatttctgc tgggagctca agacgggcga gctgcccgag atctcttcga gatacccccag      120 gggaggagga gatgggcagg atttagtagg acaactcggt tactaatgac ttggcggctg      180
gctgcgaccc cccgggaaat caggtttgcc tgtaggtacc tgagttgaca ccgaaggtgc      240 ctaaag atg ctg agc ggc gtt tgg ttc ctc agt gtg tta acc gtg gcc      288
       Met Leu Ser Gly Val Trp Phe Leu Ser Val Leu Thr Val Ala
       1               5                  10 ggg atc tta cag aca gag agt cgc aaa act gcc aaa gac att tgc aag       336
Gly Ile Leu Gln Thr Glu Ser Arg Lys Thr Ala Lys Asp Ile Cys Lys
15              20                  25                  30 atc cgc tgt ctg tgc gaa gaa aag gaa aac gta ctg aat atc aac tgt       384
Ile Arg Cys Leu Cys Glu Glu Lys Glu Asn Val Leu Asn Ile Asn Cys
                35                  40                  45 gag aac aaa gga ttt aca aca gtt agc ctg ctc cag ccc ccc cag tat       432
Glu Asn Lys Gly Phe Thr Thr Val Ser Leu Leu Gln Pro Pro Gln Tyr
            50                  55                  60 cga atc tat cag ctt ttt ctc aat gga aac ctc ttg aca aga ctg tat       480
Arg Ile Tyr Gln Leu Phe Leu Asn Gly Asn Leu Leu Thr Arg Leu Tyr
        65                  70                  75 cca aac gaa ttt gtc aat tac tcc aac gcg gtg act ctt cac cta ggt       528
Pro Asn Glu Phe Val Asn Tyr Ser Asn Ala Val Thr Leu His Leu Gly
    80                  85                  90 aac aac ggg tta cag gag atc cga aca ggg gca ttc agt ggc ctg aaa       576
Asn Asn Gly Leu Gln Glu Ile Arg Thr Gly Ala Phe Ser Gly Leu Lys
95                  100                 105                 110 act ctc aaa aga ctg cat ctc aac aac aac aag ctt gag ata ttg agg       624
Thr Leu Lys Arg Leu His Leu Asn Asn Asn Lys Leu Glu Ile Leu Arg
                115                 120                 125 gag gac acc ttc cta ggc ctg gag agc ctg gag tat ctc cag gcc gac       672
Glu Asp Thr Phe Leu Gly Leu Glu Ser Leu Glu Tyr Leu Gln Ala Asp
```

-continued

|  |  |  |  |  |  |  |  |  |  |  |  |  |  |  |  |
|---|---|---|---|---|---|---|---|---|---|---|---|---|---|---|---|
| | | 130 | | | | 135 | | | | | 140 | | | | |
| tac | aat | tac | atc | agt | gcc | atc | gag | gct | ggg | gca | ttc | agc | aaa | ctt | aac | 720 |
| Tyr | Asn | Tyr | Ile | Ser | Ala | Ile | Glu | Ala | Gly | Ala | Phe | Ser | Lys | Leu | Asn |
| | | 145 | | | | 150 | | | | 155 | | | | | |

```
tac aat tac atc agt gcc atc gag gct ggg gca ttc agc aaa ctt aac    720
Tyr Asn Tyr Ile Ser Ala Ile Glu Ala Gly Ala Phe Ser Lys Leu Asn
        145             150                 155 aag ctc aaa gtg ctc atc ctg aat gac aac ctt ctg ctt tca ctg ccc    768
Lys Leu Lys Val Leu Ile Leu Asn Asp Asn Leu Leu Leu Ser Leu Pro
    160             165                 170 agc aat gtg ttc cgc ttt gtc ctg ctg acc cac tta gac ctc agg ggg    816
Ser Asn Val Phe Arg Phe Val Leu Leu Thr His Leu Asp Leu Arg Gly
175             180                 185                 190 aat agg cta aaa gta atg cct ttt gct ggc gtc ctt gaa cat att gga    864
Asn Arg Leu Lys Val Met Pro Phe Ala Gly Val Leu Glu His Ile Gly
            195                 200                 205 ggg atc atg gag att cag ctg gag gaa aat cca tgg aat tgc act tgt    912
Gly Ile Met Glu Ile Gln Leu Glu Glu Asn Pro Trp Asn Cys Thr Cys
        210                 215                 220 gac tta ctt cct ctc aag gcc tgg cta gac acc ata act gtt ttt gtg    960
Asp Leu Leu Pro Leu Lys Ala Trp Leu Asp Thr Ile Thr Val Phe Val
            225                 230                 235 gga gag att gtc tgt gag act ccc ttt agg ttg cat ggg aaa gac gtg   1008
Gly Glu Ile Val Cys Glu Thr Pro Phe Arg Leu His Gly Lys Asp Val
    240                 245                 250 acc cag ctg acc agg caa gac ctc tgt ccc aga aaa agt gcc agt gat   1056
Thr Gln Leu Thr Arg Gln Asp Leu Cys Pro Arg Lys Ser Ala Ser Asp
255                 260                 265                 270 tcc agt cag agg ggc agc cat gct gac acc cac gtc caa agg ctg tca   1104
Ser Ser Gln Arg Gly Ser His Ala Asp Thr His Val Gln Arg Leu Ser
            275                 280                 285 cct aca atg aat cct gct ctc aac cca acc agg gct ccg aaa gcc agc   1152
Pro Thr Met Asn Pro Ala Leu Asn Pro Thr Arg Ala Pro Lys Ala Ser
        290                 295                 300 cgg ccg ccc aaa atg aga aat cgt cca act ccc cga gtg act gtg tca   1200
Arg Pro Pro Lys Met Arg Asn Arg Pro Thr Pro Arg Val Thr Val Ser
305                 310                 315 aag gac agg caa agt ttt gga ccc atc atg gtg tac cag acc aag tct   1248
Lys Asp Arg Gln Ser Phe Gly Pro Ile Met Val Tyr Gln Thr Lys Ser
320                 325                 330 cct gtg cct ctc acc tgt ccc agc agc tgt gtc tgc acc tct cag agc   1296
Pro Val Pro Leu Thr Cys Pro Ser Ser Cys Val Cys Thr Ser Gln Ser
335                 340                 345                 350 tca gac aat ggt ctg aat gta aac tgc caa gaa agg aag ttc act aat   1344
Ser Asp Asn Gly Leu Asn Val Asn Cys Gln Glu Arg Lys Phe Thr Asn
            355                 360                 365 atc tct gac ctg cag ccc aaa ccg acc agt cca aag aaa ctc tac cta   1392
Ile Ser Asp Leu Gln Pro Lys Pro Thr Ser Pro Lys Lys Leu Tyr Leu
        370                 375                 380 aca ggg aac tat ctt caa act gtc tat aag aat gac ctc tta gaa tac   1440
Thr Gly Asn Tyr Leu Gln Thr Val Tyr Lys Asn Asp Leu Leu Glu Tyr
    385                 390                 395 agt tct ttg gac tta ctg cac tta gga aac aac agg att gca gtc att   1488
Ser Ser Leu Asp Leu Leu His Leu Gly Asn Asn Arg Ile Ala Val Ile
400                 405                 410 cag gaa ggt gcc ttt aca aac ctg acc agt tta cgc aga ctt tat ctg   1536
Gln Glu Gly Ala Phe Thr Asn Leu Thr Ser Leu Arg Arg Leu Tyr Leu
415                 420                 425                 430 aat ggc aat tac ctt gaa gtg ctg tac cct tct atg ttt gat gga ctg   1584
Asn Gly Asn Tyr Leu Glu Val Leu Tyr Pro Ser Met Phe Asp Gly Leu
            435                 440                 445 cag agc ttg caa tat ctc tat tta gag tat aat gtc att aag gaa att   1632
```

```
Gln Ser Leu Gln Tyr Leu Tyr Leu Glu Tyr Asn Val Ile Lys Glu Ile
            450                 455                 460 aag cct ctg acc ttt gat gct ttg att aac cta cag cta ctg ttt ctg      1680
Lys Pro Leu Thr Phe Asp Ala Leu Ile Asn Leu Gln Leu Leu Phe Leu
        465                 470                 475 aac aac aac ctt ctt cgg tcc tta cct gat aat ata ttt ggg ggg acg      1728
Asn Asn Asn Leu Leu Arg Ser Leu Pro Asp Asn Ile Phe Gly Gly Thr
    480                 485                 490 gcc cta acc agg ctg aat ctg aga aac aac cat ttt tct cac ctg ccc      1776
Ala Leu Thr Arg Leu Asn Leu Arg Asn Asn His Phe Ser His Leu Pro
495                 500                 505                 510 gtg aaa ggg gtt ctg gat cag ctc ccg gct ttc atc cag ata gat ctg      1824
Val Lys Gly Val Leu Asp Gln Leu Pro Ala Phe Ile Gln Ile Asp Leu
            515                 520                 525 cag gag aac ccc tgg gac tgt acc tgt gac atc atg ggg ctg aaa gac      1872
Gln Glu Asn Pro Trp Asp Cys Thr Cys Asp Ile Met Gly Leu Lys Asp
        530                 535                 540 tgg aca gaa cat gcc aat tcc cct gtc atc att aat gag gtg act tgc      1920
Trp Thr Glu His Ala Asn Ser Pro Val Ile Ile Asn Glu Val Thr Cys
    545                 550                 555 gaa tct cct gct aag cat gca ggg gag ata cta aaa ttt ctg ggg agg      1968
Glu Ser Pro Ala Lys His Ala Gly Glu Ile Leu Lys Phe Leu Gly Arg
560                 565                 570 gag gct atc tgt cca gac agc cca aac ttg tca gat gga acc gtc ttg      2016
Glu Ala Ile Cys Pro Asp Ser Pro Asn Leu Ser Asp Gly Thr Val Leu
575                 580                 585                 590 tca atg aat cac aat aca gac aca cct cgg tcg ctt agt gtg tct cct      2064
Ser Met Asn His Asn Thr Asp Thr Pro Arg Ser Leu Ser Val Ser Pro
            595                 600                 605 agt tcc tat cct gaa cta cac act gaa gtt cca ctg tct gtc tta att      2112
Ser Ser Tyr Pro Glu Leu His Thr Glu Val Pro Leu Ser Val Leu Ile
        610                 615                 620 ctg gga ttg ctt gtt gtt ttc atc tta tct gtc tgt ttt ggg gct ggt      2160
Leu Gly Leu Leu Val Val Phe Ile Leu Ser Val Cys Phe Gly Ala Gly
    625                 630                 635 tta ttc gtc ttt gtc ttg aaa cgc cga aag gga gtg ccg agc gtt ccc      2208
Leu Phe Val Phe Val Leu Lys Arg Arg Lys Gly Val Pro Ser Val Pro
640                 645                 650 agg aat acc aac aac tta gac gta agc tcc ttt caa tta cag tat ggg      2256
Arg Asn Thr Asn Asn Leu Asp Val Ser Ser Phe Gln Leu Gln Tyr Gly
655                 660                 665                 670 tct tac aac act gag act cac gat aaa aca gac ggc cat gtc tac aac      2304
Ser Tyr Asn Thr Glu Thr His Asp Lys Thr Asp Gly His Val Tyr Asn
            675                 680                 685 tat atc ccc cca cct gtg ggt cag atg tgc caa aac ccc atc tac atg      2352
Tyr Ile Pro Pro Pro Val Gly Gln Met Cys Gln Asn Pro Ile Tyr Met
        690                 695                 700 cag aag gaa gga gac cca gta gcc tat tac cga aac ctg caa gag ttc      2400
Gln Lys Glu Gly Asp Pro Val Ala Tyr Tyr Arg Asn Leu Gln Glu Phe
    705                 710                 715 agc tat agc aac ctg gag gag aaa aaa gaa gag cca gcc aca cct gct      2448
Ser Tyr Ser Asn Leu Glu Glu Lys Lys Glu Glu Pro Ala Thr Pro Ala
720                 725                 730 tac aca ata agt gcc act gag ctg cta gaa aag cag gcc aca cca aga      2496
Tyr Thr Ile Ser Ala Thr Glu Leu Leu Glu Lys Gln Ala Thr Pro Arg
735                 740                 745                 750 gag cct gag ctg ctg tat caa aat att gct gag cga gtc aag gaa ctt      2544
Glu Pro Glu Leu Leu Tyr Gln Asn Ile Ala Glu Arg Val Lys Glu Leu
            755                 760                 765
```

-continued

| | |
|---|---|
| ccc agc gca ggc cta gtc cac tat aac ttt tgt acc tta cct aaa agg<br>Pro Ser Ala Gly Leu Val His Tyr Asn Phe Cys Thr Leu Pro Lys Arg<br>770                         775                   780 | 2592 |
| cag ttt gcc cct tcc tat gaa tct cga cgc caa aac caa gac aga atc<br>Gln Phe Ala Pro Ser Tyr Glu Ser Arg Arg Gln Asn Gln Asp Arg Ile<br>785                         790                   795 | 2640 |
| aat aaa acc gtt tta tat gga act ccc agg aaa tgc ttt gtg ggg cag<br>Asn Lys Thr Val Leu Tyr Gly Thr Pro Arg Lys Cys Phe Val Gly Gln<br>800                         805                   810 | 2688 |
| tca aaa ccc aac cac cct tta ctg caa gct aag ccg caa tca gaa ccg<br>Ser Lys Pro Asn His Pro Leu Leu Gln Ala Lys Pro Gln Ser Glu Pro<br>815                         820               825                 830 | 2736 |
| gac tac ctc gaa gtt ctg gaa aaa caa act gca atc agt cag ctg<br>Asp Tyr Leu Glu Val Leu Glu Lys Gln Thr Ala Ile Ser Gln Leu<br>                       835                 840               845 | 2781 |
| tgaagggaaa tcatttacaa ccctaaggca tcagaggatg ctgctccgaa ctgttggaaa | 2841 |
| caaggacatt agcttttgtg tttgtttttg ttctcccttt cccagtgtta atggggggact | 2901 |
| ttgaaaatgt ttgggagata ggatgaagtc atgattttgc ttttgcaagt tttcctttaa | 2961 |
| attatttctc tctcgctctc ctcccctcct ttttttttt ttttttttct ttttcccttc | 3021 |
| tcttcttagg aaccatcagt ggacatgaat gtttctacaa tgcatttctt catagatttt | 3081 |
| gtttatggtt ttgtttcttt ttcttcttt gttttcagt gtgggagtgg gaagaggaga | 3141 |
| ttatagtgac tgaagaaaga ataggcaaac ttttcaaatg aaaatggata tttagtgtat | 3201 |
| tttgtagaag atctccaaag atcttttgtg actacaactt cttttgtaaa taatgatata | 3261 |
| tggtatttcc atcgtcagtt accgagtata gccactgggt atcactactt tgtgttaaag | 3321 |
| tgccttcgca ctttaagtac attacttaaa tgttgctttt agctttgata aattgaaaat | 3381 |
| attttaatgt gttgtatttt tgaaattgaa aacactgtaa aatagattga tgtgtcagct | 3441 |
| atattaagtc aacgtacagt ttgcttgagt tatagaaacc agcctgtcat caaatgattc | 3501 |
| tagttctagg actttgtagg cttaactata aaatatttcc tttcctctgg gtttaagtga | 3561 |
| ttttatttaa gtcaactaag gggatttaac agtggactag aggtaataag ccacctcagt | 3621 |
| caggattaat aattcattaa taaaatatat ttaacccaaa aaaaaaaaa aaaaaaaaa | 3681 |
| aaaaaaaaa aaaaaaaaa aaaaaaaaa aaaaaaa | 3719 |

<210> SEQ ID NO 4
<211> LENGTH: 845
<212> TYPE: PRT
<213> ORGANISM: Homo sapiens

<400> SEQUENCE: 4

Met Leu Ser Gly Val Trp Phe Leu Ser Val Leu Thr Val Ala Gly Ile
1                 5                    10                  15

Leu Gln Thr Glu Ser Arg Lys Thr Ala Lys Asp Ile Cys Lys Ile Arg
               20                   25                   30

Cys Leu Cys Glu Glu Lys Glu Asn Val Leu Asn Ile Asn Cys Glu Asn
          35                     40                   45

Lys Gly Phe Thr Thr Val Ser Leu Leu Gln Pro Gln Tyr Arg Ile
    50                     55                   60

Tyr Gln Leu Phe Leu Asn Gly Asn Leu Leu Thr Arg Leu Tyr Pro Asn
65                 70                   75                   80

Glu Phe Val Asn Tyr Ser Asn Ala Val Thr Leu His Leu Gly Asn Asn
               85                   90                   95

Gly Leu Gln Glu Ile Arg Thr Gly Ala Phe Ser Gly Leu Lys Thr Leu

```
                 100                 105                 110
Lys Arg Leu His Leu Asn Asn Lys Leu Glu Ile Leu Arg Glu Asp
            115                 120                 125

Thr Phe Leu Gly Leu Glu Ser Leu Glu Tyr Leu Gln Ala Asp Tyr Asn
130                 135                 140

Tyr Ile Ser Ala Ile Glu Ala Gly Ala Phe Ser Lys Leu Asn Lys Leu
145                 150                 155                 160

Lys Val Leu Ile Leu Asn Asp Asn Leu Leu Leu Ser Leu Pro Ser Asn
            165                 170                 175

Val Phe Arg Phe Val Leu Leu Thr His Leu Asp Leu Arg Gly Asn Arg
            180                 185                 190

Leu Lys Val Met Pro Phe Ala Gly Val Leu Glu His Ile Gly Gly Ile
            195                 200                 205

Met Glu Ile Gln Leu Glu Glu Asn Pro Trp Asn Cys Thr Cys Asp Leu
            210                 215                 220

Leu Pro Leu Lys Ala Trp Leu Asp Thr Ile Thr Val Phe Val Gly Glu
225                 230                 235                 240

Ile Val Cys Glu Thr Pro Phe Arg Leu His Gly Lys Asp Val Thr Gln
            245                 250                 255

Leu Thr Arg Gln Asp Leu Cys Pro Arg Lys Ser Ala Ser Asp Ser Ser
            260                 265                 270

Gln Arg Gly Ser His Ala Asp Thr His Val Gln Arg Leu Ser Pro Thr
            275                 280                 285

Met Asn Pro Ala Leu Asn Pro Thr Arg Ala Pro Lys Ala Ser Arg Pro
            290                 295                 300

Pro Lys Met Arg Asn Arg Pro Thr Pro Arg Val Thr Val Ser Lys Asp
305                 310                 315                 320

Arg Gln Ser Phe Gly Pro Ile Met Val Tyr Gln Thr Lys Ser Pro Val
            325                 330                 335

Pro Leu Thr Cys Pro Ser Ser Cys Val Cys Thr Ser Gln Ser Ser Asp
            340                 345                 350

Asn Gly Leu Asn Val Asn Cys Gln Glu Arg Lys Phe Thr Asn Ile Ser
            355                 360                 365

Asp Leu Gln Pro Lys Pro Thr Ser Pro Lys Lys Leu Tyr Leu Thr Gly
            370                 375                 380

Asn Tyr Leu Gln Thr Val Tyr Lys Asn Asp Leu Leu Glu Tyr Ser Ser
385                 390                 395                 400

Leu Asp Leu Leu His Leu Gly Asn Asn Arg Ile Ala Val Ile Gln Glu
            405                 410                 415

Gly Ala Phe Thr Asn Leu Thr Ser Leu Arg Arg Leu Tyr Leu Asn Gly
            420                 425                 430

Asn Tyr Leu Glu Val Leu Tyr Pro Ser Met Phe Asp Gly Leu Gln Ser
            435                 440                 445

Leu Gln Tyr Leu Tyr Leu Glu Tyr Asn Val Ile Lys Glu Ile Lys Pro
            450                 455                 460

Leu Thr Phe Asp Ala Leu Ile Asn Leu Gln Leu Leu Phe Leu Asn Asn
465                 470                 475                 480

Asn Leu Leu Arg Ser Leu Pro Asp Asn Ile Phe Gly Gly Thr Ala Leu
            485                 490                 495

Thr Arg Leu Asn Leu Arg Asn Asn His Phe Ser His Leu Pro Val Lys
            500                 505                 510

Gly Val Leu Asp Gln Leu Pro Ala Phe Ile Gln Ile Asp Leu Gln Glu
            515                 520                 525
```

```
Asn Pro Trp Asp Cys Thr Cys Asp Ile Met Gly Leu Lys Asp Trp Thr
        530                 535                 540

Glu His Ala Asn Ser Pro Val Ile Ile Asn Glu Val Thr Cys Glu Ser
545                 550                 555                 560

Pro Ala Lys His Ala Gly Glu Ile Leu Lys Phe Leu Gly Arg Glu Ala
                565                 570                 575

Ile Cys Pro Asp Ser Pro Asn Leu Ser Asp Gly Thr Val Leu Ser Met
            580                 585                 590

Asn His Asn Thr Asp Thr Pro Arg Ser Leu Ser Val Ser Pro Ser Ser
        595                 600                 605

Tyr Pro Glu Leu His Thr Glu Val Pro Leu Ser Val Leu Ile Leu Gly
610                 615                 620

Leu Leu Val Val Phe Ile Leu Ser Val Cys Phe Gly Ala Gly Leu Phe
625                 630                 635                 640

Val Phe Val Leu Lys Arg Arg Lys Gly Val Pro Ser Val Pro Arg Asn
                645                 650                 655

Thr Asn Asn Leu Asp Val Ser Ser Phe Gln Leu Gln Tyr Gly Ser Tyr
            660                 665                 670

Asn Thr Glu Thr His Asp Lys Thr Asp Gly His Val Tyr Asn Tyr Ile
        675                 680                 685

Pro Pro Pro Val Gly Gln Met Cys Gln Asn Pro Ile Tyr Met Gln Lys
690                 695                 700

Glu Gly Asp Pro Val Ala Tyr Tyr Arg Asn Leu Gln Glu Phe Ser Tyr
705                 710                 715                 720

Ser Asn Leu Glu Glu Lys Lys Glu Glu Pro Ala Thr Pro Ala Tyr Thr
                725                 730                 735

Ile Ser Ala Thr Glu Leu Leu Glu Lys Gln Ala Thr Pro Arg Glu Pro
            740                 745                 750

Glu Leu Leu Tyr Gln Asn Ile Ala Glu Arg Val Lys Glu Leu Pro Ser
        755                 760                 765

Ala Gly Leu Val His Tyr Asn Phe Cys Thr Leu Pro Lys Arg Gln Phe
770                 775                 780

Ala Pro Ser Tyr Glu Ser Arg Arg Gln Asn Gln Asp Arg Ile Asn Lys
785                 790                 795                 800

Thr Val Leu Tyr Gly Thr Pro Arg Lys Cys Phe Val Gly Gln Ser Lys
                805                 810                 815

Pro Asn His Pro Leu Leu Gln Ala Lys Pro Gln Ser Glu Pro Asp Tyr
            820                 825                 830

Leu Glu Val Leu Glu Lys Gln Thr Ala Ile Ser Gln Leu
        835                 840                 845

<210> SEQ ID NO 5
<211> LENGTH: 622
<212> TYPE: PRT
<213> ORGANISM: Homo sapiens

<400> SEQUENCE: 5

Met Cys Gly Leu Gln Phe Ser Leu Pro Cys Leu Arg Leu Phe Leu Val
1               5                   10                  15

Val Thr Cys Tyr Leu Leu Leu Leu His Lys Glu Ile Leu Gly Cys
                20                  25                  30

Ser Ser Val Cys Gln Leu Cys Thr Gly Arg Gln Ile Asn Cys Arg Asn
            35                  40                  45

Leu Gly Leu Ser Ser Ile Pro Lys Asn Phe Pro Glu Ser Thr Val Phe
```

-continued

```
             50                  55                  60
Leu Tyr Leu Thr Gly Asn Asn Ile Ser Tyr Ile Asn Glu Ser Glu Leu
 65                  70                  75                  80

Thr Gly Leu His Ser Leu Val Ala Leu Tyr Leu Asp Asn Ser Asn Ile
                 85                  90                  95

Leu Tyr Val Tyr Pro Lys Ala Phe Val Gln Leu Arg His Leu Tyr Phe
                100                 105                 110

Leu Phe Leu Asn Asn Asn Phe Ile Lys Arg Leu Asp Pro Gly Ile Phe
            115                 120                 125

Lys Gly Leu Leu Asn Leu Arg Asn Leu Tyr Leu Gln Tyr Asn Gln Val
130                 135                 140

Ser Phe Val Pro Arg Gly Val Phe Asn Asp Leu Val Ser Val Gln Tyr
145                 150                 155                 160

Leu Asn Leu Gln Arg Asn Arg Leu Thr Val Leu Gly Ser Gly Thr Phe
                165                 170                 175

Val Gly Met Val Ala Leu Arg Ile Leu Asp Leu Ser Asn Asn Asn Ile
            180                 185                 190

Leu Arg Ile Ser Glu Ser Gly Phe Gln His Leu Glu Asn Leu Ala Cys
        195                 200                 205

Leu Tyr Leu Gly Ser Asn Asn Leu Thr Lys Val Pro Ser Asn Ala Phe
    210                 215                 220

Glu Val Leu Lys Ser Leu Arg Arg Leu Ser Leu Ser His Asn Pro Ile
225                 230                 235                 240

Glu Ala Ile Gln Pro Phe Ala Phe Lys Gly Leu Ala Asn Leu Glu Tyr
                245                 250                 255

Leu Leu Leu Lys Asn Ser Arg Ile Arg Asn Val Thr Arg Asp Gly Phe
            260                 265                 270

Ser Gly Ile Asn Asn Leu Lys His Leu Ile Leu Ser His Asn Asp Leu
            275                 280                 285

Glu Asn Leu Asn Ser Asp Thr Phe Ser Leu Leu Lys Asn Leu Ile Tyr
        290                 295                 300

Leu Lys Leu Asp Arg Asn Arg Ile Ile Ser Ile Asp Asn Asp Thr Phe
305                 310                 315                 320

Glu Asn Met Gly Ala Ser Leu Lys Ile Leu Asn Leu Ser Phe Asn Asn
                325                 330                 335

Leu Thr Ala Leu His Pro Arg Val Leu Lys Pro Leu Ser Ser Leu Ile
            340                 345                 350

His Leu Gln Ala Asn Ser Asn Pro Trp Glu Cys Asn Cys Lys Leu Leu
        355                 360                 365

Gly Leu Arg Asp Trp Leu Ala Ser Ser Ala Ile Thr Leu Asn Ile Tyr
    370                 375                 380

Cys Gln Asn Pro Pro Ser Met Arg Gly Arg Ala Leu Arg Tyr Ile Asn
385                 390                 395                 400

Ile Thr Asn Cys Val Thr Ser Ser Ile Asn Val Ser Arg Ala Trp Ala
                405                 410                 415

Val Val Lys Ser Pro His Ile His His Lys Thr Thr Ala Leu Met Met
            420                 425                 430

Ala Trp His Lys Val Thr Thr Asn Gly Ser Pro Leu Glu Asn Thr Glu
        435                 440                 445

Thr Glu Asn Ile Thr Phe Trp Glu Arg Ile Pro Thr Ser Pro Ala Gly
    450                 455                 460

Arg Phe Phe Gln Glu Asn Ala Phe Gly Asn Pro Leu Glu Thr Thr Ala
465                 470                 475                 480
```

Val Leu Pro Val Gln Ile Gln Leu Thr Thr Ser Val Thr Leu Asn Leu
            485                 490                 495

Glu Lys Asn Ser Ala Leu Pro Asn Asp Ala Ala Ser Met Ser Gly Lys
        500                 505                 510

Thr Ser Leu Ile Cys Thr Gln Glu Val Glu Lys Leu Asn Glu Ala Phe
        515                 520                 525

Asp Ile Leu Leu Ala Phe Phe Ile Leu Ala Cys Val Leu Ile Ile Phe
    530                 535                 540

Leu Ile Tyr Lys Val Val Gln Phe Lys Gln Lys Leu Lys Ala Ser Glu
545                 550                 555                 560

Asn Ser Arg Glu Asn Arg Leu Glu Tyr Tyr Ser Phe Tyr Gln Ser Ala
            565                 570                 575

Arg Tyr Asn Val Thr Ala Ser Ile Cys Asn Thr Ser Pro Asn Ser Leu
        580                 585                 590

Glu Ser Pro Gly Leu Glu Gln Ile Arg Leu His Lys Gln Ile Val Pro
        595                 600                 605

Glu Asn Glu Ala Gln Val Ile Leu Phe Glu His Ser Ala Leu
    610                 615                 620

<210> SEQ ID NO 6
<211> LENGTH: 591
<212> TYPE: PRT
<213> ORGANISM: Homo sapiens

<400> SEQUENCE: 6

Cys Ser Ser Val Cys Gln Leu Cys Thr Gly Arg Gln Ile Asn Cys Arg
1               5                   10                  15

Asn Leu Gly Leu Ser Ser Ile Pro Lys Asn Phe Pro Glu Ser Thr Val
            20                  25                  30

Phe Leu Tyr Leu Thr Gly Asn Asn Ile Ser Tyr Ile Asn Glu Ser Glu
        35                  40                  45

Leu Thr Gly Leu His Ser Leu Ala Leu Tyr Leu Asp Asn Ser Asn
    50                  55                  60

Ile Leu Tyr Val Tyr Pro Lys Ala Phe Val Gln Leu Arg His Leu Tyr
65                  70                  75                  80

Phe Leu Phe Leu Asn Asn Asn Phe Ile Lys Arg Leu Asp Pro Gly Ile
                85                  90                  95

Phe Lys Gly Leu Leu Asn Leu Arg Asn Leu Tyr Leu Gln Tyr Asn Gln
            100                 105                 110

Val Ser Phe Val Pro Arg Gly Val Phe Asn Asp Leu Val Ser Val Gln
        115                 120                 125

Tyr Leu Asn Leu Gln Arg Asn Arg Leu Thr Val Leu Gly Ser Gly Thr
    130                 135                 140

Phe Val Gly Met Val Ala Leu Arg Ile Leu Asp Leu Ser Asn Asn Asn
145                 150                 155                 160

Ile Leu Arg Ile Ser Glu Ser Gly Phe Gln His Leu Glu Asn Leu Ala
                165                 170                 175

Cys Leu Tyr Leu Gly Ser Asn Asn Leu Thr Lys Val Pro Ser Asn Ala
            180                 185                 190

Phe Glu Val Leu Lys Ser Leu Arg Arg Leu Ser Leu Ser His Asn Pro
        195                 200                 205

Ile Glu Ala Ile Gln Pro Phe Ala Phe Lys Gly Leu Ala Asn Leu Glu
    210                 215                 220

Tyr Leu Leu Leu Lys Asn Ser Arg Ile Arg Asn Val Thr Arg Asp Gly

```
             225                 230                 235                 240
     Phe Ser Gly Ile Asn Asn Leu Lys His Leu Ile Leu Ser His Asn Asp
                     245                 250                 255
     Leu Glu Asn Leu Asn Ser Asp Thr Phe Ser Leu Leu Lys Asn Leu Ile
                 260                 265                 270
     Tyr Leu Lys Leu Asp Arg Asn Arg Ile Ile Ser Ile Asp Asn Asp Thr
                 275                 280                 285
     Phe Glu Asn Met Gly Ala Ser Leu Lys Ile Leu Asn Leu Ser Phe Asn
                 290                 295                 300
     Asn Leu Thr Ala Leu His Pro Arg Val Leu Lys Pro Leu Ser Ser Leu
     305                 310                 315                 320
     Ile His Leu Gln Ala Asn Ser Asn Pro Trp Glu Cys Asn Cys Lys Leu
                         325                 330                 335
     Leu Gly Leu Arg Asp Trp Leu Ala Ser Ala Ile Thr Leu Asn Ile
                     340                 345                 350
     Tyr Cys Gln Asn Pro Pro Ser Met Arg Gly Arg Ala Leu Arg Tyr Ile
                     355                 360                 365
     Asn Ile Thr Asn Cys Val Thr Ser Ser Ile Asn Val Ser Arg Ala Trp
     370                 375                 380
     Ala Val Val Lys Ser Pro His Ile His His Lys Thr Thr Ala Leu Met
     385                 390                 395                 400
     Met Ala Trp His Lys Val Thr Thr Asn Gly Ser Pro Leu Glu Asn Thr
                     405                 410                 415
     Glu Thr Glu Asn Ile Thr Phe Trp Glu Arg Ile Pro Thr Ser Pro Ala
                 420                 425                 430
     Gly Arg Phe Phe Gln Glu Asn Ala Phe Gly Asn Pro Leu Glu Thr Thr
                     435                 440                 445
     Ala Val Leu Pro Val Gln Ile Gln Leu Thr Thr Ser Val Thr Leu Asn
                 450                 455                 460
     Leu Glu Lys Asn Ser Ala Leu Pro Asn Asp Ala Ala Ser Met Ser Gly
     465                 470                 475                 480
     Lys Thr Ser Leu Ile Cys Thr Gln Glu Val Glu Lys Leu Asn Glu Ala
                     485                 490                 495
     Phe Asp Ile Leu Leu Ala Phe Ile Leu Ala Cys Val Leu Ile Ile
                 500                 505                 510
     Phe Leu Ile Tyr Lys Val Val Gln Phe Lys Gln Lys Leu Lys Ala Ser
                 515                 520                 525
     Glu Asn Ser Arg Glu Asn Arg Leu Glu Tyr Tyr Ser Phe Tyr Gln Ser
                 530                 535                 540
     Ala Arg Tyr Asn Val Thr Ala Ser Ile Cys Asn Thr Ser Pro Asn Ser
     545                 550                 555                 560
     Leu Glu Ser Pro Gly Leu Glu Gln Ile Arg Leu His Lys Gln Ile Val
                     565                 570                 575
     Pro Glu Asn Glu Ala Gln Val Ile Leu Phe Glu His Ser Ala Leu
                     580                 585                 590

<210> SEQ ID NO 7
<211> LENGTH: 498
<212> TYPE: PRT
<213> ORGANISM: Homo sapiens

<400> SEQUENCE: 7

Cys Ser Ser Val Cys Gln Leu Cys Thr Gly Arg Gln Ile Asn Cys Arg
1               5                   10                  15
```

```
Asn Leu Gly Leu Ser Ser Ile Pro Lys Asn Phe Pro Glu Ser Thr Val
                20                  25                  30

Phe Leu Tyr Leu Thr Gly Asn Asn Ile Ser Tyr Ile Asn Glu Ser Glu
            35                  40                  45

Leu Thr Gly Leu His Ser Leu Val Ala Leu Tyr Leu Asp Asn Ser Asn
    50                  55                  60

Ile Leu Tyr Val Tyr Pro Lys Ala Phe Val Gln Leu Arg His Leu Tyr
 65                  70                  75                  80

Phe Leu Phe Leu Asn Asn Asn Phe Ile Lys Arg Leu Asp Pro Gly Ile
                85                  90                  95

Phe Lys Gly Leu Leu Asn Leu Arg Asn Leu Tyr Leu Gln Tyr Asn Gln
               100                 105                 110

Val Ser Phe Val Pro Arg Gly Val Phe Asn Asp Leu Val Ser Val Gln
            115                 120                 125

Tyr Leu Asn Leu Gln Arg Asn Arg Leu Thr Val Leu Gly Ser Gly Thr
    130                 135                 140

Phe Val Gly Met Val Ala Leu Arg Ile Leu Asp Leu Ser Asn Asn Asn
145                 150                 155                 160

Ile Leu Arg Ile Ser Glu Ser Gly Phe Gln His Leu Glu Asn Leu Ala
                165                 170                 175

Cys Leu Tyr Leu Gly Ser Asn Asn Leu Thr Lys Val Pro Ser Asn Ala
            180                 185                 190

Phe Glu Val Leu Lys Ser Leu Arg Arg Leu Ser Leu His Asn Pro
                195                 200                 205

Ile Glu Ala Ile Gln Pro Phe Ala Phe Lys Gly Leu Ala Asn Leu Glu
    210                 215                 220

Tyr Leu Leu Lys Asn Ser Arg Ile Arg Asn Val Thr Arg Asp Gly
225                 230                 235                 240

Phe Ser Gly Ile Asn Asn Leu Lys His Leu Ile Leu Ser His Asn Asp
                245                 250                 255

Leu Glu Asn Leu Asn Ser Asp Thr Phe Ser Leu Leu Lys Asn Leu Ile
            260                 265                 270

Tyr Leu Lys Leu Asp Arg Asn Arg Ile Ile Ser Ile Asp Asn Asp Thr
    275                 280                 285

Phe Glu Asn Met Gly Ala Ser Leu Lys Ile Leu Asn Leu Ser Phe Asn
290                 295                 300

Asn Leu Thr Ala Leu His Pro Arg Val Leu Lys Pro Leu Ser Ser Leu
305                 310                 315                 320

Ile His Leu Gln Ala Asn Ser Asn Pro Trp Glu Cys Asn Cys Lys Leu
                325                 330                 335

Leu Gly Leu Arg Asp Trp Leu Ala Ser Ser Ala Ile Thr Leu Asn Ile
            340                 345                 350

Tyr Cys Gln Asn Pro Pro Ser Met Arg Gly Arg Ala Leu Arg Tyr Ile
    355                 360                 365

Asn Ile Thr Asn Cys Val Thr Ser Ser Ile Asn Val Ser Arg Ala Trp
370                 375                 380

Ala Val Val Lys Ser Pro His Ile His Lys Thr Thr Ala Leu Met
385                 390                 395                 400

Met Ala Trp His Lys Val Thr Thr Asn Gly Ser Pro Leu Glu Asn Thr
                405                 410                 415

Glu Thr Glu Asn Ile Thr Phe Trp Glu Arg Ile Pro Thr Ser Pro Ala
            420                 425                 430

Gly Arg Phe Phe Gln Glu Asn Ala Phe Gly Asn Pro Leu Glu Thr Thr
```

```
                435                 440                 445
Ala Val Leu Pro Val Gln Ile Gln Leu Thr Thr Ser Val Thr Leu Asn
            450                 455                 460

Leu Glu Lys Asn Ser Ala Leu Pro Asn Asp Ala Ala Ser Met Ser Gly
465                 470                 475                 480

Lys Thr Ser Leu Ile Cys Thr Gln Glu Val Glu Lys Leu Asn Glu Ala
                485                 490                 495

Phe Asp

<210> SEQ ID NO 8
<211> LENGTH: 622
<212> TYPE: PRT
<213> ORGANISM: Homo sapiens

<400> SEQUENCE: 8

Met Cys Gly Leu Gln Phe Ser Leu Pro Cys Leu Arg Leu Phe Leu Val
1               5                   10                  15

Val Thr Cys Tyr Leu Leu Leu Leu His Lys Glu Ile Leu Gly Cys
            20                  25                  30

Ser Ser Val Cys Gln Leu Cys Thr Gly Arg Gln Ile Asn Cys Arg Asn
        35                  40                  45

Leu Gly Leu Ser Ser Ile Pro Lys Asn Phe Pro Glu Ser Thr Val Phe
    50                  55                  60

Leu Tyr Leu Thr Gly Asn Asn Ile Ser Tyr Ile Asn Glu Ser Glu Leu
65                  70                  75                  80

Thr Gly Leu His Ser Leu Val Ala Leu Tyr Leu Asp Asn Ser Asn Ile
                85                  90                  95

Leu Tyr Val Tyr Pro Lys Ala Phe Val Gln Leu Arg His Leu Tyr Phe
            100                 105                 110

Leu Phe Leu Asn Asn Asn Phe Ile Lys Arg Leu Asp Pro Gly Ile Phe
        115                 120                 125

Lys Gly Leu Leu Asn Leu Arg Asn Leu Tyr Leu Gln Tyr Asn Gln Val
    130                 135                 140

Ser Phe Val Pro Arg Gly Val Phe Asn Asp Leu Val Ser Val Gln Tyr
145                 150                 155                 160

Leu Asn Leu Gln Arg Asn Arg Leu Thr Val Leu Gly Ser Gly Thr Phe
                165                 170                 175

Val Gly Met Val Ala Leu Arg Ile Leu Asp Leu Ser Asn Asn Asn Ile
            180                 185                 190

Leu Arg Ile Ser Glu Ser Gly Phe Gln His Leu Glu Asn Leu Ala Cys
        195                 200                 205

Leu Tyr Leu Gly Ser Asn Asn Leu Thr Lys Val Pro Ser Asn Ala Phe
    210                 215                 220

Glu Val Leu Lys Ser Leu Arg Arg Leu Ser Leu Ser His Asn Pro Ile
225                 230                 235                 240

Glu Ala Ile Gln Pro Phe Ala Phe Lys Gly Leu Ala Asn Leu Glu Tyr
                245                 250                 255

Leu Leu Leu Lys Asn Ser Arg Ile Arg Asn Val Thr Arg Asp Gly Phe
            260                 265                 270

Ser Gly Ile Asn Asn Leu Lys His Leu Ile Leu Ser His Asn Asp Leu
        275                 280                 285

Glu Asn Leu Asn Ser Asp Thr Phe Ser Leu Leu Lys Asn Leu Ile Tyr
    290                 295                 300

Leu Lys Leu Asp Arg Asn Arg Ile Ile Ser Ile Asp Asn Asp Thr Phe
```

```
                305                 310                 315                 320
        Glu Asn Met Gly Ala Ser Leu Lys Ile Leu Asn Leu Ser Phe Asn Asn
                        325                 330                 335

Leu Thr Ala Leu His Pro Arg Val Leu Lys Pro Leu Ser Ser Leu Ile
                        340                 345                 350

His Leu Gln Ala Asn Ser Asn Pro Trp Glu Cys Asn Cys Lys Leu Leu
                        355                 360                 365

Gly Leu Arg Asp Trp Leu Ala Ser Ala Ile Thr Leu Asn Ile Tyr
                370                 375                 380

Cys Gln Asn Pro Pro Ser Met Arg Gly Arg Ala Leu Arg Tyr Ile Asn
        385                 390                 395                 400

Ile Thr Asn Cys Val Thr Ser Ser Ile Asn Val Ser Arg Ala Trp Ala
                        405                 410                 415

Val Val Lys Ser Pro His Ile His Lys Thr Thr Ala Leu Met Met
                        420                 425                 430

Ala Trp His Lys Val Thr Thr Asn Gly Ser Pro Leu Glu Asn Thr Glu
                        435                 440                 445

Thr Glu Asn Ile Thr Phe Trp Glu Arg Ile Pro Thr Ser Pro Ala Gly
                450                 455                 460

Arg Phe Phe Gln Glu Asn Ala Phe Gly Asn Pro Leu Glu Thr Thr Ala
        465                 470                 475                 480

Val Leu Pro Val Gln Ile Gln Leu Thr Thr Ser Val Thr Leu Asn Leu
                        485                 490                 495

Glu Lys Asn Ser Ala Leu Pro Asn Asp Ala Ala Ser Met Ser Gly Lys
                        500                 505                 510

Thr Ser Leu Ile Cys Thr Gln Glu Val Glu Lys Leu Asn Glu Ala Phe
                        515                 520                 525

Asp Ile Leu Leu Ala Phe Phe Ile Leu Ala Cys Val Leu Ile Ile Phe
                        530                 535                 540

Leu Ile Tyr Lys Val Val Gln Phe Lys Gln Lys Leu Lys Ala Ser Glu
        545                 550                 555                 560

Asn Ser Arg Glu Asn Arg Leu Glu Tyr Tyr Ser Phe Tyr Gln Ser Ala
                        565                 570                 575

Arg Tyr Asn Val Thr Ala Ser Ile Cys Asn Thr Ser Pro Asn Ser Leu
                        580                 585                 590

Glu Ser Pro Gly Leu Glu Gln Ile Arg Leu His Lys Gln Ile Val Pro
                        595                 600                 605

Glu Asn Glu Ala Gln Val Ile Leu Phe Glu His Ser Ala Leu
                610                 615                 620

<210> SEQ ID NO 9
<211> LENGTH: 597
<212> TYPE: PRT
<213> ORGANISM: Homo sapiens

<400> SEQUENCE: 9

His Lys Glu Ile Leu Gly Cys Ser Ser Val Cys Gln Leu Cys Thr Gly
        1               5                   10                  15

Arg Gln Ile Asn Cys Arg Asn Leu Gly Leu Ser Ser Ile Pro Lys Asn
                        20                  25                  30

Phe Pro Glu Ser Thr Val Phe Leu Tyr Leu Thr Gly Asn Asn Ile Ser
                        35                  40                  45

Tyr Ile Asn Glu Ser Glu Leu Thr Gly Leu His Ser Leu Val Ala Leu
                50                  55                  60
```

```
Tyr Leu Asp Asn Ser Asn Ile Leu Tyr Val Tyr Pro Lys Ala Phe Val
 65                  70                  75                  80

Gln Leu Arg His Leu Tyr Phe Leu Phe Leu Asn Asn Asn Phe Ile Lys
                 85                  90                  95

Arg Leu Asp Pro Gly Ile Phe Lys Gly Leu Leu Asn Leu Arg Asn Leu
            100                 105                 110

Tyr Leu Gln Tyr Asn Gln Val Ser Phe Val Pro Arg Gly Val Phe Asn
            115                 120                 125

Asp Leu Val Ser Val Gln Tyr Leu Asn Leu Gln Arg Asn Arg Leu Thr
130                 135                 140

Val Leu Gly Ser Gly Thr Phe Val Gly Met Val Ala Leu Arg Ile Leu
145                 150                 155                 160

Asp Leu Ser Asn Asn Ile Leu Arg Ile Ser Glu Ser Gly Phe Gln
                165                 170                 175

His Leu Glu Asn Leu Ala Cys Leu Tyr Leu Gly Ser Asn Asn Leu Thr
            180                 185                 190

Lys Val Pro Ser Asn Ala Phe Glu Val Leu Lys Ser Leu Arg Arg Leu
            195                 200                 205

Ser Leu Ser His Asn Pro Ile Glu Ala Ile Gln Pro Phe Ala Phe Lys
210                 215                 220

Gly Leu Ala Asn Leu Glu Tyr Leu Leu Leu Lys Asn Ser Arg Ile Arg
225                 230                 235                 240

Asn Val Thr Arg Asp Gly Phe Ser Gly Ile Asn Asn Leu Lys His Leu
                245                 250                 255

Ile Leu Ser His Asn Asp Leu Glu Asn Leu Asn Ser Asp Thr Phe Ser
            260                 265                 270

Leu Leu Lys Asn Leu Ile Tyr Leu Lys Leu Asp Arg Asn Arg Ile Ile
            275                 280                 285

Ser Ile Asp Asn Asp Thr Phe Glu Asn Met Gly Ala Ser Leu Lys Ile
290                 295                 300

Leu Asn Leu Ser Phe Asn Asn Leu Thr Ala Leu His Pro Arg Val Leu
305                 310                 315                 320

Lys Pro Leu Ser Ser Leu Ile His Leu Gln Ala Asn Ser Asn Pro Trp
                325                 330                 335

Glu Cys Asn Cys Lys Leu Leu Gly Leu Arg Asp Trp Leu Ala Ser Ser
            340                 345                 350

Ala Ile Thr Leu Asn Ile Tyr Cys Gln Asn Pro Pro Ser Met Arg Gly
            355                 360                 365

Arg Ala Leu Arg Tyr Ile Asn Ile Thr Asn Cys Val Thr Ser Ser Ile
370                 375                 380

Asn Val Ser Arg Ala Trp Ala Val Lys Ser Pro His Ile His His
385                 390                 395                 400

Lys Thr Thr Ala Leu Met Met Ala Trp His Lys Val Thr Thr Asn Gly
                405                 410                 415

Ser Pro Leu Glu Asn Thr Glu Thr Glu Asn Ile Thr Phe Trp Glu Arg
            420                 425                 430

Ile Pro Thr Ser Pro Ala Gly Arg Phe Phe Gln Glu Asn Ala Phe Gly
            435                 440                 445

Asn Pro Leu Glu Thr Thr Ala Val Leu Pro Val Gln Ile Gln Leu Thr
450                 455                 460

Thr Ser Val Thr Leu Asn Leu Glu Lys Asn Ser Ala Leu Pro Asn Asp
465                 470                 475                 480

Ala Ala Ser Met Ser Gly Lys Thr Ser Leu Ile Cys Thr Gln Glu Val
```

```
                    485                 490                 495
Glu Lys Leu Asn Glu Ala Phe Asp Ile Leu Leu Ala Phe Phe Ile Leu
            500                 505                 510

Ala Cys Val Leu Ile Ile Phe Leu Ile Tyr Lys Val Val Gln Phe Lys
            515                 520                 525

Gln Lys Leu Lys Ala Ser Glu Asn Ser Arg Glu Asn Arg Leu Glu Tyr
            530                 535                 540

Tyr Ser Phe Tyr Gln Ser Ala Arg Tyr Asn Val Thr Ala Ser Ile Cys
545                 550                 555                 560

Asn Thr Ser Pro Asn Ser Leu Glu Ser Pro Gly Leu Glu Gln Ile Arg
            565                 570                 575

Leu His Lys Gln Ile Val Pro Glu Asn Glu Ala Gln Val Ile Leu Phe
            580                 585                 590

Glu His Ser Ala Leu
            595

<210> SEQ ID NO 10
<211> LENGTH: 522
<212> TYPE: PRT
<213> ORGANISM: Homo sapiens

<400> SEQUENCE: 10

Met Asp Phe Leu Leu Gly Leu Cys Leu Tyr Trp Leu Leu Arg Arg
1               5                   10                  15

Pro Ser Gly Val Val Leu Cys Leu Leu Gly Ala Cys Phe Gln Met Leu
            20                  25                  30

Pro Ala Ala Pro Ser Gly Cys Pro Gln Leu Cys Arg Cys Glu Gly Arg
            35                  40                  45

Leu Leu Tyr Cys Glu Ala Leu Asn Leu Thr Glu Ala Pro His Asn Leu
    50                  55                  60

Ser Gly Leu Leu Gly Leu Ser Leu Arg Tyr Asn Ser Leu Ser Glu Leu
65                  70                  75                  80

Arg Ala Gly Gln Phe Thr Gly Leu Met Gln Leu Thr Trp Leu Tyr Leu
                85                  90                  95

Asp His Asn His Ile Cys Ser Val Gln Gly Asp Ala Phe Gln Lys Leu
            100                 105                 110

Arg Arg Val Lys Glu Leu Thr Leu Ser Ser Asn Gln Ile Thr Gln Leu
            115                 120                 125

Pro Asn Thr Thr Phe Arg Pro Met Pro Asn Leu Arg Ser Val Asp Leu
        130                 135                 140

Ser Tyr Asn Lys Leu Gln Ala Leu Ala Pro Asp Leu Phe His Gly Leu
145                 150                 155                 160

Arg Lys Leu Thr Thr Leu His Met Arg Ala Asn Ala Ile Gln Phe Val
                165                 170                 175

Pro Val Arg Ile Phe Gln Asp Cys Arg Ser Leu Lys Phe Leu Asp Ile
            180                 185                 190

Gly Tyr Asn Gln Leu Lys Ser Leu Ala Arg Asn Ser Phe Ala Gly Leu
        195                 200                 205

Phe Lys Leu Thr Glu Leu His Leu Glu His Asn Asp Leu Val Lys Val
    210                 215                 220

Asn Phe Ala His Phe Pro Arg Leu Ile Ser His Ser Leu Cys Leu
225                 230                 235                 240

Arg Arg Asn Lys Val Ala Ile Val Val Ser Ser Leu Asp Trp Val Trp
                245                 250                 255
```

-continued

Asn Leu Glu Lys Met Asp Leu Ser Gly Asn Glu Ile Glu Tyr Met Glu
                260                 265                 270

Pro His Val Phe Glu Thr Val Pro His Leu Gln Ser Leu Gln Leu Asp
            275                 280                 285

Ser Asn Arg Leu Thr Tyr Ile Glu Pro Arg Ile Leu Asn Ser Trp Lys
        290                 295                 300

Ser Leu Thr Ser Ile Thr Leu Ala Gly Asn Leu Trp Asp Cys Gly Arg
305                 310                 315                 320

Asn Val Cys Ala Leu Ala Ser Trp Leu Ser Asn Phe Gln Gly Arg Tyr
                325                 330                 335

Asp Gly Asn Leu Gln Cys Ala Ser Pro Glu Tyr Ala Gln Gly Glu Asp
            340                 345                 350

Val Leu Asp Ala Val Tyr Ala Phe His Leu Cys Glu Asp Gly Ala Glu
        355                 360                 365

Pro Thr Ser Gly His Leu Leu Ser Ala Val Thr Asn Arg Ser Asp Leu
370                 375                 380

Gly Pro Pro Ala Ser Ser Ala Thr Thr Leu Ala Asp Gly Gly Glu Gly
385                 390                 395                 400

Gln His Asp Gly Thr Phe Glu Pro Ala Thr Val Ala Leu Pro Gly Gly
                405                 410                 415

Glu His Ala Glu Asn Ala Val Gln Ile His Lys Val Val Thr Gly Thr
            420                 425                 430

Met Ala Leu Ile Phe Ser Phe Leu Ile Val Val Leu Val Leu Tyr Val
        435                 440                 445

Ser Trp Lys Cys Phe Pro Ala Ser Leu Arg Gln Leu Arg Gln Cys Phe
450                 455                 460

Val Thr Gln Arg Arg Lys Gln Lys Gln Thr Met His Gln Met
465                 470                 475                 480

Ala Ala Met Ser Ala Gln Glu Tyr Tyr Val Asp Tyr Lys Pro Asn His
                485                 490                 495

Ile Glu Gly Ala Leu Val Ile Ile Asn Glu Tyr Gly Ser Cys Thr Cys
            500                 505                 510

His Gln Gln Pro Ala Arg Glu Cys Glu Val
        515                 520

<210> SEQ ID NO 11
<211> LENGTH: 516
<212> TYPE: PRT
<213> ORGANISM: Homo sapiens

<400> SEQUENCE: 11

Met Gly Leu His Phe Lys Trp Pro Leu Gly Ala Pro Met Leu Ala Ala
1               5                   10                  15

Ile Tyr Ala Met Ser Met Val Leu Lys Met Leu Pro Ala Leu Gly Met
                20                  25                  30

Ala Cys Pro Pro Lys Cys Arg Cys Glu Lys Leu Leu Phe Tyr Cys Asp
            35                  40                  45

Ser Gln Gly Phe His Ser Val Pro Asn Ala Thr Asp Lys Gly Ser Leu
        50                  55                  60

Gly Leu Ser Leu Arg His Asn His Ile Thr Glu Leu Glu Arg Asp Gln
65                  70                  75                  80

Phe Ala Ser Phe Ser Gln Leu Thr Trp Leu His Leu Asp His Asn Gln
                85                  90                  95

Ile Ser Thr Val Lys Glu Asp Ala Phe Gln Gly Leu Tyr Lys Leu Lys
            100                 105                 110

```
Glu Leu Ile Leu Ser Ser Asn Lys Ile Phe Tyr Leu Pro Asn Thr Thr
            115                 120                 125
Phe Thr Gln Leu Ile Asn Leu Gln Asn Leu Asp Leu Ser Phe Asn Gln
        130                 135                 140
Leu Ser Ser Leu His Pro Glu Leu Phe Tyr Gly Leu Arg Lys Leu Gln
145                 150                 155                 160
Thr Leu His Leu Arg Ser Asn Ser Leu Arg Thr Ile Pro Val Arg Leu
                165                 170                 175
Phe Trp Asp Cys Arg Ser Leu Glu Phe Leu Asp Leu Ser Thr Asn Arg
            180                 185                 190
Leu Arg Ser Leu Ala Arg Asn Gly Phe Ala Gly Leu Ile Lys Leu Arg
        195                 200                 205
Glu Leu His Leu Glu His Asn Gln Leu Thr Lys Ile Asn Phe Ala His
        210                 215                 220
Phe Leu Arg Leu Ser Ser Leu His Thr Leu Phe Leu Gln Trp Asn Lys
225                 230                 235                 240
Ile Ser Asn Leu Thr Cys Gly Met Glu Trp Thr Trp Gly Thr Leu Glu
                245                 250                 255
Lys Leu Asp Leu Thr Gly Asn Glu Ile Lys Ala Ile Asp Leu Thr Val
            260                 265                 270
Phe Glu Thr Met Pro Asn Leu Lys Ile Leu Leu Met Asp Asn Asn Lys
        275                 280                 285
Leu Asn Ser Leu Asp Ser Lys Ile Leu Asn Ser Leu Arg Ser Leu Thr
        290                 295                 300
Thr Val Gly Leu Ser Gly Asn Leu Trp Glu Cys Ser Ala Arg Ile Cys
305                 310                 315                 320
Ala Leu Ala Ser Trp Leu Gly Ser Phe Gln Gly Arg Trp Glu His Ser
                325                 330                 335
Ile Leu Cys His Ser Pro Asp His Thr Gln Gly Glu Asp Ile Leu Asp
            340                 345                 350
Ala Val His Gly Phe Gln Leu Cys Trp Asn Leu Ser Thr Thr Val Thr
        355                 360                 365
Val Met Ala Thr Thr Tyr Arg Asp Pro Thr Thr Glu Tyr Thr Lys Arg
        370                 375                 380
Ile Ser Ser Ser Ser Tyr His Val Gly Asp Lys Glu Ile Pro Thr Thr
385                 390                 395                 400
Ala Gly Ile Ala Val Thr Thr Glu Glu His Phe Pro Glu Pro Asp Asn
                405                 410                 415
Ala Ile Phe Thr Gln Arg Val Ile Thr Gly Thr Met Ala Leu Leu Phe
            420                 425                 430
Ser Phe Phe Phe Ile Ile Phe Ile Val Phe Ile Ser Arg Lys Cys Cys
        435                 440                 445
Pro Pro Thr Leu Arg Arg Ile Arg Gln Cys Ser Met Val Gln Asn His
        450                 455                 460
Arg Gln Leu Arg Ser Gln Thr Arg Leu His Met Ser Asn Met Ser Asp
465                 470                 475                 480
Gln Gly Pro Tyr Asn Glu Tyr Glu Pro Thr His His Glu Gly Pro Phe Ile
                485                 490                 495
Ile Ile Asn Gly Tyr Gly Gln Cys Lys Cys Gln Gln Leu Pro Tyr Lys
            500                 505                 510
Glu Cys Glu Val
        515
```

<210> SEQ ID NO 12
<211> LENGTH: 581
<212> TYPE: PRT
<213> ORGANISM: Macaca fascicularis

<400> SEQUENCE: 12

```
Met Gly Phe Asn Val Ile Arg Leu Leu Ser Gly Ser Ala Val Ala Leu
1               5                   10                  15

Val Ile Ala Pro Thr Val Leu Leu Thr Met Leu Ser Ser Ala Glu Arg
            20                  25                  30

Gly Cys Pro Lys Gly Cys Arg Cys Glu Gly Lys Met Val Tyr Cys Glu
        35                  40                  45

Ser Gln Lys Leu Gln Glu Ile Pro Ser Ser Ile Ser Ala Gly Cys Leu
    50                  55                  60

Gly Leu Ser Leu Arg Tyr Asn Ser Leu Gln Lys Leu Lys Tyr Asn Gln
65                  70                  75                  80

Phe Lys Gly Leu Asn Gln Leu Thr Trp Leu Tyr Leu Asp His Asn His
                85                  90                  95

Ile Ser Asn Ile Asp Glu Asn Ala Phe Asn Gly Ile Arg Arg Leu Lys
            100                 105                 110

Glu Leu Ile Leu Ser Ser Asn Arg Ile Ser Tyr Phe Leu Asn Asn Thr
        115                 120                 125

Phe Arg Pro Val Thr Asn Leu Arg Asn Leu Asp Leu Ser Tyr Asn Gln
    130                 135                 140

Leu His Ser Leu Gly Ser Glu Gln Phe Arg Gly Leu Arg Lys Leu Leu
145                 150                 155                 160

Ser Leu His Leu Arg Ser Asn Ser Leu Arg Thr Ile Pro Val Arg Ile
                165                 170                 175

Phe Gln Asp Cys Arg Asn Leu Glu Leu Leu Asp Leu Gly Tyr Asn Arg
            180                 185                 190

Ile Arg Ser Leu Ala Arg Asn Val Phe Ala Gly Met Ile Arg Leu Lys
        195                 200                 205

Glu Leu His Leu Glu His Asn Gln Phe Ser Lys Leu Asn Leu Ala Leu
    210                 215                 220

Phe Pro Arg Leu Val Ser Leu Gln Asn Leu Tyr Leu Gln Trp Asn Lys
225                 230                 235                 240

Ile Ser Val Ile Gly Gln Thr Met Ser Trp Thr Trp Ser Ser Leu Gln
                245                 250                 255

Arg Leu Asp Leu Ser Gly Asn Glu Ile Glu Ala Phe Ser Gly Pro Ser
            260                 265                 270

Val Phe Gln Cys Val Pro Asn Leu Gln Arg Leu Asn Leu Asp Ser Asn
        275                 280                 285

Lys Leu Thr Phe Ile Gly Gln Glu Ile Leu Asp Ser Trp Ile Ser Leu
    290                 295                 300

Asn Asp Ile Ser Leu Ala Gly Asn Ile Trp Glu Cys Ser Arg Asn Ile
305                 310                 315                 320

Cys Ser Leu Val Asn Trp Leu Lys Ser Phe Lys Gly Leu Arg Glu Asn
                325                 330                 335

Thr Ile Ile Cys Ala Ser Pro Lys Glu Leu Gln Gly Val Asn Val Ile
            340                 345                 350

Asp Ala Val Lys Asn Tyr Ser Ile Cys Gly Lys Ser Thr Thr Glu Arg
        355                 360                 365

Phe Asp Leu Ala Arg Ala Leu Pro Lys Pro Thr Phe Lys Pro Lys Leu
    370                 375                 380
```

```
Pro Arg Pro Lys His Glu Ser Lys Pro Pro Leu Pro Pro Thr Val Gly
385                 390                 395                 400

Ala Thr Glu Pro Gly Pro Glu Thr Asp Ala Asp Ala Glu His Ile Ser
            405                 410                 415

Phe His Lys Ile Ile Ala Gly Ser Val Ala Leu Phe Leu Ser Val Leu
            420                 425                 430

Val Ile Leu Leu Val Ile Tyr Val Ser Trp Lys Arg Tyr Pro Ala Ser
            435                 440                 445

Met Lys Gln Leu Gln Gln Arg Ser Leu Met Arg Arg His Arg Lys Lys
450                 455                 460

Lys Arg Gln Ser Leu Lys Gln Met Thr Pro Ser Thr Gln Glu Phe Tyr
465                 470                 475                 480

Val Asp Tyr Lys Pro Thr Asn Thr Glu Thr Ser Glu Met Leu Leu Asn
            485                 490                 495

Gly Thr Gly Pro Cys Thr Tyr Asn Lys Ser Gly Ser Arg Glu Cys Glu
            500                 505                 510

Ile Pro Leu Ser Met Asn Val Ser Thr Phe Leu Ala Tyr Asp Gln Pro
515                 520                 525

Thr Ile Ser Tyr Cys Gly Val His His Glu Leu Leu Ser His Lys Ser
530                 535                 540

Phe Glu Thr Asn Ala Gln Glu Asp Thr Met Glu Thr His Leu Glu Thr
545                 550                 555                 560

Glu Leu Asp Leu Ser Thr Ile Thr Thr Ala Gly Arg Ile Ser Asp His
            565                 570                 575

Lys Gln Gln Leu Ala
            580

<210> SEQ ID NO 13
<211> LENGTH: 384
<212> TYPE: PRT
<213> ORGANISM: Mus musculus

<400> SEQUENCE: 13

Met Asp Phe Leu Leu Gly Leu Cys Leu His Trp Leu Leu Arg Arg
1               5                   10                  15

Pro Ser Gly Val Val Leu Cys Leu Leu Gly Ala Cys Phe Gln Met Leu
            20                  25                  30

Pro Ala Ala Pro Ser Gly Cys Pro Gly Gln Cys Arg Cys Glu Gly Arg
            35                  40                  45

Leu Leu Tyr Cys Glu Ala Leu Asn Leu Thr Glu Ala Pro His Asn Leu
50                  55                  60

Ser Gly Leu Leu Gly Leu Ser Leu Arg Tyr Asn Ser Leu Ser Glu Leu
65                  70                  75                  80

Arg Ala Gly Gln Phe Thr Gly Leu Met Gln Leu Thr Trp Leu Tyr Leu
            85                  90                  95

Asp His Asn His Ile Cys Ser Val Gln Gly Asp Ala Phe Gln Lys Leu
            100                 105                 110

Arg Arg Val Lys Glu Leu Thr Leu Ser Ser Asn Gln Ile Thr Glu Leu
            115                 120                 125

Ala Asn Thr Thr Phe Arg Pro Met Pro Asn Leu Arg Ser Val Asp Leu
130                 135                 140

Ser Tyr Asn Lys Leu Gln Ala Leu Ala Pro Asp Leu Phe His Gly Leu
145                 150                 155                 160

Arg Lys Leu Thr Thr Leu His Met Arg Ala Asn Ala Ile Gln Phe Val
```

```
                      165                 170                 175
Pro Val Arg Ile Phe Gln Asp Cys Arg Ser Leu Lys Phe Leu Asp Ile
            180                 185                 190
Gly Tyr Asn Gln Leu Lys Ser Leu Ala Arg Asn Ser Phe Ala Gly Leu
        195                 200                 205
Phe Lys Leu Thr Glu Leu His Leu Glu His Asn Asp Leu Ile Lys Val
        210                 215                 220
Asn Phe Ala His Phe Pro Arg Leu Ile Ser Leu His Ser Leu Cys Leu
225                 230                 235                 240
Arg Arg Asn Lys Val Ala Ile Val Ser Ser Leu Asp Trp Val Trp
            245                 250                 255
Asn Leu Glu Lys Met Asp Leu Ser Gly Asn Glu Ile Glu Tyr Met Glu
            260                 265                 270
Pro His Val Phe Glu Thr Val Pro Tyr Leu Gln Thr Leu Gln Leu Asp
            275                 280                 285
Ser Asn Arg Leu Thr Tyr Ile Glu Pro Arg Ile Leu Asn Ser Trp Lys
        290                 295                 300
Ser Leu Thr Ser Ile Thr Leu Ala Gly Asn Leu Trp Asp Cys Gly Arg
305                 310                 315                 320
Asn Val Cys Ala Leu Ala Ser Trp Leu Ser Asn Phe Gln Gly Arg Tyr
            325                 330                 335
Asp Ala Asn Leu Gln Cys Ala Ser Pro Glu Tyr Ala Gln Gly Arg Thr
            340                 345                 350
Ser Trp Met Gln Cys Met Leu Ser Thr Cys Val Arg Met Gly Pro Ser
            355                 360                 365
Pro Pro Ala Ala Thr Ser Cys Arg Trp Pro Ser Leu Thr Ala Val Thr
        370                 375                 380

<210> SEQ ID NO 14
<211> LENGTH: 570
<212> TYPE: PRT
<213> ORGANISM: Mus musculus

<400> SEQUENCE: 14

Met Lys Phe Ser Ser Val Ser Glu Glu Lys Pro Gly Leu Leu Ala Pro
1               5                   10                  15
Pro Ala Gln Pro Leu Thr Thr Met Phe Pro Gly Ala Trp Leu Cys Trp
            20                  25                  30
Val Ser Leu Leu Leu Leu Ala Arg Leu Thr Gln Pro Cys Pro Val Gly
        35                  40                  45
Cys Asp Cys Phe Gly Arg Glu Val Phe Cys Ser Asp Glu Gln Leu Ala
    50                  55                  60
Asp Ile Pro Pro Asp Ile Pro Pro His Ile Thr Asp Ile Val Phe Val
65                  70                  75                  80
Glu Thr Ala Phe Thr Thr Val Arg Thr Arg Ala Phe Ser Gly Pro
            85                  90                  95
Asn Leu Thr Lys Val Val Phe Leu Asn Thr Gln Val Arg His Leu Glu
            100                 105                 110
Pro Asp Ala Phe Gly Gly Leu Pro Arg Leu Gln Asp Leu Glu Ile Thr
        115                 120                 125
Gly Ser Pro Val Ser Asn Leu Ser Ala His Ile Phe Ser Asn Leu Ser
    130                 135                 140
Ser Leu Glu Lys Leu Thr Leu Asp Phe Asp Arg Leu Ala Gly Leu Pro
145                 150                 155                 160
```

```
Glu Asp Leu Phe Cys His Met Asp Ile Leu Glu Ser Leu Gln Leu Gln
                165                 170                 175
Gly Asn Gln Leu Arg Thr Leu Pro Gly Arg Leu Phe Gln Ser Leu Arg
            180                 185                 190
Asp Leu Arg Thr Leu Asn Leu Ala Gln Asn Leu Leu Thr Gln Leu Pro
        195                 200                 205
Lys Gly Ala Phe Gln Ser Leu Thr Gly Leu Gln Met Leu Lys Leu Ser
    210                 215                 220
Asn Asn Met Leu Ala Arg Leu Pro Glu Gly Ala Leu Gly Ser Leu Ser
225                 230                 235                 240
Ser Leu Gln Glu Leu Phe Leu Asp Gly Asn Ala Ile Thr Glu Leu Ser
                245                 250                 255
Pro His Leu Phe Ser Gln Leu Phe Ser Leu Glu Met Leu Trp Leu Gln
                260                 265                 270
His Asn Ala Ile Cys His Leu Pro Val Ser Leu Phe Ser Ser Leu His
            275                 280                 285
Asn Leu Thr Phe Leu Ser Leu Lys Asp Asn Ala Leu Arg Thr Leu Pro
    290                 295                 300
Glu Gly Leu Phe Ala His Asn Gln Gly Leu Leu His Leu Ser Leu Ser
305                 310                 315                 320
Tyr Asn Gln Leu Glu Thr Ile Pro Glu Gly Ala Phe Thr Asn Leu Ser
                325                 330                 335
Arg Leu Val Ser Leu Thr Leu Ser His Asn Ala Ile Thr Asp Leu Pro
            340                 345                 350
Glu His Val Phe Arg Asn Leu Glu Gln Leu Val Lys Leu Ser Leu Asp
        355                 360                 365
Ser Asn Asn Leu Thr Ala Leu His Pro Ala Leu Phe His Asn Leu Ser
    370                 375                 380
Arg Leu Gln Leu Leu Asn Leu Ser Arg Asn Gln Leu Thr Thr Leu Pro
385                 390                 395                 400
Gly Gly Ile Phe Asp Thr Asn Tyr Asp Leu Phe Asn Leu Ala Leu Leu
                405                 410                 415
Gly Asn Pro Trp Gln Cys Asp Cys His Leu Ser Tyr Leu Thr Ser Trp
            420                 425                 430
Leu Arg Leu Tyr Asn Asn Gln Ile Ser Asn Thr His Thr Phe Cys Ala
        435                 440                 445
Gly Pro Ala Tyr Leu Lys Gly Gln Leu Val Pro Asn Leu Lys Gln Glu
    450                 455                 460
Gln Leu Ile Cys Pro Val Asn Pro Gly His Leu Ser Phe Arg Ala Leu
465                 470                 475                 480
Gly Leu Asp Glu Gly Glu Pro Ala Gly Ser Trp Asp Leu Thr Val Glu
                485                 490                 495
Gly Arg Ala Ala His Ser Gln Cys Ala Tyr Ser Asn Pro Glu Gly Thr
            500                 505                 510
Val Leu Leu Ala Cys Glu Glu Ser Arg Cys Arg Trp Leu Asn Ile Gln
        515                 520                 525
Leu Ser Ser Arg Asp Gly Ser Asp Ser Ala Ala Met Val Tyr Asn Ser
    530                 535                 540
Ser Gln Glu Trp Gly Leu Arg Ser Ser Cys Gly Leu Leu Arg Val Thr
545                 550                 555                 560
Val Ser Ile Glu Ala Pro Ala Ala Gly Pro
                565                 570
```

-continued

<210> SEQ ID NO 15
<211> LENGTH: 207
<212> TYPE: PRT
<213> ORGANISM: Homo sapiens

<400> SEQUENCE: 15

Met Trp Glu Cys Ser Arg Ser Ile Cys Pro Leu Phe Tyr Trp Leu Lys
1               5                   10                  15

Asn Phe Lys Gly Asn Lys Glu Ser Thr Met Ile Cys Ala Gly Pro Lys
            20                  25                  30

His Ile Gln Gly Glu Lys Val Ser Asp Ala Val Glu Thr Tyr Asn Ile
        35                  40                  45

Cys Ser Glu Val Gln Val Val Asn Thr Glu Arg Ser His Leu Val Pro
    50                  55                  60

Gln Thr Pro Gln Lys Pro Leu Ile Ile Pro Arg Pro Thr Ile Phe Lys
65                  70                  75                  80

Pro Asp Val Thr Gln Ser Thr Phe Glu Thr Pro Ser Pro Ser Pro Gly
                85                  90                  95

Phe Gln Ile Pro Gly Ala Glu Gln Tyr Glu His Val Ser Phe His
            100                 105                 110

Lys Ile Ile Ala Gly Ser Val Ala Leu Phe Leu Ser Val Ala Met Ile
        115                 120                 125

Leu Leu Val Ile Tyr Val Ser Trp Lys Arg Tyr Pro Ala Ser Met Lys
    130                 135                 140

Gln Leu Gln Gln His Ser Leu Met Lys Arg Arg Arg Lys Lys Ala Arg
145                 150                 155                 160

Glu Ser Glu Arg Gln Met Asn Ser Pro Leu Gln Glu Tyr Tyr Val Asp
                165                 170                 175

Tyr Lys Pro Thr Asn Ser Glu Thr Met Asp Ile Ser Val Asn Gly Ser
            180                 185                 190

Gly Pro Cys Thr Tyr Thr Ile Ser Gly Ser Arg Glu Cys Glu Val
        195                 200                 205

<210> SEQ ID NO 16
<211> LENGTH: 797
<212> TYPE: PRT
<213> ORGANISM: Homo sapiens

<400> SEQUENCE: 16

Met Val Gln Gly Gly Ile Gln Ser Ser Val Ala Ser Gly Lys Ser
1               5                   10                  15

Leu Pro Pro Leu Gly Leu Ser Glu Ala Gly Gly Gln Gly Leu Trp Gly
            20                  25                  30

Leu Pro Gly Val Leu Gln Glu Gly Gly Leu Pro Arg Pro Arg Ser Ser
        35                  40                  45

Thr His Val Pro Leu Val Leu Pro Leu Leu Val Leu Leu Leu Leu Ala
    50                  55                  60

Pro Ala Arg Gln Ala Ala Ala Gln Arg Cys Pro Gln Ala Cys Ile Cys
65                  70                  75                  80

Asp Asn Ser Arg Arg His Val Ala Cys Arg Tyr Gln Asn Leu Thr Glu
                85                  90                  95

Val Pro Asp Ala Ile Pro Glu Leu Thr Gln Arg Leu Asp Leu Gln Gly
            100                 105                 110

Asn Leu Leu Lys Val Ile Pro Ala Ala Ala Phe Gln Gly Val Pro His
        115                 120                 125

Leu Thr His Leu Asp Leu Arg His Cys Glu Val Glu Leu Val Ala Glu

-continued

```
            130                 135                 140
Gly Ala Phe Arg Gly Leu Gly Arg Leu Leu Leu Asn Leu Ala Ser
145                 150                 155                 160

Asn His Leu Arg Glu Leu Pro Gln Ala Leu Asp Gly Leu Gly Ser
                165                 170                 175

Leu Arg Arg Leu Glu Leu Glu Gly Asn Ala Leu Glu Glu Leu Arg Pro
                180                 185                 190

Gly Thr Phe Gly Ala Leu Gly Ala Leu Ala Thr Leu Asn Leu Ala His
                195                 200                 205

Asn Ala Leu Val Tyr Leu Pro Ala Met Ala Phe Gln Gly Leu Leu Arg
210                 215                 220

Val Arg Trp Leu Arg Leu Ser His Asn Ala Leu Ser Val Leu Ala Pro
225                 230                 235                 240

Glu Ala Leu Ala Gly Leu Pro Ala Leu Arg Arg Leu Ser Leu His His
                245                 250                 255

Asn Glu Leu Gln Ala Leu Pro Gly Pro Val Leu Ser Gln Ala Arg Gly
                260                 265                 270

Leu Ala Arg Leu Glu Leu Gly His Asn Pro Leu Thr Tyr Ala Gly Glu
                275                 280                 285

Glu Asp Gly Leu Ala Leu Pro Gly Leu Arg Glu Leu Leu Leu Asp Gly
290                 295                 300

Gly Ala Leu Gln Ala Leu Gly Pro Arg Ala Phe Ala His Cys Pro Arg
305                 310                 315                 320

Leu His Thr Leu Asp Leu Arg Gly Asn Gln Leu Asp Thr Leu Pro Pro
                325                 330                 335

Leu Gln Gly Pro Gly Gln Leu Arg Arg Leu Arg Leu Gln Gly Asn Pro
                340                 345                 350

Leu Trp Cys Gly Cys Gln Ala Arg Pro Leu Leu Glu Trp Leu Ala Arg
                355                 360                 365

Ala Arg Val Arg Ser Asp Gly Ala Cys Gln Gly Pro Arg Arg Leu Arg
                370                 375                 380

Gly Glu Ala Leu Asp Ala Leu Arg Pro Trp Asp Leu Arg Cys Pro Gly
385                 390                 395                 400

Asp Ala Ala Gln Glu Glu Glu Leu Glu Glu Arg Ala Val Ala Gly
                405                 410                 415

Pro Arg Ala Pro Pro Arg Gly Pro Pro Arg Gly Pro Gly Glu Glu Arg
                420                 425                 430

Ala Val Ala Pro Cys Pro Arg Ala Cys Val Cys Val Pro Glu Ser Arg
                435                 440                 445

His Ser Ser Cys Glu Gly Cys Gly Leu Gln Ala Val Pro Arg Gly Phe
450                 455                 460

Pro Ser Asp Thr Gln Leu Leu Asp Leu Arg Arg Asn His Phe Pro Ser
465                 470                 475                 480

Val Pro Arg Ala Ala Phe Pro Gly Leu Gly His Leu Val Ser Leu His
                485                 490                 495

Leu Gln His Cys Gly Ile Ala Glu Leu Glu Ala Gly Ala Leu Ala Gly
                500                 505                 510

Leu Gly Arg Leu Ile Tyr Leu Tyr Leu Ser Asp Asn Gln Leu Ala Gly
                515                 520                 525

Leu Ser Ala Ala Ala Leu Glu Gly Ala Pro Arg Leu Gly Tyr Leu Tyr
530                 535                 540

Leu Glu Arg Asn Arg Phe Leu Gln Val Pro Gly Ala Ala Leu Arg Ala
545                 550                 555                 560
```

```
Leu Pro Ser Leu Phe Ser Leu His Leu Gln Asp Asn Ala Val Asp Arg
                565                 570                 575
Leu Ala Pro Gly Asp Leu Gly Arg Thr Arg Ala Leu Arg Trp Val Tyr
            580                 585                 590
Leu Ser Gly Asn Arg Ile Thr Glu Val Ser Leu Gly Ala Leu Gly Pro
        595                 600                 605
Ala Arg Glu Leu Glu Lys Leu His Leu Asp Arg Asn Gln Leu Arg Glu
    610                 615                 620
Val Pro Thr Gly Ala Leu Glu Gly Leu Pro Ala Leu Glu Leu Gln
625                 630                 635                 640
Leu Ser Gly Asn Pro Leu Arg Ala Leu Arg Asp Gly Ala Phe Gln Pro
                645                 650                 655
Val Gly Arg Ser Leu Gln His Leu Phe Leu Asn Ser Ser Leu Glu
            660                 665                 670
Gln Ile Cys Pro Gly Ala Phe Ser Gly Leu Gly Pro Gly Leu Gln Ser
        675                 680                 685
Leu His Leu Gln Lys Asn Gln Leu Arg Ala Leu Pro Ala Leu Pro Ser
    690                 695                 700
Leu Ser Gln Leu Glu Leu Ile Asp Leu Ser Ser Asn Pro Phe His Cys
705                 710                 715                 720
Asp Cys Gln Leu Leu Pro Leu His Arg Trp Leu Thr Gly Leu Asn Leu
                725                 730                 735
Arg Val Gly Ala Thr Cys Ala Thr Pro Pro Asn Ala Arg Gly Gln Arg
            740                 745                 750
Val Lys Ala Ala Ala Val Phe Glu Asp Cys Pro Gly Trp Ala Ala
        755                 760                 765
Arg Lys Ala Lys Arg Thr Pro Ala Ser Arg Pro Ser Ala Arg Arg Thr
    770                 775                 780
Pro Ile Lys Gly Arg Gln Cys Gly Ala Asp Lys Val Gly
785                 790                 795

<210> SEQ ID NO 17
<211> LENGTH: 696
<212> TYPE: PRT
<213> ORGANISM: Homo sapiens

<400> SEQUENCE: 17

Met Leu Leu Trp Ile Leu Leu Glu Thr Ser Leu Cys Phe Ala Ala
1               5                   10                  15
Gly Asn Val Thr Gly Asp Val Cys Lys Glu Lys Ile Cys Ser Cys Asn
            20                  25                  30
Glu Ile Glu Gly Asp Leu His Val Asp Cys Glu Lys Lys Gly Phe Thr
        35                  40                  45
Ser Leu Gln Arg Phe Thr Ala Pro Thr Ser Gln Phe Tyr His Leu Phe
    50                  55                  60
Leu His Gly Asn Ser Leu Thr Arg Leu Phe Pro Asn Glu Phe Ala Asn
65                  70                  75                  80
Phe Tyr Asn Ala Val Ser Leu His Met Glu Asn Asn Gly Leu His Glu
                85                  90                  95
Ile Val Pro Gly Ala Phe Leu Gly Leu Gln Leu Val Lys Arg Leu His
            100                 105                 110
Ile Asn Asn Asn Lys Ile Lys Ser Phe Arg Lys Gln Thr Phe Leu Gly
        115                 120                 125
Leu Asp Asp Leu Glu Tyr Leu Gln Ala Asp Phe Asn Leu Leu Arg Asp
```

-continued

```
            130                 135                 140
Ile Asp Pro Gly Ala Phe Gln Asp Leu Asn Lys Leu Glu Val Leu Ile
145                 150                 155                 160

Leu Asn Asp Asn Leu Ile Ser Thr Leu Pro Ala Asn Val Phe Gln Tyr
                165                 170                 175

Val Pro Ile Thr His Leu Asp Leu Arg Gly Asn Arg Leu Lys Thr Leu
                180                 185                 190

Pro Tyr Glu Glu Val Leu Glu Gln Ile Pro Gly Ile Ala Glu Ile Leu
                195                 200                 205

Leu Glu Asp Asn Pro Trp Asp Cys Thr Cys Asp Leu Leu Ser Leu Lys
210                 215                 220

Glu Trp Leu Glu Asn Ile Pro Lys Asn Ala Leu Ile Gly Arg Val Val
225                 230                 235                 240

Cys Glu Ala Pro Thr Arg Leu Gln Gly Lys Asp Leu Asn Glu Thr Thr
                245                 250                 255

Glu Gln Asp Leu Cys Pro Leu Lys Asn Arg Val Asp Ser Ser Leu Pro
                260                 265                 270

Ala Pro Pro Ala Gln Glu Glu Thr Phe Ala Pro Gly Pro Leu Pro Thr
                275                 280                 285

Pro Phe Lys Thr Asn Gly Gln Glu Asp His Ala Thr Pro Gly Ser Ala
                290                 295                 300

Pro Asn Gly Gly Thr Lys Ile Pro Gly Asn Trp Gln Ile Lys Ile Arg
305                 310                 315                 320

Pro Thr Ala Ala Ile Ala Thr Gly Ser Ser Arg Asn Lys Pro Leu Ala
                325                 330                 335

Asn Ser Leu Pro Cys Pro Gly Gly Cys Ser Cys Asp His Ile Pro Gly
                340                 345                 350

Ser Gly Leu Lys Met Asn Cys Asn Asn Arg Asn Val Ser Ser Leu Ala
                355                 360                 365

Asp Leu Lys Pro Lys Leu Ser Asn Val Gln Glu Leu Phe Leu Arg Asp
                370                 375                 380

Asn Lys Ile His Ser Ile Arg Lys Ser His Phe Val Asp Tyr Lys Asn
385                 390                 395                 400

Leu Ile Leu Leu Asp Leu Gly Asn Asn Asn Ile Ala Thr Val Glu Asn
                405                 410                 415

Asn Thr Phe Lys Asn Leu Leu Asp Leu Arg Trp Leu Tyr Met Asp Ser
                420                 425                 430

Asn Tyr Leu Asp Thr Leu Ser Arg Glu Lys Phe Ala Gly Leu Gln Asn
                435                 440                 445

Leu Glu Tyr Leu Asn Val Glu Tyr Asn Ala Ile Gln Leu Ile Leu Pro
                450                 455                 460

Gly Thr Phe Asn Ala Met Pro Lys Leu Arg Ile Leu Ile Leu Asn Asn
465                 470                 475                 480

Asn Leu Leu Arg Ser Leu Pro Val Asp Val Phe Ala Gly Val Ser Leu
                485                 490                 495

Ser Lys Leu Ser Leu His Asn Asn Tyr Phe Met Tyr Leu Pro Val Ala
                500                 505                 510

Gly Val Leu Asp Gln Leu Thr Ser Ile Ile Gln Ile Asp Leu His Gly
                515                 520                 525

Asn Pro Trp Glu Cys Ser Cys Thr Ile Val Pro Phe Lys Gln Trp Ala
                530                 535                 540

Glu Arg Leu Gly Ser Glu Val Leu Met Ser Asp Leu Lys Cys Glu Thr
545                 550                 555                 560
```

-continued

```
Pro Val Asn Phe Phe Arg Lys Asp Phe Met Leu Leu Ser Asn Asp Glu
            565                 570                 575

Ile Cys Pro Gln Leu Tyr Ala Arg Ile Ser Pro Thr Leu Thr Ser His
        580                 585                 590

Ser Lys Asn Ser Thr Gly Leu Ala Glu Thr Gly Thr His Ser Asn Ser
    595                 600                 605

Tyr Leu Asp Thr Ser Arg Val Ser Ile Ser Val Leu Val Pro Gly Leu
610                 615                 620

Leu Leu Val Phe Val Thr Ser Ala Phe Thr Val Val Gly Met Leu Val
625                 630                 635                 640

Phe Ile Leu Arg Asn Arg Lys Arg Ser Lys Arg Asp Ala Asn Ser
            645                 650                 655

Ser Ala Ser Glu Ile Asn Ser Leu Gln Thr Val Cys Asp Ser Ser Tyr
            660                 665                 670

Trp His Asn Gly Pro Tyr Asn Ala Asp Gly Ala His Arg Val Tyr Asp
            675                 680                 685

Cys Gly Ser His Ser Leu Ser Asp
690                 695

<210> SEQ ID NO 18
<211> LENGTH: 596
<212> TYPE: PRT
<213> ORGANISM: Homo sapiens
<220> FEATURE:
<221> NAME/KEY: misc_feature
<222> LOCATION: (456)..(456)
<223> OTHER INFORMATION: Xaa can be any naturally occurring amino acid

<400> SEQUENCE: 18

Arg Lys Thr Ala Lys Asp Ile Cys Lys Ile Arg Cys Leu Cys Glu Glu
1               5                   10                  15

Lys Glu Asn Val Leu Asn Ile Asn Cys Glu Asn Lys Gly Phe Thr Thr
            20                  25                  30

Val Ser Leu Leu Gln Pro Pro Gln Tyr Arg Ile Tyr Gln Leu Phe Leu
        35                  40                  45

Asn Gly Asn Leu Leu Thr Arg Leu Tyr Pro Asn Glu Phe Val Asn Tyr
    50                  55                  60

Ser Asn Ala Val Thr Leu His Leu Gly Asn Asn Gly Leu Gln Glu Ile
65                  70                  75                  80

Arg Thr Gly Ala Phe Ser Gly Leu Lys Thr Leu Lys Arg Leu His Leu
                85                  90                  95

Asn Asn Asn Lys Leu Glu Ile Leu Arg Glu Asp Thr Phe Leu Gly Leu
            100                 105                 110

Glu Ser Leu Glu Tyr Leu Gln Ala Asp Tyr Asn Tyr Ile Ser Ala Ile
        115                 120                 125

Glu Ala Gly Ala Phe Ser Lys Leu Asn Lys Leu Lys Val Leu Ile Leu
    130                 135                 140

Asn Asp Asn Leu Leu Leu Ser Leu Pro Ser Asn Val Phe Arg Phe Val
145                 150                 155                 160

Leu Leu Thr His Leu Asp Leu Arg Gly Asn Arg Leu Lys Val Met Pro
                165                 170                 175

Phe Ala Gly Val Leu Glu His Ile Gly Gly Ile Met Glu Ile Gln Leu
            180                 185                 190

Glu Glu Asn Pro Trp Asn Cys Thr Cys Asp Leu Leu Pro Leu Lys Ala
        195                 200                 205
```

-continued

```
Trp Leu Asp Thr Ile Thr Val Phe Val Gly Glu Ile Val Cys Glu Thr
    210                 215                 220
Pro Phe Arg Leu His Gly Lys Asp Val Thr Gln Leu Thr Arg Gln Asp
225                 230                 235                 240
Leu Cys Pro Arg Lys Ser Ala Ser Asp Ser Gln Arg Gly Ser His
                245                 250                 255
Ala Asp Thr His Val Gln Arg Leu Ser Pro Thr Met Asn Pro Ala Leu
            260                 265                 270
Asn Pro Thr Arg Ala Pro Lys Ala Ser Arg Pro Pro Lys Met Arg Asn
        275                 280                 285
Arg Pro Thr Pro Arg Val Thr Val Ser Lys Asp Arg Gln Ser Phe Gly
    290                 295                 300
Pro Ile Met Val Tyr Gln Thr Lys Ser Pro Val Pro Leu Thr Cys Pro
305                 310                 315                 320
Ser Ser Cys Val Cys Thr Ser Gln Ser Ser Asp Asn Gly Leu Asn Val
                325                 330                 335
Asn Cys Gln Glu Arg Lys Phe Thr Asn Ile Ser Asp Leu Gln Pro Lys
            340                 345                 350
Pro Thr Ser Pro Lys Lys Leu Tyr Leu Thr Gly Asn Tyr Leu Gln Thr
        355                 360                 365
Val Tyr Lys Asn Asp Leu Leu Glu Tyr Ser Ser Leu Asp Leu Leu His
    370                 375                 380
Leu Gly Asn Asn Arg Ile Ala Val Ile Gln Glu Gly Ala Phe Thr Asn
385                 390                 395                 400
Leu Thr Ser Leu Arg Arg Leu Tyr Leu Asn Gly Asn Tyr Leu Glu Val
                405                 410                 415
Leu Tyr Pro Ser Met Phe Asp Gly Leu Gln Ser Leu Gln Tyr Leu Tyr
            420                 425                 430
Leu Glu Tyr Asn Val Ile Lys Glu Ile Lys Pro Leu Thr Phe Asp Ala
        435                 440                 445
Leu Ile Asn Leu Gln Leu Leu Xaa Leu Asn Asn Asn Leu Leu Arg Ser
    450                 455                 460
Leu Pro Asp Asn Ile Phe Gly Gly Thr Ala Leu Thr Arg Leu Asn Leu
465                 470                 475                 480
Arg Asn Asn His Phe Ser His Leu Pro Val Lys Gly Val Leu Asp Gln
                485                 490                 495
Leu Pro Ala Phe Ile Gln Ile Asp Leu Gln Glu Asn Pro Trp Asp Cys
            500                 505                 510
Thr Cys Asp Ile Met Gly Leu Lys Asp Trp Thr Glu His Ala Asn Ser
        515                 520                 525
Pro Val Ile Ile Asn Glu Val Thr Cys Glu Ser Pro Ala Lys His Ala
    530                 535                 540
Gly Glu Ile Leu Lys Phe Leu Gly Arg Glu Ala Ile Cys Pro Asp Ser
545                 550                 555                 560
Pro Asn Leu Ser Asp Gly Thr Val Leu Ser Met Asn His Asn Thr Asp
                565                 570                 575
Thr Pro Arg Ser Leu Ser Val Ser Pro Ser Ser Tyr Pro Glu Leu His
            580                 585                 590
Thr Glu Val Pro
        595

<210> SEQ ID NO 19
<211> LENGTH: 635
<212> TYPE: PRT
```

<213> ORGANISM: Homo sapiens

<400> SEQUENCE: 19

```
Met Leu Leu Trp Ile Leu Leu Glu Thr Ser Leu Cys Phe Ala Ala
1               5                   10                  15

Gly Asn Val Thr Gly Asp Val Cys Lys Glu Lys Ile Cys Ser Cys Asn
            20                  25                  30

Glu Ile Glu Gly Asp Leu His Val Asp Cys Glu Lys Lys Gly Phe Thr
        35                  40                  45

Ser Leu Gln Arg Phe Thr Ala Pro Thr Ser Gln Phe Tyr His Leu Phe
    50                  55                  60

Leu His Gly Asn Ser Leu Thr Arg Leu Phe Pro Asn Glu Phe Ala Asn
65                  70                  75                  80

Phe Tyr Asn Ala Val Ser Leu His Met Glu Asn Asn Gly Leu His Glu
                85                  90                  95

Glu Val Leu Ile Leu Asn Asp Asn Leu Ile Ser Thr Leu Pro Ala Asn
            100                 105                 110

Val Phe Gln Tyr Val Pro Ile Thr His Leu Asp Leu Arg Gly Asn Arg
        115                 120                 125

Leu Lys Arg Cys Pro Met Arg Ser Leu Gly Ala Asn Pro Trp Tyr Cys
    130                 135                 140

Gly Asp Pro Ala Arg Asp Asn Pro Trp Asp Cys Thr Cys Asp Leu Leu
145                 150                 155                 160

Ser Leu Lys Glu Trp Leu Glu Asn Ile Pro Lys Asn Ala Leu Ile Gly
                165                 170                 175

Arg Val Val Cys Glu Ala Pro Thr Arg Leu Gln Gly Lys Asp Leu Asn
            180                 185                 190

Glu Thr Thr Glu Gln Asp Leu Cys Pro Leu Lys Asn Arg Val Asp Ser
        195                 200                 205

Ser Leu Pro Ala Pro Ala Gln Glu Thr Phe Ala Pro Gly Pro
    210                 215                 220

Leu Pro Thr Pro Phe Lys Thr Asn Gly Gln Glu Asp His Ala Thr Pro
225                 230                 235                 240

Gly Ser Ala Pro Asn Gly Gly Thr Lys Ile Pro Gly Asn Trp Gln Ile
                245                 250                 255

Lys Ile Arg Pro Thr Ala Ala Ile Ala Thr Gly Ser Ser Arg Asn Lys
            260                 265                 270

Pro Leu Ala Asn Ser Leu Pro Cys Pro Gly Gly Cys Ser Cys Asp His
        275                 280                 285

Ile Pro Gly Ser Gly Leu Lys Met Asn Cys Asn Asn Arg Asn Val Ser
290                 295                 300

Ser Leu Ala Asp Leu Lys Pro Lys Leu Ser Asn Val Gln Glu Leu Phe
305                 310                 315                 320

Leu Arg Asp Asn Lys Ile His Ser Ile Arg Lys Ser His Phe Val Asp
            325                 330                 335

Tyr Lys Asn Leu Ile Leu Leu Asp Leu Gly Asn Asn Ile Ala Thr
        340                 345                 350

Val Glu Asn Asn Thr Phe Lys Asn Leu Leu Asp Leu Arg Trp Leu Tyr
    355                 360                 365

Met Asp Ser Asn Tyr Leu Asp Thr Leu Ser Arg Glu Lys Phe Ala Gly
370                 375                 380

Leu Gln Asn Leu Glu Tyr Leu Asn Val Glu Tyr Asn Ala Ile Gln Leu
385                 390                 395                 400
```

```
Ile Leu Pro Gly Thr Phe Asn Ala Met Pro Lys Leu Arg Ile Leu Ile
                405                 410                 415
Leu Asn Asn Asn Leu Leu Arg Ser Leu Pro Val Asp Val Phe Ala Gly
            420                 425                 430
Val Ser Leu Ser Lys Leu Ser Leu His Asn Asn Tyr Phe Met Tyr Leu
        435                 440                 445
Pro Val Ala Gly Val Leu Asp Gln Leu Thr Ser Ile Ile Gln Ile Asp
    450                 455                 460
Leu His Gly Asn Pro Trp Glu Cys Ser Cys Thr Ile Val Pro Phe Lys
465                 470                 475                 480
Gln Trp Ala Glu Arg Leu Gly Ser Glu Val Leu Met Ser Asp Leu Lys
                485                 490                 495
Cys Glu Thr Pro Val Asn Phe Phe Arg Lys Asp Phe Met Leu Leu Ser
            500                 505                 510
Asn Asp Glu Ile Cys Pro Gln Leu Tyr Ala Arg Ile Ser Pro Thr Leu
        515                 520                 525
Thr Ser His Ser Lys Asn Ser Thr Gly Leu Ala Glu Thr Gly Thr His
    530                 535                 540
Ser Asn Ser Tyr Leu Asp Thr Ser Arg Val Ser Ile Ser Val Leu Val
545                 550                 555                 560
Pro Gly Leu Leu Leu Val Phe Val Thr Ser Ala Phe Thr Val Val Gly
                565                 570                 575
Met Leu Val Phe Ile Leu Arg Asn Arg Lys Ser Lys Arg Arg Asp
            580                 585                 590
Ala Asn Ser Ser Ala Ser Glu Ile Asn Ser Leu Gln Thr Val Cys Asp
        595                 600                 605
Ser Ser Tyr Trp His Asn Gly Pro Tyr Asn Ala Asp Gly Ala His Arg
    610                 615                 620
Val Tyr Asp Cys Gly Ser His Ser Leu Ser Asp
625                 630                 635

<210> SEQ ID NO 20
<211> LENGTH: 440
<212> TYPE: PRT
<213> ORGANISM: Homo sapiens

<400> SEQUENCE: 20

Met Leu Ile Asn Cys Glu Ala Lys Gly Ile Lys Met Val Ser Glu Ile
1               5                   10                  15
Ser Val Pro Pro Ser Arg Pro Phe Gln Leu Ser Leu Leu Asn Asn Gly
                20                  25                  30
Leu Thr Met Leu His Thr Asn Asp Phe Ser Gly Leu Thr Asn Ala Ile
            35                  40                  45
Ser Ile His Leu Gly Phe Asn Asn Ile Ala Asp Ile Glu Ile Gly Ala
    50                  55                  60
Phe Asn Gly Leu Gly Leu Leu Lys Gln Leu His Ile Asn His Asn Ser
65                  70                  75                  80
Leu Glu Ile Leu Lys Glu Asp Thr Phe His Gly Leu Glu Asn Leu Glu
                85                  90                  95
Phe Leu Gln Ala Asp Asn Asn Phe Ile Thr Val Ile Glu Pro Ser Ala
            100                 105                 110
Phe Ser Lys Leu Asn Arg Leu Lys Val Leu Ile Leu Asn Asp Asn Ala
        115                 120                 125
Ile Glu Ser Leu Pro Pro Asn Ile Phe Arg Phe Val Pro Leu Thr His
    130                 135                 140
```

-continued

Leu Asp Leu Arg Gly Asn Gln Leu Gln Thr Leu Pro Tyr Val Gly Phe
145                 150                 155                 160

Leu Glu His Ile Gly Arg Ile Leu Asp Leu Gln Leu Glu Asp Asn Lys
                165                 170                 175

Trp Ala Cys Asn Cys Asp Leu Gln Leu Lys Thr Trp Leu Glu Asn
            180                 185                 190

Met Pro Pro Gln Ser Ile Ile Gly Asp Val Val Cys Asn Ser Pro Pro
            195                 200                 205

Phe Phe Lys Gly Ser Ile Leu Ser Arg Leu Lys Lys Glu Ser Ile Cys
        210                 215                 220

Pro Thr Pro Pro Val Tyr Glu Glu His Glu Asp Pro Ser Gly Ser Leu
225                 230                 235                 240

His Leu Ala Ala Thr Ser Ser Ile Asn Asp Ser Arg Met Ser Thr Lys
                245                 250                 255

Thr Thr Ser Ile Leu Lys Leu Pro Thr Lys Ala Pro Gly Leu Ile Pro
            260                 265                 270

Tyr Ile Thr Lys Pro Ser Thr Gln Leu Pro Gly Pro Tyr Cys Pro Ile
        275                 280                 285

Pro Cys Asn Cys Lys Val Leu Ser Pro Ser Gly Leu Leu Ile His Cys
290                 295                 300

Gln Glu Arg Asn Ile Glu Ser Leu Ser Asp Leu Arg Pro Pro Gln
305                 310                 315                 320

Asn Pro Arg Lys Leu Ile Leu Ala Gly Asn Ile Ile His Ser Leu Met
                325                 330                 335

Lys Ser Asp Leu Val Glu Tyr Phe Thr Leu Glu Met Leu His Leu Gly
            340                 345                 350

Asn Asn Arg Ile Glu Val Leu Glu Glu Gly Ser Phe Met Asn Leu Thr
        355                 360                 365

Arg Leu Gln Lys Leu Tyr Leu Asn Gly Asn His Leu Thr Lys Leu Ser
370                 375                 380

Lys Gly Met Phe Leu Gly Leu His Asn Leu Glu Tyr Leu Tyr Leu Glu
385                 390                 395                 400

Tyr Asn Ala Ile Lys Glu Ile Leu Pro Gly Thr Phe Asn Pro Met Pro
                405                 410                 415

Lys Leu Lys Val Leu Tyr Leu Asn Asn Thr Ser Ser Lys Phe Tyr His
            420                 425                 430

His Ile Phe Gln Gly Phe Leu
        435                 440

<210> SEQ ID NO 21
<211> LENGTH: 977
<212> TYPE: PRT
<213> ORGANISM: Homo sapiens

<400> SEQUENCE: 21

Met Lys Pro Ser Ile Ala Glu Met Leu His Arg Gly Arg Met Leu Trp
1               5                   10                  15

Ile Ile Leu Leu Ser Thr Ile Ala Leu Gly Trp Thr Thr Pro Ile Pro
                20                  25                  30

Leu Ile Glu Asp Ser Glu Ile Asp Glu Pro Cys Phe Asp Pro Cys
            35                  40                  45

Tyr Cys Glu Val Lys Glu Ser Leu Phe His Ile His Cys Asp Ser Lys
        50                  55                  60

Gly Phe Thr Asn Ile Ser Gln Ile Thr Glu Phe Trp Ser Arg Pro Phe

```
            65                  70                  75                  80
Lys Leu Tyr Leu Gln Arg Asn Ser Met Arg Lys Leu Tyr Thr Asn Ser
                    85                  90                  95
Phe Leu His Leu Asn Asn Ala Val Ser Ile Asn Leu Gly Asn Asn Ala
                100                 105                 110
Leu Gln Asp Ile Gln Thr Gly Ala Phe Asn Gly Leu Lys Ile Leu Lys
            115                 120                 125
Arg Leu Tyr Leu His Glu Asn Lys Leu Asp Val Phe Arg Asn Asp Thr
        130                 135                 140
Phe Leu Gly Leu Glu Ser Leu Glu Tyr Leu Gln Ala Asp Tyr Asn Val
145                 150                 155                 160
Ile Lys Arg Ile Glu Ser Gly Ala Phe Arg Asn Leu Ser Lys Leu Arg
                165                 170                 175
Val Leu Ile Leu Asn Asp Asn Leu Ile Pro Met Leu Pro Thr Asn Leu
                180                 185                 190
Phe Lys Ala Val Ser Leu Thr His Leu Asp Leu Arg Gly Asn Arg Leu
            195                 200                 205
Lys Val Leu Phe Tyr Arg Gly Met Leu Asp His Ile Gly Arg Ser Leu
        210                 215                 220
Met Glu Leu Gln Leu Glu Glu Asn Pro Trp Asn Cys Thr Cys Glu Ile
225                 230                 235                 240
Val Gln Leu Lys Ser Trp Leu Glu Arg Ile Pro Tyr Thr Ala Leu Val
                245                 250                 255
Gly Asp Ile Thr Cys Glu Thr Pro Phe His Phe His Gly Lys Asp Leu
                260                 265                 270
Arg Glu Ile Arg Lys Thr Glu Leu Cys Pro Leu Leu Ser Asp Ser Glu
            275                 280                 285
Val Glu Ala Ser Leu Gly Ile Pro His Ser Ser Ser Lys Glu Asn
        290                 295                 300
Ala Trp Pro Thr Lys Pro Ser Ser Met Leu Ser Ser Val His Phe Thr
305                 310                 315                 320
Ala Ser Ser Val Glu Tyr Lys Ser Ser Asn Lys Gln Pro Lys Pro Thr
                325                 330                 335
Lys Gln Pro Arg Thr Pro Arg Pro Ser Thr Ser Gln Ala Leu Tyr
                340                 345                 350
Pro Gly Pro Asn Gln Pro Pro Ile Ala Pro Tyr Gln Thr Arg Pro Pro
            355                 360                 365
Ile Pro Ile Ile Cys Pro Thr Gly Cys Thr Cys Asn Leu His Ile Asn
        370                 375                 380
Asp Leu Gly Leu Thr Val Asn Cys Lys Glu Arg Gly Phe Asn Ile
385                 390                 395                 400
Ser Glu Leu Leu Pro Arg Pro Leu Asn Ala Lys Lys Leu Tyr Leu Ser
                405                 410                 415
Ser Asn Leu Ile Gln Lys Ile Tyr Arg Ser Asp Phe Trp Asn Phe Ser
            420                 425                 430
Ser Leu Asp Leu Leu His Leu Gly Asn Asn Arg Ile Ser Tyr Val Gln
        435                 440                 445
Asp Gly Ala Phe Ile Asn Leu Pro Asn Leu Lys Ser Leu Phe Leu Asn
    450                 455                 460
Gly Asn Asp Ile Glu Lys Leu Thr Pro Gly Met Phe Arg Gly Leu Gln
465                 470                 475                 480
Ser Leu His Tyr Leu Tyr Phe Glu Phe Asn Val Ile Arg Glu Ile Gln
                485                 490                 495
```

-continued

```
Pro Ala Ala Phe Ser Leu Met Pro Asn Leu Lys Leu Leu Phe Leu Asn
            500                 505                 510

Asn Asn Leu Leu Arg Thr Leu Pro Thr Asp Ala Phe Ala Gly Thr Ser
        515                 520                 525

Leu Ala Arg Leu Asn Leu Arg Lys Asn Tyr Phe Leu Tyr Leu Pro Val
        530                 535                 540

Ala Gly Val Leu Glu His Leu Asn Ala Ile Val Gln Ile Asp Leu Asn
545                 550                 555                 560

Glu Asn Pro Trp Asp Cys Thr Cys Asp Leu Val Pro Phe Lys Gln Trp
                565                 570                 575

Ile Glu Thr Ile Ser Ser Val Ser Val Val Gly Asp Val Leu Cys Arg
            580                 585                 590

Ser Pro Glu Asn Leu Thr His Arg Asp Val Arg Thr Ile Glu Leu Glu
        595                 600                 605

Val Leu Cys Pro Glu Met Leu His Val Ala Pro Ala Gly Glu Ser Pro
    610                 615                 620

Ala Gln Pro Gly Asp Ser His Leu Ile Gly Ala Pro Thr Ser Ala Ser
625                 630                 635                 640

Pro Tyr Glu Phe Ser Pro Gly Gly Pro Val Pro Leu Ser Val Leu
                645                 650                 655

Ile Leu Ser Leu Leu Val Leu Phe Phe Ser Ala Val Phe Val Ala Ala
            660                 665                 670

Gly Leu Phe Ala Tyr Val Leu Arg Arg Arg Lys Lys Leu Pro Phe
                675                 680                 685

Arg Ser Lys Arg Gln Glu Gly Val Asp Leu Thr Gly Ile Gln Met Gln
690                 695                 700

Cys His Arg Leu Phe Glu Asp Gly Gly Gly Gly Gly Gly Ser Gly
705                 710                 715                 720

Gly Gly Gly Arg Pro Thr Leu Ser Ser Pro Glu Lys Ala Pro Pro Val
                725                 730                 735

Gly His Val Tyr Glu Tyr Ile Pro His Pro Val Thr Gln Met Cys Asn
            740                 745                 750

Asn Pro Ile Tyr Lys Pro Arg Glu Glu Glu Val Ala Val Ser Ser
        755                 760                 765

Ala Gln Glu Ala Gly Ser Ala Glu Arg Gly Gly Pro Gly Thr Gln Pro
        770                 775                 780

Pro Gly Met Gly Glu Ala Leu Leu Gly Ser Glu Gln Phe Ala Glu Thr
785                 790                 795                 800

Pro Lys Glu Asn His Ser Asn Tyr Arg Thr Leu Leu Glu Lys Glu Lys
                805                 810                 815

Glu Trp Ala Leu Ala Val Ser Ser Gln Leu Asn Thr Ile Val Thr
            820                 825                 830

Val Asn His His His Pro His His Pro Ala Val Gly Gly Val Ser Gly
                835                 840                 845

Val Val Gly Gly Thr Gly Gly Asp Leu Ala Gly Phe Arg His His Glu
    850                 855                 860

Lys Asn Gly Gly Val Val Leu Phe Pro Pro Gly Gly Cys Gly Ser
865                 870                 875                 880

Gly Ser Met Leu Leu Asp Arg Glu Arg Pro Gln Pro Ala Pro Cys Thr
                885                 890                 895

Val Gly Phe Val Asp Cys Leu Tyr Gly Thr Val Pro Lys Leu Lys Glu
                900                 905                 910
```

```
Leu His Val His Pro Pro Gly Met Gln Tyr Pro Asp Leu Gln Gln Asp
        915                 920                 925

Ala Arg Leu Lys Glu Thr Leu Leu Phe Ser Ala Glu Lys Gly Phe Thr
        930                 935                 940

Asp His Gln Thr Gln Lys Ser Asp Tyr Leu Glu Leu Arg Ala Lys Leu
945                 950                 955                 960

Gln Thr Lys Pro Asp Tyr Leu Glu Val Leu Glu Lys Thr Thr Tyr Arg
                965                 970                 975

Phe

<210> SEQ ID NO 22
<211> LENGTH: 966
<212> TYPE: PRT
<213> ORGANISM: Homo sapiens

<400> SEQUENCE: 22

Arg Arg Gly Ala Gln Gly Gly Lys Met His Thr Cys Cys Pro Pro Val
1               5                   10                  15

Thr Leu Glu Gln Asp Leu His Arg Lys Met His Ser Trp Met Leu Gln
            20                  25                  30

Thr Leu Ala Phe Ala Val Thr Ser Leu Val Leu Ser Cys Ala Glu Thr
        35                  40                  45

Ile Asp Tyr Tyr Gly Glu Ile Cys Asp Asn Ala Cys Pro Cys Glu Glu
    50                  55                  60

Lys Asp Gly Ile Leu Thr Val Ser Cys Glu Asn Arg Gly Ile Ile Ser
65                  70                  75                  80

Leu Ser Glu Ile Ser Pro Pro Arg Phe Pro Ile Tyr His Leu Leu Leu
                85                  90                  95

Ser Gly Asn Leu Leu Asn Arg Leu Tyr Pro Asn Glu Phe Val Asn Tyr
            100                 105                 110

Thr Gly Ala Ser Ile Leu His Leu Gly Ser Asn Val Ile Gln Asp Ile
        115                 120                 125

Glu Thr Gly Ala Phe His Gly Leu Arg Gly Leu Arg Arg Leu His Leu
    130                 135                 140

Asn Asn Asn Lys Leu Glu Leu Leu Arg Asp Asp Thr Phe Leu Gly Leu
145                 150                 155                 160

Glu Asn Leu Glu Tyr Leu Gln Val Asp Tyr Asn Tyr Ile Ser Val Ile
                165                 170                 175

Glu Pro Asn Ala Phe Gly Lys Leu His Leu Leu Gln Val Leu Ile Leu
            180                 185                 190

Asn Asp Asn Leu Leu Ser Ser Leu Pro Asn Asn Leu Phe Arg Phe Val
        195                 200                 205

Pro Leu Thr His Leu Asp Leu Arg Gly Asn Arg Leu Lys Leu Leu Pro
    210                 215                 220

Tyr Val Gly Leu Leu Gln His Met Asp Lys Val Val Glu Leu Gln Leu
225                 230                 235                 240

Glu Glu Asn Pro Trp Asn Cys Ser Cys Glu Leu Ile Ser Leu Lys Asp
                245                 250                 255

Trp Leu Asp Ser Ile Ser Tyr Ser Ala Leu Val Gly Asp Val Val Cys
            260                 265                 270

Glu Thr Pro Phe Arg Leu His Gly Arg Asp Leu Asp Glu Val Ser Lys
        275                 280                 285

Gln Glu Leu Cys Pro Arg Arg Leu Ile Ser Asp Tyr Glu Met Arg Pro
    290                 295                 300
```

-continued

```
Gln Thr Pro Leu Ser Thr Thr Gly Tyr Leu His Thr Thr Pro Ala Ser
305                 310                 315                 320

Val Asn Ser Val Ala Thr Ser Ser Ala Val Tyr Lys Pro Pro Leu
            325                 330                 335

Lys Pro Pro Lys Gly Thr Arg Gln Pro Asn Lys Pro Arg Val Arg Pro
                340                 345                 350

Thr Ser Arg Gln Pro Ser Lys Asp Leu Gly Tyr Ser Asn Tyr Gly Pro
        355                 360                 365

Ser Ile Ala Tyr Gln Thr Lys Ser Pro Val Pro Leu Glu Cys Pro Thr
370                 375                 380

Ala Cys Ser Cys Asn Leu Gln Ile Ser Asp Leu Gly Leu Asn Val Asn
385                 390                 395                 400

Cys Gln Glu Arg Lys Ile Glu Ser Ile Ala Glu Leu Gln Pro Lys Pro
                405                 410                 415

Tyr Asn Pro Lys Lys Met Tyr Leu Thr Glu Asn Tyr Ile Ala Val Val
            420                 425                 430

Arg Arg Thr Asp Phe Leu Glu Ala Thr Gly Leu Asp Leu Leu His Leu
        435                 440                 445

Gly Asn Asn Arg Ile Ser Met Ile Gln Asp Arg Ala Phe Gly Asp Leu
    450                 455                 460

Thr Asn Leu Arg Arg Leu Tyr Leu Asn Gly Asn Arg Ile Glu Arg Leu
465                 470                 475                 480

Ser Pro Glu Leu Phe Tyr Gly Leu Gln Ser Leu Gln Tyr Leu Phe Leu
                485                 490                 495

Gln Tyr Asn Leu Ile Arg Glu Ile Gln Ser Gly Thr Phe Asp Pro Val
            500                 505                 510

Pro Asn Leu Gln Leu Leu Phe Leu Asn Asn Asn Leu Leu Gln Ala Met
        515                 520                 525

Pro Ser Gly Val Phe Ser Gly Leu Thr Leu Leu Arg Leu Asn Leu Arg
    530                 535                 540

Ser Asn His Phe Thr Ser Leu Pro Val Ser Gly Val Leu Asp Gln Leu
545                 550                 555                 560

Lys Ser Leu Ile Gln Ile Asp Leu His Asp Asn Pro Trp Asp Cys Thr
                565                 570                 575

Cys Asp Ile Val Gly Met Lys Leu Trp Val Glu Gln Leu Lys Val Gly
            580                 585                 590

Val Leu Val Asp Glu Val Ile Cys Lys Ala Pro Lys Lys Phe Ala Glu
        595                 600                 605

Thr Asp Met Arg Ser Ile Lys Ser Glu Leu Leu Cys Pro Asp Tyr Ser
    610                 615                 620

Asp Val Val Ser Thr Pro Thr Pro Ser Ser Ile Gln Val Pro Ala
625                 630                 635                 640

Arg Thr Ser Ala Val Thr Pro Ala Val Arg Leu Asn Ser Thr Gly Ala
                645                 650                 655

Pro Ala Ser Leu Gly Ala Gly Gly Ala Ser Ser Val Pro Leu Ser
            660                 665                 670

Val Leu Ile Leu Ser Leu Leu Val Phe Ile Met Ser Val Phe Val
        675                 680                 685

Ala Ala Gly Leu Phe Val Leu Val Met Lys Arg Arg Lys Lys Asn Gln
    690                 695                 700

Ser Asp His Thr Ser Thr Asn Asn Ser Asp Val Ser Ser Phe Asn Met
705                 710                 715                 720

Gln Tyr Ser Val Tyr Gly Gly Gly Gly Thr Gly Gly His Pro His
```

```
                       725                 730                 735
Ala His Val His His Arg Gly Pro Ala Leu Pro Lys Val Lys Thr Pro
                740                 745                 750
Ala Gly His Val Tyr Glu Tyr Ile Pro His Pro Leu Gly His Met Cys
            755                 760                 765
Lys Asn Pro Ile Tyr Arg Ser Arg Glu Gly Asn Ser Val Glu Asp Tyr
        770                 775                 780
Lys Asp Leu His Glu Leu Lys Val Thr Tyr Ser Ser Asn His His Leu
785                 790                 795                 800
Gln Gln Gln Gln Gln Pro Pro Pro Gln Gln Pro Gln Gln Gln
                805                 810                 815
Pro Pro Pro Gln Leu Gln Leu Gln Pro Gly Glu Glu Arg Arg Glu
                820                 825                 830
Ser His His Leu Arg Ser Pro Ala Tyr Ser Val Ser Thr Ile Glu Pro
            835                 840                 845
Arg Glu Asp Leu Leu Ser Pro Val Gln Asp Ala Asp Arg Phe Tyr Arg
        850                 855                 860
Gly Ile Leu Glu Pro Asp Lys His Cys Ser Thr Thr Pro Ala Gly Asn
865                 870                 875                 880
Ser Leu Pro Glu Tyr Pro Lys Phe Pro Cys Ser Pro Ala Ala Tyr Thr
                885                 890                 895
Phe Ser Pro Asn Tyr Asp Leu Arg Arg Pro His Gln Tyr Leu His Pro
                900                 905                 910
Gly Ala Gly Asp Ser Arg Leu Arg Glu Pro Val Leu Tyr Ser Pro Pro
            915                 920                 925
Ser Ala Val Phe Val Glu Pro Asn Arg Asn Glu Tyr Leu Glu Leu Lys
        930                 935                 940
Ala Lys Leu Asn Val Glu Pro Asp Tyr Leu Glu Val Leu Glu Lys Gln
945                 950                 955                 960
Thr Thr Phe Ser Gln Phe
                965

<210> SEQ ID NO 23
<211> LENGTH: 720
<212> TYPE: DNA
<213> ORGANISM: Homo sapiens

<400> SEQUENCE: 23
gaaactcatc atttgcactt gagatctaac ttcactaaag actgtgcccc ataagagttt      60
tttccaagac tgtcggaatc ttgatttttt ggatttgggt tacaatcgtc ttcgaagctt     120
gtcccgaaat gcatttgctg gcctcttgaa gttaaaggag ctccacctgg agcacaacca     180
gttttccaag atcaactttg ctcatttttcc acgtctcttc aacctccgct caatttactt     240
acaatggaac aggattcgct ccattagcca aggtttgaca tggacttgga gttccttaca     300
caacttggat ttatcaggga tgacatccaa ggaattgag ccgggcacat ttaaatgcct     360
ccccaattta caaaaattga atttggattc caacaagctc accatatatct cacaggaaac     420 tgtcaatgcg tggatatcat taatatccat cacattgtct ggaaatatgt gggaatgcag     480
tcggagcatt tgtcctttat tttattggct taagaatttc aaaggaaata aggaaagcac     540
catgatatgt gcgggaccta agcacatcca gggtgaaaag gttagtgatg cagtggaaac     600
atataatatc tgttctgaag tccaggtggt caacacagaa agatcacacc tggtgcccca     660
aactccccag aaacctctga ttatccctag acctaccatc ttcaaacctg acgtcaccca     720
```

<210> SEQ ID NO 24
<211> LENGTH: 2080
<212> TYPE: DNA
<213> ORGANISM: Homo sapiens

<400> SEQUENCE: 24

```
ccagtccctc cctggcagct cggcttccct cagctccaac tcttctcttc cgctcctgcc      60
tcctgtcgga ttttaatttt ctgcgcaccc ccagtcaaat taaatcaacc aacaaaaagc     120
aggcatcccc cctggaagca gcgtcttatt ttaccttgtt ctcccacttc ctgaagatgc     180
taaactcctg gtggactgca gaggagaggg attcagtctt ctcctgatgt cgattgcgat     240
ttctgctggg agctcaagac gggcgagctg cccgagatct cttcgagata ccccagggga     300
ggaggagatg ggcaggattt agtaggacaa ctcggttact aatgacttgg cggctggctg     360
cgaccccccg ggaaatcagg tttgcctgta ggtacctgag ttgacaccga aggtgcctaa     420
agatgctgag cggcgtttgg ttcctcagtg tgttaaccgt ggccgggatc ttacagacag     480
agagtcgcaa aactgccaaa gacatttgca agatccgctg tctgtgcgaa gaaaaggaaa     540
acgtactgaa tatcaactgt gagaacaaag gatttacaac agttagcctg ctccagcccc     600
cccagtatcg aatctatcag cttttttctca atggaaacct cttgacaaga ctgtatccaa     660
acgaatttgt caattactcc aacgcggtga ctcttcacct aggtaacaac gggttacagg     720
agatccgaac gggggcattc agtggcctga aaactctcaa aagactgcat ctcaacaaca     780
acaagcttga gatattgagg gaggacacct tcctaggcct ggagagcctg gagtatctcc     840
aggccgacta caattacatc agtgccatcg aggctggggc attcagcaaa cttaacaagc     900
tcaaagtgct catcctgaat gacaaccttc tgctttcact gcccagcaat gtgttccgct     960
ttgtcctgct gacccactta gacctcaggg ggaataggct aaaagtaatg ccttttgctg    1020
gcgtccttga acatattgga gggatcatgg agattcagct ggaggaaaat ccatggaatt    1080
gcacttgtga cttacttcct ctcaaggcct ggctagacac cataactgtt tttgtgggag    1140
agattgtctg tgagactccc tttaggttgc atgggaaaga cgtgacccag ctgaccaggc    1200
aagacctctg tccagaaaaa agtgccagtg attccagtca gaggggcagc catgctgaca    1260
cccacgtcca aaggctgtca cctacaatga atcctgctct caacccaacc agggctccga    1320
aagccagccg gccgcccaaa atgagaaatc gtccaactcc ccgagtgact gtgtcaaagg    1380
acaggcaaag ttttggaccc atcatggtgt accagaccaa gtctcctgtg cctctcacct    1440
gtcccagcag ctgtgtctgc acctctcaga gctcagacaa tggtctgaat gtaaactgcc    1500
aagaaaggaa gttcactaat atctctgacc tgcagcccaa accgaccagt ccaaagaaac    1560
tctacctaac agggaactat cttcaaactg tctataagaa tgacctctta gaatacagtt    1620
ctttggactt actgcactta ggaaacaaca ggattgcagt cattcaggaa ggtgccttta    1680
caaacctgac cagtttacgc agactttatc tgaatgcaa ttaccttgaa gtgctgtacc    1740
cttctatgtt tgatggactg cagagcttgc aatatctcta tttagagtat aatgtcatta    1800
aggaaattaa gcctctgacc tttgatgctt tgattaacct acagctactg tttctgaaca    1860
acaaccttct tcggtcctta cctgataata tatttgggg gacggcccta accaggctga    1920
atctgagaaa caaccatttt tctcacctgc ccgtgaaagg ggttctggat cagctcccgg    1980
cttttcatcca gatagatctg caggagaacc ccctggggact gtcctgtgac atcatggggc    2040
tgaaagactg gacagaacat gccaattccc ctgtcatcat                          2080
```

-continued

<210> SEQ ID NO 25
<211> LENGTH: 32
<212> TYPE: PRT
<213> ORGANISM: Homo sapiens

<400> SEQUENCE: 25

Met Gly Phe His Leu Ile Thr Gln Leu Lys Gly Met Ser Val Val Leu
1               5                   10                  15
Val Leu Leu Pro Thr Leu Leu Leu Val Met Leu Thr Gly Ala Gln Arg
            20                  25                  30

<210> SEQ ID NO 26
<211> LENGTH: 25
<212> TYPE: PRT
<213> ORGANISM: Homo sapiens

<400> SEQUENCE: 26

Asn Leu Gln His Leu Asp Leu Ser His Asn Gln Leu Thr Gly Ser Ile
1               5                   10                  15
Pro Pro Glu Ser Phe Gly Asn Leu Pro
            20                  25

<210> SEQ ID NO 27
<211> LENGTH: 31
<212> TYPE: PRT
<213> ORGANISM: Homo sapiens

<400> SEQUENCE: 27

Gln Cys Pro Arg Pro Cys His Cys His Pro Phe His Thr His Val Tyr
1               5                   10                  15
Cys Asp Asp Arg Asn Leu Thr Asn Glu Val Pro Arg Asp Ile Pro
            20                  25                  30

<210> SEQ ID NO 28
<211> LENGTH: 54
<212> TYPE: PRT
<213> ORGANISM: Homo sapiens

<400> SEQUENCE: 28

Asn Pro Trp His Cys Asp Cys His Leu Arg Trp Phe Gln Arg Trp Leu
1               5                   10                  15
Arg Glu Trp His Pro Arg His Ile Trp Asp Gln Glu Asp Tyr Arg Cys
            20                  25                  30
Ala Asn Pro Pro His Leu Arg Gly Gln Pro Val Leu Asp Tyr Pro His
        35                  40                  45
Ser Asp Phe Ser Cys Pro
    50

<210> SEQ ID NO 29
<211> LENGTH: 24
<212> TYPE: PRT
<213> ORGANISM: Homo sapiens

<400> SEQUENCE: 29

Gln Leu Ile Trp Leu Tyr Leu Asp His Asn Tyr Ile Ser Ser Val Asp
1               5                   10                  15
Glu Asp Ala Phe Gln Gly Ile Arg
            20

<210> SEQ ID NO 30
<211> LENGTH: 24
<212> TYPE: PRT

<213> ORGANISM: Homo sapiens

<400> SEQUENCE: 30

Arg Leu Lys Glu Leu Ile Leu Ser Ser Asn Lys Ile Thr Tyr Leu His
1               5                   10                  15

Asn Lys Thr Phe His Pro Val Pro
            20

<210> SEQ ID NO 31
<211> LENGTH: 24
<212> TYPE: PRT
<213> ORGANISM: Homo sapiens

<400> SEQUENCE: 31

Asn Leu Arg Asn Leu Asp Leu Ser Tyr Asn Lys Leu Gln Thr Leu Gln
1               5                   10                  15

Ser Glu Gln Phe Lys Gly Leu Arg
            20

<210> SEQ ID NO 32
<211> LENGTH: 24
<212> TYPE: PRT
<213> ORGANISM: Homo sapiens

<400> SEQUENCE: 32

Lys Leu Ile Ile Leu His Leu Arg Ser Asn Ser Leu Lys Thr Val Pro
1               5                   10                  15

Ile Arg Val Phe Gln Asp Cys Arg
            20

<210> SEQ ID NO 33
<211> LENGTH: 24
<212> TYPE: PRT
<213> ORGANISM: Homo sapiens

<400> SEQUENCE: 33

Asn Leu Asp Phe Leu Asp Leu Gly Tyr Asn Arg Leu Arg Ser Leu Ser
1               5                   10                  15

Arg Asn Ala Phe Ala Gly Leu Leu
            20

<210> SEQ ID NO 34
<211> LENGTH: 24
<212> TYPE: PRT
<213> ORGANISM: Homo sapiens

<400> SEQUENCE: 34

Lys Leu Lys Glu Leu His Leu Glu His Asn Gln Phe Ser Lys Ile Asn
1               5                   10                  15

Phe Ala His Phe Pro Arg Leu Phe
            20

<210> SEQ ID NO 35
<211> LENGTH: 24
<212> TYPE: PRT
<213> ORGANISM: Homo sapiens

<400> SEQUENCE: 35

Asn Leu Arg Ser Ile Tyr Leu Gln Trp Asn Arg Ile Arg Ser Ile Ser
1               5                   10                  15

Gln Gly Leu Thr Trp Thr Trp Ser
            20

<210> SEQ ID NO 36
<211> LENGTH: 24
<212> TYPE: PRT
<213> ORGANISM: Homo sapiens

<400> SEQUENCE: 36

Ser Leu His Asn Leu Asp Leu Ser Gly Asn Asp Ile Gln Gly Ile Glu
1               5                   10                  15

Pro Gly Thr Phe Lys Cys Leu Pro
            20

<210> SEQ ID NO 37
<211> LENGTH: 24
<212> TYPE: PRT
<213> ORGANISM: Homo sapiens

<400> SEQUENCE: 37

Asn Leu Gln Lys Leu Asn Leu Asp Ser Asn Lys Leu Thr Asn Ile Ser
1               5                   10                  15

Gln Glu Thr Val Asn Ala Trp Ile
            20

<210> SEQ ID NO 38
<211> LENGTH: 28
<212> TYPE: PRT
<213> ORGANISM: Homo sapiens

<400> SEQUENCE: 38

Ala Cys Pro Lys Asn Cys Arg Cys Asp Gly Lys Ile Val Tyr Cys Glu
1               5                   10                  15

Ser His Ala Phe Ala Asp Ile Pro Glu Asn Ile Ser
            20                  25

<210> SEQ ID NO 39
<211> LENGTH: 51
<212> TYPE: PRT
<213> ORGANISM: Homo sapiens

<400> SEQUENCE: 39

Asn Met Trp Glu Cys Ser Arg Ser Ile Cys Pro Leu Phe Tyr Trp Leu
1               5                   10                  15

Lys Asn Phe Lys Gly Asn Lys Glu Ser Thr Met Ile Cys Ala Gly Pro
            20                  25                  30

Lys His Ile Gln Gly Glu Lys Val Ser Asp Ala Val Glu Thr Tyr Asn
        35                  40                  45

Ile Cys Ser
    50

<210> SEQ ID NO 40
<211> LENGTH: 20
<212> TYPE: DNA
<213> ORGANISM: Homo sapiens

<400> SEQUENCE: 40
ccattagcca aggtttgaca                                            20

<210> SEQ ID NO 41
<211> LENGTH: 20
<212> TYPE: DNA
<213> ORGANISM: Homo sapiens

```
<400> SEQUENCE: 41
ttggtgagct tgttggaatc                                                   20

<210> SEQ ID NO 42
<211> LENGTH: 20
<212> TYPE: DNA
<213> ORGANISM: Homo sapiens

<400> SEQUENCE: 42
tgtcctgctg acccacttag                                                   20

<210> SEQ ID NO 43
<211> LENGTH: 20
<212> TYPE: DNA
<213> ORGANISM: Homo sapiens

<400> SEQUENCE: 43
ccaggccttg agaggaagta                                                   20

<210> SEQ ID NO 44
<211> LENGTH: 24
<212> TYPE: PRT
<213> ORGANISM: Homo sapiens

<400> SEQUENCE: 44

Asn Ala Val Thr Leu His Leu Gly Asn Asn Gly Leu Gln Glu Ile Arg
1               5                   10                  15

Thr Gly Ala Phe Ser Gly Leu Lys
            20

<210> SEQ ID NO 45
<211> LENGTH: 24
<212> TYPE: PRT
<213> ORGANISM: Homo sapiens

<400> SEQUENCE: 45

Thr Leu Lys Arg Leu His Leu Asn Asn Asn Lys Leu Glu Ile Leu Arg
1               5                   10                  15

Glu Asp Thr Phe Leu Gly Leu Glu
            20

<210> SEQ ID NO 46
<211> LENGTH: 24
<212> TYPE: PRT
<213> ORGANISM: Homo sapiens

<400> SEQUENCE: 46

Ser Leu Glu Tyr Leu Gln Ala Asp Tyr Asn Tyr Ile Ser Ala Ile Glu
1               5                   10                  15

Ala Gly Ala Phe Ser Lys Leu Asn
            20

<210> SEQ ID NO 47
<211> LENGTH: 23
<212> TYPE: PRT
<213> ORGANISM: Homo sapiens

<400> SEQUENCE: 47

Lys Leu Lys Val Leu Ile Leu Asn Asp Asn Leu Leu Leu Ser Leu Pro
1               5                   10                  15

Ser Asn Val Phe Arg Phe Val
            20
```

<210> SEQ ID NO 48
<211> LENGTH: 22
<212> TYPE: PRT
<213> ORGANISM: Homo sapiens

<400> SEQUENCE: 48

Leu Leu Thr His Leu Asp Leu Arg Gly Asn Arg Leu Lys Val Met Pro
1               5                   10                  15

Phe Ala Gly Val Leu Glu
            20

<210> SEQ ID NO 49
<211> LENGTH: 24
<212> TYPE: PRT
<213> ORGANISM: Homo sapiens

<400> SEQUENCE: 49

Ser Leu Asp Leu Leu His Leu Gly Asn Asn Arg Ile Ala Val Ile Gln
1               5                   10                  15

Glu Gly Ala Phe Thr Asn Leu Thr
            20

<210> SEQ ID NO 50
<211> LENGTH: 24
<212> TYPE: PRT
<213> ORGANISM: Homo sapiens

<400> SEQUENCE: 50

Ser Leu Arg Arg Leu Tyr Leu Asn Gly Asn Tyr Leu Glu Val Leu Tyr
1               5                   10                  15

Pro Ser Met Phe Asp Gly Leu Gln
            20

<210> SEQ ID NO 51
<211> LENGTH: 24
<212> TYPE: PRT
<213> ORGANISM: Homo sapiens

<400> SEQUENCE: 51

Ser Leu Gln Tyr Leu Tyr Leu Glu Tyr Asn Val Ile Lys Glu Ile Lys
1               5                   10                  15

Pro Leu Thr Phe Asp Ala Leu Ile
            20

<210> SEQ ID NO 52
<211> LENGTH: 23
<212> TYPE: PRT
<213> ORGANISM: Homo sapiens

<400> SEQUENCE: 52

Asn Leu Gln Leu Leu Phe Leu Asn Asn Asn Leu Leu Arg Ser Leu Pro
1               5                   10                  15

Asp Asn Ile Phe Gly Gly Thr
            20

<210> SEQ ID NO 53
<211> LENGTH: 25
<212> TYPE: PRT
<213> ORGANISM: Homo sapiens

<400> SEQUENCE: 53

```
Ala Leu Thr Arg Leu Asn Leu Arg Asn Asn His Phe Ser His Leu Pro
1               5                   10                  15

Val Lys Gly Val Leu Asp Gln Leu Pro
            20                  25
```

<210> SEQ ID NO 54
<211> LENGTH: 32
<212> TYPE: PRT
<213> ORGANISM: Homo sapiens

<400> SEQUENCE: 54

```
Ile Cys Lys Ile Arg Cys Leu Cys Glu Glu Lys Glu Asn Val Leu Asn
1               5                   10                  15

Ile Asn Cys Glu Asn Lys Gly Phe Thr Thr Val Ser Leu Leu Gln Pro
            20                  25                  30
```

<210> SEQ ID NO 55
<211> LENGTH: 34
<212> TYPE: PRT
<213> ORGANISM: Homo sapiens

<400> SEQUENCE: 55

```
Thr Cys Pro Ser Ser Cys Val Cys Thr Ser Gln Ser Ser Asp Asn Gly
1               5                   10                  15

Leu Asn Val Asn Cys Gln Glu Arg Lys Phe Thr Asn Ile Ser Asp Leu
            20                  25                  30

Gln Pro
```

<210> SEQ ID NO 56
<211> LENGTH: 49
<212> TYPE: PRT
<213> ORGANISM: Homo sapiens

<400> SEQUENCE: 56

```
Asn Pro Trp Asn Cys Thr Cys Asp Leu Leu Pro Leu Lys Ala Trp Leu
1               5                   10                  15

Asp Thr Ile Thr Val Phe Val Gly Glu Ile Val Cys Glu Thr Pro Phe
            20                  25                  30

Arg Leu His Gly Lys Asp Val Thr Gln Leu Thr Arg Gln Asp Leu Cys
        35                  40                  45

Pro
```

<210> SEQ ID NO 57
<211> LENGTH: 51
<212> TYPE: PRT
<213> ORGANISM: Homo sapiens

<400> SEQUENCE: 57

```
Asn Pro Trp Asp Cys Thr Cys Asp Ile Met Gly Leu Lys Asp Trp Thr
1               5                   10                  15

Glu His Ala Asn Ser Pro Val Ile Ile Asn Glu Val Thr Cys Glu Ser
            20                  25                  30

Pro Ala Lys His Ala Gly Glu Ile Leu Lys Phe Leu Gly Arg Glu Ala
        35                  40                  45

Ile Cys Pro
    50
```

<210> SEQ ID NO 58
<211> LENGTH: 80
<212> TYPE: DNA

<213> ORGANISM: Homo sapiens

<400> SEQUENCE: 58
ggggaggcat ttaaatgtgc ccggctcaat tccttggatg tcattccctg ataaatccaa      60
gttgtgtaag gaactccaag                                                  80

<210> SEQ ID NO 59
<211> LENGTH: 80
<212> TYPE: DNA
<213> ORGANISM: Homo sapiens

<400> SEQUENCE: 59
cacaagtgca attccatgga ttttcctcca gctgaatctc catgatccct ccaatatgtt      60
caaggacgcc agcaaaaggc                                                  80

<210> SEQ ID NO 60
<211> LENGTH: 19
<212> TYPE: DNA
<213> ORGANISM: Homo sapiens

<400> SEQUENCE: 60
gctacccagc cagcatgaa                                                   19

<210> SEQ ID NO 61
<211> LENGTH: 22
<212> TYPE: DNA
<213> ORGANISM: Homo sapiens

<400> SEQUENCE: 61
tcagactctc tggccttttt cc                                               22

<210> SEQ ID NO 62
<211> LENGTH: 30
<212> TYPE: DNA
<213> ORGANISM: Homo sapiens

<400> SEQUENCE: 62
actccagcaa cactctctta tgaagaggcg                                       30

<210> SEQ ID NO 63
<211> LENGTH: 19
<212> TYPE: DNA
<213> ORGANISM: Homo sapiens

<400> SEQUENCE: 63
cctgctctca acccaacca                                                   19

<210> SEQ ID NO 64
<211> LENGTH: 24
<212> TYPE: DNA
<213> ORGANISM: Homo sapiens

<400> SEQUENCE: 64
ggagttggac gatttctcat tttg                                             24

<210> SEQ ID NO 65
<211> LENGTH: 18
<212> TYPE: DNA
<213> ORGANISM: Homo sapiens

<400> SEQUENCE: 65
ccgaaagcca gccggccg                                                    18

<210> SEQ ID NO 66
<211> LENGTH: 38
<212> TYPE: DNA
<213> ORGANISM: Homo sapiens

<400> SEQUENCE: 66
gcagcagcgg ccgcgctcag agagcttgcc caaagaac                    38

<210> SEQ ID NO 67
<211> LENGTH: 37
<212> TYPE: DNA
<213> ORGANISM: Homo sapiens

<400> SEQUENCE: 67
gcagcagtcg acgtttgcaa ttctctctag gtagatg                     37

<210> SEQ ID NO 68
<211> LENGTH: 39
<212> TYPE: DNA
<213> ORGANISM: Homo sapiens

<400> SEQUENCE: 68
gcagcagcgg ccgcatgggt ttccatttaa ttacgcagc                   39

<210> SEQ ID NO 69
<211> LENGTH: 36
<212> TYPE: DNA
<213> ORGANISM: Homo sapiens

<400> SEQUENCE: 69
gcagcagtcg actatccacg cattgacagt ttcctg                      36

<210> SEQ ID NO 70
<211> LENGTH: 37
<212> TYPE: DNA
<213> ORGANISM: Homo sapiens

<400> SEQUENCE: 70
gcagcagcgg ccgcaacgcg gtgactcttc acctagg                     37

<210> SEQ ID NO 71
<211> LENGTH: 33
<212> TYPE: DNA
<213> ORGANISM: Homo sapiens

<400> SEQUENCE: 71
gcagcagtcg accagctgac tgattgcagt ttg                         33

<210> SEQ ID NO 72
<211> LENGTH: 38
<212> TYPE: DNA
<213> ORGANISM: Homo sapiens

<400> SEQUENCE: 72
gcagcagcgg ccgcatgctg agcggcgttt ggttcctc                    38

<210> SEQ ID NO 73
<211> LENGTH: 37
<212> TYPE: DNA
<213> ORGANISM: Homo sapiens

<400> SEQUENCE: 73

```
                                         -continued
gcagcagtcg accgggagct gatccagaac ccctttc                          37

<210> SEQ ID NO 74
<211> LENGTH: 733
<212> TYPE: DNA
<213> ORGANISM: homo sapiens

<400> SEQUENCE: 74
gggatccgga gcccaaatct tctgacaaaa ctcacacatg cccaccgtgc ccagcacctg   60
aattcgaggg tgcaccgtca gtcttcctct tccccccaaa acccaaggac accctcatga  120
tctcccggac tcctgaggtc acatgcgtgg tggtggacgt aagccacgaa gaccctgagg  180
tcaagttcaa ctggtacgtg gacggcgtgg aggtgcataa tgccaagaca aagccgcggg  240
aggagcagta caacagcacg taccgtgtgg tcagcgtcct caccgtcctg caccaggact  300
ggctgaatgg caaggagtac aagtgcaagg tctccaacaa agccctccca accccatcg  360 agaaaaccat ctccaaagcc aaagggcagc ccgagaacc acaggtgtac accctgcccc  420
catcccggga tgagctgacc aagaaccagg tcagcctgac ctgcctggtc aaaggcttct  480
atccaagcga catcgccgtg gagtgggaga gcaatgggca gccggagaac aactacaaga  540
ccacgcctcc cgtgctggac tccgacggct ccttcttcct ctacagcaag ctcaccgtgg  600
acaagagcag gtggcagcag gggaacgtct tctcatgctc cgtgatgcat gaggctctgc  660
acaaccacta cacgcagaag agcctctccc tgtctccggg taaatgagtg cgacggccgc  720
gactctagag gat                                                    733

<210> SEQ ID NO 75
<211> LENGTH: 20
<212> TYPE: PRT
<213> ORGANISM: Artificial Sequence
<220> FEATURE:
<223> OTHER INFORMATION: LRR Concensus Sequence.
<220> FEATURE:
<221> NAME/KEY: MISC_FEATURE
<222> LOCATION: (1)..(20)
<223> OTHER INFORMATION: wherein "X" equals any naturally occurring
      amino acid.
<220> FEATURE:
<221> NAME/KEY: MISC_FEATURE
<222> LOCATION: (12)..(12)
<223> OTHER INFORMATION: wherein "A" equals an aliphatic residue, such
      as glycine, alanine, valine, leucine and isoleucine.
<220> FEATURE:
<221> NAME/KEY: MISC_FEATURE
<222> LOCATION: (16)..(16)
<223> OTHER INFORMATION: wherein "A" equals an aliphatic residue, such
      as glycine, alanine, valine, leucine and isoleucine.

<400> SEQUENCE: 75

Xaa Leu Xaa Xaa Leu Xaa Leu Xaa Xaa Asn Xaa Ala Xaa Xaa Xaa Ala
 1               5                  10                  15

Xaa Xaa Leu Xaa
             20
```